US008828998B2

(12) United States Patent
Palombella et al.

(10) Patent No.: US 8,828,998 B2
(45) Date of Patent: Sep. 9, 2014

(54) TREATMENT OF LUPUS, FIBROTIC CONDITIONS, AND INFLAMMATORY MYOPATHIES AND OTHER DISORDERS USING PI3 KINASE INHIBITORS

(71) Applicant: Infinity Pharmaceuticals, Inc., Cambridge, MA (US)

(72) Inventors: Vito J. Palombella, Needham, MA (US); David G. Winkler, Arlington, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/837,195

(22) Filed: Mar. 15, 2013

(65) Prior Publication Data

US 2013/0344061 A1  Dec. 26, 2013

Related U.S. Application Data

(60) Provisional application No. 61/664,025, filed on Jun. 25, 2012, provisional application No. 61/664,037, filed on Jun. 25, 2012, provisional application No. 61/673,113, filed on Jul. 18, 2012, provisional application No. 61/673,187, filed on Jul. 18, 2012, provisional application No. 61/673,195, filed on Jul. 18, 2012.

(51) Int. Cl.
| | | |
|---|---|---|
| *A61K 31/535* | (2006.01) | |
| *A61K 31/519* | (2006.01) | |
| *A61K 31/52* | (2006.01) | |
| *A61K 31/44* | (2006.01) | |
| *A61K 39/00* | (2006.01) | |
| *A01N 43/54* | (2006.01) | |

(52) U.S. Cl.
USPC .................... 514/234.2; 514/256; 514/262.1; 514/263.22; 514/300; 514/302; 424/133.1; 424/134.1; 424/142.1

(58) Field of Classification Search
USPC ............. 514/234.2, 256, 262.1, 263.22, 300, 514/302; 424/133.1, 134.1, 142.1
See application file for complete search history.

(56) References Cited

U.S. PATENT DOCUMENTS

| | | | |
|---|---|---|---|
| 4,547,508 A | 10/1985 | Konz et al. | |
| 4,656,159 A | 4/1987 | McPherson et al. | |
| 4,704,381 A | 11/1987 | Schaumann et al. | |
| 4,795,627 A | 1/1989 | Fisher et al. | |
| 5,240,941 A | 8/1993 | Bruneau | |
| 5,294,612 A | 3/1994 | Bacon et al. | |
| 5,310,731 A | 5/1994 | Olsson et al. | |
| 5,364,862 A | 11/1994 | Spada et al. | |
| 5,409,930 A | 4/1995 | Spada et al. | |
| 5,420,419 A | 5/1995 | Wood | |
| 5,428,125 A | 6/1995 | Hefner, Jr. et al. |
| 5,442,039 A | 8/1995 | Hefner, Jr. et al. |
| 5,480,883 A | 1/1996 | Spada et al. |
| 5,504,103 A | 4/1996 | Bonjouklian et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,646,153 A | 7/1997 | Spada et al. |
| 5,652,366 A | 7/1997 | Spada et al. |
| 5,654,307 A | 8/1997 | Bridges et al. |
| 5,656,643 A | 8/1997 | Spada et al. |
| 5,665,721 A | 9/1997 | Bhagwat et al. |
| 5,674,998 A | 10/1997 | Boyer et al. |
| 5,686,455 A | 11/1997 | Adams et al. |
| 5,710,158 A | 1/1998 | Spada et al. |
| 5,714,493 A | 2/1998 | Spada et al. |
| 5,721,237 A | 2/1998 | Spada et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| RE36,256 E | 7/1999 | Spada et al. |
| 5,919,808 A | 7/1999 | Petrie et al. |
| 5,922,753 A | 7/1999 | Petrie et al. |
| 5,948,776 A | 9/1999 | Petrie et al. |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

Abdel-Mohsen, "Synthesis, Reactions and Antimicrobial Activity of 2-Amino-4-(8-quinolinol-5-yl)-1-(p-tolyl)-pyrrole-3-carbonitrile," *Bull. Korean Chem. Soc.* 26(5):719-728 (2005).
Abe et al., "T cell receptor-mediated recognition of self-ligand induces signaling in immature thymocytes before negative selection," *J. Exp. Med.* 176(2):459-468 (1992).
Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).
Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).
Ames et al., "Heterocyclic Syntheses from o-Halogeno-acids. Part II. Thienopyridinones and Thienopyranones from 3-Bromothiophen-2- and 4-Bromothiophen-3-carboxylic Acids," *J.C.S. Perkin I* 1390-1395 (1975).

(Continued)

*Primary Examiner* — Raymond Henley, III
(74) *Attorney, Agent, or Firm* — Jones Day

(57) ABSTRACT

Provided herein are methods, kits, and pharmaceutical compositions that include a PI3 kinase inhibitor for treating lupus, a fibrotic condition, or inflammatory myopathies and other conditions (e.g., skin conditions).

48 Claims, 27 Drawing Sheets

(56) References Cited

U.S. PATENT DOCUMENTS

| | | | |
|---|---|---|---|
| 5,965,573 A | 10/1999 | Petrie et al. | |
| 5,977,061 A | 11/1999 | Holy et al. | |
| 5,981,533 A | 11/1999 | Traxler et al. | |
| 5,985,589 A | 11/1999 | Chantry et al. | |
| 5,990,109 A * | 11/1999 | Chen et al. | 514/250 |
| 5,990,169 A | 11/1999 | Petrie et al. | |
| 5,994,358 A | 11/1999 | Petrie et al. | |
| 6,001,839 A | 12/1999 | Calderwood et al. | |
| 6,057,305 A | 5/2000 | Holy et al. | |
| 6,057,320 A | 5/2000 | Spada et al. | |
| 6,057,371 A | 5/2000 | Glennon | |
| 6,084,095 A | 7/2000 | Bridges et al. | |
| 6,093,737 A | 7/2000 | Anthony et al. | |
| 6,127,121 A | 10/2000 | Meyer, Jr. et al. | |
| 6,153,631 A | 11/2000 | Petrie et al. | |
| 6,191,170 B1 | 2/2001 | Medina | |
| 6,242,453 B1 * | 6/2001 | Cirillo et al. | 514/267 |
| 6,251,901 B1 | 6/2001 | Petrie et al. | |
| 6,265,410 B1 | 7/2001 | Bridges et al. | |
| 6,268,370 B1 | 7/2001 | Adams et al. | |
| 6,312,894 B1 | 11/2001 | Hedgpeth et al. | |
| 6,323,201 B1 | 11/2001 | Carson et al. | |
| 6,342,514 B1 | 1/2002 | Petrie et al. | |
| 6,350,741 B1 | 2/2002 | Golec et al. | |
| 6,358,945 B1 * | 3/2002 | Breitfelder et al. | 514/227.8 |
| 6,362,216 B1 | 3/2002 | Burgess et al. | |
| RE37,650 E | 4/2002 | Spada et al. | |
| 6,383,790 B1 | 5/2002 | Shokat | |
| 6,384,039 B1 | 5/2002 | Fossa | |
| 6,387,894 B1 | 5/2002 | Fossa | |
| 6,390,821 B1 | 5/2002 | Shokat | |
| 6,455,534 B2 | 9/2002 | Bridges et al. | |
| 6,472,153 B1 | 10/2002 | Dempcy et al. | |
| 6,472,562 B1 | 10/2002 | Klingler et al. | |
| 6,482,623 B1 | 11/2002 | Vanhaesebroeck et al. | |
| 6,485,906 B2 | 11/2002 | Meyer, Jr. et al. | |
| 6,492,346 B1 | 12/2002 | Hedgpeth et al. | |
| 6,506,769 B2 | 1/2003 | Snow et al. | |
| 6,518,277 B1 | 2/2003 | Sadhu et al. | |
| 6,521,417 B1 | 2/2003 | Shokat | |
| 6,521,620 B1 | 2/2003 | Bridges et al. | |
| 6,531,491 B1 | 3/2003 | Kania et al. | |
| 6,534,524 B1 | 3/2003 | Kania et al. | |
| 6,545,005 B1 | 4/2003 | Baxter et al. | |
| 6,552,192 B1 | 4/2003 | Hanus et al. | |
| 6,562,819 B2 | 5/2003 | Carson et al. | |
| 6,583,161 B1 | 6/2003 | Medina | |
| 6,613,798 B1 | 9/2003 | Porter et al. | |
| 6,630,495 B1 | 10/2003 | Cooke et al. | |
| 6,632,789 B1 | 10/2003 | June | |
| 6,645,969 B1 | 11/2003 | Spada et al. | |
| 6,645,989 B2 | 11/2003 | Adams et al. | |
| 6,649,631 B1 | 11/2003 | Orme et al. | |
| 6,653,296 B1 | 11/2003 | Holy et al. | |
| 6,653,306 B1 | 11/2003 | Alexander et al. | |
| 6,660,744 B1 | 12/2003 | Hirst et al. | |
| 6,660,845 B1 | 12/2003 | Gall et al. | |
| 6,664,269 B2 | 12/2003 | Martin et al. | |
| 6,664,393 B2 | 12/2003 | Klingler et al. | |
| 6,667,300 B2 | 12/2003 | Sadhu et al. | |
| 6,667,398 B2 | 12/2003 | Dunn et al. | |
| 6,690,583 B1 | 2/2004 | Bergstedt et al. | |
| 6,713,484 B2 | 3/2004 | Bridges et al. | |
| 6,720,344 B2 | 4/2004 | Kerwin et al. | |
| 6,734,187 B1 | 5/2004 | Tanaka et al. | |
| 6,770,639 B2 | 8/2004 | Snow et al. | |
| 6,777,425 B2 | 8/2004 | Burli et al. | |
| 6,777,439 B2 | 8/2004 | Durden | |
| 6,790,844 B2 | 9/2004 | Ueno et al. | |
| 6,800,620 B2 | 10/2004 | Sadhu et al. | |
| 6,825,219 B2 * | 11/2004 | Cywin et al. | 514/338 |
| 6,849,420 B2 | 2/2005 | Vanhasebroeck et al. | |
| 6,849,637 B2 | 2/2005 | Andrianjara et al. | |
| 6,849,713 B2 | 2/2005 | Zhang et al. | |
| 6,852,727 B2 | 2/2005 | Goulet et al. | |
| 6,858,756 B2 | 2/2005 | Rampf et al. | |
| 6,906,103 B2 | 6/2005 | Zhang et al. | |
| 6,916,949 B2 | 7/2005 | Springer et al. | |
| 6,919,332 B2 | 7/2005 | Noe et al. | |
| 6,921,763 B2 | 7/2005 | Hirst et al. | |
| 6,949,535 B2 | 9/2005 | Sadhu et al. | |
| 7,005,520 B2 | 2/2006 | Dunn et al. | |
| 7,026,461 B1 | 4/2006 | Shokat | |
| 7,041,676 B2 | 5/2006 | McDonald et al. | |
| 7,049,116 B2 | 5/2006 | Shokat | |
| 7,049,312 B1 | 5/2006 | Rafferty et al. | |
| 7,064,218 B2 | 6/2006 | Dyatkina et al. | |
| 7,071,355 B2 | 7/2006 | Leban et al. | |
| 7,087,597 B1 | 8/2006 | Miwa et al. | |
| 7,102,046 B2 | 9/2006 | Rampf et al. | |
| 7,115,627 B2 | 10/2006 | Pinto et al. | |
| 7,115,653 B2 | 10/2006 | Baxter et al. | |
| 7,144,903 B2 | 12/2006 | Collins et al. | |
| 7,157,487 B2 | 1/2007 | Nakayama et al. | |
| 7,166,293 B2 | 1/2007 | Teng et al. | |
| 7,208,493 B2 | 4/2007 | Wrasidlo et al. | |
| 7,208,601 B2 | 4/2007 | Mjalli et al. | |
| 7,217,794 B2 | 5/2007 | Abdel-Meguid et al. | |
| 7,223,780 B2 | 5/2007 | Nazare et al. | |
| 7,235,585 B2 | 6/2007 | Springer et al. | |
| 7,244,741 B2 | 7/2007 | Simon et al. | |
| 7,247,736 B2 | 7/2007 | Leban et al. | |
| 7,262,204 B2 | 8/2007 | Collins et al. | |
| 7,265,111 B2 | 9/2007 | Bigot et al. | |
| 7,265,131 B2 | 9/2007 | Johnson et al. | |
| 7,317,027 B2 | 1/2008 | Nazare et al. | |
| 7,329,765 B2 | 2/2008 | Burli et al. | |
| 7,332,497 B2 | 2/2008 | Hirst et al. | |
| 7,348,427 B2 | 3/2008 | Burli et al. | |
| 7,365,088 B2 | 4/2008 | Nazare et al. | |
| 7,365,094 B2 | 4/2008 | Leban et al. | |
| 7,384,967 B2 | 6/2008 | Polisetti et al. | |
| 7,396,836 B2 | 7/2008 | Harada et al. | |
| 7,414,036 B2 | 8/2008 | Sevillano et al. | |
| 7,429,596 B2 | 9/2008 | Tanaka et al. | |
| 7,439,254 B2 | 10/2008 | Bergnes | |
| 7,449,477 B2 | 11/2008 | Barda et al. | |
| 7,459,462 B2 | 12/2008 | Simon et al. | |
| 7,459,472 B2 | 12/2008 | Mjalli et al. | |
| 7,465,806 B2 | 12/2008 | Bauer et al. | |
| 7,470,721 B2 | 12/2008 | Durden | |
| 7,501,538 B2 | 3/2009 | Mjalli et al. | |
| 7,514,445 B2 | 4/2009 | Freyne et al. | |
| 7,534,797 B2 | 5/2009 | Arnold et al. | |
| 7,541,373 B2 | 6/2009 | Polisetti et al. | |
| 7,569,571 B2 | 8/2009 | Dong et al. | |
| 7,572,913 B2 | 8/2009 | McKerracher et al. | |
| 7,579,348 B2 | 8/2009 | Wang et al. | |
| 7,585,868 B2 | 9/2009 | Knight et al. | |
| 7,608,594 B2 | 10/2009 | Blagg et al. | |
| 7,615,552 B2 | 11/2009 | Ono et al. | |
| 7,622,451 B2 | 11/2009 | Blagg et al. | |
| 7,642,272 B2 | 1/2010 | Shankar et al. | |
| 7,678,803 B2 | 3/2010 | Huang et al. | |
| 7,700,552 B2 | 4/2010 | Waehling et al. | |
| 7,700,607 B2 | 4/2010 | Hu et al. | |
| 7,705,018 B2 | 4/2010 | Chen et al. | |
| 7,745,485 B2 | 6/2010 | Durden | |
| 7,829,590 B2 | 11/2010 | Brenchley et al. | |
| 7,919,046 B2 | 4/2011 | Delapierre et al. | |
| 7,932,260 B2 | 4/2011 | Fowler et al. | |
| 8,053,445 B2 | 11/2011 | Yamamori et al. | |
| 8,053,603 B2 | 11/2011 | Shao et al. | |
| 8,088,385 B2 | 1/2012 | Chesney et al. | |
| 8,101,637 B2 | 1/2012 | Bessis et al. | |
| 8,106,146 B2 | 1/2012 | Benz et al. | |
| 8,124,625 B2 | 2/2012 | Yamamori et al. | |
| 8,188,134 B2 | 5/2012 | Brenchley et al. | |
| 8,193,182 B2 | 6/2012 | Ren et al. | |
| 8,399,483 B2 | 3/2013 | Allen et al. | |
| 8,557,823 B2 | 10/2013 | Tapolsky et al. | |
| 2001/0019829 A1 | 9/2001 | Nelson et al. | |
| 2001/0027197 A1 | 10/2001 | Bridges et al. | |
| 2002/0016460 A1 | 2/2002 | Snow et al. | |

(56) References Cited

U.S. PATENT DOCUMENTS

| | | |
|---|---|---|
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0107245 A1 | 8/2002 | Wagle et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156073 A1 | 10/2002 | Wagle et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0193377 A1 | 12/2002 | Andrianjara et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0029875 A1 | 2/2004 | Fauchere et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0072871 A1 | 4/2004 | Dublanchet et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0146941 A1 | 7/2004 | Zhang et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0235849 A1 | 11/2004 | Beyreuther et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282814 A1 | 12/2005 | Wrasidlo et al. |
| 2006/0019967 A1 | 1/2006 | Wu et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179122 A1 | 8/2007 | Urmann et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0254318 A1 | 11/2007 | Sebti et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0125432 A1 | 5/2008 | Blom et al. |
| 2008/0200461 A1 | 8/2008 | Anderson et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0318503 A1 | 12/2009 | Crooks et al. |
| 2009/0325967 A1 | 12/2009 | Fairhurst et al. |

(56) References Cited

U.S. PATENT DOCUMENTS

| | | | |
|---|---|---|---|
| 2010/0009963 A1 | 1/2010 | Knight et al. |
| 2010/0022531 A1 | 1/2010 | Kincaid et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0063047 A1 | 3/2010 | Borchardt et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2010/0216791 A1 | 8/2010 | Aquila et al. |
| 2010/0278811 A1 | 11/2010 | Wrasidlo et al. |
| 2010/0280067 A1 | 11/2010 | Sarma et al. |
| 2010/0280255 A1 | 11/2010 | Moniz et al. |
| 2010/0298290 A1 | 11/2010 | Anand et al. |
| 2011/0009378 A1 | 1/2011 | Lange et al. |
| 2011/0046165 A1 | 2/2011 | Ren et al. |
| 2011/0112137 A1 | 5/2011 | Eissenstat et al. |
| 2011/0124641 A1 | 5/2011 | Ren et al. |
| 2011/0135655 A1 | 6/2011 | Katsikis et al. |
| 2011/0144134 A1 | 6/2011 | Shokat et al. |
| 2011/0160463 A1 | 6/2011 | Moniz et al. |
| 2011/0172228 A1 | 7/2011 | Ren et al. |
| 2011/0172335 A1 | 7/2011 | Deshpande |
| 2011/0212975 A1 | 9/2011 | Kao et al. |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0275803 A1 | 11/2011 | Remenar et al. |
| 2011/0281866 A1 | 11/2011 | Ren et al. |
| 2011/0301144 A1 | 12/2011 | Knight et al. |
| 2012/0004198 A1 | 1/2012 | Liao et al. |
| 2012/0046307 A1 | 2/2012 | Engel et al. |
| 2012/0059000 A1 | 3/2012 | Ren et al. |
| 2012/0065154 A1 | 3/2012 | Tanaka et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0149715 A1 | 6/2012 | Kao et al. |
| 2012/0157696 A1 | 6/2012 | Yu et al. |
| 2012/0177749 A1 | 7/2012 | Tapolsky et al. |
| 2012/0184568 A1* | 7/2012 | Ren et al. ............... 514/263.22 |
| 2012/0196905 A1 | 8/2012 | Cashman |
| 2012/0202784 A1 | 8/2012 | Aronov et al. |
| 2012/0220575 A1 | 8/2012 | Chang et al. |
| 2012/0225851 A1 | 9/2012 | Cardone et al. |
| 2012/0238549 A1 | 9/2012 | Cusack et al. |
| 2012/0238559 A1* | 9/2012 | Baldwin et al. ............ 514/228.2 |
| 2012/0245169 A1 | 9/2012 | Ren et al. |
| 2012/0258953 A1 | 10/2012 | Aay et al. |
| 2012/0293063 A1 | 11/2012 | Kang et al. |
| 2012/0322769 A1 | 12/2012 | Yang et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0039945 A1 | 2/2013 | Iadonato et al. |
| 2013/0045229 A1 | 2/2013 | Iadonato et al. |
| 2013/0053362 A1 | 2/2013 | Castro et al. |
| 2013/0102608 A1 | 4/2013 | Hoelzemann et al. |
| 2013/0109713 A1 | 5/2013 | Lavoie et al. |
| 2013/0158003 A1 | 6/2013 | Campbell et al. |
| 2013/0172388 A1 | 7/2013 | Xie et al. |
| 2014/0024637 A1 | 1/2014 | Rice |
| 2014/0031547 A1 | 1/2014 | Sheridan et al. |

FOREIGN PATENT DOCUMENTS

| | | |
|---|---|---|
| CN | 102206172 | 10/2011 |
| CN | 102731492 | 10/2012 |
| DE | 2139107 A1 | 2/1973 |
| EP | 773023 A1 | 5/1997 |
| EP | 1020445 B1 | 8/2008 |
| GB | 812366 A | 4/1959 |
| GB | 937725 A | 9/1963 |
| JP | 61-109797 A | 5/1986 |
| JP | H04211063 | 8/1992 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| JP | 4834699 | 12/2011 |
| JP | 4846769 | 12/2011 |
| WO | WO 83/01446 A1 | 4/1983 |
| WO | WO 91/17161 A1 | 11/1991 |
| WO | WO 92/14733 A1 | 9/1992 |
| WO | WO 93/16091 A1 | 8/1993 |
| WO | WO 93/16092 A1 | 8/1993 |
| WO | WO 93/18035 A1 | 9/1993 |
| WO | WO 93/19767 A1 | 10/1993 |
| WO | WO 93/22443 A1 | 11/1993 |
| WO | WO 94/13677 A1 | 6/1994 |
| WO | WO 94/17803 A1 | 8/1994 |
| WO | WO 94/29436 A1 | 12/1994 |
| WO | WO 95/10628 A2 | 4/1995 |
| WO | WO 95/12588 A1 | 5/1995 |
| WO | WO 95/29673 A1 | 11/1995 |
| WO | WO 95/32984 A1 | 12/1995 |
| WO | WO 95/10628 A3 | 9/1996 |
| WO | WO 96/40706 A1 | 12/1996 |
| WO | WO 97/28133 A1 | 8/1997 |
| WO | WO 97/28161 A1 | 8/1997 |
| WO | WO 98/41525 A1 | 9/1998 |
| WO | WO 98/52611 A1 | 11/1998 |
| WO | WO 98/57952 A1 | 12/1998 |
| WO | WO 00/17202 A1 | 3/2000 |
| WO | WO 01/02369 A2 | 1/2001 |
| WO | WO 01/16114 A2 | 3/2001 |
| WO | WO 01/19829 A2 | 3/2001 |
| WO | WO 01/21160 | 3/2001 |
| WO | WO 01/25238 A2 | 4/2001 |
| WO | WO 01/31063 A1 | 5/2001 |
| WO | WO 01/38584 A2 | 5/2001 |
| WO | WO 01/16114 A3 | 8/2001 |
| WO | WO 01/55140 A1 | 8/2001 |
| WO | WO 01/56988 A1 | 8/2001 |
| WO | WO 01/60824 | 8/2001 |
| WO | WO 01/19829 A3 | 9/2001 |
| WO | WO 01/25238 A3 | 10/2001 |
| WO | WO 01/38584 A3 | 10/2001 |
| WO | WO 01/81346 A2 | 11/2001 |
| WO | WO 02/06192 A1 | 1/2002 |
| WO | WO 01/81346 A3 | 3/2002 |
| WO | WO 01/02369 A3 | 4/2002 |
| WO | WO 02/30944 A2 | 4/2002 |
| WO | WO 02/057425 A2 | 7/2002 |
| WO | WO 02/076986 A1 | 10/2002 |
| WO | WO 02/080926 A1 | 10/2002 |
| WO | WO 02/083143 A1 | 10/2002 |
| WO | WO 02/088025 A1 | 11/2002 |
| WO | WO 02/090334 A1 | 11/2002 |
| WO | WO 02/30944 A3 | 1/2003 |
| WO | WO 03/000187 A2 | 1/2003 |
| WO | WO 03/016275 A1 | 2/2003 |
| WO | WO 03/020880 A2 | 3/2003 |
| WO | WO 03/024969 A1 | 3/2003 |
| WO | WO 03/028341 A2 | 4/2003 |
| WO | WO 03/035075 A1 | 5/2003 |
| WO | WO 03/059884 A1 | 7/2003 |
| WO | WO 03/020880 A3 | 10/2003 |
| WO | WO 03/082341 A1 | 10/2003 |
| WO | WO 03/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/031177 A1 | 4/2004 |
| WO | WO 2004/039774 A2 | 5/2004 |

(56) References Cited

FOREIGN PATENT DOCUMENTS

| | | |
|---|---|---|
| WO | WO 2004/046128 | 6/2004 |
| WO | WO 2004/018058 A3 | 7/2004 |
| WO | WO 2004/039774 A3 | 7/2004 |
| WO | WO 2004/058717 A1 | 7/2004 |
| WO | WO 03/000187 A3 | 8/2004 |
| WO | WO 2004/075917 | 9/2004 |
| WO | WO 2004/087053 A2 | 10/2004 |
| WO | WO 2004/087679 | 10/2004 |
| WO | WO 2004/089877 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/016348 A1 | 2/2005 |
| WO | WO 2005/016349 A1 | 2/2005 |
| WO | WO 2005/016528 A2 | 2/2005 |
| WO | WO 2005/021533 A1 | 3/2005 |
| WO | WO 2002/057425 A3 | 4/2005 |
| WO | WO 2005/012323 A3 | 5/2005 |
| WO | WO 2005/016528 A3 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2006/015279 | 2/2006 |
| WO | WO 2005/044181 A3 | 3/2006 |
| WO | WO 2006/030032 A1 | 3/2006 |
| WO | WO 2006/038865 A1 | 4/2006 |
| WO | WO 2006/050501 A2 | 5/2006 |
| WO | WO 2006/050946 A1 | 5/2006 |
| WO | WO 2006/068760 A2 | 6/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/025090 A2 | 3/2007 |
| WO | WO 2007/029121 | 3/2007 |
| WO | WO 2006/050501 A3 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/063625 A2 | 5/2008 |
| WO | WO 2008/064018 A1 | 5/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2007/121924 A3 | 9/2008 |
| WO | WO 2008/112715 A2 | 9/2008 |
| WO | WO 2007/114926 A3 | 10/2008 |
| WO | WO 2008/117050 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/100406 A2 | 8/2009 |
| WO | WO 2009/103022 | 8/2009 |
| WO | WO 2009/117157 A1 | 9/2009 |
| WO | WO 2009/118765 | 10/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/053998 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/133836 A1 | 11/2010 |
| WO | WO 2011/008302 A1 | 1/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/094890 | 8/2011 |
| WO | WO 2011/111880 | 9/2011 |
| WO | WO 2011/146882 A1 | 11/2011 |
| WO | WO 2012/032334 A1 | 3/2012 |
| WO | WO 2012/037204 | 3/2012 |
| WO | WO 2012/052540 | 4/2012 |
| WO | WO 2012/061696 A1 | 5/2012 |
| WO | WO 2012/064973 A2 | 5/2012 |

(56) References Cited

FOREIGN PATENT DOCUMENTS

| WO | WO 2012/068096 | 5/2012 |
|---|---|---|
| WO | WO 2012/068106 | 5/2012 |
| WO | WO 2012/071519 | 5/2012 |
| WO | WO 2012/097000 A1 | 7/2012 |
| WO | WO 2012/129562 | 9/2012 |
| WO | WO 2013/012915 | 1/2013 |
| WO | WO 2013/013504 | 1/2013 |
| WO | WO 2013/013505 | 1/2013 |
| WO | WO 2013/025498 | 2/2013 |
| WO | WO 2013/044169 | 3/2013 |
| WO | WO 2013/074583 | 5/2013 |
| WO | WO 2013/086131 | 6/2013 |
| WO | WO 2013/090725 | 6/2013 |
| WO | WO 2013/113838 | 8/2013 |
| WO | WO 2013/113841 | 8/2013 |

OTHER PUBLICATIONS

Anderson et al., "Paradoxical inhibition of T-cell function in response to CTLA-4 blockade; heterogeneity within the human T-cell population," *Nat. Med.* 6(2):211-214 (2000).

Andrews et al., "Effects of the 11β-hydroxysteroid dehydrogenase inhibitor carbenoxolone on insulin sensitive in men with type 2 diabetes," *J. Clin. Endocrinol. Metab.* 88(1):285-291 (2003).

Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).

Arnold et al., "Pyrrolo[2,3-d]pyrimidines containing an extended 5-substituent as potent and selective inhibitors of Ick I," *Bioorg. Med. Chem. Lett.* 10(19):2167-2170 (2000).

Augustine et al., "Interleukin 2- and polyomavirus middle T antigen-induced modification of phosphatidylinositol 3-kinase activity in activated T lymphocytes," *Mol. Cell. Biol.* 11(9):4431-4440 (1991).

Baggiolini et al., "Inhibition of the phagocytosis-induced respiratory burst by the fungal metabolite wortmannin and some analogues," *Exp. Cell. Res.* 169(2): 408-418 (1987).

Ballell et al. "New Thiopyrazolo[3,4-d] pyrimidine derivatives as anti-mycobacterial agents," *Bioorg. Med. Chem. Lett.* 17(6):1736-1740 (2007).

Banker et al., Modern Pharmaceutics, pp. 451, 596, 3$^{rd}$ ed, Marcel Dekker, New York (1996).

Bansal et al., "The Molecular Biology of Endometrial Cancers and the Implications for Pathogenesis, Classification, and Targeted Therapies," *Cancer Control* 16(1):8-13 (2009).

Barber et al., "PI3Kgamma inhibition blocks glomerulonephritis and extends lifespan in a mouse model of systemic lupus," *Nat. Med.* 11(9):933-935 (2005). (Epub Aug. 28, 2005).

Barf et al., "Arylsulfonamidothiazoles as a new class of potential antidiabetic drugs. Discovery of potent and selective inhibitors of the 11β-hydroxysteroid dehydrogenase Type 1," *J. Med. Chem.* 45(18):3813-3815 (2002).

Barnes et al., "Efficacy and Safety of Inhaled Corticosteroids in Asthma—Report of a Workshop Held in Eze, France Oct. 1992," *Am. Rev. Respir. Dis.* 148:S1-S26 (1993).

Bartholomeusz et al., "Targeting the PI3K Signaling Pathway in Cancer Therapy," *Expert Opin. Ther. Targets* 16(1):121-130 (2012).

Basotest®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retreived from the Internet Nov. 29, 2011.

Beeram et al., "Akt-induced endocrine therapy resistance is reversed by inhibition of mTOR signaling," *Ann Oncol.* 18(8):1323-1328 (2007).

Bell et al., "Glucokinase mutations insulin secretion, and diabetes mellitus", *Annu. Rev. Physiol.* 58:171-186 (1996).

Berndt et al., "The p110δ crystal structure uncovers mechanisms for selectivity and potency of novel PI3K inhibitors," *Nat. Chem. Biol.* 6(2):117-124 (2010).

Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).

Bhatt et al., "Dual inhibition of PI3K and mTOR inhibits autocrine and paracrine proliferative loops in PI3K/Akt/mTOR-addicted lymphomas," *Blood* 115(22):4455-4463 (2010).

Bi et al., "Proliferative defect and embryonic lethality in mice homozygous for a deletion in the p110α subunit of phosphoinositide 3-kinase," *J. Biol. Chem.* 274:10963-10968 (1999).

Billottet et al., "A selective inhibitor of the p110δ isoform of PI 3-kinase inhibits AML cell proliferation and survival and increases the cytotoxic effects of VP16," *Oncogene* 25:6648-6659 (2006).

Billottet et al., "Inhibition of Class 1 Phosphoinositide 3-Kinase Activity Impairs Proliferation and Triggers Apoptosis in Acute Promyelocytic Leukemia without Affecting Atra-Induced Differentiation," *Cancer Res.* 69(3):1027-1036 (2009).

Bishop et al., "Generation of monospecific nanomolar tyrosine kinase inhibitors via a chemical genetic approach," *J. Am. Chem. Soc.* 121(4):627-631 (1999).

Blunden et al., "Mycotoxins in food," *Med. Lab. Sci.* 48(4):271-282 (1991).

Bochner et al., "Immunological aspects of allergic asthma," *Annu. Rev. Immunol.* 12:295-335 (1994).

Bohren et al., "Expression, crystallization and preliminary crystallographic analysis of human carbonyl reductase," *J. Mol. Biol.* 224:659-664 (1994).

Bone et al., "Phosphoinositide 3-kinase signalling regulates early development and developmental haemopoiesis," *J. Cell. Sci.* 120(Pt 10):1752-1762 (2007).

Bowers et al., "A platelet biomarker for assessing phosphoinositide 3-kinase inhibition during cancer chemotherapy," *Mol. Cancer Ther.* 6(9):2600-2607 (2007).

Brzezianska et al., "A Minireview: The Role of MAPK/ERK and PI3K/Akt Pathways in Thyroid Follicular Cell-Derived Neoplasm," *Front. Biosci.* 16:422-439 (2011).

Buitenhuis et al., "The role of the PI3k-PKB signaling module in regulation of hematopoiesis," *Cell Cycle* 8(4):560-566 (2009).

Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).

Burger et al., "Phosphoinositide 3'-kinase delta: turning off BCR signaling in Chronic Lymphocytic Leukemia," *Oncotarget* 2(10):737-738 (2011).

Burger, "Inhibiting B-Cell Receptor Signaling Pathways in Chronic Lymphocytic Leukemia," *Curr. Mematol. Malig. Rep.* 7:26-33 (2012).

Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).

Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).

Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).

Camps et al., "Blockade of PI3Kγ suppresses joint inflammation and damage in mouse models of rheumatoid arthritis," *Nat. Med.* 11(9):936-943 (2005).

Chaisuparat et al., "Dual inhibition of PI3Kα and mTOR as an alternative treatment for Kaposi's Sarcoma," *Cancer Res.* 68:8361-8368 (2008).

Chang et al., "The Bruton tyrosine kinase inhibitor PCI-32765 ameliorates autoimmune arthritis by inhibition of multiple effector cells," *Arthritis Research & Therapy* 13:R115 (2011).

Chappelow et al., "Neovascular age-related macular degeneration: potential therapies," *Drugs* 68(8):1029-1036 (2008).

Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).

Chawla et. al., "Challenges in Polymorphism of Pharmaceuticals," *Current Research & Information on Pharmaceutical Science* 5(1):9-12 (2004).

(56) References Cited

OTHER PUBLICATIONS

Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.*(Tokyo) 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).
Courtney et al., "The PI3K Pathway as Drug Target in Human Cancer," *J. Clin. Oncol.* 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).
Dijksman et al., "271.1: 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
Donati, G., "Emerging therapies for neovascular age-related macular degeneration: state of the art," *Ophthalmologica* 221(6):366-377 (2007).

European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," *Diabet. Med.* 13(9 Suppl 6):S90-S95 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).
Feldman et al., "Active-Site Inhibitors of mTOR Target Rapamycin-Resistant Outputs of mTORC1 and mTORC2," *PLoS Biol.* 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C—C bonds on solid support," *Can. J. Chem.* 78:957-962 (2000).
Funder et al., "Mineralocorticoid action: target tissue specificity is enzyme, not receptor, mediated," *Science* 242:583-585 (1988).
Fung-Leung, W. P., "Phosphoinositide 3-kinase delta (PI3Kδ) in leukocyte signaling and function," *Cell Signal* 23:603-608 (2011).
Furukawa, T., "Molecular Targeting Therapy for Pancreatic Cancer: Current Knowledge and Perspectives from Bench to Bedside," *J. Gastroenterol.* 43(12):905-911 (2008).
Garber et al., "Diversity of gene expression in adenocarcinoma of the lung," *Proc. Natl. Acad. Sci. U.S.A.* 98(24):13784-13789 (2001).
Gillespie et al., "Antagonists of the human adenosine $A_{2A}$ receptor. Part 3: Design synthesis of pyrazolo[3,4-d]pyrimidines, pyrrolo[2,3-d]pyrimidines and 6-arylpurines," *Bioorg. Med. Chem. Lett.* 18(9):2924-2929 (2008).
Gonzalez et al., "Protection against daunorubicin cytotoxicity by expression of a cloned human carbonyl reductase cDNA in K562 leukemia cells," *Cancer Res.* 55(20):4646-4650 (1995).
Graber et al., "The protein tyrosine kinase inhibitor herbimycin A, but not genistein, specifically inhibits signal transduction by the T cell antigen receptor," *Int. Immunol.* 4(1):1201-1210 (1992).
Graupera et al., "Angiogenesis selectively requires the p110α isoform of PI3K to control endothelial cell migration," *Nature* 453(7195):662-666 (2008).
Gunther et al., "Acute pathological effects on rats of orally administered wortmannin-containing preparations and purified wortmannin from *Fusarium oxysporum*," *Food Chem. Toxicol.* 27(3):173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).

(56) References Cited

OTHER PUBLICATIONS

Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistry," *J. Chem. Soc. Perkin 1* 1545-1552 (1996).
Harada et al., "Novel role of phosphatidylinositol 3-kinase in CD28-mediated costimulation," *J. Biol. Chem.* 276(12):9003-9008 (2001).
Harding et al., "CD28-mediated signalling co-stimulates murine T cells and prevents induction of anergy in T-cell clones," *Nature* 356(6370):607-609 (1992).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Hellwinkel et al., "Heterocyclensynthesen mit MF/A1203-basensystemen; 2-arylbenzofurane and 2,3-diarylisochinolin-1(2H)-one," *Synthesis* 1995( 9):1135-1141 (1995).
Herishanu et al., "The lymph node microenvironment promotes B-cell receptor signaling, NF-κB activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "PI3K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).
June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).

(56) References Cited

OTHER PUBLICATIONS

Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -65, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).
Khwaja, A., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific substrates," *J. Am. Chem. Soc.* 124(41):12118-12128 (2002).
Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio-and stereoselective synthesis of (Z)-3-aryl(alykl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viabaility," *Blood* 117(2):591-594 (2011).
Larabi et al., "Crystal Structure and Mechanism of Activation of TANK-Binding Kinase 1," *Cell Reports* 3:734-746 (2013).
Ledbetter et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).
Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).

Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," Curr. Med. Chem. 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," *Blood (ASH Annual Meeting Abstracts)*, 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV—synthesis of methyl, 3-formyl & other 3-substituted N-arylisoquinolones." *Indian J. Chem.* 18B:304-306 (1979).
Moon et al., "A novel microtubule destabilizing entity from orthogonal synthesis of triazine library and zebrafish embryo screening," *J. Am. Chem. Soc.* 124(39):11608-11609 (2002).
Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11β-hydroxysteriod dehydrogenases with retained oxidoreductase activities," *Protein Expr. Purif.* 26(3):349-356 (2002).
Norman, "Selective PI3K-delta Inhibitors, A Review of the Patent Literature," Expert Opinion on Therapeutic Patents, 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).

(56) References Cited

OTHER PUBLICATIONS

Oda et al., "PIK3CA cooperates with other phosphatidylinositol 3'-kinase pathway mutations to effect oncogenic transformation," *Cancer Res.* 68(19):8127-8136 (2008).

Office Action dated Dec. 13, 2012 for 7004 US1, U.S. Appl. No. 13/112,611.

Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).

Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).

Oppermann et al., "Forms and functions of human SDR enzyemes," *Chem. Biol. Interact.* 130-132(1-3):699-705 (2001).

O'Shea et al., "Activation of human peripheral blood T lymphocytes by pharmacological induction of protein-tyrosine phosphorylation," *Proc. Natl. Acad. Sci. U.S.A.* 89(21):10306-10310 (1992).

Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).

Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).

Patel et al., "Immunopathological aspects of age-related macular degeneration," *Semin. Immunopathol.* 30(2):97-110 (2008).

Pérez-Blas et al., "Impaired T cell signal transduction through CD28 in a patient with idiopathic thrombocytopenia," *Clin. Exp. Immunol.* 85(3):424-428 (1991).

Persson, "Glucocorticoids for asthma—early contributions," *Pulm. Pharmacol.* 2(3):163-166 (1989).

Petrie et al., "Novel biotinylated adenylate analogue derived from pyrazolo[3,4-d]pyrimidine for labeling DNA probes," *Bioconjug. Chem.* 2(6):441-446 (1991).

Pighi et al., "Phospho-proteomic analysis of mantle cell lymphoma cells suggests a pro-survival role of B-cell receptor signaling," *Cell Oncol. (Dordr)* 34(2):141-153 (2011).

Polak et al., "The PI3K/PKB signaling module as key regulator of hematopoiesis: implications for therapeutic strategies in leukemia," *Blood* 119(4):911-923 (2012).

Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).

Prasad et al., "Phosphatidylinositol (PI) 3-kinase and PI 4-kinase binding to the CD4-p56$^{lck}$ complex: the p$^{56lck}$ SH3 domain binds to PI 3-kinase but not PI 4-kinase," *Mol. Cell. Biol.* 13(12): 7708-7717 (1993).

Prasad et al., "Src-homology 3 domain of protein kinase p59$^{fyn}$ mediates binding to phosphatidylinositol 3-kinase in T cells," *Proc. Natl. Acad. Sci. U. S. A.* 90(15): 7366-7370 (1993).

Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).

Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," *J. Med. Chem.* 33(7):1984-1992 (1990).

Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).

Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).

Reif et al., "Divergent regulation of phosphatidylinositol 3-kinase P85α and P85β isoforms upon T cell activation," *J. Biol. Chem.* 268(15):10780-10788 (1993).

Report of the Expert Committee on the Diagnosis and Classification of Diabetes Mellitus, *Diabetes Care* 2( Suppl. 1):S5-S19 (1992).

Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).

Robertson, "Eicosanoids and human disease", Harrison's Principles of Internal Medicine, Isselbacher K.J. et al. (eds.), vol. 1, pp. 431-435, McGraw-Hill, New York City (1994).

Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).

Romero et al., "Cloning and expression of the bovine 1 1b-hydroxysteroid dehydrogenase type-2," *J. Steroid Biochem. Mol. Biol.* 72(5):231-237 (2000).

Rommel et al., "PI3Kδ and PI3Kγ: partners in crime in inflammation in rheumatoid arthritis and beyond?" *Nat. Rev. Immunol.* 7:191-201 (2007).

Rott et al., "Recent developments in the use of biologics in psoriasis and autoimmune disorders. The role of autoantibodies," *BMJ* 330(7493):716-720 (2005).

Rudelius et al., "Constitutive activation of Akt contributes to the pathogenesis and survival of mantle cell lymphoma," *Blood* 108(5):1668-1676 (2006).

Saif and Chu, "Biology of colorectal cancer," *Cancer J.* 16(3):196-201 (2010).

Salmena et al., "Tenets of PTEN Tumor Suppression," *Cell* 133(3):403-414 (2008).

Sarker et al., "Targeting the PI3K/AKT pathway for the treatment of prostate cancer," *Clin. Cancer Res.* 15(15):4799-4805 (2009).

Sasaki et al., "Function of PI3Kγ in Thymocyte Development, T Cell Activation, and Neutrophil Migration," *Science* 287:1040-1046 (2000).

Schwartz et al., "Quercetin inhibition of the induction and function of cytotoxic T lymphocytes," *Immunopharmacology* 4(2):125-138 (1982).

Schwartz, "A cell culture model for T lymphocyte clonal anergy," *Science* 248(4961):1349-1356 (1990).

Shapiro et al., "Phase I Dose-Escalation Study of XL147, A PI3K Inhibitor Administered Orally to Patients with Solid Tumors," *J. Clin. Oncol.* 27:146x (Suppl Abstr 3500) (2009).

Shibasaki et al., "Different properties of monomer and heterodimer forms of phosphatidylinositol 3-kinases," *Biochem. J.* 289 ( Pt 1):227-231 (1993).

Sinclair et al., "Phosphatidylinositol-3 Kinase Delta (PI3Kδ) Inhibitor AMG 319 Is a Potent, Selective and Orally Bioavailable Small Molecule Inhibitor That Supresses PI3K-Mediated Signaling and Viability in Neoplastic B Cells," *Blood (ASH Annual Meeting Abstracts)* 118:Abstract 4964 (2011).

Singer et al., "Optimization of in situ hybridization using isotopic and non-isotopic detection methods," *Biotechniques* 4(3):230-250 (1986).

Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).

Soldan et al., "Induction of daunorubicin carbonyl reducing enzymes by daunorubicin in sensitive and resistant pancreas carcinoma cells," *Biochem. Pharmacol.* 51(2):117-123 (1996).

Soond et al., "PI3K p110δ regulates T-cell cytokine production during primary and secondary immune responses in mice and humans," *Blood* 115(11):2203-2213 (2010).

Srinivasan et al., "PI3 Kinase Signals BCR-Dependent Mature B Cell Survival," *Cell* 139:573-586 (2009).

Stanoeva et al., "Homophthalic anhydrides and their application to the synthesis of heterocyclic compounds (review)," *Chemistry of Heterocyclic Compounds* 20(12):1305-1315 (1984).

Subramaniam et al., "Targeting Nonclassical Oncogenes for Therapy in T-ALL," *Cancer Cell* 21:459-472 (2012).

(56) References Cited

OTHER PUBLICATIONS

Sujobert et al., "Essential role for the p110δ isoform in phosphoinositide 3-kinase activation and cell proliferation in acute myeloid leukemia," *Blood* 106(3):1063-1066 (2005).

Supplementary European Examination Report EP Application No. 07754845.1 dated Sep. 20, 2011.

Supplementary European Search Report for EP Application No. 07754845 (4 pages) dated Feb. 24, 2010.

Supplementary European Search Report for EP Application No. 10800175.1 dated Nov. 7, 2012.

Sykes et al., "Treatment of severe autoimmune disease by stem-cell transplantation," *Nature* 35(7042):620-627 (2005).

Takeuchi et al., "Synergistic Augmentation of Rapamycin-Induced Autophagy in Malignant Glioma Cells by Phosphatidylinositol 3-Kinase/Protein Kinase B Inhibitors," *Cancer Res.* 65(8):3336-3346 (2005).

Tanaka et al., "An unbiased cell morphology-based screen for new, biologically active small molecules," *PLoS Biol.* 3(5):0764-0776 (2005).

Thompson et al., "Identification of distinct populations of PI-3 kinase activity following T-cell activation," *Oncogene* 7(4):719-725 (1992).

Torbett et al., "A chemical screen in diverse breast cancer cell lines reveals genetic enhancers and suppressors of sensitivity to PI3K isoform-selective inhibition," *Biochem. J.* 415(1):97-110 (2008).

Truitt et al., "Stimulation of CD28 triggers an association between CD28 and phosphatidylinositol 3-kinase in Jurkat T cells," *J. Exp. Med.* 179(3):1071-1076 (1994).

Tyukavkina et al., Bioorganicheskaya Khimiya, Moskva, DROFA, pp. 83-85 (2004).

Uddin et al., "Role of phosphatidylinositol 3'-kinase/AKT pathway in diffuse large B-cell lymphoma survival," *Blood* 108(13):4178-4186 (2006).

Ugarkar et al., "Adenosine kinase inhibitors. 2. Synthesis, enzyme inhibition, and antiseizure activity of diaryltubercidin analogues," *J. Med. Chem.* 43(15):2894-2905 (2000).

Vandenberghe et al., "Antibody and B7/BB1-mediated ligation of the CD28 receptor induces tyrosine phosphorylation in human T cells," *J. Exp. Med.* 175(4):951-960 (1992).

Vanhaesebroeck et al., "PI3K: from the bench to the clinic and back," *Curr. Top. Microbiol. Immunol.* 347:1-19 (2010).

Vara et al., "PI3K/Akt Signalling Pathway and Cancer," *Cancer Treat. Rev.* 30(2):193-204 (2004).

Vasilevsky et al., "Study of the Heterocyclization of vic-Substituted Hydrazides of Acetylenylpyrazolecarboxylic Acids into N-Amino Pyrazolopyridinones," *Journal of Heterocyclic Chemistry* 39(6):1229-1233 (2002).

Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).

Vippagunta et al., "Crystalline Solids," *Adv. Drug Deliv. Rev.* 48(1):3-26 (2001).

Vitali et al., "Immunotherapy in rheumatoid arthritis: a review," *Int. J. Artif. Organs* 16 Suppl. 5:196-200 (1993).

Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).

Vogt et al., "Phosphatidylinositol 3-kinase: the oncoprotein," *Curr. Top. Microbiol. Immunol.* 347:79-104 (2010).

Vogt et al., "Phosphoinositide 3-kinase: from viral oncoprotein to drug target," *Virology* 344(1):131-138 (2006).

Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).

Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood* (*ASH Annual Meeting Abstracts*) 118: Abstract 3490 (2011).

Ward et al, "Inhibition of CD28-mediated T cell costimulation by the phosphoinositide 3-kinase inhibitor wortmannin," *Eur. J. Immunol.* 25(2):526-532 (1995).

Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).

Ward et al., "Regulation of D-3 phosphoinositides during T cell activation via the T cell antigen receptor/CD3 complex and CD2 antigens," *Eur. J. Immunol.* 22(1):45-49 (1992).

Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).

Ward et al., "Therapeutic potential of phosphoinositide 3-kinase inhibitors," *Chem. Biol.* 10(3):207-213 (2003).

White et al., "11β-Hydroxysteroid Dehyrdogenase and the Syndrome of Apparent Mineralocorticoid Excess," *Endocr. Rev.* 18(1):135-156 (1997).

Widler et al., "7-alkyl- and 7-Cycloalkyl-5-aryl-pyrrolo[2,3-d]pyrimidines—potent inhibitors of the tyrosine kinase c-Src," *Bioorg. Med. Chem. Lett.* 11(6):849-852 (2001).

Wiesinger et al., "Antiinflammatory activity of the new mould metabolite 11-desacetoxy-wortmannin and of some of its derivatives," *Experientia* 30(2):135-136 (1974).

Wolff, Burger's Medicinal Chemistry, $5^{th}$ ed, Part 1, pp. 975-977, John Wiley & Sons (1995).

Woscholski et al., "A comparison of demethoxyviridin and wortmannin as inhibitors of phosphatidylinositol 3-kinase," *FEBS Lett.* 342(2):109-114 (1994).

Wu et al., "Decreased immunological responses by wortmannin-containing rice culture of *Fusarium oxysporum* and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al., "Inhibition of histamine secretion by wortmannin through the blockade of phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(40:5486-5496 (2008).
Song et al., "The antagonistic effect of PI3K-gamma inhibitor AS605240 on cardiac hypertrophy and cardiac fibrosis induced by isoproterenol in rats," Sichuan Da Xue Xue Bao Yi Xue Ban 42(4):471-474 (2011) (abstract only).
Wei et al., "A phosphoinositide 3-kinase-γ inhibitor, AS605240 prevents bleomycin-induced pulmonary fibrosis in rats," Biochem. Biophy. Res. Comm. 397:311-317 (2010).
Conte et al., "Inhibition of PI3K Prevents the Proliferation and Differentiation of Human Lung Fibroblasts into Myofibroblasts: The Role of Class I P110 Isoforms," PLoS One 6(10):e24663 (2011).

* cited by examiner

TREATMENT OF LUPUS, FIBROTIC CONDITIONS, AND INFLAMMATORY MYOPATHIES AND OTHER DISORDERS USING PI3 KINASE INHIBITORS

This application claims priority to U.S. Provisional Application Nos. 61/664,025, filed Jun. 25, 2012, 61/664,037, filed Jun. 25, 2012, 61/673,113, filed Jul. 18, 2012, 61/673,187, filed Jul. 18, 2012, and 61/673,195, filed Jul. 18, 2012, the entireties of which are incorporated herein by reference.

BACKGROUND OF THE INVENTION

Lupus is a group of conditions with similar underlying mechanisms involving autoimmunity. In these conditions antibodies created by the body to attack antigens (e.g., viruses, bacteria) became unable to differentiate between antigens and healthy tissue. Thus, the antibodies that should protect the body begin to attack the body's own healthy tissues. Triggers for lupus include viruses, bacteria, allergens (both IgE and hypersensitivity), hormones (e.g., estrogens), environmental stimulants (e.g., ultraviolet light, sunlight, stress, smoking, trauma, scratching, burn, coldness), and certain medications.

Lupus is generally a chronic disease in which the signs and symptoms tend to come and go. Common signs or symptoms of lupus include, for example, joint pain and stiffness; muscle aches, pains, or weakness, fever with no known cause; feeling very tired; butterfly-shaped rash across the nose and cheeks; other skin rashes; unusual weight loss or weight gain; anemia; trouble thinking, memory problems, and confusion; kidney problems with no known cause; chest pain when taking a deep breath; sun or light sensitivity; hair loss; and purple or pale fingers or toes from cold or stress. Less common symptoms include blood clots, seizures, strokes, sores in the mouth or nose, severe headache, dizzy spells, "seeing things" or not being able to judge reality, feeling sad, and dry or irritated eyes. Lupus also increases the risk of developing various other diseases and/or causes other diseases to occur earlier in life. Such diseases include heart disease, osteoporosis, and kidney disease. See, e.g., Lupus Fact Sheet by the U.S. Department of Health and Human Services, Office on Women's Health (womenshealth.gov/publications/our-publications/fact-sheet/lupus.cfm; accessed Jun. 18, 2012).

Types of lupus include, for example, systemic lupus erythematosus (SLE), cutaneous lupus erythematosus (CLE) (CLE includes, e.g., acute cutaneous lupus erythematosus (ACLE), subacute cutaneous lupus erythematosus (SCLE), intermittent cutaneous lupus erythematosus, and chronic cutaneous lupus), drug-induced lupus, and neonatal lupus. About 70% of all cases of lupus are SLE. CLE can have symptoms that are limited to the skin or can be seen in those with SLE.

Lupus affects predominately young women. More than 90% of people with lupus are women between the ages of 15 and 45. African-American, Latina, Asian, and Native American women are at greater risk of developing lupus than are white women. Men are at higher risk for developing lupus before puberty and after age 50. For African-American women between the ages of 15 and 64, the prevalence is one per 245 women. This prevalence rate for African-American women makes lupus one of the most common chronic diseases of this population. See, e.g., lupus.org/webmodules/webarticlesnet/templates/new_empty.aspx?articleid=413&zoneid=99, accessed Jun. 18, 2012.

Fibrotic conditions include diseases that involve the formation and/or deposition of fibrous tissue that builds up and/or spreads over or replaces normal organ tissue. Fibrotic conditions occur when processes that normally contribute to wound healing go awry, resulting in extra scar tissue that can be harmful. Fibrotic conditions can affect single organs or tissues, or they can be systemic and affect multiple organs or tissues of the body. Examples of systemic fibrotic diseases include atherosclerosis, scleroderma, nephrogenic systemic fibrosis, cystic fibrosis, and chronic graft vs. host disease. Fibrotic conditions can affect almost any part of the body. For example, fibrotic conditions can affect the lungs, heart, skin, kidneys, bone marrow, liver, and eyes.

Fibrotic conditions affect a large portion of the population; atherosclerosis alone will affect about 25% of Americans in their lifetime. Fibrotic conditions have serious consequences for quality of life. Examples of serious consequences of fibrotic conditions include difficulty breathing, kidney failure, and blindness. Furthermore, fibrotic conditions are often fatal. Indeed, tissue fibrosis contributes to 45 percent of all deaths in developed countries.

Inflammatory myopathies are diseases that typically involve inflammation of the muscles and associated symptoms, such as muscle weakness. The muscle weakness can be progressive and can lead to difficulty moving, including difficulty walking, breathing, swallowing, and talking. Inflammatory myopathies can be caused by allergic reactions, other diseases, exposure to a drug or toxin, or exposure to an infectious agent, or they can be idiopathic (no known cause). Inflammatory myopathies include dermatomyositis, polymyositis, inclusion body myositis and immune-mediated necrotizing myopathies. In some cases, dermatomyositis involves predominantly skin symtoms, without muscle symptoms, or without noticeable muscle symptoms. Inflammatory myopathies can affect both adults and children (e.g., juvenile dermatomyositis). Inflammatory myopathies can include symptoms that affect other organs or systems of the body, such as the skin, lungs, heart, eyes, and gastrointestinal system. Although inflammatory myopathies are relatively rare, their prevalence has likely been underestimated (see, e.g., Smoyer Tomic, K. C. (2012) *BMC Musculoskeletal Disorders*, 13:103) and they can cause serious and even fatal symptoms or complications.

Inflammatory skin conditions, such as skin rashes, including rashes caused by allergens or other diseases, are commonplace. Skin rashes are frequently painful and/or itchy (pruritic) and can be debilitating. Associated symptoms such as hay fever are likewise uncomfortable and can be debilitating. Allergic reactions can also have serious consequences, such as anaphalaxis.

Accordingly, there is a need for effective treatments for lupus, fibrotic conditions, inflammatory myopathies, skin conditions, and associated symptoms.

SUMMARY OF THE INVENTION

Methods, compositions, and kits for treating or preventing lupus, a fibrotic condition (e.g., fibrosis), inflammatory myopathies (e.g., myositis, e.g., dermatomyositis, polymyositis, and inclusion body myositis) and other disorders (e.g., skin conditions, e.g., skin rashes) are provided herein. The methods, compositions and kits include administering a PI3K inhibitor, alone or in combination with other agents or therapeutic modalities, to a subject, e.g., a mammalian subject, e.g., a human.

The invention discloses, at least in part, that a PI3 kinase (PI3K) inhibitor, as a single agent or in combination with one or more additional therapies, can ameliorate lupus (e.g., by decreasing one or more lupus-associated symptoms) in a subject, e.g., a mammalian subject. Symptoms of lupus that can be ameliorated include any one or combination of symptoms of lupus, as known the art and/or as disclosed herein. Experimental conditions for evaluating the effects of a PI3K inhibitor in ameliorating lupus in animal models of lupus, such as systemic lupus erythematosus, are disclosed.

In one aspect, a method of reducing a lupus-associated symptom (e.g., one or more lupus-associated symptoms) in a subject is disclosed. The method includes administering to the subject a PI3K inhibitor (e.g., as a single agent or in combination with another agent or therapeutic modality), in an amount sufficient to decrease or inhibit lupus (e.g., to decrease one or more lupus-associated symptoms). In one embodiment, the method is carried out in vivo, for example, in a mammalian subject, e.g., an animal model or as part of therapeutic protocol. In some embodiments, the method is carried out in a biological sample present within or derived from a subject who has lupus, or from a subject at risk for developing lupus. In some embodiments, the biological sample can be contacted with the PI3K inhibitor outside the body and then introduced into the body of a subject.

In another aspect, the invention features a method of treating or preventing lupus in a subject. The method includes administering a PI3K inhibitor (e.g., as a single agent or in combination with another agent or therapeutic modality), to a subject in need thereof, in an amount sufficient to decrease lupus or a symptom associated with lupus in the subject.

In some embodiments, the lupus is chosen from one or more of systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, haematological, gastrointestinal and musculoskeletal manifestations; neonatal lupus erythematosus; childhood systemic lupus erythematosus; drug-induced lupus erythematosus; anti-phospholipid syndrome; or complement deficiency syndromes resulting in lupus manifestations.

In some embodiments, the lupus is selected from systemic lupus erythematosus (SLE), cutaneous lupus erythematosus (CLE), drug-induced lupus, and/or neonatal lupus.

In some embodiments, the lupus is a CLE, e.g., acute cutaneous lupus erythematosus (ACLE), subacute cutaneous lupus erythematosus (SCLE), intermittent cutaneous lupus erythematosus (also known as lupus erythematosus tumidus (LET)), or chronic cutaneous lupus. In some embodiments, the intermittent CLE is selected from chronic discloid lupus erythematosus (CDLE) and lupus erythematosus profundus (LEP) (also known as lupus erythematosus panniculitis).

Exemplary symptoms associated with lupus include, but are not limited to, for example, joint pain and stiffness; muscle aches, pains, or weakness, fever; malaise; cutaneous manifestations (e.g., butterfly-shaped rash across the nose and cheeks; other skin rashes); unusual weight loss or weight gain; anemia; neurological or neuropsychiatric manifestations (e.g., trouble thinking, memory problems, confusion, depression, headache, seizures, strokes); kidney problems (e.g., nephritis, e.g., glomerulonephritis); chest pain; sun or light sensitivity; hair loss; Raynaud's phenomenon; vascular lesions or other vascular manifestations (e.g., Raynaud's phenomenon, nail fold telangiectasia and infarct, splinter haemorrhages, chilblain LE, acquired C1 esterase deficiency, vasculitis, urticarial vasculitis, purpura, thrombophlebitis, livedo reticularis, antiphospholipid syndrome, Degos syndrome and calcinosis)), as well as biological concomitants of lupus as disclosed herein or as known in the art (e.g., immune complexes, elevated levels of cytokines (e.g., interferons (e.g., Type I interferons, e.g., IFN-α and/or IFN-β); interleukins (e.g., IL-6, IL-8, IL-1, and IL-18) and TNF-α), elevated levels of antibodies associated with lupus (e.g., antinuclear antibodies (e.g., anti-Smith antibodies, anti-double stranded DNA (dsDNA) antibodies, anti-U1 RNP, SS-a (or anti-Ro), SS-b (or anti-La)), antiphospholipid antibodies, anti-ss DNA antibodies, anti-histone antibodies, or anticardiolipin antibodies), and overexpression of IFN inducible genes. Symptoms can be assessed using assays and scales (e.g., Systemic Lupus Activity Measure-Revised (SLAM-R) disclosed and/or exemplified herein and/or as known in the art.

In some embodiments, the symptom associated with lupus is nephritis (e.g., glomerulonephritis, interstitial nephritis, perivascular inflammation, or protein cast severity), proteinuria, or spleen inflammation. In certain embodiments, the symptom is glomerulonephritis. In some embodiments, the symptom is an immune complex. In some embodiments, the symptom is a cutaneous manifestation of lupus. In some embodiments, the symptom is overexpression of IFN-α, TNF-α, IL-6, IL-8, or IL-1. In certain embodiments, the symptom is overexpression of IFN-α.

Disclosed herein, at least in part, are PI3 kinase (PI3K) inhibitors, for use as a single agent or in combination with one or more additional therapies (e.g., an additional agent), to reduce a fibrotic condition in a mammalian subject Inhibition of a PI3K is useful for ameliorating fibrotic conditions and disorders, including reducing fibrosis and/or having a protective effect by decreasing signs or symptoms of fibrosis (e.g., one or more of: reducing the formation or deposition of tissue fibrosis; reducing the size, cellularity, or composition, of a fibrotic lesion; reducing the collagen or hydroxyproline content, of a fibrotic lesion; reducing the expression or activity of a fibrogenic protein; reducing the fibrosis associated with an inflammatory response; decreasing weight loss associated with fibrosis; or increasing survival. Experimental conditions for evaluating the anti-fibrotic effects of a PI3K inhibitor in animal models for fibrosis, such as liver fibrosis, bone marrow fibrosis (e.g., myelofibrosis) and kidney fibrosis, are disclosed.

Accordingly, in one aspect, the present invention features a method of reducing fibrosis in a cell or tissue. The method includes contacting a fibrotic cell or tissue with a PI3K inhibitor (e.g., as a single agent or in combination with another agent or therapeutic modality), in an amount sufficient to decrease or inhibit the fibrosis. In one embodiment, the method is carried out in vivo, for example, in a mammalian subject, e.g., an animal model or as part of therapeutic protocol. In one embodiment, the fibrosis is present in a subject with a fibrotic condition, e.g., a fibrotic condition as described herein.

In another aspect, the invention features a method of treating or preventing a fibrotic condition in a subject. The method includes administering a PI3K inhibitor (e.g., as a single agent or in combination with another agent or therapeutic modality), to a subject in need thereof, in an amount sufficient to decrease or inhibit the fibrotic condition in the subject.

The invention also features a method of treating or preventing scleroderma in a subject. The method includes administering a PI3K inhibitor (e.g., as a single agent or in combination with another agent or therapeutic modality), to a subject in need thereof, in an amount sufficient to decrease or inhibit the scleroderma. In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

In certain embodiments, reducing fibrosis, or treatment of a fibrotic condition, includes reducing or inhibiting one or more of: formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is associated with an autoimmune disease selected from scleroderma or lupus, e.g., systemic lupus erythematosus.

In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs. host disease, or atherosclerosis.

In some embodiments, the fibrotic condition is scleroderma. In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

In certain embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In other embodiment, the fibrotic condition affects a tissue chosen from one or more of: muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods of the invention is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g, endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, or focal segmental glomerulosclerosis (FSGS).

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In certain embodiments, the fibrotic condition is found in a tissue exhibiting PI3K activity. In one embodiment, the PI3K inhibitor modulates (e.g., inhibits or activates) one or more components of a PI3K signaling pathway. For example, the PI3K inhibitor modulates the activity of Akt (PKB), mTOR, Tec kinases (e.g., Btk, Itk, Tec), phospholipase C, PDK1, PKCs, NFκB, Rac GEF (e.g., Vav-1), Rac, PDGF, TGF-beta, INF-alpha, or IL-1.

The invention discloses, at least in part, that a PI3 kinase (PI3K) inhibitor, as a single agent or in combination with one or more additional therapies, can ameliorate inflammatory myopathies (e.g., by decreasing one or more signs, symptoms, or complications associated with inflammatory myopathy) and/or skin disorders (e.g., skin rashes, e.g., urtricaria) in a subject, e.g., a mammalian subject. Signs, symptoms, or complications associated with inflammatory myopathy that can be ameliorated by the methods disclosed herein include any one or combination of such signs, symptoms, or complications, as known the art and/or as disclosed herein. Methods for evaluating the effects of a PI3K inhibitor in ameliorating inflammatory myopathies, e.g., in animal models of inflammatory myopathies, are disclosed.

In one aspect, methods of treating or preventing an inflammatory myopathy in a subject are disclosed. The methods include administering a PI3K inhibitor (e.g., as a single agent or in combination with another agent or therapeutic modality), to a subject in need thereof, in an amount sufficient to decrease or inhibit an inflammatory myopathy (e.g., by decreasing the severity and/or frequency of one or more symptoms associated with the inflammatory myopathy) in the subject.

In a related aspect, a method of reducing a symptom of an inflammatory myopathy (e.g., one or more symptoms associated with an inflammatory myopathy) in a subject is disclosed. The method includes administering to the subject a PI3K inhibitor (e.g., as a single agent or in combination with another therapeutic (e.g., another therapeutic agent)), in an amount sufficient to decrease or inhibit the symptom(s). In one embodiment, the method is carried out in vivo, for example, in a mammalian subject, e.g., an animal model or as part of therapeutic protocol. In some embodiments, the method is carried out in a biological sample present within or derived from a subject who has an inflammatory myopathy, or from a subject at risk for developing an inflammatory myopathy. In some embodiments, a biological sample (e.g., a sample derived from a subject who has or is at risk for developing an inflammatory myopathy, or a sample derived from a healthy subject) is contacted with the PI3K inhibitor outside the body and then introduced into the body of the subject.

The inflammatory myopathy can be an acute inflammatory myopathy or a chronic inflammatory myopathy.

In some embodiments, the inflammatory myopathy is a chronic inflammatory myopathy (e.g., dermatomyositis, polymyositis, or inclusion body myositis).

In some embodiments, the inflammatory myopathy is caused by an allergic reaction, another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic.

In some embodiments, the inflammatory myopathy is selected from polymyositis, dermatomyositis, inclusion body myositis, and immune-mediated necrotizing myopathy.

In some embodiments, the inflammatory myopathy is dermatomyositis.

Symptoms associated with inflammatory myopathies (e.g., dermatomyositis) can include, for example, muscle weakness (e.g. proximal muscle weakness), skin rash, fatigue after walking or standing, tripping or falling, dysphagia, dysphonia, difficulty breathing, muscle pain, tender muscles, weight loss, low-grade fever, inflamed lungs, light sensitivity, calcium deposits (calcinosis) under the skin or in the muscle, as well as biological concomitants of inflammatory myopathies as disclosed herein or as known in the art. Biological concomitants of inflammatory myopathies (e.g., dermatomyositis) include, e.g., altered (e.g., increased) levels of cytokines (e.g., Type I interferons (e.g., IFN-α and/or IFN-β), interleukins (e.g., IL-6, IL-10, IL-15, IL-17 and IL-18), and TNF-α), TGF-β, B-cell activating factor (BAFF), overexpression of IFN inducible genes (e.g., Type I IFN inducible genes). Other biological concomitants of inflammatory myopathies can include, e.g., an increased erythrocyte sedimentation rate (ESR) and/or elevated level of creatine kinase. Further biological concomitants of inflammatory myopathies can include autoantibodies, e.g., anti-synthetase autoantibodies (e.g., anti-Jo1 antibodies), anti-signal recognition particle antibodies (anti-SRP), anti-Mi-2 antibodies, anti-p155 antibodies, anti-PM/Sci antibodies, and anti-RNP antibodies.

In some embodiments, the symptom associated with inflammatory myopathy is an elevated level or increased biological activity of one or more of the following: IFN-α, TNF-α, IL-6, IL-8, IL-1, IL-10, TGFβ, IL-17, IL-18, and IL-15.

In some embodiments, decreasing or inhibiting the inflammatory myopathy comprises inhibiting (e.g., decreasing a level of, or decreasing a biological activity of) one or more of IFN-α, TNF-α, IL-6, IL-8, IL-1, IL-10, TGFβ, IL-17, IL-18, and IL-15 in the subject or in a sample derived from the subject.

In a related aspect, methods of treating or preventing a skin condition (e.g., a dermatitis) in a subject are disclosed. The methods include administering a PI3K inhibitor (e.g., as a single agent or in combination with another agent or therapeutic modality), to a subject in need thereof, in an amount sufficient to decrease or inhibit the skin condition (e.g., by decreasing the severity and/or frequency of one or more symptoms (e.g., inflammation or itchiness) associated with the skin condition) in the subject.

In some embodiments, the methods of the invention reduce symptoms associated with a skin condition (e.g., itchiness and/or inflammation). In some such embodiments, the PI3K inhibitor is administered topically (e.g., as a topical cream, eyedrop, nose drop or nasal spray). In some such embodiments, the PI3K inhibitor is a PI3K delta inhibitor (e.g., a PI3K inhibitor that demonstrates greater inhibition of PI3K delta than of other PI3K isoforms). In some embodiments, the PI3K delta inhibitor prevents mast cell degranulation.

The skin condition (e.g., the skin rash) may be spontaneous, or it may be induced, e.g., by exposure to an allergen (e.g., poison ivy, poison oak, or poison sumac), drugs, food, insect bite, inhalants, emotional stress, exposure to heat, exposure to cold, or exercise. In some embodiments, the skin condition is a skin rash (e.g., a pruritic rash, e.g., urticaria). In some embodiments, the skin condition is an insect bite. In some embodiments, the skin condition is associated with another disease (e.g., dermatomyositis).

In some embodiments, treating (e.g., decreasing or inhibiting) the inflammatory myopathy, or the skin condition, comprises inhibiting (e.g., decreasing a level of, or decreasing a biological activity of) one or more of IFN-α, TNF-α, IL-6, IL-8, or IL-1 in the subject or in a sample derived from the subject. In some embodiments, the method decreases a level of IFN-α, TNF-α, IL-6, IL-8, IL-1, or a combination thereof, in the subject or in a sample derived from the subject. In some embodiments, the method decreases a level of IFN-α in the subject or in a sample derived from the subject. In some embodiments, the level of IFN-α, TNF-α, IL-6, IL-8, or IL-1 is the level assessed in a sample of whole blood or PBMCs. In some embodiments, the level of IFN-α, TNF-α, IL-6, IL-8, or IL-1 is the level assessed in a sample obtained by a skin biopsy or a muscle biopsy. In some embodiments, the sample is obtained by a skin biopsy.

In some embodiments, the symptom (e.g., a symptom associated with lupus, a symptom associated with a fibrotic condition, a symptom associated with inflammatory myopathy, and/or a symptom associated with a skin condition) is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have lupus, a fibrotic condition, an inflammatory myopathy, and/or a skin condition or the level in samples derived from subjects who do not have lupus, a fibrotic condition, an inflammatory myopathy, and/or a skin condition). In some embodiments, the decrease is statistically significant, for example, as assessed using an appropriate parametric or nonparametric statistical comparison.

In certain embodiments, the symptom is found in, or is associated with, a tissue exhibiting PI3K activity.

In one embodiment, the PI3K inhibitor modulates (e.g., inhibits or activates) one or more components of a PI3K signaling pathway. For example, the PI3K inhibitor modulates the activity of Akt (PKB), mTOR, Tec kinases (e.g., Btk, Itk, Tec), phospholipase C, PDK1, PKCs, NFκB, Rac GEF (e.g., Vav-1), or Rac.

In some embodiments, the subject is a mammal. In some embodiments, the subject is a human.

In certain embodiments, the subject is an animal model of lupus, a fibrotic condition, or an inflammatory myopathy, a human with lupus, a fibrotic condition, or an inflammatory myopathy, or a subject (e.g., a human) at risk for developing lupus, a fibrotic condition, or an inflammatory myopathy. In some embodiments, the subject has a family history of lupus, a fibrotic condition, or an inflammatory myopathy; who carries a gene associated with lupus, a fibrotic condition, or an inflammatory myopathy; who is positive for a biomarker associated with lupus, a fibrotic condition, or an inflammatory myopathy; or a combination thereof. In some embodiments, the subject has been diagnosed with lupus, a fibrotic condition, or an inflammatory myopathy (e.g., dermatomyositis). In some embodiments, the subject has one or more signs or symptoms associated with lupus, a fibrotic condition, or an inflammatory myopathy, e.g., one or more of the symptoms described herein. In some embodiments, the subject is at risk for developing lupus, a fibrotic condition, or an inflammatory myopathy. In one embodiment, the subject has a mutation (e.g., an SNP) in a gene selected from STAT4, IRF5, BANK1, ITGAM, PD1, FAM167A-BLK, IRF5-TNP03, KIAA1542, TNFAIP3, XKR6, 1q25.1, PXK, ATG5, ICA1, XKR6, LYN and SCUB2 or a combination thereof. In one embodiment, the subject carries a human leukocyte antigen (HLA) type associated with development of an inflammatory myopathy (e.g., dermatomyositis) (e.g., DR3, DR5, or DR7). In one embodiment, the subject has a polymorphism of tumor necrosis factor (e.g., the −308A allele).

In some embodiments, the subject exhibits elevated levels of IFN-α, TNF-α, IL-6, IL-8, or IL-1. In certain embodiments, the subject exhibits elevated levels of IFN-α.

In some embodiments, the subject exhibits elevated levels of antinuclear antibodies (e.g., anti-Smith antibodies, anti-double stranded DNA (dsDNA) antibodies, anti-U1 RNP, SS-a (or anti-Ro), SS-b (or anti-La)), antiphospholipid antibodies, anti-ss DNA antibodies, anti-histone antibodies, or anticardiolipin antibodies. In some embodiments, the subject exhibits elevated levels of anti-dsDNA antibodies. In some embodiments, the subject exhibits elevated levels of anti-Sm antibodies.

In one embodiment of the present disclosure, the PI3 kinase inhibitor is a compound of Formula I below or a pharmaceutically acceptable salt thereof, wherein Formula I

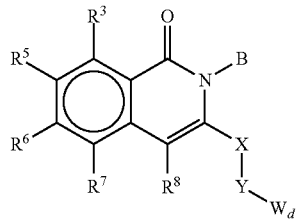

$W_d$ is heterocycloalkyl, aryl or heteroaryl;
B is alkyl or a moiety of Formula II;

Formula II

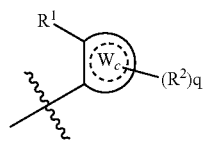

wherein $W_c$ is aryl, heteroaryl, heterocycloalkyl, or cycloalkyl, and q is an integer of 0, 1, 2, 3, or 4;
X is absent or —(CH($R^9$))$_z$—, and z is an integer of 1;
Y is absent, or —N($R^9$)—;
$R^1$ is hydrogen, alkyl, alkenyl, alkynyl, alkoxy, amido, alkoxycarbonyl, sulfonamido, halo, cyano, or nitro;
$R^2$ is alkyl, alkenyl, alkynyl, cycloalkyl, heterocycloalkyl, aryl, heteroaryl, heteroarylalkyl, alkoxy, amino, halo, cyano, hydroxy or nitro;
$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro;
$R^5$, $R^6$, $R^7$, and $R^8$ are independently hydrogen, alkyl, alkenyl, alkynyl, cycloalkyl, heterocycloalkyl, alkoxy, amido, amino, acyl, acyloxy, sulfonamido, halo, cyano, hydroxy or nitro; and
each instance of $R^9$ is independently hydrogen, alkyl, cycloalkyl, or heterocycloalkyl.

In some embodiments of the compounds of Formula I, when both X and Y are present then Y is —NH—.

In some embodiments of the compounds of Formula I, X is absent or is —(CH($R^9$))$_z$—, and z is independently an integer of 1, 2, 3, or 4; and Y is absent, —O—, —S—, —S(=O)—, —S(=O)$_2$—, —N($R^9$)—, —C(=O)—(CH($R^9$)$_z$—, —C(=O)—, —N($R^9$)(C=O)—, —N($R^9$)(C=O)NH—, or —N($R^9$)C($R^9$)$_2$—.

In some of the embodiments, X is —CH$_2$—, —CH(CH$_2$CH$_3$), or —CH(CH$_3$)—.

In some embodiments, X—Y is —CH$_2$—N(CH$_3$), —CH$_2$—N(CH$_2$CH$_3$), —CH(CH$_2$CH$_3$)—NH— or —CH(CH$_3$)—NH—.

In some embodiments, $W_d$ is a pyrazolopyrimidine of Formula III(a), or purine of Formula III(b), Formula III(c) or Formula III(d) below:

Formula III(a)

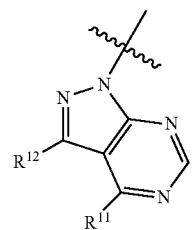

Formula III(b)

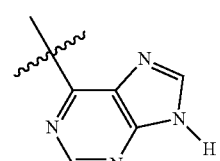

Formula III(c)

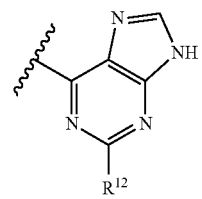

Formula III(d)

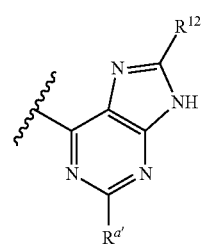

wherein $R^{a'}$ if Formula III(d) is hydrogen, halo, phosphate, urea, a carbonate, amino, alkyl, alkenyl, alkynyl, cycloalkyl, heteroalkyl, or heterocycloalkyl; $R^{11}$ of Formula III(a) is H, alkyl, halo, amino, amido, hydroxy, or alkoxy, and $R^{12}$ of Formula III(a), Formula III(c) or Formula III(d) is H, alkyl, alkynyl, alkenyl, halo, aryl, heteroaryl, heterocycloalkyl, or cycloalkyl. In some embodiments, $W_d$ is a pyrazolopyrimidine of Formula III(a), wherein $R^{11}$ is H, alkyl, halo, amino, amido, hydroxy, or alkoxy, and $R^{12}$ is cyano, amino, carboxylic acid, or amido.

In some embodiments, the compound of Formula I has the structure of Formula IV:

Formula IV

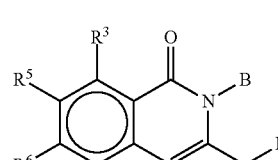
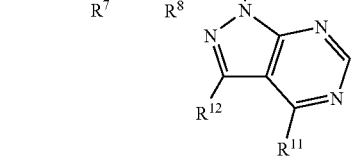

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, the compound of Formula I has the structure of Formula IV wherein $R^{11}$ is H, alkyl, halo, amino, amido, hydroxy, or alkoxy, and $R^{12}$ is cyano, amino, carboxylic acid, or amido.

In some embodiments of the compound of Formula IV, $R^{11}$ is amino. In some embodiments of the compound of Formula IV, $R^{12}$ is alkyl, alkenyl, alkynyl, heteroaryl, aryl, or heterocycloalkyl. In some embodiments of the compound of Formula IV, $R^{12}$ is cyano, amino, carboxylic acid, amido, monocyclic heteroaryl, or bicyclic heteroaryl.

In some embodiments of the compound of Formula I, the compound has the structure of Formula V:

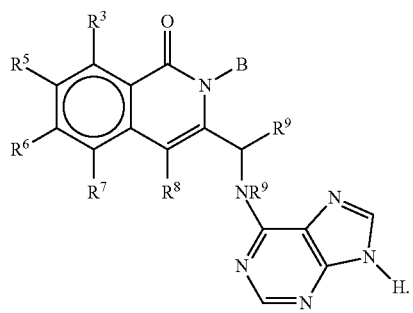

Formula V

In some of the embodiments of Formula V, $NR^9$ is —$N(CH_2CH_3)CH_2$— or $N(CH_3)CH_2$—.

In some of the embodiments of Formula I, the compound has a structure of Formula VI:

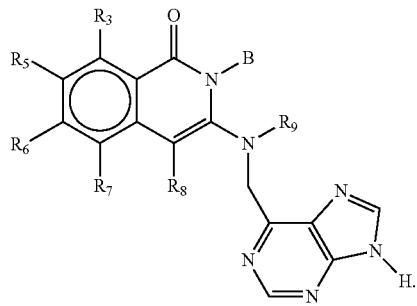

Formula VI

In some of the embodiments of the compound of Formula VI, $R^3$ is —H, —$CH_3$, —Cl, or —F, and $R^5$, $R^6$, $R^7$, and $R^8$ are independently hydrogen.

In some of the embodiments of Formula VI, B is a moiety of Formula II;

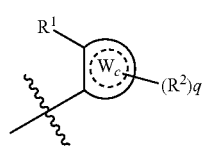

Formula II wherein $W_c$ is aryl, heteroaryl, heterocycloalkyl, or cycloalkyl, and q is an integer of 0, 1, 2, 3, or 4.

In one embodiment of the present disclosure, the PI3 kinase inhibitor is a compound, or pharmaceutically acceptable salt thereof, having the structure of Formula I-1, wherein:

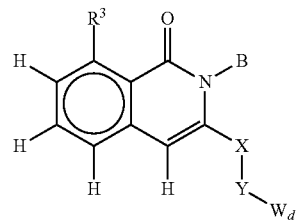

Formula I-1

B is a moiety of Formula II;

wherein $W_c$ in B is aryl, heteroaryl, heterocycloalkyl, or cycloalkyl, and q is an integer of 0, 1, 2, 3, or 4;

X is absent or —$(CH(R^9))_z$—, and z is an integer of 1;

Y is absent, or —$N(R^9)$—;

when Y is absent, Wd is:

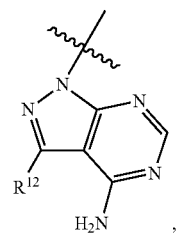

or when Y is present, Wd is:

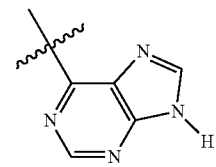 [SMILES: *c1ncnc2[nH]cnc12]

$R^1$ is hydrogen, alkyl, alkenyl, alkynyl, alkoxy, amido, alkoxycarbonyl, sulfonamido, halo, cyano, or nitro;

$R^2$ is alkyl, alkenyl, alkynyl, cycloalkyl, heterocycloalkyl, aryl, heteroaryl, heteroarylalkyl, alkoxy, amino, halo, cyano, hydroxy or nitro;

$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro;

each instance of $R^9$ is independently hydrogen, $C_1$-$C_{10}$alkyl, cycloalkyl, or heterocyclooalkyl; and $R^{12}$ is H, alkyl, alkynyl, alkenyl, halo, aryl, heteroaryl, heterocycloalkyl, or cycloalkyl.

In some embodiments, a compound of Formula I or Formula I-1 has the structure of Formula IV-A:

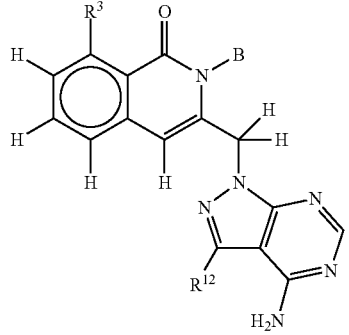

Formula IV-A

In some embodiments of the compound of Formula IV-A, $R^{12}$ is substituted benzoxazole.

In some embodiments, a compound of Formula I or Formula I-1 has the structure of Formula V-A:

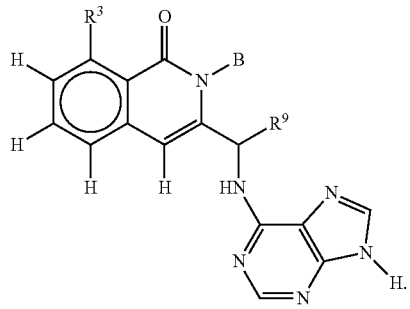

Formula V-A

In some embodiments, a compound of Formula I or Formula I-1 has the structure of Formula IV-A or Formula V-A.

In some embodiments, a compound of Formula I or Formula I-1 has the structure of Formula V-B:

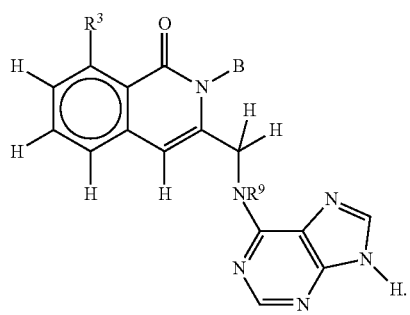

Formula V-B

In some embodiments, a compound of Formula I or Formula I-1 has the structure of Formula VI-A:

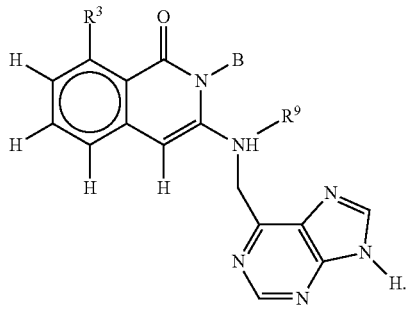

Formula VI-A

In some embodiments, a compound of Formula I or Formula I-1 is the compound wherein B is a moiety of Formula II;

Formula II

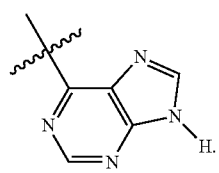

wherein $W_c$ is aryl, heteroaryl, heterocycloalkyl, or cycloalkyl; q is an integer of 0 or 1; $R^1$ is hydrogen, alkyl, or halo; $R^2$ is alkyl or halo; and $R^3$ is hydrogen, alkyl, or halo. In some embodiments, when both X and Y are present then Y is —NH—. In other embodiments, $R^3$ is —H, —CH$_3$, —CH$_2$CH$_3$, —CF$_3$, —Cl or —F. In further embodiments, $R^3$ is methyl or chloro.

In some embodiments of the compound of Formula I or Formula I-1, X is —(CH($R^9$))$_z$—, wherein $R^9$ is methyl and z=1; and
Wd is

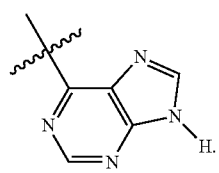

In other embodiments of the compound of Formula I or Formula I-1, the compound is predominately in an (S)-stereochemical configuration.

In further embodiments of the compound of Formula I or Formula I-1, the compound has a structure of Formula V-A2:

Formula V-A2

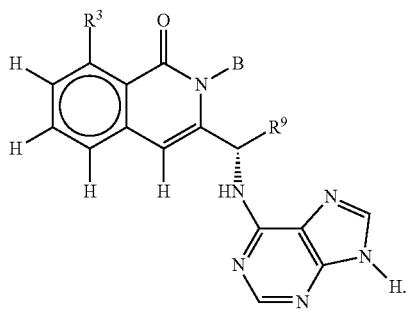

In some other embodiments of the compound of Formula I or Formula I-1, $R^{12}$ is a monocyclic heteroaryl, bicyclic heteroaryl, or heterocycloalkyl.

In some other embodiments of the compound of Formula I or Formula I-1, B is a moiety of Formula II:

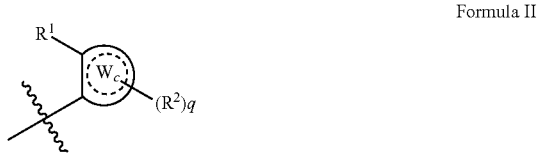

Formula II wherein $W_c$ is aryl or cycloalkyl.

In some embodiments, the compound is a polymorph Form C as disclosed herein.

In some embodiments, the compound inhibits a class I PI3K. In certain embodiments, the class I PI3K is selected from p110α, p110β, p110γ, and p110δ.

In some embodiments, the compound inhibits one or more class I PI3K isoforms selected from the group consisting of PI3 kinase-α, PI3 kinase-β, PI3 kinase-γ, and PI3 kinase-δ.

In some embodiments, the compound selectively inhibits a class I PI3 kinase-δ isoform, or selectively inhibits a class I PI3 kinase-δ and a PI3 kinase-γ isoform, as compared with other class I PI3 kinase isoforms.

In some embodiments, a pharmaceutical composition is used, wherein the composition comprises a pharmaceutically acceptable excipient and one or more compounds of any formulae provided herein, including but not limited to Formula I, I-1, IV, IV-A, V, V-A, V-A2, V-B, VI, and VI-A. In some embodiments, the composition is a liquid, solid, semi-solid, gel, or an aerosol form.

In other embodiments, one or more PI3K inhibitors (e.g., one or more PI3K inhibitors described herein) are administered in combination. In one embodiment, the PI3K inhibitors are administered concurrently. In another embodiment the inhibitors are administered sequentially. For example, a combination of e.g., Compound 292 and a second PI3K inhibitor, can be administered concurrently or sequentially. In one embodiment, the second PI3K inhibitor, is administered first, followed, with or without a period of overlap, by administration of Compound 292.

In another embodiment, Compound 292 is administered first, followed, with or without a period of overlap, by administration of the second PI3K inhibitor.

In one embodiment, the subject treated is a mammal, e.g., a primate, typically a human (e.g., a patient having, or at risk of having, lupus, a fibrotic condition, or an inflammatory myopathy as described herein). In some embodiments, the subject treated is in need of PI3 kinase inhibition (e.g., has been evaluated to show elevated PI3K levels or alterations in another component of the PI3K pathway). In some embodiments, the subject treated is in need of PI3 kinase inhibition (e.g., has been evaluated to show elevated PI3K levels or alterations in another component of the PI3K pathway, a fibrotic marker, or a genetic abnormality associated with a fibrotic condition). In other embodiments, the subject has a mutation associated with a disorder having a fibrotic component. For example, the subject is a patient having, or at risk of having, primary myelofibrosis having a gain-of-function mutation in a gene that regulates hematopoiesis, such as Janus kinase 2 (JAK2) (e.g., JAK2$^{V617F}$) or the thrombopoietin receptor (MPL). In other embodiments, the subject has, or is at risk of having, a mutation in Bcr-abl. In other embodiments, the subject has, or is at risk of having, a cytogenic abnormality associated with a malignancy or cancer (e.g., a cytogenic abnormality associated with a myeloplastic syndrome, hairy cell leukemia, a lymphoma or multiple myeloma). In other embodiments, the subject has, or is at risk of having, a SMAD mutation. Any of these mutations or abnormalities can be evaluating prior to, during, or after the course of therapy.

In some embodiments, the PI3K inhibitor is administered as a pharmaceutical composition comprising the PI3K inhibitor, or a pharmaceutically acceptable salt thereof, and a pharmaceutically acceptable excipient.

In certain embodiments, the PI3K inhibitor is administered or is present in the composition, e.g., the pharmaceutical composition.

The PI3K inhibitors described herein can be administered to the subject systemically (e.g., orally, parenterally, subcutaneously, intravenously, rectally, intramuscularly, intraperitoneally, intranasally, transdermally, or by inhalation or intracavitary installation). Typically, the PI3K inhibitors are administered orally. In some embodiments, the PI3K inhibitor is administered topically. In some embodiments, the PI3K inhibitor is administered as a topical ointment (e.g., a topical cream), eyedrop, nose drop or nasal spray.

In one embodiment, the PI3K inhibitor is Compound 292, as disclosed in Table 4, or a pharmaceutically acceptable salt thereof. Compound 292, or a pharmaceutically acceptable salt thereof, can be administered orally. Other routes of administration are also provided herein.

The methods and compositions of the invention can, optionally, be used in combination with other therapies (e.g., one or more agents, surgical procedures, or radiation procedures). Any combination of one or more PI3K inhibitor(s) and one or more other agents or therapies can be used. The PI3K inhibitor(s) and other therapies can be administered before treatment, concurrently with treatment, post-treatment, or during remission of the disorder. In one embodiment, a second agent is administered simultaneously or sequentially with the PI3K inhibitor.

In some embodiments, the PI3K inhibitor and the second agent are administered as separate compositions, e.g., pharmaceutical compositions. In some embodiments, the PI3K inhibitor and the agent are administered separately, but via the same route (e.g., both orally or both intravenously). In other embodiments, the PI3K inhibitor and the agent are administered in the same composition, e.g., pharmaceutical composition.

In some embodiments, where lupus is treated, the second agent is selected from belimumab, AGS-009, rontalizumab, vitamin D3, sifalimumab, AMG 811, IFNα Kinoid, CEP33457, epratuzumab, LY2127399, Ocrelizumab, Atacicept, A-623, SBI-087, AMG557, laquinimod, rapamycin, cyclophosphamide, azathioprine, mycophenolate, leflunomide, methotrexate, CNTO 136, tamibarotene, N-acetylcysteine, CDP7657, hydroxychloroquine, rituximab, carfilzomib, bortezomib, ONX 0914, IMO-3100, or DV1179.

In embodiments where a fibrotic condition of the heart is treated, the PI3K inhibitor can be administered in combination with eplerenone, furosemide, pycnogenol, spironolactone, TcNC100692, torasemide (e.g., prolonged release form of torasemide), or a combination thereof. In embodiments where a fibrotic condition of the kidney is treated, the PI3K inhibitor can be administered in combination with cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, or a combination thereof.

In embodiments where a fibrotic condition of the skin is treated, the PI3K inhibitor can be administered in combination with Bosentan (Tracleer), p144, pentoxifylline; pirfenidone; pravastatin, STI571, Vitamin E, or a combination thereof.

In embodiments where a fibrotic condition of the bone marrow is treated, the PI3K inhibitor can be administered in combination with an agent chosen from a Jak2 inhibitor (including, but not limited to, INCB018424, XL019, TG101348, or TG101209), an immunomodulator, e.g., an IMID (including, but not limited to thalidomide, lenalidomide, or panolinomide), hydroxyurea, an androgen, erythropoietic stimulating agents, prednisone, danazol, HDAC inhibitors, or other agents or therapeutic modalities (e.g., stem cell transplants, or radiation).

In embodiments where a fibrotic condition of the gastrointestinal fibrosis is treated, the PI3K inhibitor can be administered in combination with ALTU-135, bucelipase alfa (INN), DCI1020, EUR-1008 (ZENPEP™) ibuprofen, Lym-X-Sorb powder, pancrease MT, pancrelipase (e.g., pancrelipase delayed release), pentade canoic acid (PA), repaglinide, TheraCLEC™, triheptadecanoin (THA), ULTRASE MT20, ursodiol, or a combination thereof.

In other embodiments, the PI3K inhibitor is administered in combination with one or more of allogeneic bone marrow transplant, erythropoietin, radiation, or a histone deacetylase inhibitor.

In some embodiments, where an inflammatory myopathy is treated, the second agent is selected from one or more of a corticosteroid (e.g., prednisone, methylprednisone), methotrexate, azathioprine, intravenous immunoglobulin, tacrolimus, pimecrolimus, cyclophosphamide, cyclosporine, hydroxychloroquine, chloroquine, total body irradiation, rituximab, a TNF inhibitor, infliximab, AGS-009, Rontalizumab, Vitamin D3, Sifalimumab, AMG 811, IFN$\alpha$ Kinoid, or CEP33457.

The methods of the invention can further include the step of monitoring the subject, e.g., for a change (e.g., an increase or decrease) in levels of one or more signs or symptoms or biological concomitants of lupus, as disclosed herein. For example, biological concomitants can include immune complexes, elevated levels of cytokines (e.g., interferons (e.g., Type I interferons, e.g., IFN-$\alpha$ and/or IFN-$\beta$); interleukins (e.g., IL-6, IL-8, IL-1, and IL-18) and TNF-$\alpha$), elevated levels of antibodies associated with lupus (e.g., antinuclear antibodies (e.g., anti-Smith antibodies, anti-double stranded DNA (dsDNA) antibodies, anti-U1 RNP, SS-a (or anti-Ro), SS-b (or anti-La)), antiphospholipid antibodies, anti-ss DNA antibodies, anti-histone antibodies, or anticardiolipin antibodies), overexpression of IFN-$\alpha$ and/or IFN-$\beta$ inducible genes, elevated levels of IP-10, elevated levels of sCD40L, reduced levels of C3-derived C3b, reduced peripheral iNKT cell frequencies, defective B cell-mediated stimulation of iNKT cells, altered CD1d expression on B cells, and reduced numbers of natural regulatory T cells (Treg)). In some embodiments, one or more of these biological concomitants correlates with a decrease in one or more clinical symptoms associated with lupus.

The methods of the invention can further include the step of monitoring the subject, e.g., for a change (e.g., an increase or decrease) in one or more of: fibrotic lesion size (e.g., Sirius red staining, collagen or hydroxyproline content); cellularity; composition; fibrogenic gene expression (e.g., Col1a1, Acta2, TIMP-1, Lox); alpha-SMA immunohistochemistry (IHC) and/or Western Blot; immune/inflammatory levels; PI3K levels or signaling; stromal activation; levels of one or more markers (e.g., cancer markers); or any other parameter related to clinical outcome. In additional embodiments, the method further includes monitoring in a subject with bone marrow fibrosis one or more of: monitoring peripheral blood counts (e.g., red blood cells, white blood cells, platelets), wherein an increase in peripheral blood counts is indicative of an improved outcome. In other embodiments, the method further includes monitoring in a subject with bone marrow fibrosis one or more of: spleen size, liver size, and size of extramedullary hematopoiesis, wherein a decrease in one or more of these parameters is indicative of an improved outcome. The subject can be monitored in one or more of the following periods: prior to beginning of treatment; during the treatment; or after one or more elements of the treatment have been administered. Monitoring can be used to evaluate the need for further treatment with the same PI3K inhibitior, alone or in combination with, another agent, or for additional treatment with additional agents. Generally, a decrease in one or more of the parameters described above is indicative of the improved condition of the subject.

The methods of the invention can further include the step of monitoring the subject, e.g., for a change (e.g., an increase or decrease) in levels of one or more signs or symptoms or biological concomitants of an inflammatory myopathy, as disclosed herein. In some embodiments, the change in one or more of these biological concomitants correlates with a decrease in one or more clinical symptoms (e.g., symptoms associated with an inflammatory myopathy and/or a skin condition, as disclosed herein).

In some embodiments, a normalization (e.g., a decrease in an elevated level or increase in a diminished level) of a biological concomitant is indicative of treatment efficacy and/or is predictive of improvement in clinical symptoms. For example, in some embodiments, a decrease in IFN-$\alpha$ is indicative of treatment efficacy. In some embodiments, a decrease in IFN-$\alpha$ correlates with a decrease in one or more clinical symptoms associated with lupus, a fibrotic condition, an inflammatory myopathy and/or a skin condition. In some embodiments, the subject is monitored for a change in urine protein levels (e.g., a decrease in urine protein levels, which can be indicative of treatment efficacy). In some embodiments, the subject is monitored for a change in spleen inflammation (e.g., by monitoring spleen size, wherein a decrease or lack of increase in spleen size can be indicative of treatment efficacy). In some embodiments, the subject is monitored for a change in nephritis. A reduction in nephritis can be indicative of treatment efficacy. In some embodiments, the subject is monitored for a change in formation of immune complexes. A decrease in immune complexes can be indicative of treatment efficacy.

The subject can be monitored in one or more of the following periods: prior to beginning of treatment; during the treatment; or after one or more elements of the treatment have been administered. Monitoring can be used to evaluate the need for further treatment with the same PI3K inhibitior, alone or in combination with, another agent, or for additional treatment with additional agents.

The methods of the invention can further include the step of analyzing a nucleic acid or protein from the subject, e.g., analyzing the genotype of the subject. In one embodiment, a PI3K protein, or a nucleic acid encoding a PI3K protein, and/or an upstream or downstream component(s) of a PI3K signaling pathway is analyzed. The nucleic acid or protein can be detected in any biological sample (e.g., blood, urine, circulating cells, a tissue biopsy or a bone marrow biopsy) using any method disclosed herein or known in the art. For example, the PI3K protein can be detected by systemic administration of a labeled form of an antibody to PI3K followed by imaging.

The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the PI3K inhibitior and/or agent, to thereby determine appropriate dosage(s) and treatment regimen(s) of the PI3K inhibitior (e.g., amount per treatment or frequency of treatments) for prophylactic or therapeutic treatment of the subject.

In other embodiments, the method further includes analyzing a nucleic acid or a protein from a cancer marker, e.g., Janus kinase 2 (JAK2) (e.g., $JAK2^{V617F}$); the thrombopoietin receptor (MPL) for bone marrow fibrotic conditions, such as myeloproliferative neoplasms; a mutation in Bcr-abl; or a cytogenic abnormality associated with a malignancy.

In certain embodiments, the methods of the invention further include the step of detecting an altered PI3K level in the subject, prior to, or after, administering a PI3K inhibitior to the patient. The PI3K level can be assessed in any biological sample, e.g., blood, urine, circulating cells, a tissue biopsy, or a bone marrow biopsy. In some embodiments, the PI3K level is assessed by systemic administration of a labeled form of an antibody to PI3K followed by imaging.

In another aspect, the invention features a composition, e.g., a pharmaceutical composition, that includes one or more PI3K inhibitiors, e.g., a PI3K inhibitior as described herein, and optionally, one or more additional therapeutic agents (e.g., an agent as disclosed herein). The composition can further include a pharmaceutically-acceptable carrier or excipient.

In another aspect, the invention features a composition for use, or the use, of a PI3K inhibitor, alone or in combination with a second agent or therapeutic modality described herein for the treatment of lupus, a fibrotic condition (e.g., a fibrotic condition), an inflammatory myopathy (e.g., dermatomyositis, polymyositis, or inclusion body myositis), or a skin condition, as described herein.

In another aspect, the invention features therapeutic kits that include the PI3K inhibitior, alone or in combination with one or more additional agents, and instructions for use the treatment of lupus, a fibrotic condition (e.g., a fibrotic condition), an inflammatory myopathy (e.g., dermatomyositis, polymyositis, or inclusion body myositis), or a skin condition, as described herein.

INCORPORATION BY REFERENCE

All publications, patents, and patent applications mentioned in this specification are herein incorporated by reference in their entirety and to the same extent as if each individual publication, patent, or patent application was specifically and individually indicated to be incorporated by reference.

DETAILED DESCRIPTION OF THE INVENTION

Figure 1:
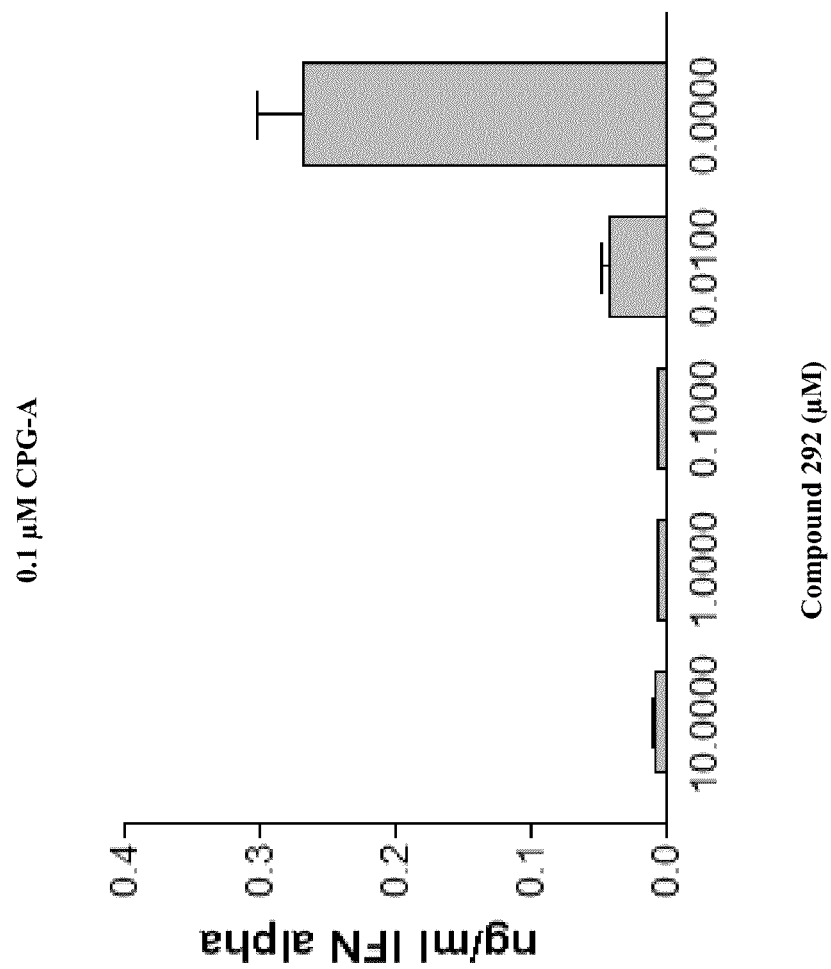
FIG. 1 depicts the effect of Compound 292 on IFN-α production induced by 0.1 μM CPG-A.

While preferred embodiments of the present invention have been shown and described herein, such embodiments are provided by way of example only. Numerous variations, changes, and substitutions will occur to those skilled in the art without departing from the invention. It should be understood that various alternatives to the embodiments of the invention described herein can be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, the term "patient" or "subject" refers to an animal, typically a human (i.e., a male or female of any age group, e.g., a pediatric patient (e.g, infant, child, adolescent) or adult patient (e.g., young adult, middle-aged adult or senior adult) or other mammal, such as a primate (e.g., cynomolgus monkey, rhesus monkey); other mammals such as rodents (mice, rats), cattle, pigs, horses, sheep, goats, cats, dogs; and/or birds, that will be or has been the object of treatment, observation, and/or experiment. When the term is used in conjunction with administration of a compound or drug, then the patient has been the object of treatment, observation, and/or administration of the compound or drug.

"Treating," "treat," and "treatment" as used herein, refers to partially or completely inhibiting or reducing the condition from which the subject is suffering. In one embodiment, this term refers to an action that occurs while a patient is suffering from, or is diagnosed with, the condition, which reduces the severity of the condition, or retards or slows the progression of the condition. Treatment need not result in a complete cure of the condition; partial inhibition or reduction of the condition is encompassed by this term. Treatment is intended to encompass prevention or prophylaxis.

"Therapeutically effective amount," as used herein, refers to a minimal amount or concentration of a PI3K inhibitor that, when administered alone or in combination, is sufficient to provide a therapeutic benefit in the treatment of the condition, or to delay or minimize one or more symptoms associated with the condition. The term "therapeutically effective amount" can encompass an amount that improves overall therapy, reduces or avoids symptoms or causes of the condition, or enhances the therapeutic efficacy of another therapeutic agent. The therapeutic amount need not result in a complete cure of the condition; partial inhibition or reduction of the condition is encompassed by this term. The therapeutically effective amount can also encompass a prophylactically effective amount.

As used herein, unless otherwise specified, the terms "prevent," "preventing" and "prevention" refers to an action that occurs before the subject begins to suffer from the condition, or relapse of the condition. The prevention need not result in a complete prevention of the condition; partial prevention or reduction of the condition to be treated, or reduction of the risk of the condition to be treated, is encompassed by this term.

As used herein, unless otherwise specified, a "prophylactically effective amount" of a PI3K inhibitor that, when administered alone or in combination, prevents or reduces the risk of developing the condition, or one or more symptoms associated with the condition, or prevents its recurrence. The term "prophylactically effective amount" can encompass an amount that improves overall prophylaxis or enhances the prophylactic efficacy of another prophylactic agent. The prophylactic amount need not result in a complete prevention of the condition; partial prevention or reduction of the condition is encompassed by this term.

As used herein, to "decrease", "ameliorate," "reduce," "treat" (or the like) a condition or a sumptom associated with the condition includes reducing the severity and/or frequency of symptoms of the condition, as well as preventing the condition and/or symptoms of the condition (e.g., by reducing the severity and/or frequency of flares of symptoms). In some embodiments, the symptom is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the condition or the level in samples derived from subjects who do not have the condition). In some embodiments, the decrease is statistically significant, for example, as assessed using an appropriate parametric or non-parametric statistical comparison.

In the context of biological molecules, to "decrease", "ameliorate," "reduce," "inhibit," or the like, includes decreasing the level (e.g., the level, e.g., of mRNA or protein, that can be measured in a biological sample) or the activity (e.g., the function) of the molecule. In some embodiments, the level or activity is reduced by at least 10%, at least 20%, at least 30%, at least 40%, at least 50%, at least 60%, at least 70%, at least 80%, at least 90%, or at least 95% relative to a control level.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The terms "antagonist" and "inhibitor" are used interchangeably, and they refer to a compound having the ability to inhibit a biological function of a target protein (e.g., a PI3K, e.g., PI3K-δ), whether by inhibiting the activity or expression of the target protein. Accordingly, the terms "antagonist" and "inhibitors" are defined in the context of the biological role of the target protein. While antagonists can specifically interact with (e.g., bind to) the target, compounds that inhibit a biological activity of the target protein by interacting with other members of the signal transduction pathway of which the target protein is a member are also specifically included within this definition.

As used herein, a "phosphoinositide 3-kinase (PI3K) inhibitor" or "PI3K inhibitor" refers to an inhibitor of any PI3K. PI3Ks are members of a unique and conserved family of intracellular lipid kinases that phosphorylate the 3'-OH group on phosphatidylinositols or phosphoinositides. The PI3K family includes kinases with distinct substrate specificities, expression patterns, and modes of regulation (see, e.g., Katso et al., 2001, *Annu. Rev. Cell Dev. Biol.* 17, 615-675; Foster, F. M. et al., 2003, *J Cell Sci* 116, 3037-3040). The class I PI3Ks (e.g., p110α, p110β, p110γ, and p110δ) are typically activated by tyrosine kinases or G-protein coupled receptors to generate PIP3, which engages downstream mediators such as those in the Akt/PDK1 pathway, mTOR, the Tec family kinases, and the Rho family GTPases. The class II PI3Ks (e.g., PI3K-C2α, PI3K-C2β, PI3K-C2γ) and III PI3Ks (e.g., Vps34) play a key role in intracellular trafficking through the synthesis of PI(3)P and PI(3,4)P2. Specific exemplary PI3K inhibitors are disclosed herein.

The class I PI3Ks comprise a p110 catalytic subunit and a regulatory adapter subunit. See, e.g., Cantrell, D. A. (2001) *Journal of Cell Science* 114: 1439-1445. Four isoforms of the p110 subunit (including PI3K-α (alpha), PI3K-β (beta), PI3K-γ (gamma), and PI3K-δ (delta) isoforms) have been implicated in various biological functions. Class I PI3Kα is involved, for example, in insulin signaling, and has been found to be mutated in solid tumors. Class I PI3K-β is involved, for example, in platelet activation and insulin signaling. Class I PI3K-γ plays a role in mast cell activation, innate immune function, and immune cell trafficking (chemokines). Class I PI3K-δ is involved, for example, in B-cell and T-cell activation and function and in Fc receptor signaling in mast cells. In some embodiments provided herein, the PI3K inhibitor is a class I PI3K inhibitor. In some such embodiments, the PI3K inhibitor inhibits a PI3K-α (alpha), PI3K-β (beta), PI3K-γ (gamma), or PI3K-δ (delta) isoform, or a combination thereof.

Downstream mediators of PI3K signal transduction include Akt and mammalian target of rapamycin (mTOR). Akt possesses a plckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

The term "selective inhibition" or "selectively inhibit" as applied to a biologically active agent refers to the agent's ability to selectively reduce the target signaling activity as compared to off-target signaling activity, via direct or interact interaction with the target.

"Radiation therapy" means exposing a patient, using routine methods and compositions known to the practitioner, to radiation emitters such as alpha-particle emitting radionucleotides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Prodrug" is meant to indicate a compound that can be converted under physiological conditions or by solvolysis to a biologically active compound described herein. Thus, the term "prodrug" refers to a precursor of a biologically active compound that is pharmaceutically acceptable. A prodrug can be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in *Bioreversible Carriers in Drug Design*, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds having the present structures wherein hydrogen is replaced by deuterium or tritium, or wherein carbon atom is replaced by $^{13}$C- or $^{14}$C-enriched carbon, are within the scope of this invention.

The compounds described herein can also contain unnatural proportions of atomic isotopes at one or more of atoms that constitute such compounds. For example, the compounds can be radiolabeled with radioactive isotopes, such as for example tritium ($^{3}$H), iodine-125 ($^{125}$I) or carbon-14 ($^{14}$C). All isotopic variations of the compounds described herein, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range can vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HIV=Human Immunodeficiency Virus; MeI=Methyl Iodide; POCl$_3$=Phosphorous Oxychloride; KCNS=Potassium IsoThiocyanate; TLC=Thin Layer Chromatography; MeOH=Methanol; and CHCl$_3$=Chloroform.

Abbreviations used herein have their conventional meaning within the chemical and biological arts.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, can be branched, straight chain, or cyclic.

"Alkenyl" refers to a straight or branched hydrocarbon chain radical group consisting solely of carbon and hydrogen atoms, containing at least one double bond, and having from two to ten carbon atoms (ie. $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (ie. $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)R$^a$, —OC(O)N(R$^a$)$_2$, —C(O)N(R$^a$)$_2$, —N(R$^a$)C(O)R$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cyclo alkyl are as disclosed herein and which are optionally substituted by one or more of the substituents described as suitable substituents for alkynyl and cycloalkyl respectively.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and can be saturated, or partially unsaturated. Cycloalkyl groups include groups having from 3 to 10 ring atoms (ie. $C_2$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)R$^a$, —OC(O)N(R$^a$)$_2$, —C(O)N(R$^a$)$_2$, —N(R$^a$)C(O)R$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl)heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)R$^a$, —OC(O)N(R$^a$)$_2$, —C(O)N(R$^a$)$_2$, —N(R$^a$)C(O)R$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —C(O)$R^a$, —C(O)O$R^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)R$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2-S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two Ra other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)R$^a$, —OC(O)N(R$^a$)$_2$, —C(O)N(R$^a$)$_2$, —N(R$^a$)C(O)R$^a$, —N(R$^a$) C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety can itself be optionally substituted. In some embodiments it is a $C_1$-$C_4$ amido or amide radical, which includes the amide carbonyl in the total number of carbons in the radical. The $R_2$ of —N(R)$_2$ of the amide can optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide can be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C (O)R$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis*, 3.sup.rd Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)R$^a$, —OC(O)N(R$^a$)$_2$, —C(O)N(R$^a$)$_2$, —N(R$^a$)C(O)R$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical can be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range can be given, e.g. C$_1$-C$_4$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the rest of the molecule can be through either a heteroatom or a carbon in the heteroalkyl chain. A heteroalkyl group can be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively.

"Heteroalkylheterocycloalkyl" refers to an -(heteroalkyl) heterocycloalkyl radical where heteroalkyl and heteroaryl are as disclosed herein and which are optionally substituted by one or more of the substituents described as suitable substituents for heteroalkyl and heterocycloalkyl respectively "Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively.

"Heteroaryl" or, alternatively, "heteroaromatic" refers to a 5- to 18-membered aromatic radical (e.g., C$_5$-C$_{13}$ heteroaryl) that includes one or more ring heteroatoms selected from nitrogen, oxygen and sulfur, and which can be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group can be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group can consist of 3 ring atoms, 4 ring atoms, etc., up to and including 18 ring atoms. In some embodiments, it is a C$_5$-C$_{10}$ heterocycloalkyl. In some embodiments, it is a C$_4$-C$_{10}$ heterocycloalkyl. In some embodiments, it is a C$_3$-C$_{10}$ heterocycloalkyl. Unless stated otherwise specifically in the specification, the heterocycloalkyl radical is a monocyclic, bicyclic, tricyclic or tetracyclic ring system, which can include fused or bridged ring systems. The heteroatoms in the heterocycloalkyl radical can be optionally oxidized. One or more nitrogen atoms, if present, are optionally quaternized. The heterocycloalkyl radical is partially or fully saturated. The heterocycloalkyl can be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Isomers" are different compounds that have the same molecular formula. "Stereoisomers" are isomers that differ only in the way the atoms are arranged in space, i.e. having a different stereochemical configuration. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which can potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

"Moiety" refers to a specific segment or functional group of a molecule. Chemical moieties are often recognized chemical entities embedded in or appended to a molecule.

"Nitro" refers to the —$NO_2$ radical.

"Oxa" refers to the —O— radical.

"Oxo" refers to the =O radical.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The compounds of the present invention can also contain unnatural proportions of atomic isotopes at one or more of atoms that constitute such compounds. For example, the compounds can be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

A "leaving group or atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups can similarly be protected.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Substituted" means that the referenced group can be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves can be substituted, for example, a cycloakyl substituent can have a halide substituted at one or more ring carbons, and the like. The protecting groups that can form the protective derivatives of the above substituents are known to those of skill in the art and can be found in references such as Greene and Wuts, above.

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —$S(O_2)$—H, —$S(O_2)$-(optionally substituted alkyl), —$S(O_2)$-(optionally substituted amino), —$S(O_2)$-(optionally substituted aryl), —$S(O_2)$-(optionally substituted heteroaryl), and —$S(O_2)$-(optionally substituted heterocycloalkyl).

"Sulfonamidyl" or "sulfonamido" refers to a —$S(=O)_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —$S(=O)_2$—NRR radical can be taken together with the nitrogen to which it is attached to form a 4-, 5-, 6-, or 7-membered ring. In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively "Sulfoxyl" refers to a —$S(=O)_2$OH radical.

"Sulfonate" refers to a —$S(=O)_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

Where substituent groups are specified by their conventional chemical formulae, written from left to right, they equally encompass the chemically identical substituents that would result from writing the structure from right to left, e.g., —$CH_2O$— is equivalent to —$OCH_2$—.

Compounds that can be used as described herein also include crystalline and amorphous forms of compounds, including, for example, polymorphs, pseudopolymorphs, solvates, hydrates, unsolvated polymorphs (including anhydrates), conformational polymorphs, and amorphous forms of the compounds, as well as mixtures thereof.

As used herein, and unless otherwise specified, "polymorph" can be used herein to describe a crystalline material, e.g., a crystalline form. In certain embodiments, "polymorph" as used herein are also meant to include all crystalline and amorphous forms of a compound or a salt thereof, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms, as well as mixtures thereof, unless a particular crystalline or amorphous form is referred to. Compounds of the present disclosure include crystalline and amorphous forms of those compounds, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms of the compounds or a salt thereof, as well as mixtures thereof.

Chemical entities include, but are not limited to, compounds of Formula I, I-1, IV, IV-A, V, V-A, V-A2, V-B, VI or VI-A, and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

In addition, if the compound of Formula I is obtained as an acid addition salt, the free base can be obtained by basifying a solution of the acid salt. Conversely, if the product is a free base, an addition salt, particularly a pharmaceutically acceptable addition salt, can be produced by dissolving the free base in a suitable organic solvent and treating the solution with an acid, in accordance with conventional procedures for preparing acid addition salts from base compounds. Those skilled in the art will recognize various synthetic methodologies that can be used to prepare non-toxic pharmaceutically acceptable addition salts.

Compounds

The compounds provided below are exemplary PI3K inhibitors that can be used in the pharmaceutical compositions, methods and kits disclosed herein.

In some aspects, the PI3K inhibitor is a compound of Formula I:

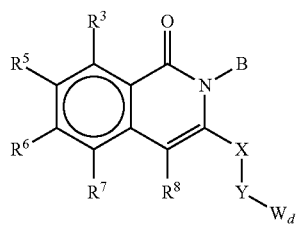

Formula I or its pharmaceutically acceptable salt thereof, wherein
$W_d$ is heterocycloalkyl, aryl or heteroaryl;
B is alkyl, amino, heteroalkyl, or a moiety of Formula II;

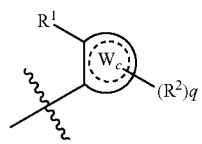

Formula II wherein $W_c$ is aryl, heteroaryl, heterocycloalkyl, or cycloalkyl, and
q is an integer of 0, 1, 2, 3, or 4;
X is absent or is —$(CH(R^9))_z$— and z is an integer of 1, 2, 3, or 4;

Y is absent, —O—, —S—, —S(=O)—, —S(=O)$_2$—, —N(R$^9$)—, —C(=O)—(CHR$^9$)$_z$—, —C(=O)—, —N(R$^9$)—C(=O)—, or —N(R$^9$)—C(=O)NH—, —N(R$^9$)C(R$^9$)$_2$—, or —C(=O)—(CHR$^9$)$_z$—;

R$^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

R$^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

R$^3$ is hydrogen, alkyl, alkenyl, alkynyl, cycloalkyl, heterocycloalkyl, alkoxy, amido, amino, acyl, acyloxy, alkoxycarbonyl, sulfonamido, halo, cyano, hydroxy, nitro, aryl, or heteroaryl;

R$^5$, R$^6$, R$^7$, and R$^8$ are independently hydrogen, C$_1$-C$_4$alkyl, C$_2$-C$_5$alkenyl, C$_2$-C$_5$alkynyl, C$_3$-C$_5$cycloalkyl, C$_1$-C$_4$heteroalkyl, C$_1$-C$_4$alkoxy, C$_1$-C$_4$amido, amino, acyl, C$_1$-C$_4$acyloxy, C$_1$-C$_4$sulfonamido, halo, cyano, hydroxy or nitro; and each instance of R$^9$ is independently hydrogen, C$_1$-C$_{10}$alkyl, C$_3$-C$_7$cycloalkyl, heterocycloalkyl, or C$_2$-C$_{10}$heteroalkyl.

In some embodiments, B is unsubstituted or substituted alkyl, including but not limited to —(CH$_2$)$_2$—NR$^a$R$^a$, wherein each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, or NR$^a$R$^a$ are combined together to form a cyclic moiety, which includes but is not limited to piperidinyl, piperazinyl, and morpholinyl. In some embodiments, B is unsubstituted or substituted amino. In some embodiments, B is unsubstituted or substituted heteroalkyl.

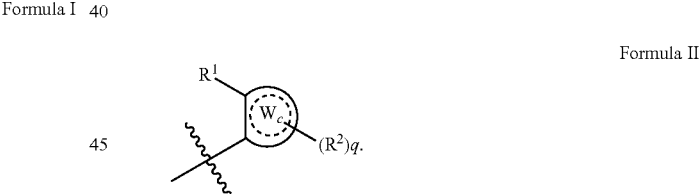

Formula II

In some embodiments, B is a moiety of Formula II and wherein $W_c$ is a member selected from the group consisting of unsubstituted or substituted aryl, substituted phenyl, unsubstituted or substituted heteroaryl including but not limited to pyridin-2-yl, pyridin-3-yl, pyridin-4-yl, pyrimidin-4-yl, pyrimidin-2-yl, pyrimidin-5-yl, or pyrazin-2-yl, unsubstituted or substituted monocyclic heteroaryl, unsubstituted or substituted bicyclic heteroaryl, a heteroaryl comprising two heteroatoms as ring atoms, unsubstituted or substituted heteroaryl comprising a nitrogen ring atom, heteroaryl comprising two nitrogen ring atoms, heteroaryl comprising a nitrogen and a sulfur as ring atoms, unsubstituted or substituted heterocycloalkyl including but not limited to morpholinyl, tetrahydropyranyl, piperazinyl, and piperidinyl, unsubstituted or substituted cycloalkyl including but not limited to cyclopentyl and cyclohexyl.

In some embodiments, B is one of the following moieties:
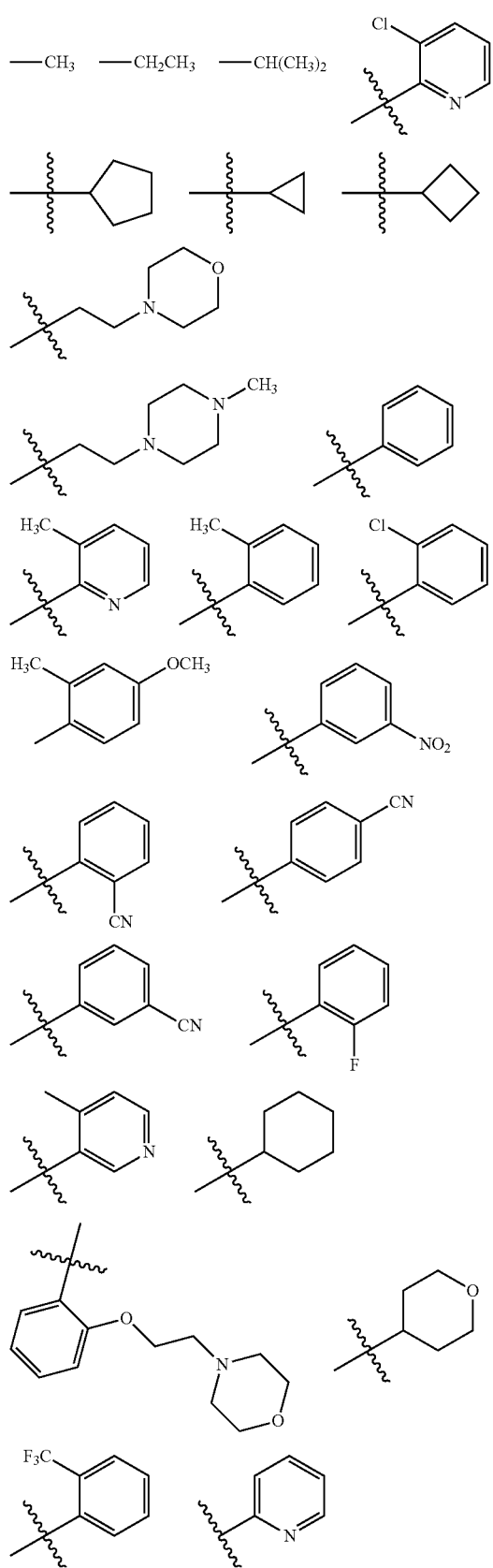
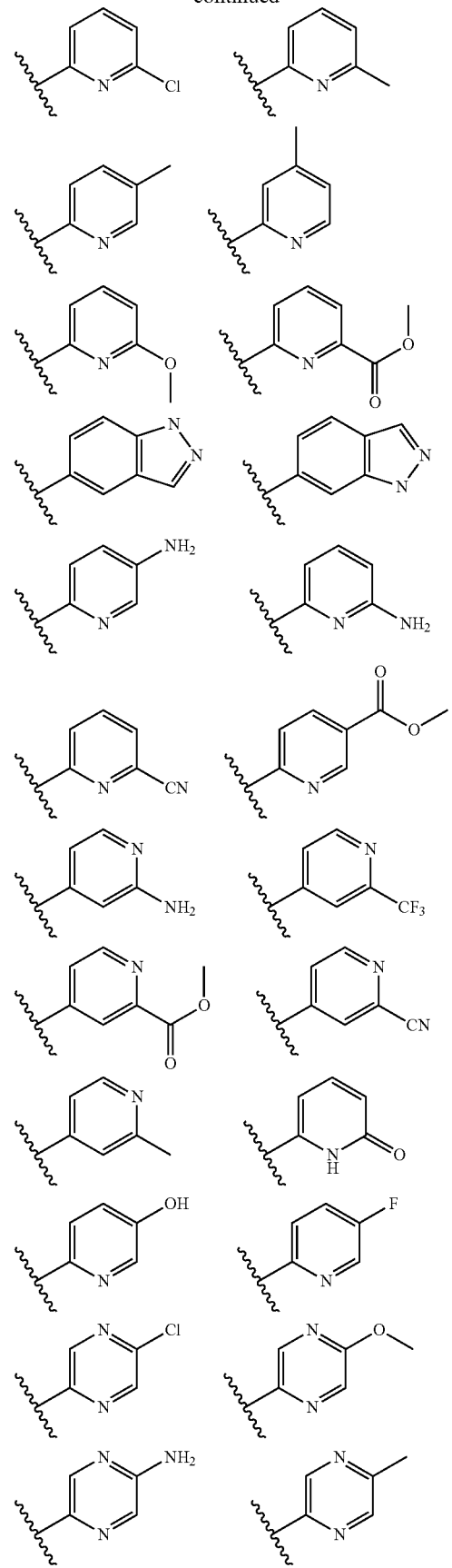
-continued -continued
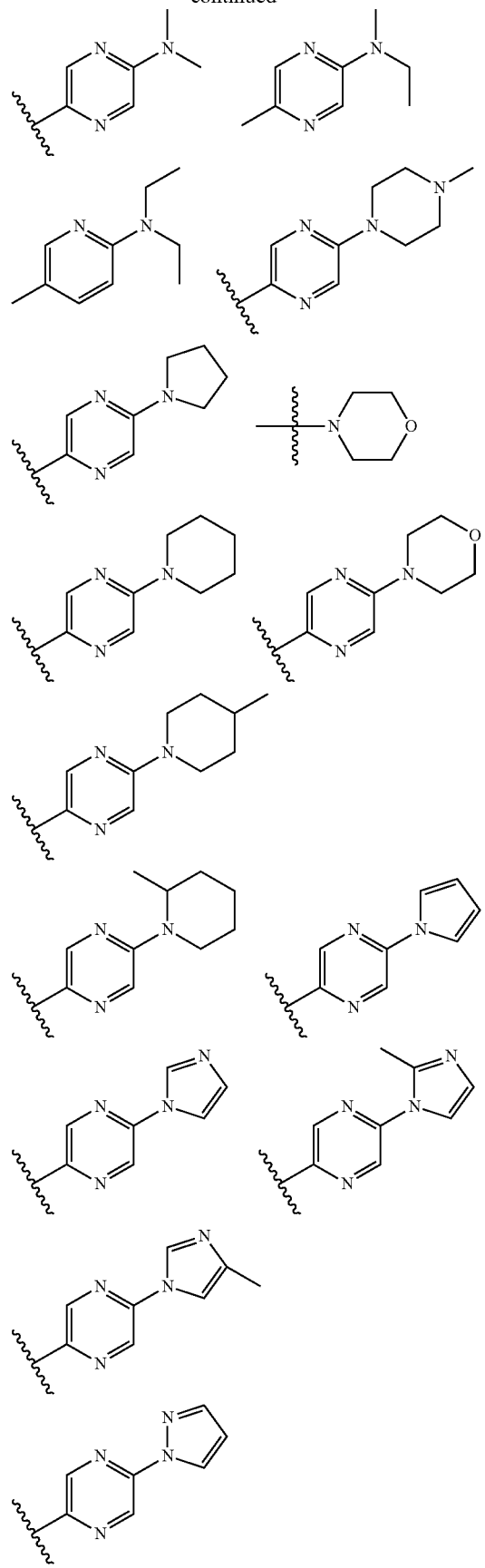
-continued
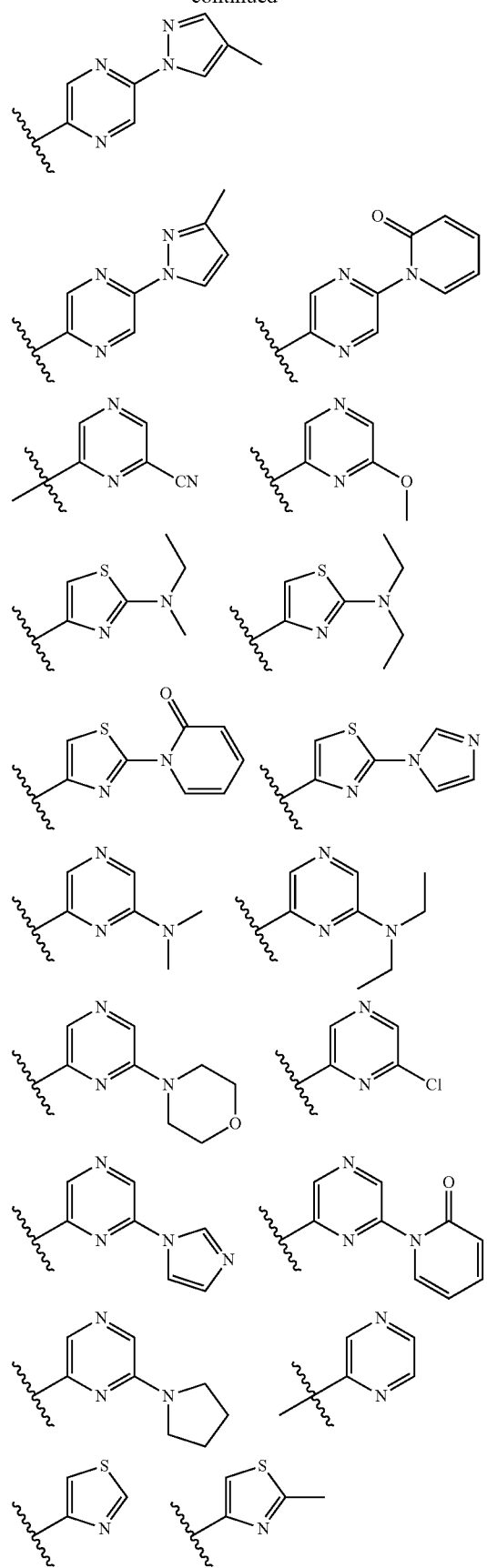

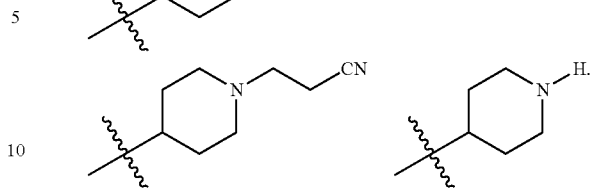
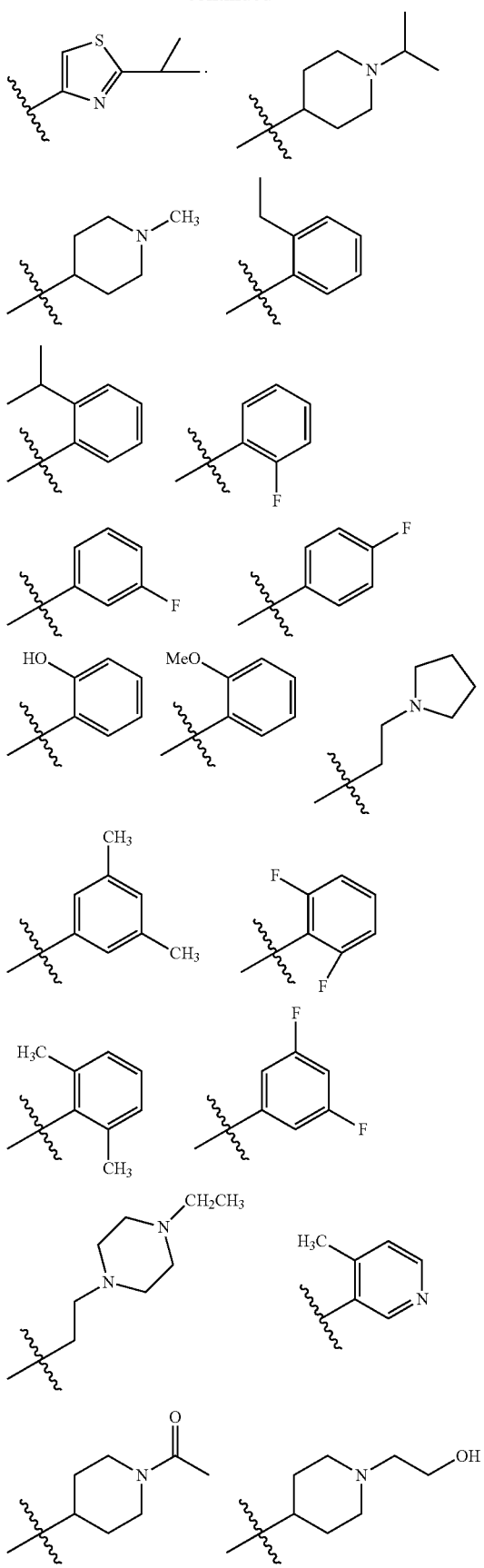

In some embodiments, B is substituted by one or more of alkyl, heteroalkyl, alkenyl, alkynyl, cycloalkyl, heterocycloalkyl, aryl, heteroaryl alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, or sulfonamido, can itself be substituted.

In some embodiments, $R^1$ is a member selected from the group consisting of hydrogen, unsubstituted or substituted alkyl, unsubstituted or substituted heteroalkyl, unsubstituted or substituted alkenyl, unsubstituted or substituted alkynyl, unsubstituted or substituted cycloalkyl, or unsubstituted or substituted heterocycloalkyl. In some embodiments, $R^1$ is unsubstituted or substituted aryl, unsubstituted or substituted arylalkyl, unsubstituted or substituted heteroaryl, or unsubstituted or substituted heteroarylalkyl. In some embodiments, $R^1$ is unsubstituted or substituted alkoxy, unsubstituted or substituted amido, unsubstituted or substituted amino. In some embodiments, $R^1$ is unsubstituted or substituted acyl, unsubstituted or substituted acyloxy, unsubstituted or substituted alkoxycarbonyl, or unsubstituted or substituted sulfonamido. In some embodiments, $R^1$ is halo which includes —Cl, —F, —I, and —Br. In some embodiments, $R^1$ is selected from the group consisting of cyano, hydroxy, nitro, unsubstituted or substituted phosphate, unsubstituted or substituted urea, and carbonate.

In some embodiments, when $R^1$ is alkyl, $R^1$ is methyl, ethyl, propyl, isopropyl, n-butyl, tert-butyl, sec-butyl, pentyl, hexyl or heptyl.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, $R^1$ is substituted by phosphate, or unsubstituted urea, or substituted urea, or carbonic acid, or carbonate.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, $R^1$ is substituted by one or more of alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido can itself be substituted.

In some embodiments, $R^2$ is a member selected from the group consisting of unsubstituted or substituted alkyl, unsubstituted or substituted heteroalkyl, unsubstituted or substituted alkenyl, unsubstituted or substituted alkynyl, unsubstituted or substituted cycloalkyl, and unsubstituted or substituted heterocycloalkyl. In some embodiments, $R^2$ is unsubstituted or substituted aryl, unsubstituted or substituted arylalkyl, unsubstituted or substituted heteroaryl, or unsubstituted or substituted heteroarylalkyl. In some embodiments, $R^2$ is unsubstituted or substituted alkoxy, unsubstituted or substituted amido, unsubstituted or substituted amino. In some embodiments, $R^2$ is unsubstituted or substituted acyl, unsubstituted or substituted acyloxy, unsubstituted or substituted alkoxycarbonyl, or unsubstituted or substituted sulfonamido. In some embodiments, $R^2$ is halo, which is —I, —F, —Cl, or —Br. In some embodiments, $R^2$ is selected from the group consisting of cyano, hydroxy, nitro, a carbonic acid, and a carbonate. In some embodiments, $R^2$ is unsubstituted or substituted phosphate. In some embodiments, $R^2$ is unsubstituted or substituted urea. In some embodiments, when $R^2$ is alkyl, $R^2$ is methyl, ethyl, propyl, isopropyl, n-butyl, tert-butyl, sec-butyl, pentyl, hexyl or heptyl.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, it is substituted by phosphate, substituted by urea, or substituted by carbonate.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, it is substituted by one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments, q is an integer of 0. In some embodiments, q is an integer of 1. In some embodiments, q is an integer of 2. In some embodiments, q is an integer of 3. In some embodiments, q is an integer of 4.

In some embodiments of the compound of Formula I, $R^3$ is a member selected from the group consisting of hydrogen, unsubstituted or substituted alkyl, unsubstituted or substituted alkenyl, and unsubstituted or substituted alkynyl. In some embodiments, $R^3$ is unsubstituted or substituted aryl, unsubstituted or substituted heteroaryl, unsubstituted or substituted cycloalkyl, or unsubstituted or substituted heterocycloalkyl. In some embodiments, $R^3$ is unsubstituted or substituted alkoxy, unsubstituted or substituted amido, unsubstituted or substituted amino. In some embodiments, $R^3$ is unsubstituted or substituted acyl, unsubstituted or substituted acyloxy, unsubstituted or substituted alkoxycarbonyl, or unsubstituted or substituted sulfonamido. In some embodiments, $R^3$ is halo, which is is —I, —F, —Cl, or —Br.

In some embodiments, $R^3$ is selected from the group consisting of cyano, hydroxy, and nitro. In some embodiments, when $R^3$ is alkyl, $R^3$ is methyl, ethyl, propyl, isopropyl, n-butyl, tert-butyl, sec-butyl, pentyl, hexyl or heptyl. In some embodiments, $R^3$ is —$CF_3$.

In some embodiments, when $R^3$ is alkyl, alkenyl, alkynyl, aryl, heteroaryl, cycloalkyl, heterocycloalkyl, alkoxy, amido, amino, acyl, acyloxy, alkoxycarbonyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^5$ is hydrogen, unsubstituted or substituted alkyl (including but not limited to unsubstituted or substituted $C_1$-$C_4$alkyl). In some embodiments, $R^5$ is unsubstituted or substituted alkenyl including but not limited to unsubstituted or substituted $C_2$-$C_5$alkenyl. In some embodiments, $R^5$ is unsubstituted or substituted alkynyl including but not limited to unsubstituted or substituted $C_2$-$C_5$alkynyl. In some embodiments, $R^5$ is unsubstituted or substituted cycloalkyl including but not limited to unsubstituted or substituted $C_3$-$C_5$cycloalkyl. In some embodiments, $R^5$ is unsubstituted or substituted heterocycloalkyl. In some embodiments, $R^5$ is unsubstituted or substituted heteroalkyl including but not limited to unsubstituted or substituted $C_1$-$C_4$heteroalkyl. In some embodiments, $R^5$ is unsubstituted or substituted alkoxy including but not limited to unsubstituted or substituted $C_1$-$C_4$alkoxy. In some embodiments, $R^5$ is unsubstituted or substituted amido including but not limited to unsubstituted or substituted $C_1$-$C_4$amido. In some embodiments, $R^5$ is unsubstituted or substituted amino. In some embodiments, $R^5$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^5$ is halo, which is —I, —F, —Cl, or —Br. In some embodiments, $R^5$ is selected from the group consisting of cyano, hydroxy, and nitro. In some other embodiments, $R^5$ is —$CH_3$, —$CH_2CH_3$, n-propyl, isopropyl, —$OCH_3$, —$OCH_2CH_3$, or —$CF_3$.

In some embodiments, when $R^5$ is alkyl, alkenyl, alkynyl, cycloalkyl, heteroalkyl, acyl, alkoxy, amido, amino, acyloxy, alkoxycarbonyl, or sulfonamido, $R^5$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^6$ is hydrogen, unsubstituted or substituted alkyl (including but not limited to unsubstituted or substituted $C_1$-$C_4$alkyl). In some embodiments, $R^6$ is unsubstituted or substituted alkenyl including but not limited to unsubstituted or substituted $C_2$-$C_5$alkenyl. In some embodiments, $R^6$ is unsubstituted or substituted alkynyl including but not limited to unsubstituted or substituted $C_2$-$C_5$alkynyl. In some embodiments, $R^6$ is unsubstituted or substituted cycloalkyl including but not limited to unsubstituted or substituted $C_3$-$C_5$cycloalkyl. In some embodiments, $R^6$ is unsubstituted or substituted heterocycloalkyl. In some embodiments, $R^6$ is unsubstituted or substituted heteroalkyl including but not limited to unsubstituted or substituted $C_1$-$C_4$heteroalkyl. In some embodiments, $R^6$ is unsubstituted or substituted alkoxy including but not limited to unsubstituted or substituted $C_1$-$C_4$alkoxy. In some embodiments, $R^6$ is unsubstituted or substituted amido including but not limited to unsubstituted or substituted $C_1$-$C_4$amido. In some embodiments, $R^6$ is unsubstituted or substituted amino. In some embodiments, $R^6$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^6$ is halo, which is —I, —F, —Cl, or —Br. In some embodiments, $R^6$ is selected from the group consisting of cyano, hydroxy, and nitro. In some other embodiments, $R^6$ is —$CH_3$, —$CH_2CH_3$, n-propyl, isopropyl, —$OCH_3$, —$OCH_2CH_3$, or —$CF_3$.

In some embodiments, when $R^6$ is alkyl, alkenyl, alkynyl, cycloalkyl, heteroalkyl, acyl, alkoxy, amido, amino, acyloxy, alkoxycarbonyl, or sulfonamido, $R^6$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^7$ is hydrogen, unsubstituted or substituted alkyl (including but not limited to unsubstituted or substituted $C_1$-$C_4$alkyl). In some embodiments, $R^7$ is unsubstituted or substituted alkenyl including but not limited to unsubstituted or substituted $C_2$-$C_5$alkenyl. In some embodiments, $R^7$ is unsubstituted or substituted alkynyl including but not limited to unsubstituted or substituted $C_2$-$C_5$alkynyl. In some embodiments, $R^7$ is unsubstituted or substituted cycloalkyl including but not limited to unsubstituted or substituted $C_3$-$C_5$cycloalkyl. In some embodiments, $R^7$ is unsubstituted or substituted heterocycloalkyl. In some embodiments, $R^7$ is unsubstituted or substituted heteroalkyl including but not limited to unsubstituted or substituted $C_1$-$C_4$heteroalkyl. In some embodiments, $R^7$ is unsubstituted or substituted alkoxy including but not limited to unsubstituted or substituted $C_1$-$C_4$alkoxy. In some embodiments, $R^7$ is unsubstituted or substituted amido including but not limited to unsubstituted or substituted $C_1$-$C_4$amido. In some embodiments, $R^7$ is unsubstituted or substituted amino. In some embodiments, $R^7$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^7$ is halo, which is —I, —F, —Cl, or —Br. In some embodiments, $R^7$ is selected from the group consisting of cyano, hydroxy, and nitro. In some other embodiments, $R^7$ is —$CH_3$, —$CH_2CH_3$, n-propyl, isopropyl, —$OCH_3$, —$OCH_2CH_3$, or —$CF_3$.

In some embodiments, when $R^7$ is alkyl, alkenyl, alkynyl, cycloalkyl, heteroalkyl, acyl, alkoxy, amido, amino, acyloxy, alkoxycarbonyl, or sulfonamido, $R^7$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^8$ is hydrogen, unsubstituted or substituted alkyl (including but not limited to unsubstituted or substituted $C_1$-$C_4$alkyl). In some embodiments, $R^8$ is unsubstituted or substituted alkenyl including but not limited to unsubstituted or substituted $C_2$-$C_5$alkenyl. In some embodiments, $R^8$ is unsubstituted or substituted alkynyl including but not limited to unsubstituted or substituted $C_2$-$C_5$alkynyl. In some embodiments, $R^8$ is unsubstituted or substituted cycloalkyl including but not limited to unsubstituted or substituted $C_3$-$C_5$cycloalkyl. In some embodiments, $R^8$ is unsubstituted or substituted heterocycloalkyl. In some embodiments, $R^8$ is unsubstituted or substituted heteroalkyl including but not limited to unsubstituted or substituted $C_1$-$C_4$heteroalkyl. In some embodiments, $R^8$ is unsubstituted or substituted alkoxy including but not limited to unsubstituted or substituted $C_1$-$C_4$alkoxy. In some embodiments, $R^8$ is unsubstituted or substituted amido including but not limited to unsubstituted or substituted $C_1$-$C_4$amido. In some embodiments, $R^8$ is unsubstituted or substituted amino. In some embodiments, $R^8$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^8$ is halo, which is —I, —F, —Cl, or —Br. In some embodiments, $R^8$ is selected from the group consisting of cyano, hydroxy, and nitro. In some other embodiments, $R^8$ is —$CH_3$, —$CH_2CH_3$, n-propyl, isopropyl, —$OCH_3$, —$OCH_2CH_3$, or —$CF_3$.

In some embodiments, when $R^8$ is alkyl, alkenyl, alkynyl, cycloalkyl, heteroalkyl, acyl, alkoxy, amido, amino, acyloxy, alkoxycarbonyl, or sulfonamido, $R^8$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido can itself be substituted.

In some embodiments of the compound of Formula I, $R^5$, $R^6$, $R^7$, and $R^8$ are H and the compound has a structure of Formula I-1:

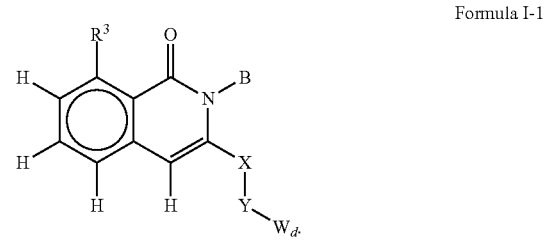

Formula I-1

In some embodiments of the compound of Formula I, X is absent. In some embodiments, X is —$(CH(R^9))_z$—, and z is an integer of 1, 2, 3 or 4.

In some embodiments, $R^9$ is unsubstituted or substituted alkyl including but not limited to unsubstituted or substituted $C_1$-$C_{10}$alkyl. In some embodiments, $R^9$ is unsubstituted or substituted cycloalkyl including but not limited to unsubstituted or substituted $C_3$-$C_7$cycloalkyl. In some embodiments, $R^9$ is ethyl, methyl or hydrogen. In some embodiments, $R^9$ is unsubstituted or substituted heterocycloalkyl including but not limited to unsubstituted or substituted $C_2$-$C_{10}$heteroalkyl. In some embodiments, $R^9$ is unsubstituted or substituted heteroalkyl including but not limited to unsubstituted or substituted $C_2$-$C_{10}$heteroalkyl.

The invention also provides a compound of Formula I wherein $R^9$ is hydrogen, and X is —$CH_2$—, —$CH_2CH_2$—, —$CH_2CH_2CH_2$—, —$CH(CH_3)$—, or —$CH(CH_2CH_3)$—. In other embodiments, X is —$(CH(R^9))_z$—, $R^9$ is not hydrogen, and z is an integer of 1. When X is —$CH(R^9)$— and $R^9$ is not hydrogen, then the compound can adopt either an (S)- or (R)-stereochemical configuration with respect to carbon X. In some embodiments, the compound is a racemic mixture of (S)- and (R) isomers with respect to carbon X. In other embodiments, the present invention provides a mixture of compounds of Formula I wherein individual compounds of the mixture exist predominately in an (S)- or (R)-isomeric configuration. For example, the compound mixture has an (S)-enantiomeric purity of greater than about 55%, about 60%, about 65%, about 70%, about 75%, about 80%, about 85%, about 90%, about 95%, about 96%, about 97%, about 98%, about 99%, about 99.5%, or more at the X carbon. In other embodiments, the compound mixture has an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5%, or more at the X carbon. In some other embodiments, the compound mixture has an (R)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture contains identical chemical entities except for their stereochemical orientations, namely (S)- or (R)-isomers. For instance, in the compounds of Formula I, when X is —CH($R^9$)—, and $R^9$ is not hydrogen, then the —CH($R^9$)— is in an (S)- or (R)-sterochemical orientation for each of the identical chemical entities. In some embodiments, the mixture of identical chemical entities of Formula I is a racemic mixture of (S)- and (R)-isomers at the carbon represented by X. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric purity greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In some embodiments, the compound of Formula I, X is —CH($R^9$)—, $R^9$ is methyl or ethyl, and the compound is the (S)-isomer.

In some embodiments of the compound of Formula I, Y is absent. In some embodiments, Y is —O—, —S—, —S(=O)—, —S(=O)$_2$—, —C(=O)—, —N($R^9$)(C=O)—, —N($R^9$)(C=O)NH—, —N($R^9$)C($R^9$)$_2$— (such as —N($R^9$)CH$_2$—, specifically —N(CH$_3$)CH$_2$—, N(CH(CH$_3$)$_2$)CH$_2$— or N(CH$_2$CH$_3$)CH$_2$—), —N($R^9$)—, —N(CH$_3$)—, —N(CH$_2$CH$_3$)—, or —N(CH(CH$_3$)$_2$)—. In some embodiments, Y is —C(=O)—(CHR$^9$)$_z$— and z is an integer of 1, 2, 3, or 4.

In some embodiments, at least one of X and Y is present. In some embodiments of the compound of Formula I, —XY— is —CH$_2$—, —CH$_2$—N(CH$_3$), —CH$_2$—N(CH$_2$CH$_3$), —CH(CH$_3$)—NH—, (S)—CH(CH$_3$)—NH—, or (R)—CH(CH$_3$)—NH—. In other embodiments, X—Y is —N(CH$_3$)—CH$_2$—, N(CH$_2$CH$_3$)CH$_2$—, —N(CH(CH$_3$)$_2$)CH$_2$—, or —NHCH$_2$—. The invention provides other compounds of Formula I wherein when X—Y is X is —(CH($R^9$))$_z$N($R^9$)—, z is an integer of 1, 2, 3 or 4, and —N($R^9$)— is not —NH—, then —XY— is not connected to purinyl.

In some embodiments, $W_d$ in a formula disclosed herein (including but not limited to I, I-1, IV, IV-A, V, V-A, V-A2, V-B, VI and VI-A), is a member selected from the group consisting of unsubstituted or substituted heterocycloalkyl, unsubstituted or substituted aryl, and unsubstituted or substituted heteroaryl.

In various embodiments, $W_d$ is unsubstituted or substituted monocyclic heteroaryl (including but not limited to pyrimidinyl, pyrrolyl, pyrazinyl, triazinyl, or pyridazinyl) or unsubstituted or substituted bicyclic heteroaryl.

In some embodiments, $W_d$ is a monocyclic heteroaryl of the following formula:

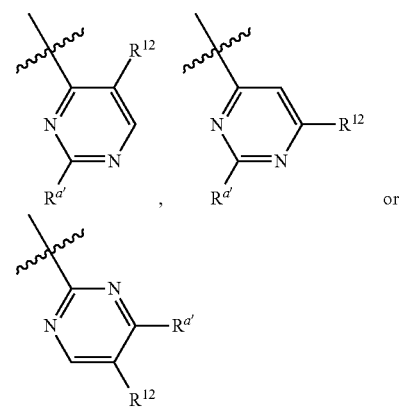

wherein $R^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl; and $R^{12}$ is H, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

Also included herein are compounds having monocyclic heteroaryl $W_d$ including but not limited to one of the following formulae:

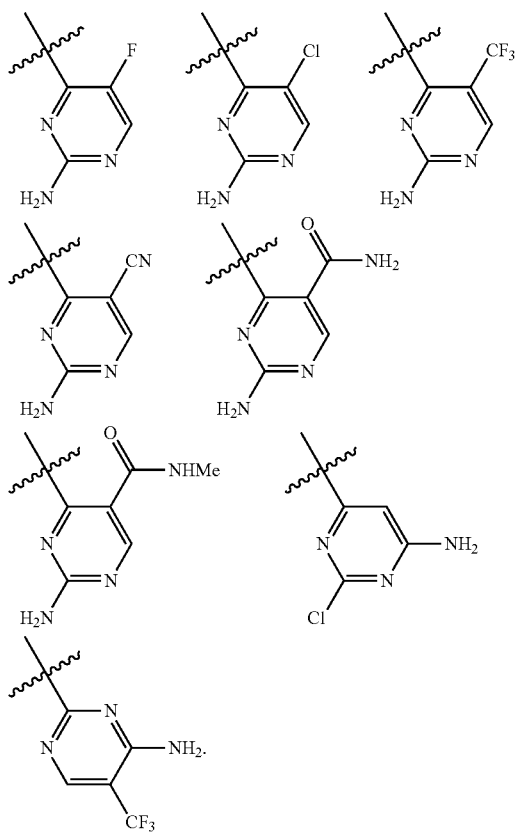

In some embodiments, $W_d$ in a formula disclosed herein (including but not limited to I, I-1, IV, IV-A, V, V-A, V-A2, V-B, VI and VI-A), is a bicyclic heteroaryl having at least one heteroatom, e.g., a bicyclic heteroaryl having at least one nitrogen ring atom. In some embodiments, $W_d$ is a bicyclic heteroaryl having at least two heteroatoms, e.g., a bicyclic heteroaryl having at least two nitrogen ring atoms. In some embodiments, $W_d$ is a bicyclic heteroaryl having two heteroatoms in the ring which is connected to XY. In some embodiments, $W_d$ is a bicyclic heteroaryl having two nitrogen ring atoms in the ring to which XY is connected. In some embodiments, $W_d$ is a bicyclic heteroaryl having four heteroatoms, e.g, a bicyclic heteroaryl having four nitrogen ring atoms. In some embodiments, $W_d$ is unsubstituted or substituted 4-amino-1H-pyrazolo[3,4-d]pyrimidin-1-yl, unsubstituted or substituted 7-amino-2-methyl-2H-pyrazolo[4,3-d]pyrimidin-3-yl. unsubstituted or substituted 6-methylenyl-9H-purin-6-yl, or unsubstituted or substituted 6-amino-9H-purin-9-yl.

In some embodiments $W_d$ is one of the following:

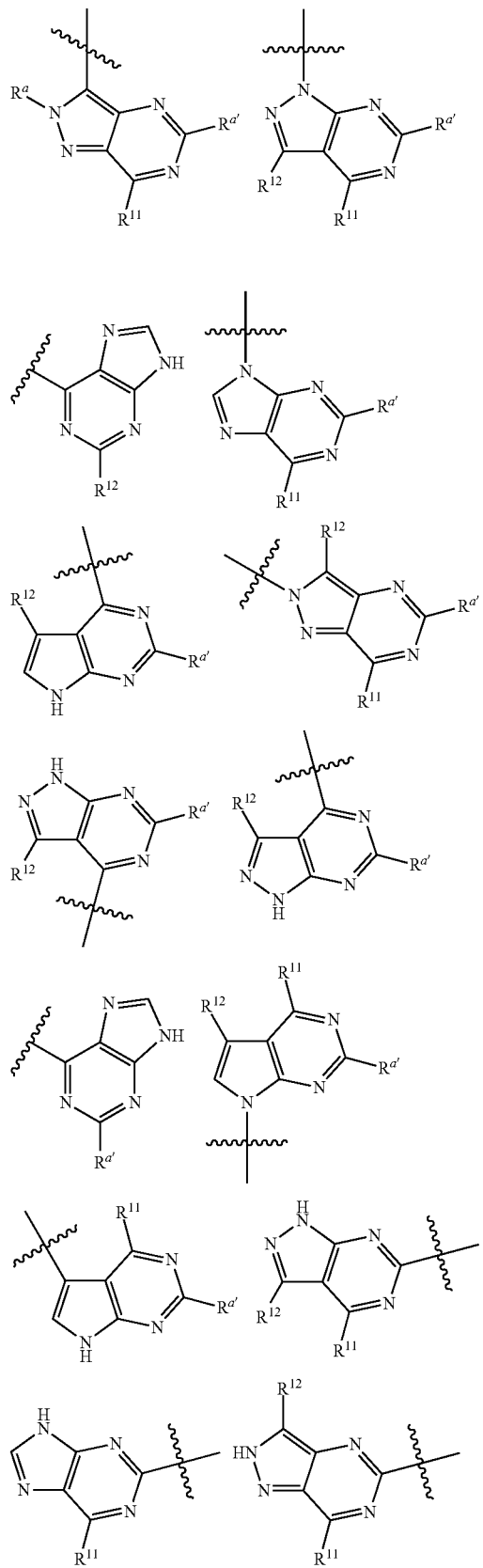

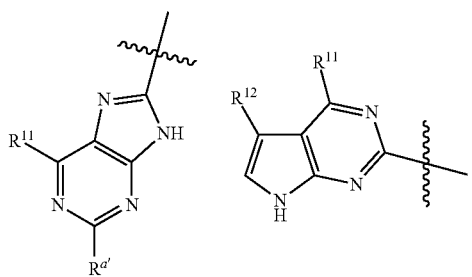
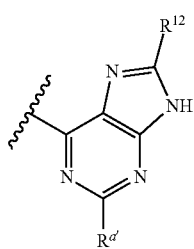

wherein $R^{a'}$ is hydrogen, halo, phosphate, urea, a carbonate, unsubstituted or substituted amino, unsubstituted or substituted alkyl, unsubstituted or substituted alkenyl, unsubstituted or substituted alkynyl, unsubstituted or substituted cycloalkyl, unsubstituted or substituted heteroalkyl, or unsubstituted or substituted heterocycloalkyl; $R^{11}$ is hydrogen, unsubstituted or substituted alkyl, halo (which includes —I, —F, —Cl, or —Br), unsubstituted or substituted amino, unsubstituted or substituted amido, hydroxy, or unsubstituted or substituted alkoxy, phosphate, unsubstituted or substituted urea, or carbonate; and $R^{12}$ is H, unsubstituted or substituted alkyl, unsubstituted or substituted cyano, unsubstituted or substituted alkynyl, unsubstituted or substituted alkenyl, halo, unsubstituted or substituted aryl, unsubstituted or substituted heteroaryl, unsubstituted or substituted heterocycloalkyl, unsubstituted or substituted cycloalkyl, unsubstituted or substituted amino, carboxylic acid, unsubstituted or substituted alkoxycarbonyl, unsubstituted or substituted amido, unsubstituted or substituted acyl, or unsubstituted or substituted sulfonamido.

In some embodiments of $W_d$ of the compounds of Formula I, when $R^{a'}$ is alkyl, alkynyl, cycloalkyl, heteroalkyl, or heterocycloalkyl, it is substituted by phosphate, urea, or carbonate.

In some embodiments of $W_d$ of the compounds of Formula I, when $R^{11}$ is alkyl, amino, amido, hydroxy, or alkoxy, it is substituted by phosphate, urea, or carbonate.

In some embodiments of the compound of Formula I, —X—Y—$W_d$ is one of the following moieties:

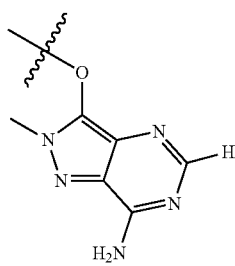
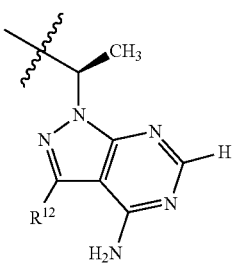
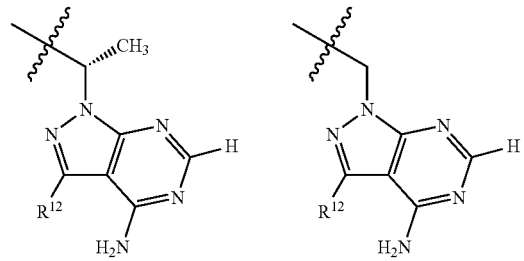
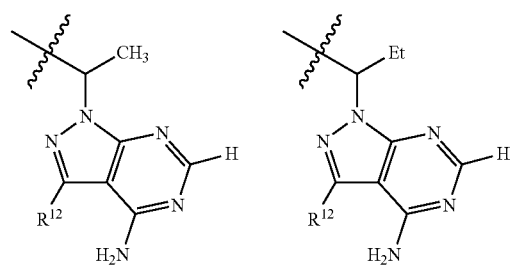
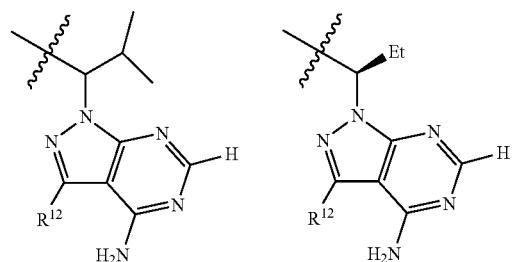
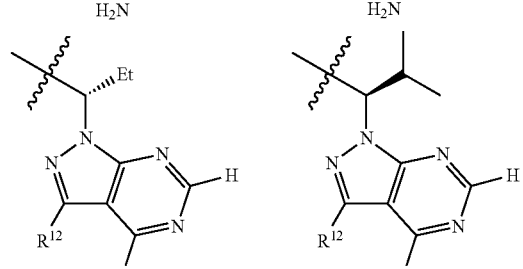
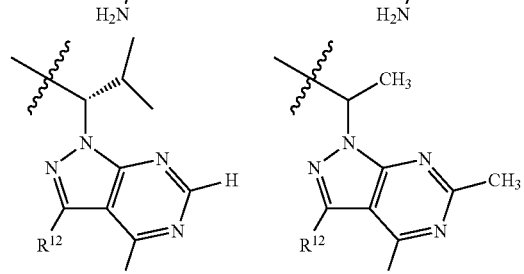
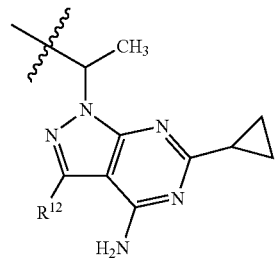

57
-continued
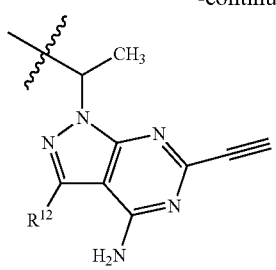
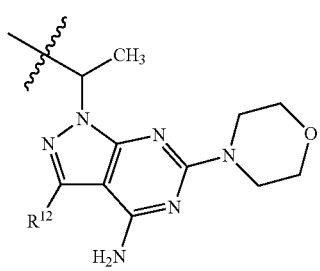
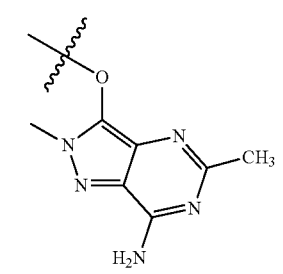 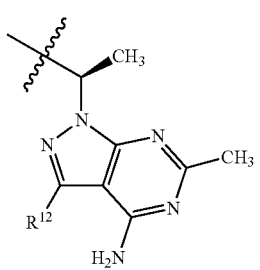
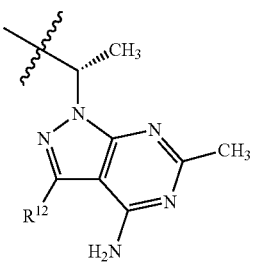
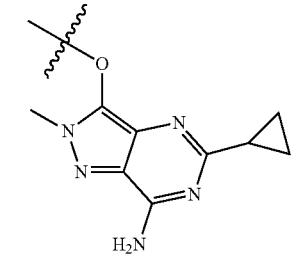
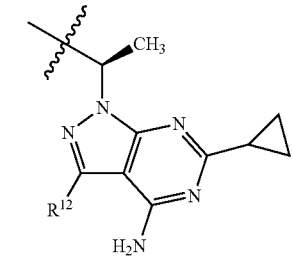
58
-continued
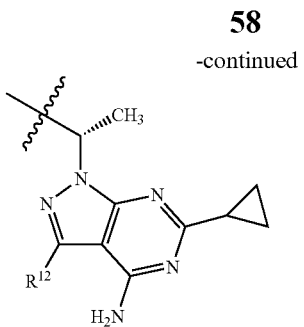
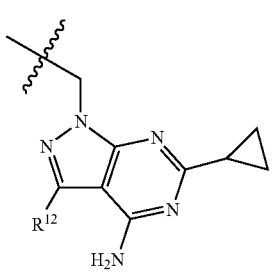
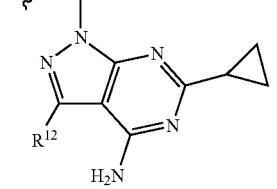
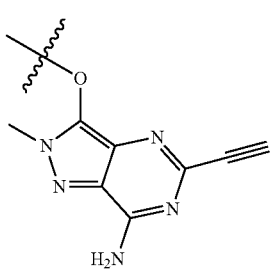
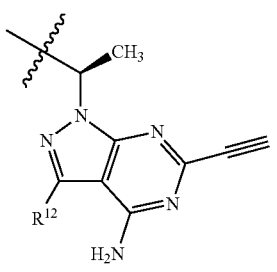
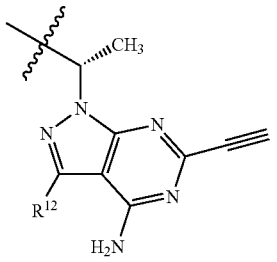
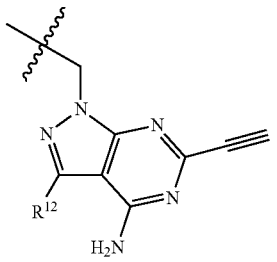

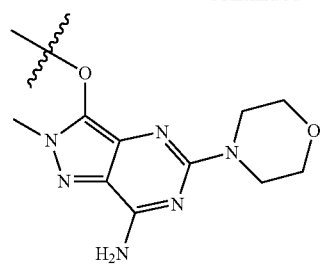
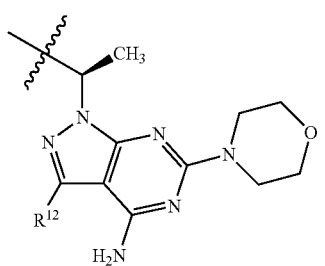
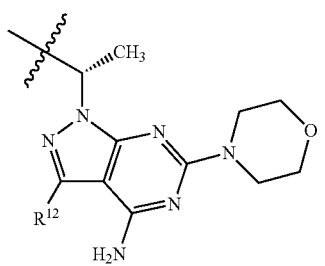
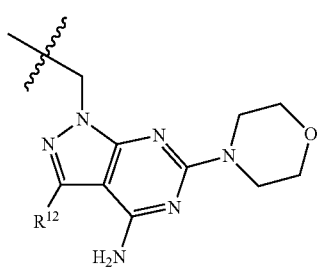
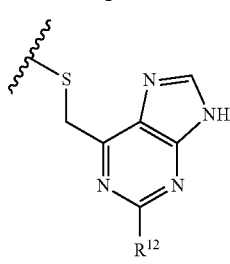
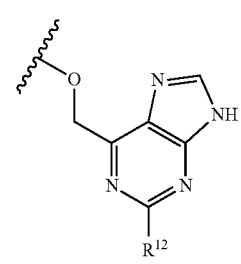
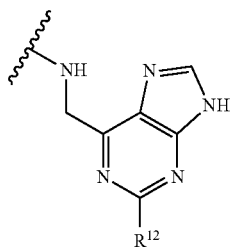
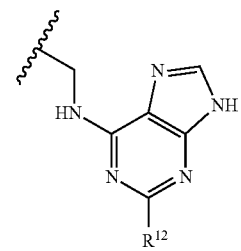
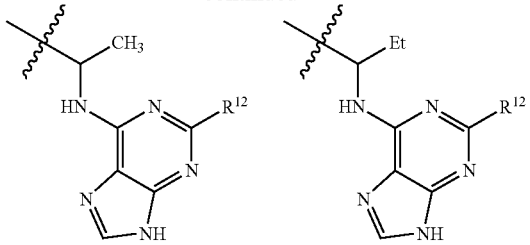
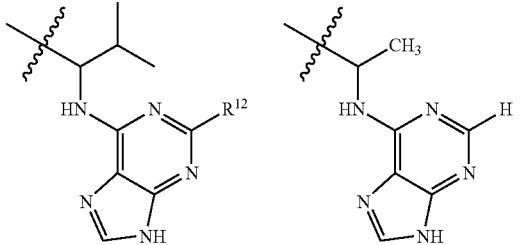
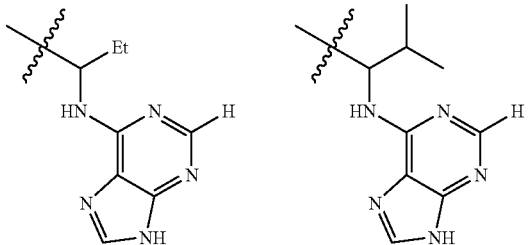
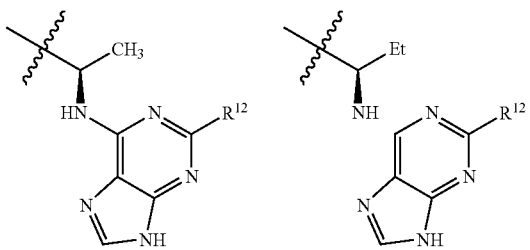
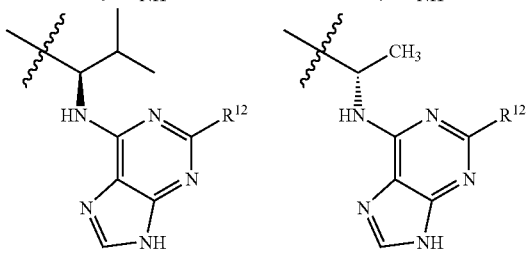
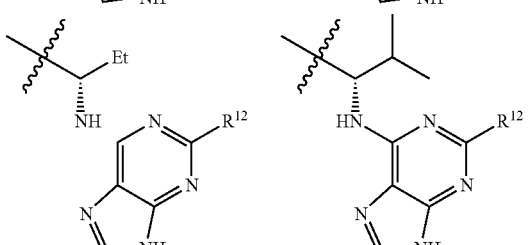
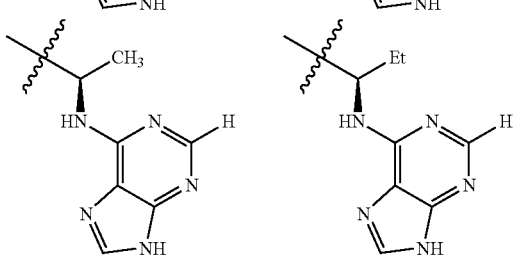

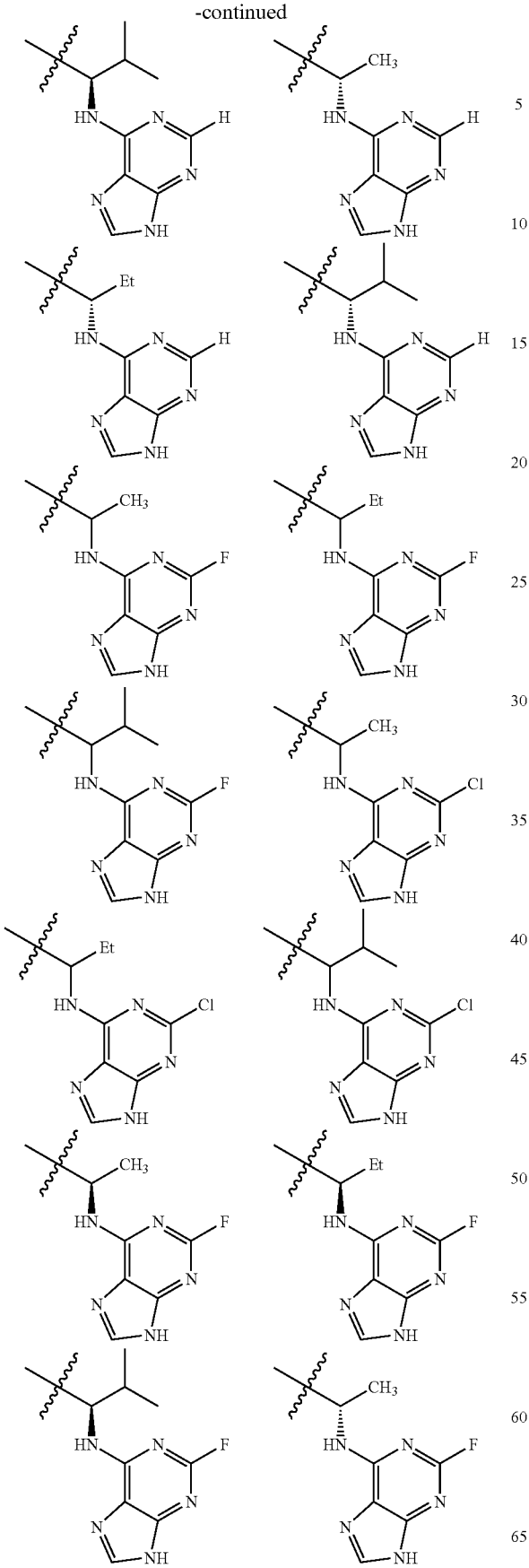
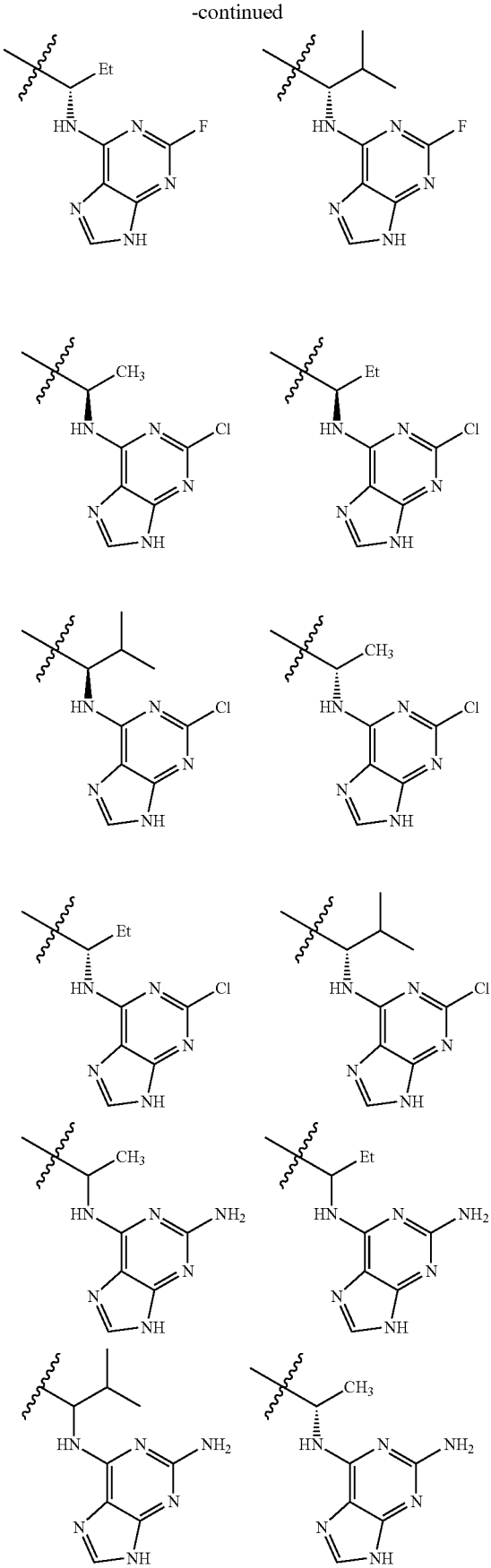

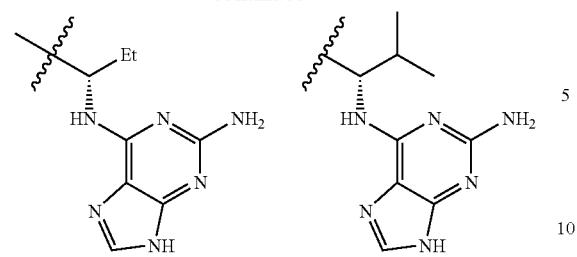
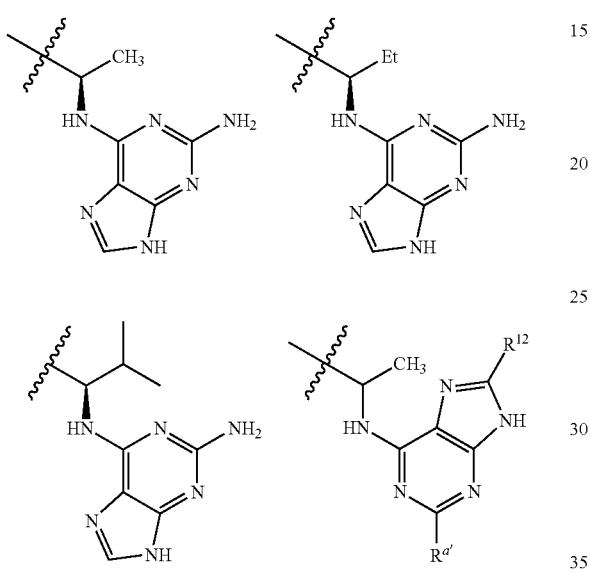
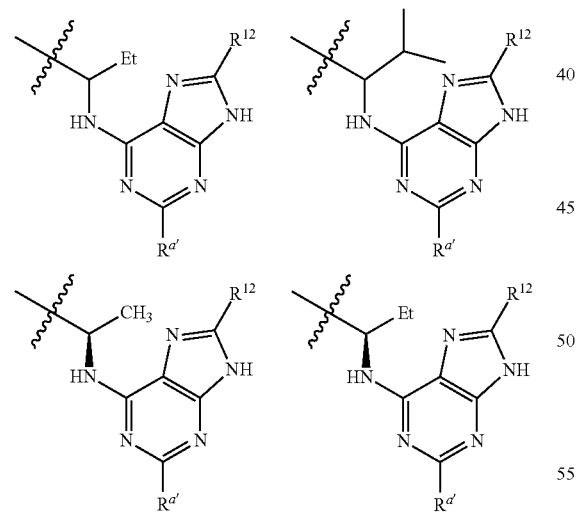
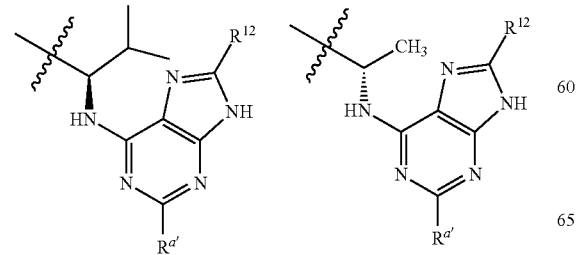
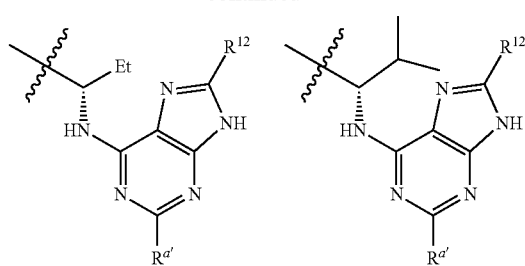
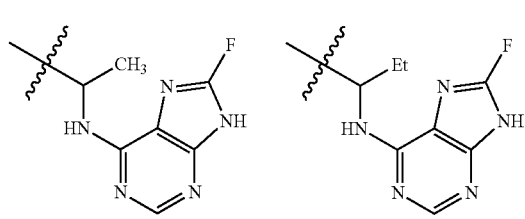
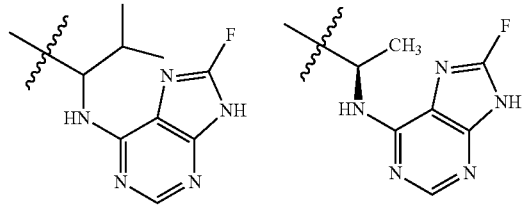
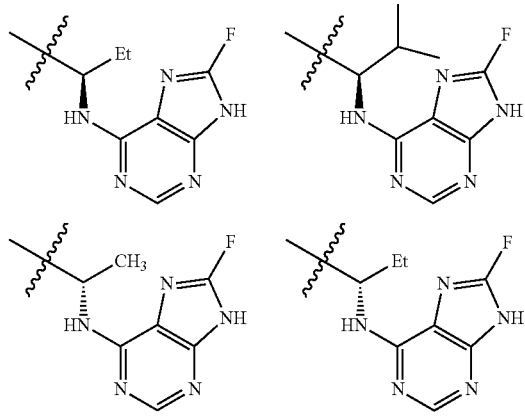
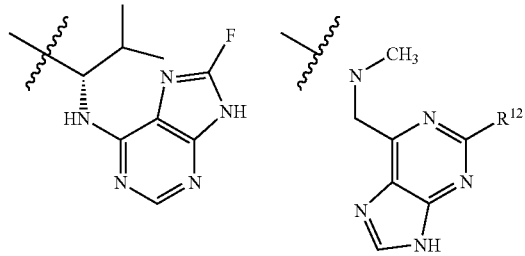
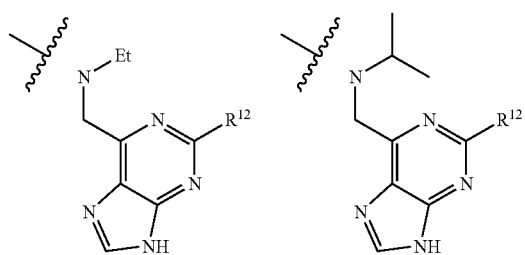

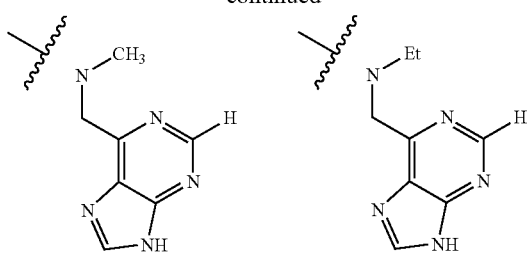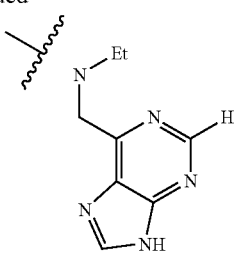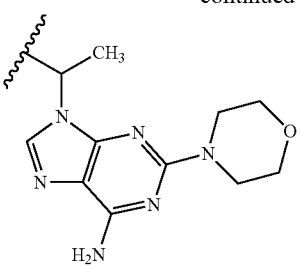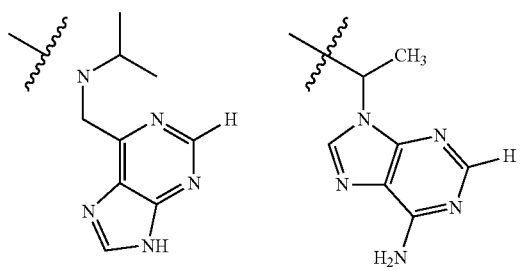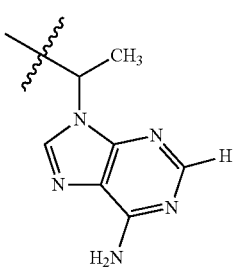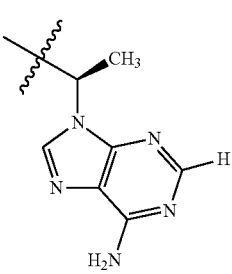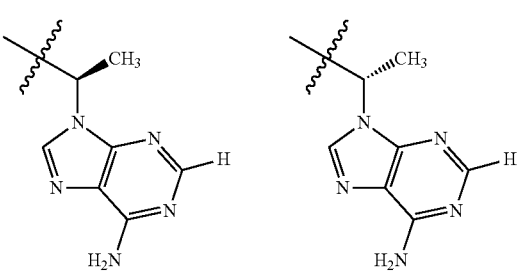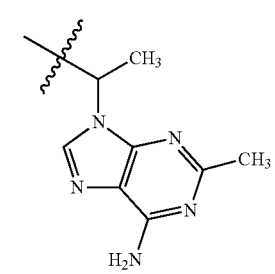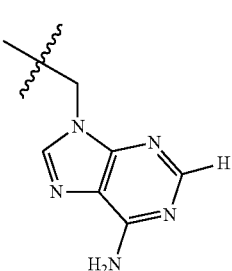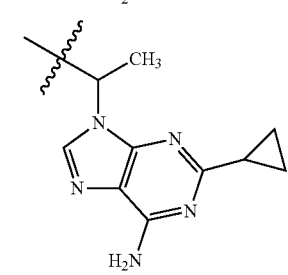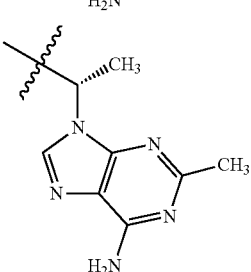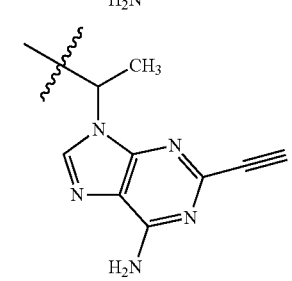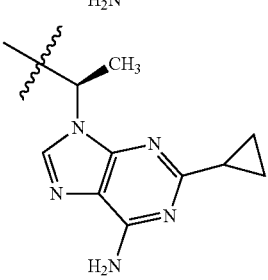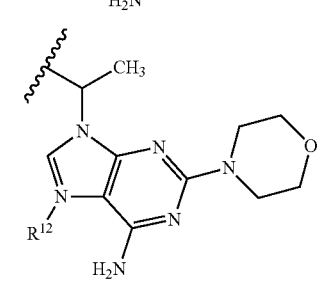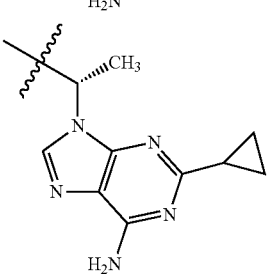

67
-continued
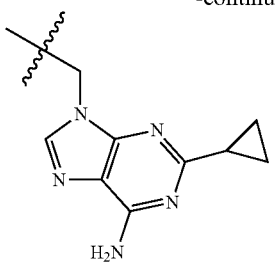
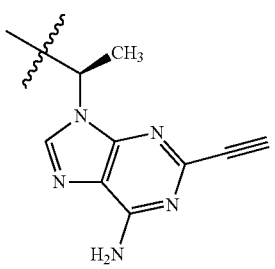
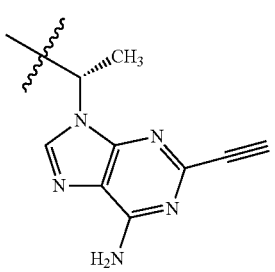
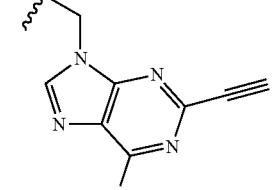
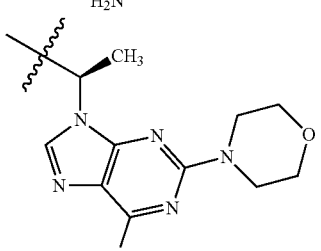
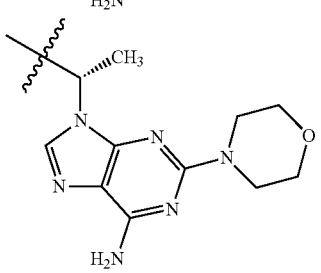
68
-continued
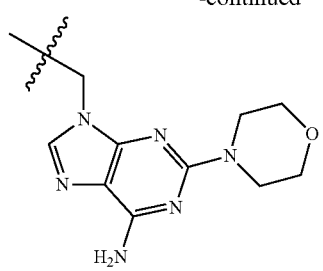
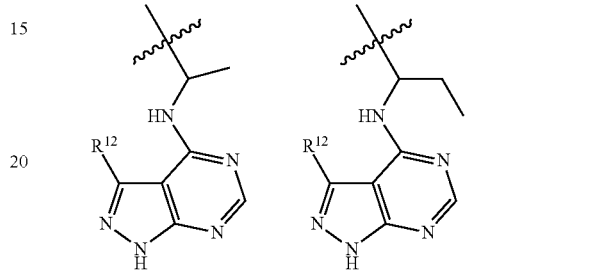
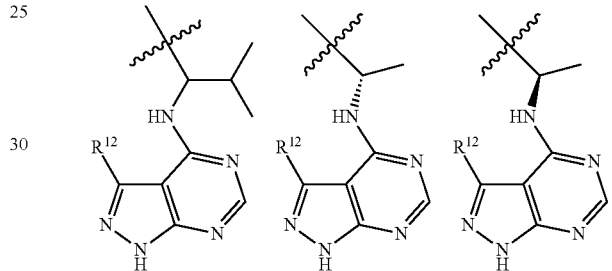
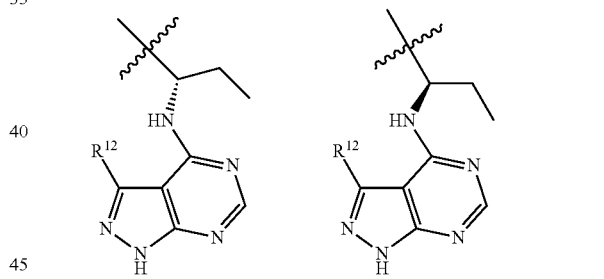
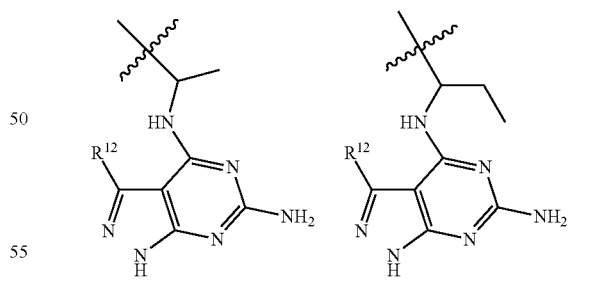
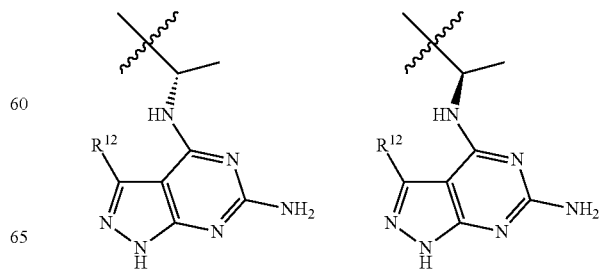

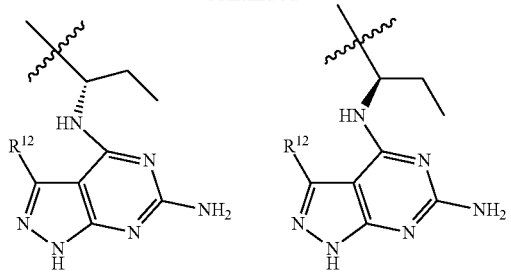
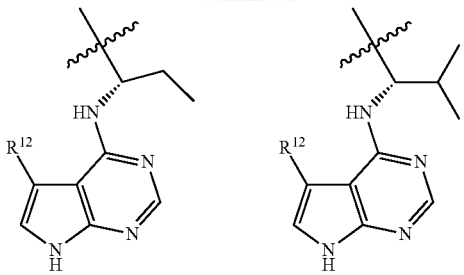
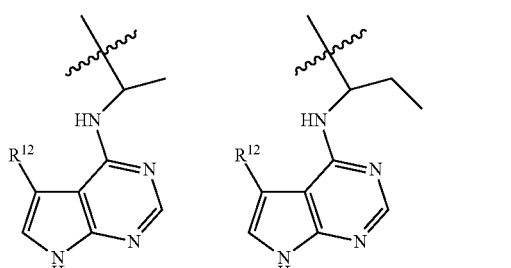
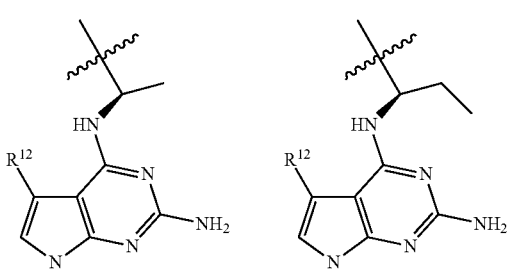
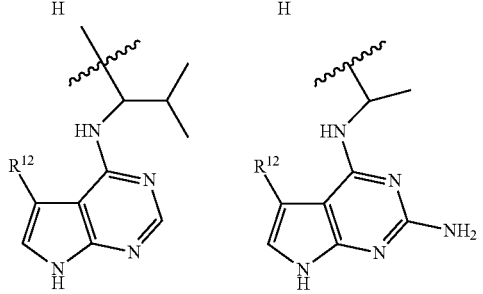
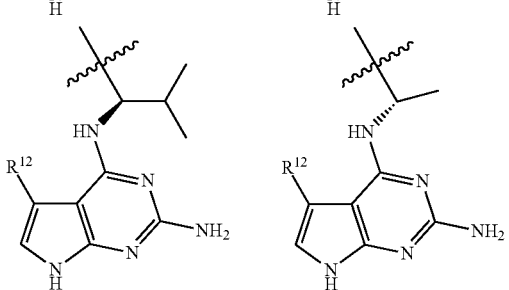
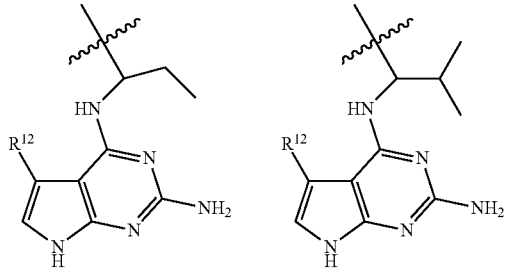
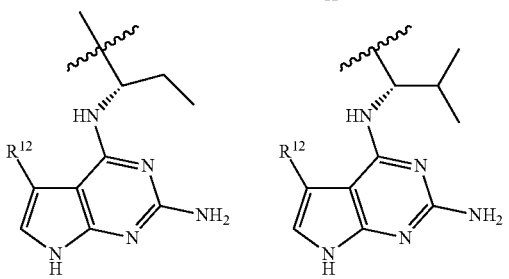
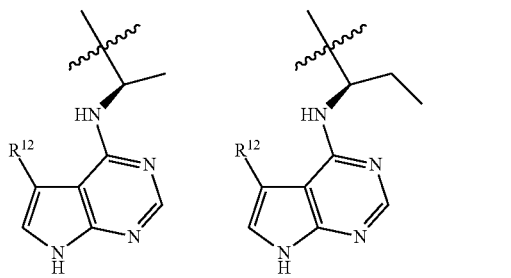
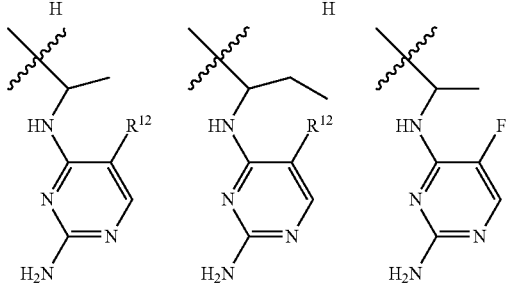
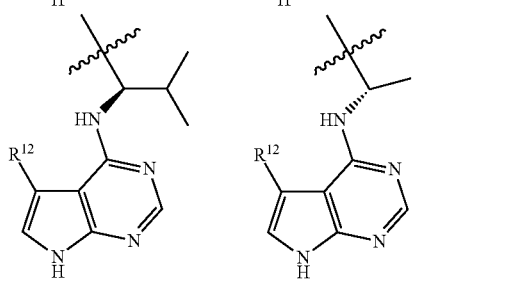
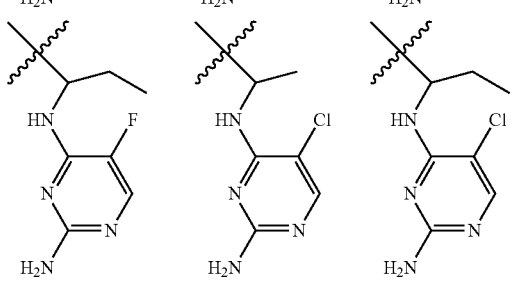

-continued
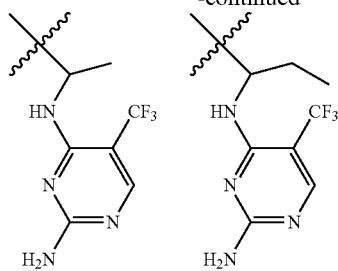 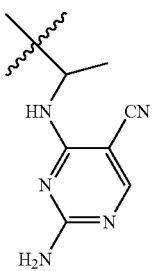 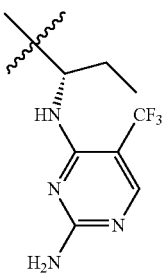 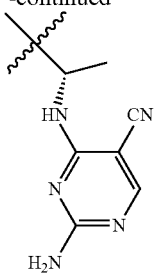 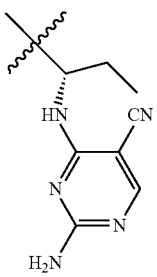
-continued
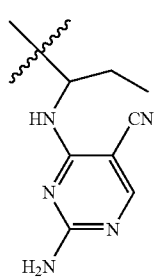 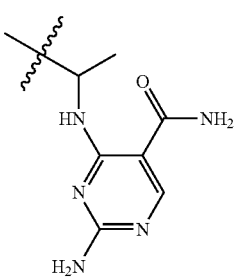 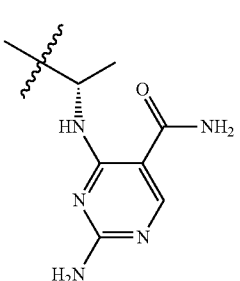 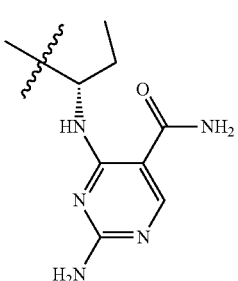
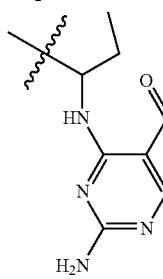 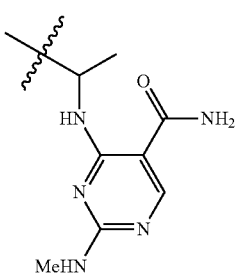 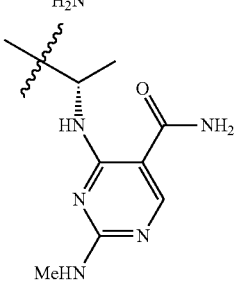 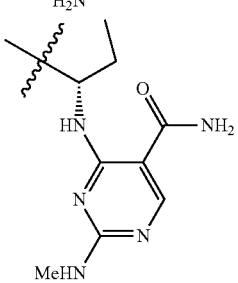
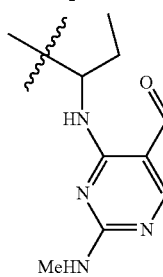 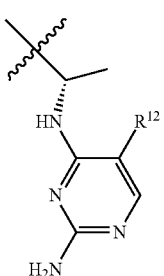 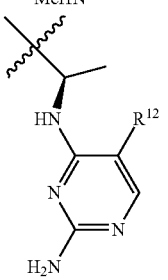 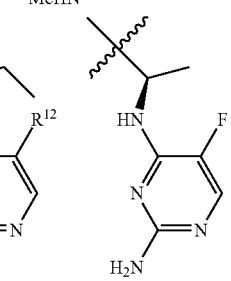
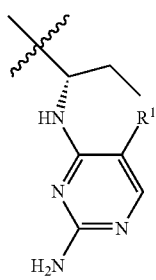 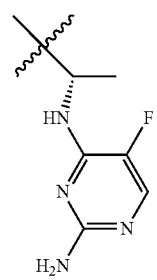 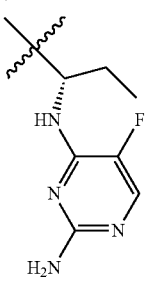 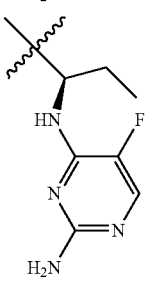 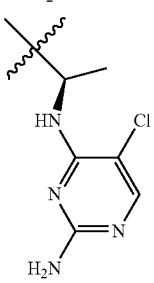 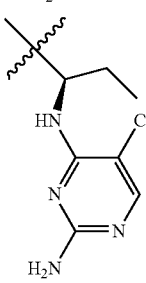
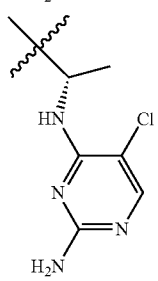 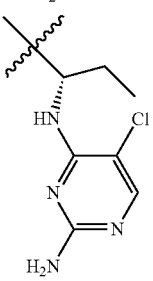 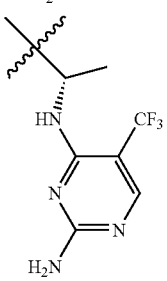 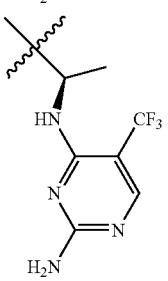 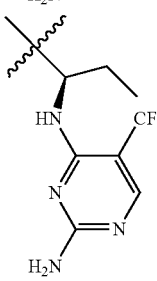 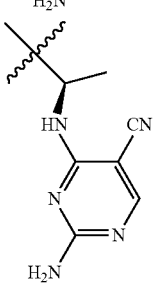

-continued
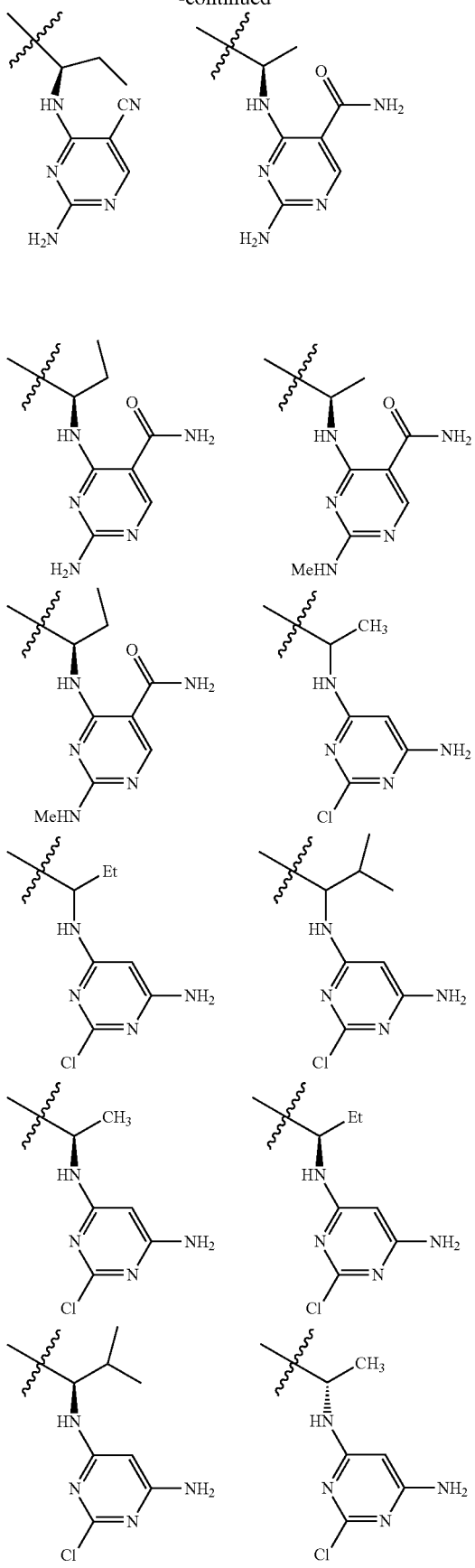
-continued
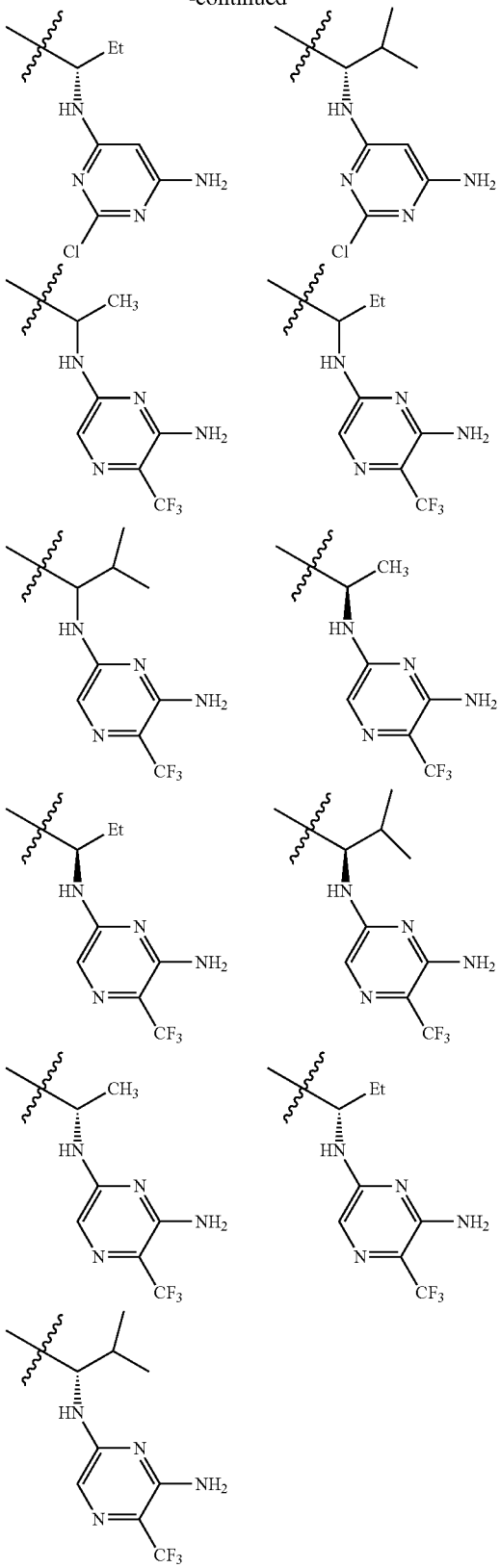
In some embodiments of the compound of Formula I, $R^{12}$ is a member of the group consisting of hydrogen, cyano, halo, unsubstituted or substituted alkyl, unsubstituted or substituted alkynyl, and unsubstituted or substituted alkenyl. In some embodiments, $R^{12}$ is unsubstituted or substituted aryl. In some embodiments, $R^{12}$ is unsubstituted or substituted heteroaryl, which includes but is not limited to heteroaryl having a 5 membered ring, heteroaryl having a six membered ring, heteroaryl with at least one nitrogen ring atom, heteroaryl with two nitrogen ring atoms, monocylic heteroaryl, and bicyclic heteroaryl. In some embodiments, $R^{12}$ is unsubstituted or substituted heterocycloalkyl, which includes but is not limited to heterocycloalkyl with one nitrogen ring atom, heterocycloalkyl with one oxygen ring atom, $R^{12}$ is heterocycloalkyl with one sulfur ring atom, 5 membered heterocycloalkyl, 6 membered heterocycloalkyl, saturated heterocycloalkyl, unsaturated heterocycloalkyl, heterocycloalkyl having an unsaturated moiety connected to the heterocycloalkyl ring, heterocycloalkyl substituted by oxo, and heterocycloalkyl substituted by two oxo. In some embodiments, $R^{12}$ is unsubstituted or substituted cycloalkyl, including but not limited to cyclopropyl, cyclobutyl, cyclopentyl, cyclohexyl, cycloalkyl substituted by one oxo, cycloalkyl having an unsaturated moiety connected to the cycloalkyl ring. In some embodiments, $R^{12}$ is unsubstituted or substituted amido, carboxylic acid, unsubstituted or substituted acyloxy, unsubstituted or substituted alkoxycarbonyl, unsubstituted or substituted acyl, or unsubstituted or substituted sulfonamido.

In some embodiments, when $R^{12}$ is alkyl, alkynyl, alkenyl, aryl, heteroaryl, heterocycloalkyl, or cycloalkyl, it is substituted with phosphate. In some embodiments, when $R^{12}$ is alkyl, alkynyl, alkenyl, aryl, heteroaryl, heterocycloalkyl, or cycloalkyl, it is substituted with urea. In some embodiments, when $R^{12}$ is alkyl, alkynyl, alkenyl, aryl, heteroaryl, heterocycloalkyl, or cycloalkyl, it is substituted with carbonate.

In some embodiments, when $R^{12}$ is alkyl, alkynyl, alkenyl, aryl, heteroaryl, heterocycloalkyl, cycloalkyl, alkoxycarbonyl, amido, acyloxy, acyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, aloxycarbonyl, or sulfonamido can itself be substituted.

In some embodiments of the compound of Formula I, $R^{12}$ of $W_d$ is one of the following moieties:

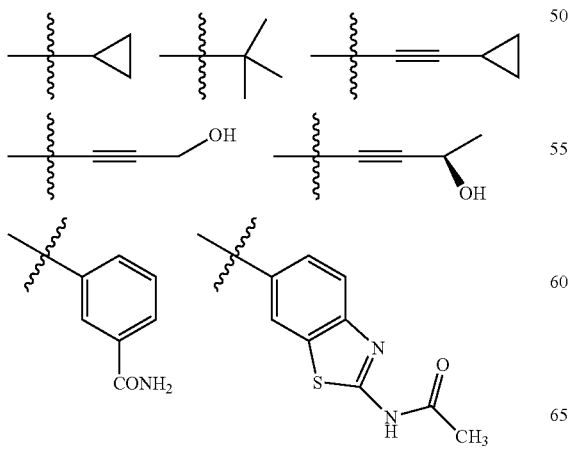

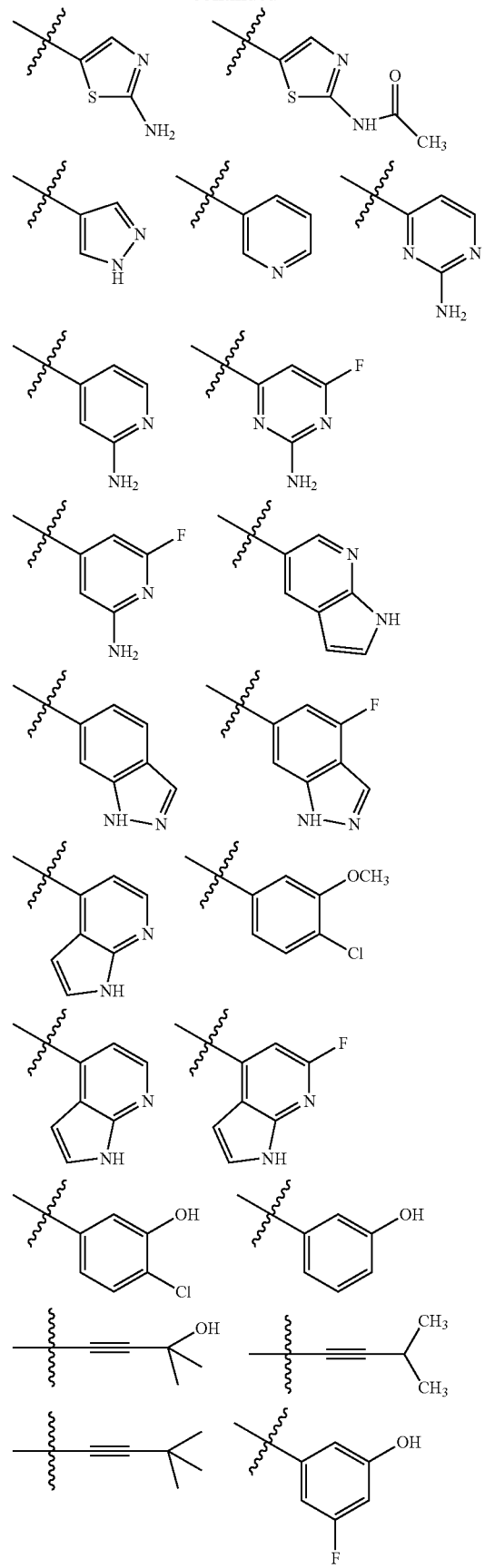

-continued
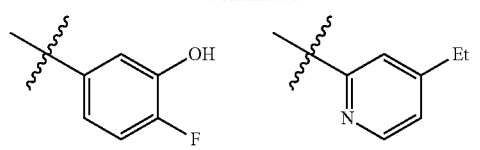
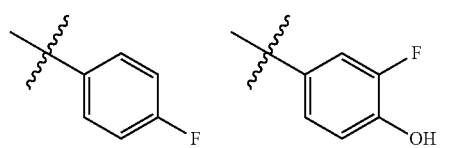
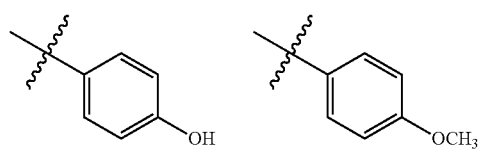
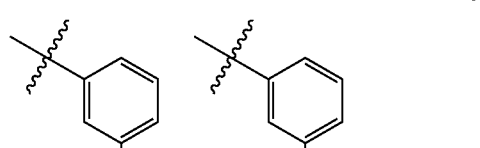
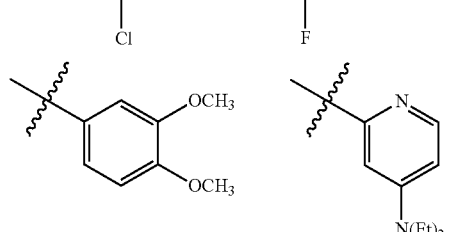
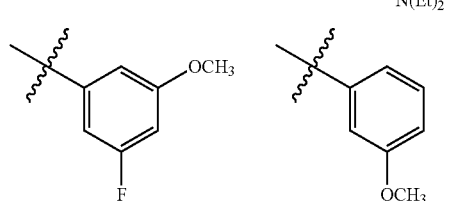
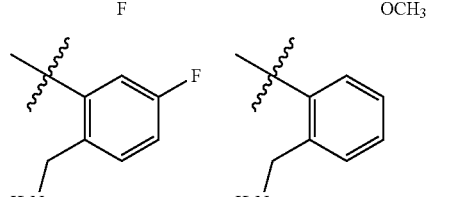
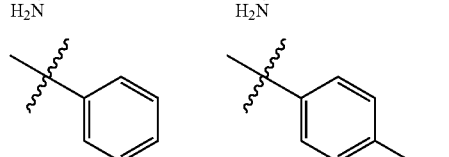
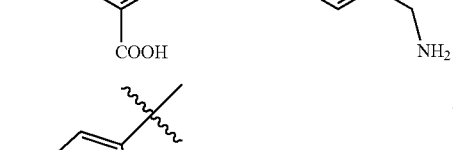
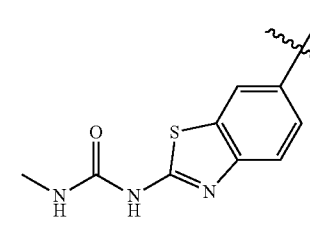
-continued
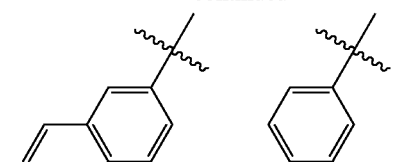
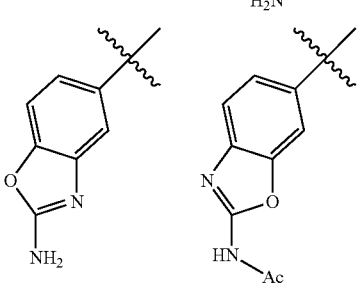
—CN, —Br, —Cl, —I, —H, —Me, —Et, —i-Pr,
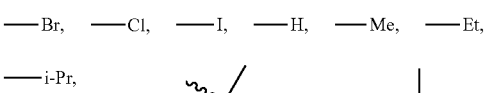
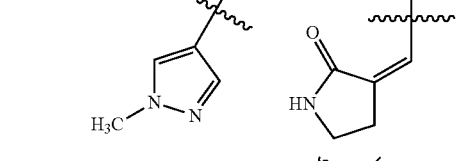
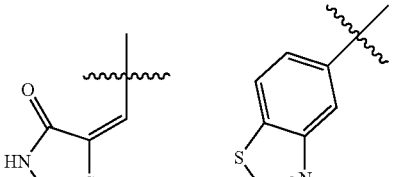
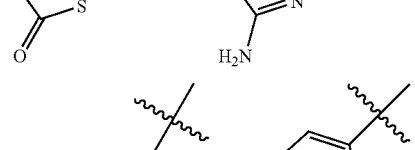
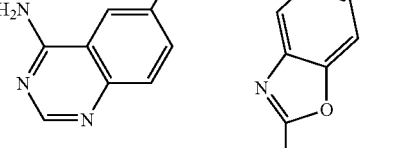
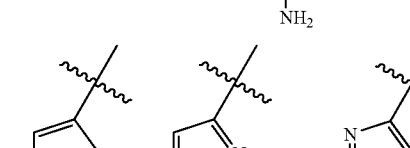
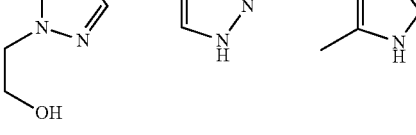
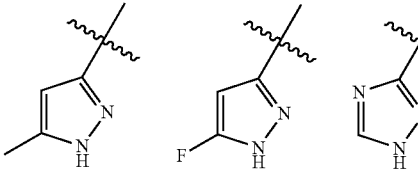

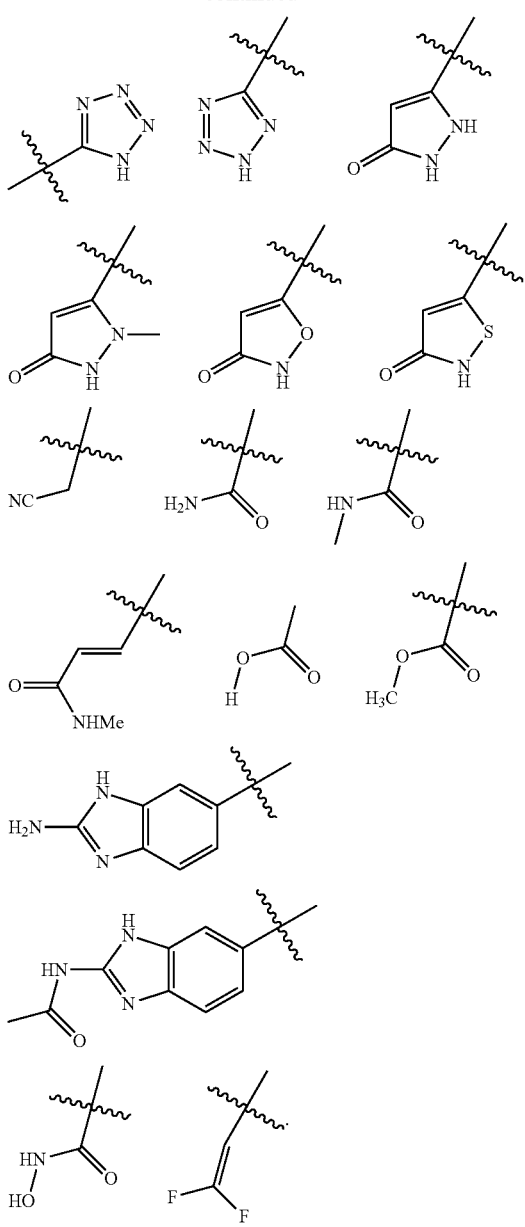

In some embodiments of the compound of Formula I, $W_d$ is a pyrazolopyrimidine of Formula III:

Formula III

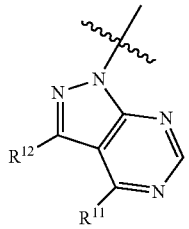

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is alkyl, halo, aryl, heteroaryl, heterocycloalkyl, or cycloalkyl. In some embodiments, $R^{11}$ is amino and $R^{12}$ is monocyclic heteroaryl. In some embodiments, $R^{11}$ is amino and $R^{12}$ is bicyclic heteroaryl. In some embodiments, $R^{11}$ is amino and $R^{12}$ is cyano, amino, carboxylic acid, acyloxy, alkoxycarbonyl, or amido.

In some embodiments of the invention, the compound of Formula I is a compound having a structure of Formula IV:

Formula IV

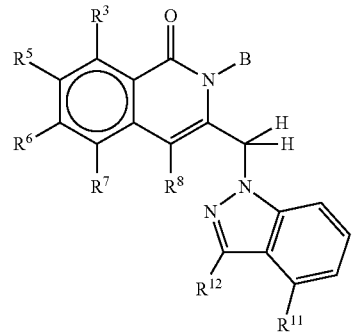

In some embodiments of the compound of Formula IV, $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In another embodiment, $R^{11}$ is amino and $R^{12}$ is alkyl, alkenyl, heteroaryl, aryl, or heterocycloalkyl. In some embodiments, $R^{11}$ is amino and $R^{12}$ is cyano, amino, carboxylic acid, alkoxycarbonyl, or amido.

In some embodiments, the compound of Formula IV is a compound of Formula IV-A:

Formula IV-A

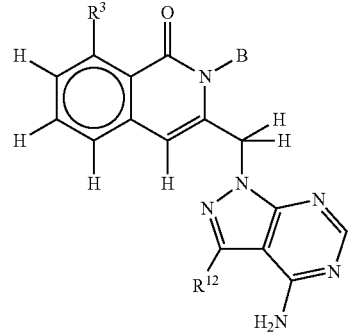

The invention also provides compounds of Formula I having a structure of any of Formulae V, V-A1, V-A2, V-B, VI, VI-A, VII-A1, VII-A2, VIII-A1, VIII-A2, IX-A1, IX-A2, X-A1, X-A2, XI-A1, X1-A2, XII-A, XII-A1, XII-A2, XIII-A, XIII-A1, XIII-A2, XIV-A, XIV-A1, XIV-A2, XV-A, XV-A1, XV-A2, XVI-A, XVI-A1, XVI-A2, XVII-A, XVII-A1, XVII-A2, XVIII-A, XVIII-A1, or XVIII-A2:

Formula V
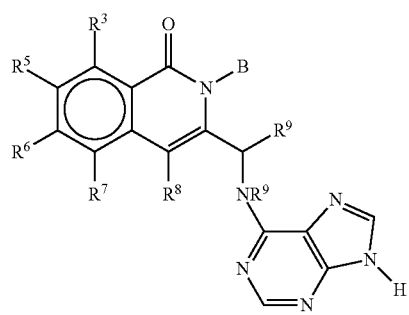
Formula V-A
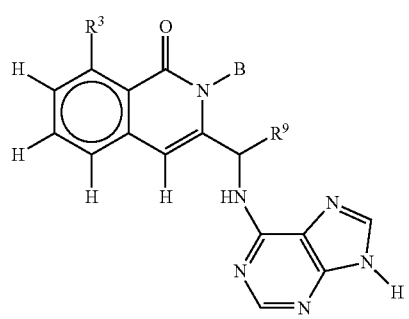
Formula VI
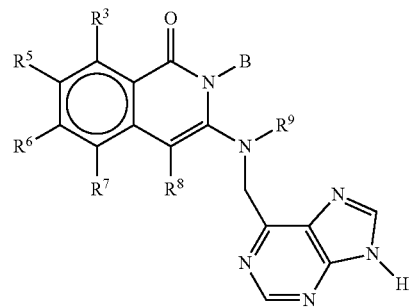
Formula VI-A
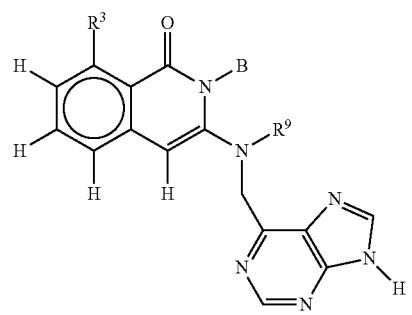
Formula VII-A
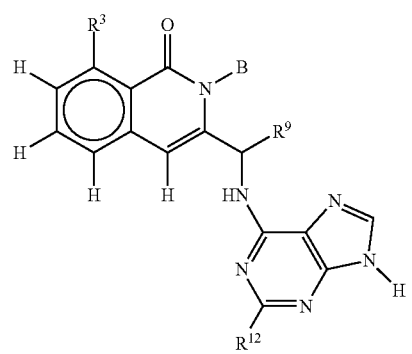
Formula VII-A1
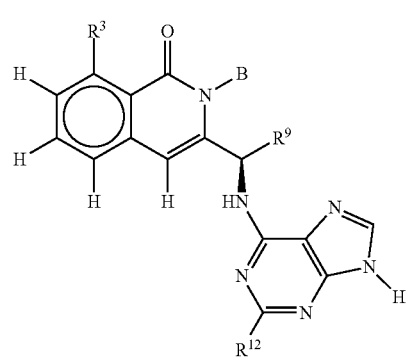
Formula V-A1
Formula V-A2
Formula V-B Formula VII-A2

Formula VIII-A

Formula VIII-A1

Formula VIII-A2

Formula IX-A

Formula IX-A1

Formula IX-A2

Formula X-A

Formula X-A1
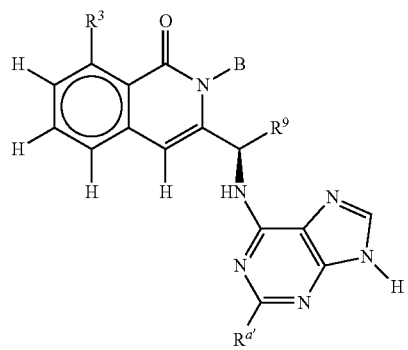
Formula X-A2
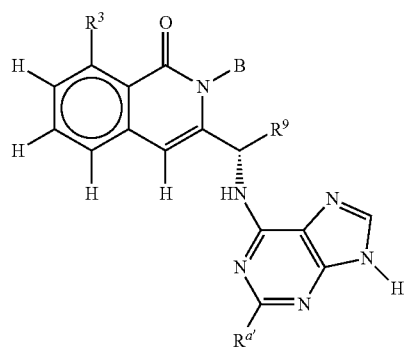
Formula XI-A
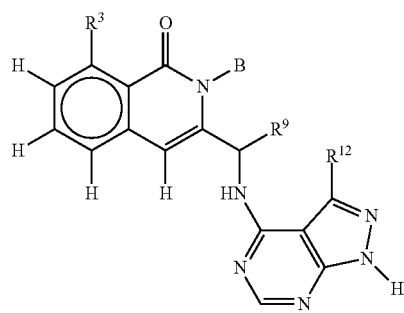
Formula XI-A1
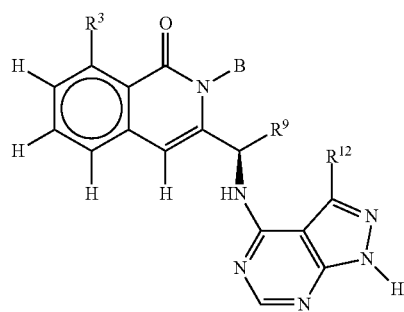
Formula XI-A2
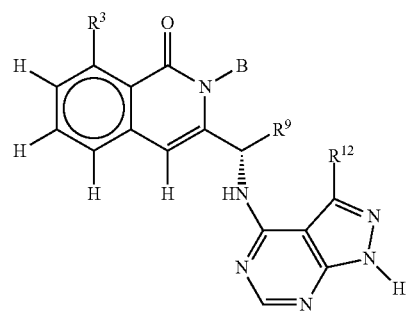
Formula XII-A
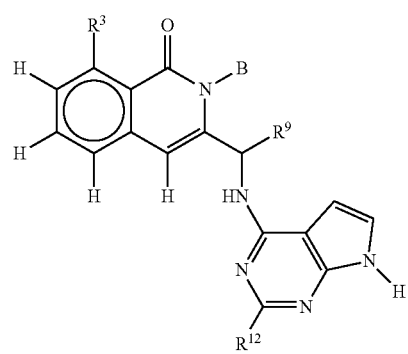
Formula XII-A1
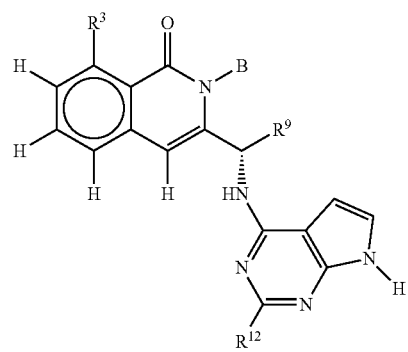
Formula XII-A2
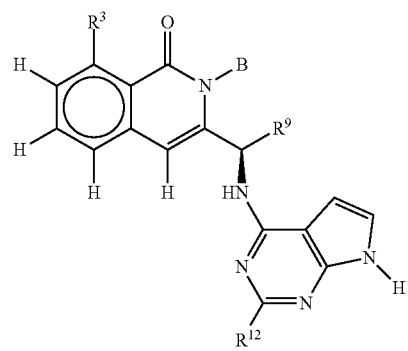

Formula XIII-A
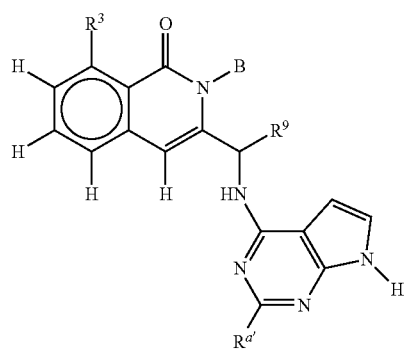
Formula XIII-A1
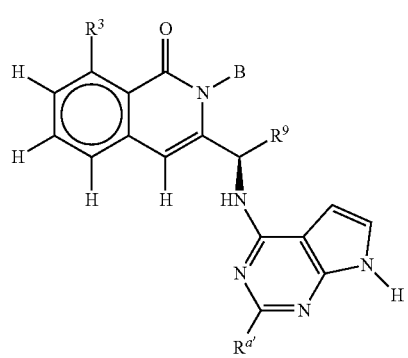
Formula XIII-A2
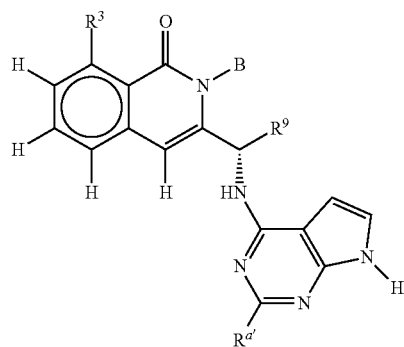
Formula XIV-A
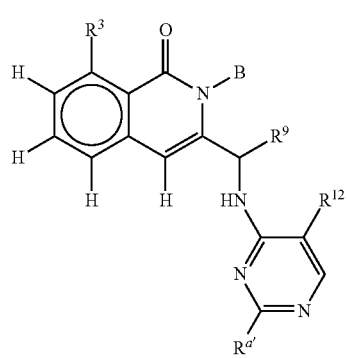
Formula XIV-A1
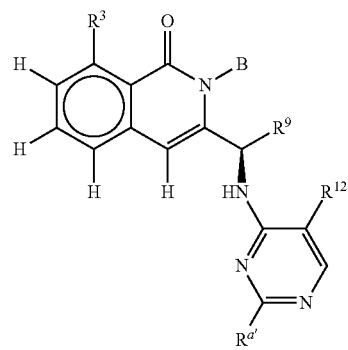
Formula XIV-A2
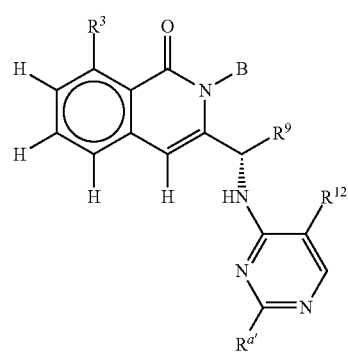
Formula XV-A
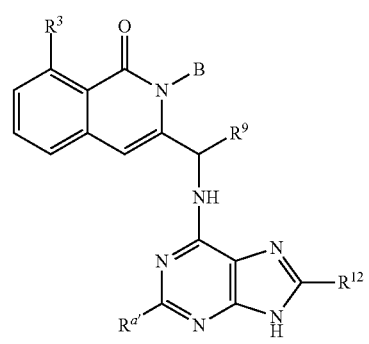
Formula XV-A1
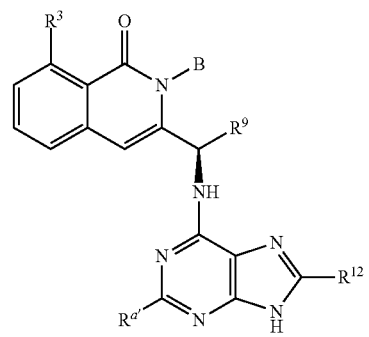

Formula XV-A2
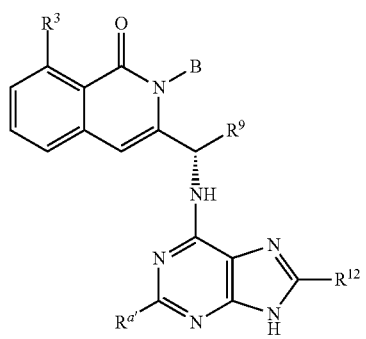
Formula XVI-A
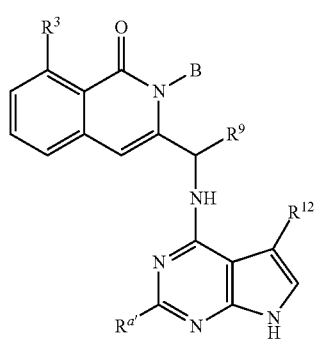
Formula XVI-A1
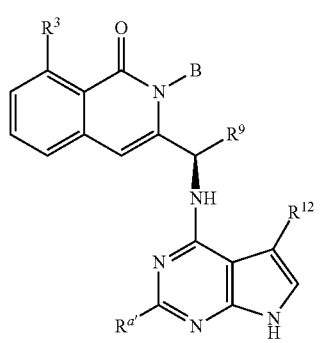
Formula XVI-A2
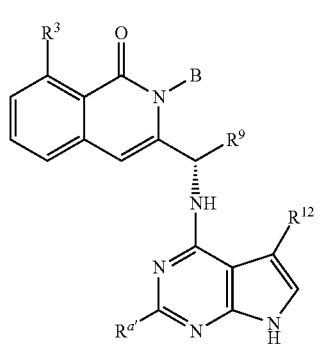
Formula XVII-A
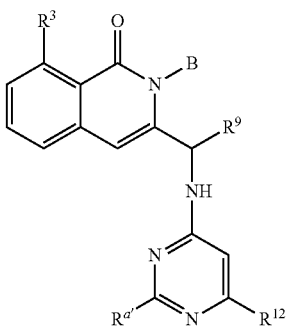
Formula XVII-A1
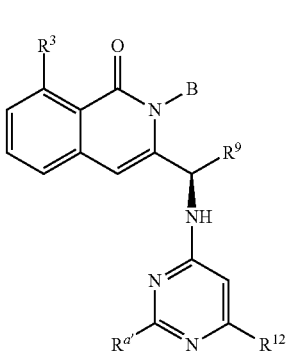
Formula XVII-A2
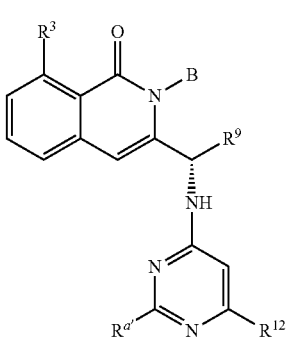
Formula XVIII-A
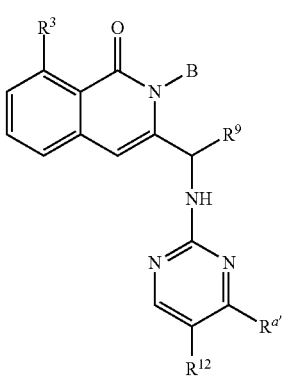

Formula XVIiI-A1

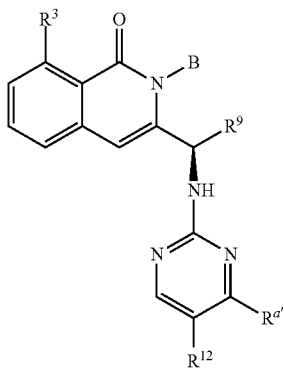

Formula XVIII-A2

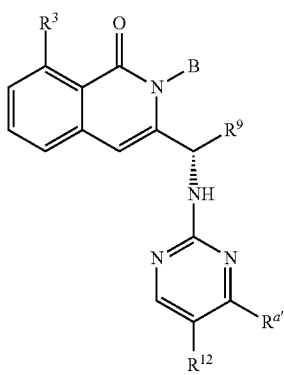

Any of the disclosed elements and their substituents for the compounds of Formula I can be used in any combination.

In one aspect, for the compounds of Formula I, $R_3$ is H, $CH_3$, $CF_3$, Cl, or F; and B is a moiety of Formula II:

Formula II

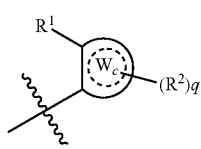

wherein $W_c$ is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, or nitro; q is an integer of 0, 1, 2, 3, or 4; $R^5$, $R^6$, $R^7$, and $R^8$ are H; X is absent or $(CH_2)_z$; z is 1; Y is absent or —N($R^9$)—; $R^9$ is hydrogen, $C_1$-$C_{10}$alkyl, $C_3$-$C_7$cycloalkyl, or $C_2$-$C_{10}$heteroalkyl; at least one of X and Y is present; and $W_d$ is pyrazolopyrimidine or purine. In some embodiments, when X and Y are present and $W_d$ is purine, then —N($R^9$)— is —NH—.

In another aspect, for the compounds of Formula I, $R_3$ is H, $CH_3$, $CF_3$, Cl, or F; B is a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, or nitro; q is 0, 1 or 2; $R^5$, $R^6$, $R^7$, and $R^8$ are H; X is absent or $(CH_2)_z$; z is 1; Y is absent or —N($R^9$)—; $R^9$ is hydrogen, methyl, or ethyl; at least one of X and Y is present; $W_d$ is:

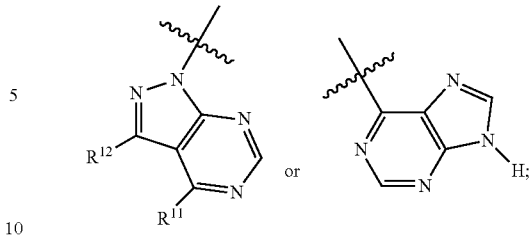

$R^{11}$ is amino; and $R^{12}$ is H, alkyl, alkynyl, alkenyl, halo, aryl, heteroaryl, heterocycloalkyl, or cycloalkyl. In some embodiments, when X and Y are present and $W_d$ is purine, then —N($R^9$)— is —NH—.

In another aspect, for the compounds of Formula I, $R_3$ is H, $CH_3$, $CF_3$, Cl, or F; B is a moiety of Formula II, which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, or nitro; q is 0, 1 or 2; X is $(CH_2)_z$; z is 1; $R^5$, $R^6$, $R^7$, and $R^8$ are H; Y is absent and $W_d$ is:

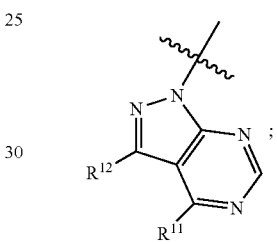

$R^{11}$ is amino; and $R^{12}$ is H, alkyl, alkynyl, alkenyl, halo, aryl, heteroaryl, heterocycloalkyl, or cycloalkyl.

In another aspect, $R_3$ is H, $CH_3$, $CF_3$, Cl, or F; B is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, or nitro; q is 0, 1 or 2; $R^5$, $R^6$, $R^7$, and $R^8$ are H; X is $(CH_2)_z$; z is 1; X is $(CH_2)_z$; z is 1; Y is —N($R^9$)—; $R^9$ is hydrogen, methyl, or ethyl; and $W_d$ is

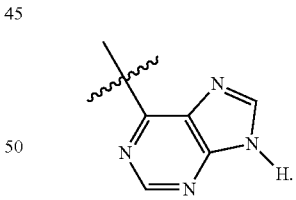

In some embodiments, Y is —NH—.

In another aspect, for the compounds of Formula I $R_3$ is aryl, heteroaryl, H, $CH_3$, $CF_3$, Cl, or F; B is alkyl or a moiety of Formula II;
wherein $W_c$ is aryl, heteroaryl, heterocycloalkyl, or cycloalkyl, and q is an integer of 0, 1, 2, 3, or 4; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1, 2, 3, or 4; Y is absent, —N($R^9$)—, or —N($R^9$)CH($R^9$)—; $R^9$ is hydrogen, alkyl, cycloalkyl, or heteroalkyl; at least one of X and Y is present; and $W_d$ is pyrazolopyrimidine or purine. In some embodiments, when X is present, Y is —N($R^9$)—, and $W_d$ is purine, then Y is —NH—.

In another aspect, for the compounds of Formula I, $R_3$ is aryl, heteroaryl, H, $CH_3$, $CF_3$, Cl, or F; B is alkyl or a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1, 2, 3, or 4; Y is absent, —$N(R^9)$—, or —$N(R^9)CH(R^9)$—; $R^9$ is hydrogen, methyl, or ethyl; at least one of X and Y is present; $W_d$ is:

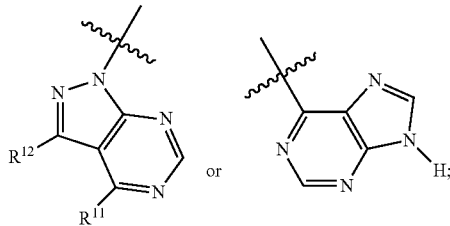

$R^{11}$ is amino; and $R^{12}$ is H, alkyl, alkynyl, alkenyl, halo, aryl, heteroaryl, heterocycloalkyl, cycloalkyl, cyano, amino, carboxylic acid, aloxycarbonyl, or amido. In some embodiments, when X is present, Y is —$N(R^9)$—, and $W_d$ is purine, then Y is —NH—.

In another aspect, for the compounds of Formula I, $R_3$ is H, $CH_3$, $CF_3$, Cl, or F; B is alkyl or a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is $(CH(R^9))_z$; z is an integer of 1; Y is absent-; $R^9$ is hydrogen, methyl, or ethyl; $W_d$ is:

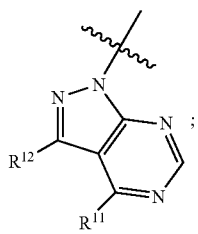

$R^{11}$ is amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido.

In another aspect, for the compounds of Formula I, $R_3$ is aryl, heteroaryl, H, $CH_3$, $CF_3$, Cl, or F; B is a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1; Y is absent, —$N(R^9)$—, or —$N(R^9)CH(R^9)$—; $R^9$ is hydrogen, methyl, or ethyl; at least one of X and Y is present, and $W_d$ is:

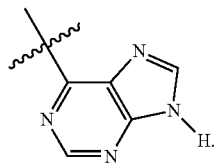

In some embodiments, when X is present, Y is —$N(R^9)$—, and $W_d$ is purine, then Y is —NH—.

In another aspect, for the compounds of Formula I, $R_3$ is aryl, heteroaryl, H, $CH_3$, $CF_3$, Cl, or F; B is a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent; Y is —$N(R^9)CH(R^9)$—; $R^9$ is hydrogen, methyl, or ethyl; and $W_d$ is:

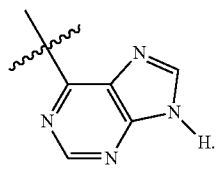

In another aspect, for the compounds of Formula I, $R_3$ is aryl, heteroaryl, H, $CH_3$, $CF_3$, Cl, or F; B is alkyl or a moiety of Formula II which is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH(R^9))_z$; z is an integer of 1, 2, 3, or 4; Y is absent, —$N(R^9)$—, or —$N(R^9)CH(R^9)$—; $R^9$ is hydrogen, methyl, or ethyl; at least one of X and Y is present; $W_d$ is:

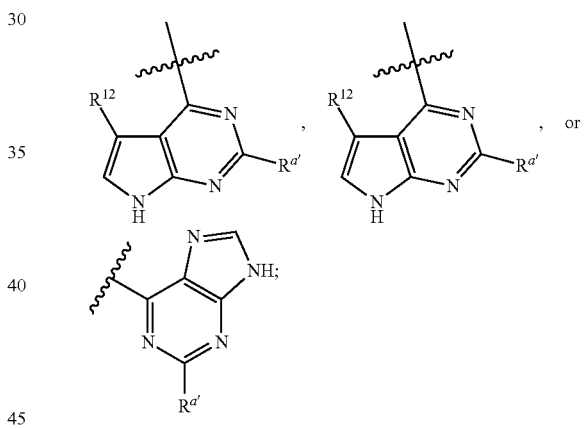

$R^{a'}$ is hydrogen, halo, or amino; and $R^{12}$ is H, alkyl, alkynyl, alkenyl, halo, aryl, heteroaryl, heterocycloalkyl, cycloalkyl, cyano, amino, carboxylic acid, aloxycarbonyl, or amido. In some embodiments, when X is present, Y is —$N(R^9)$—, and $W_d$ is purine, then Y is —NH—.

Additional exemplary compounds of the present invention are disclosed having a sub-structure of Formula IV-A.

Formula IV-A

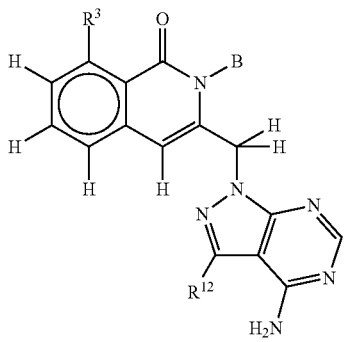

Some illustrative compounds of the present invention having a structure of Formula IV-A include those in which $R^3$ is —H, —Cl, —F, or —CH$_3$ in combination with any B moiety described in Table 1, and any $R^{12}$ as described in Table 2. A compound of Formula IV-A includes any combination of $R^3$, B, and $R^{12}$. Additional exemplary compounds of Formula IV-A are illustrated in Table 4.

TABLE 1

Illustrative B moiethies of the compounds of Formula I.

| Sub-class # | B |
|---|---|
| B-1 | 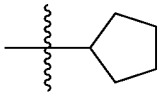 [SMILES: *C1CCCC1] |
| B-2 | 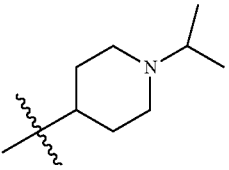 [SMILES: *C1CCN(C(C)C)CC1] |
| B-3 | —CH(CH$_3$)2 |
| B-4 | 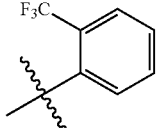 [SMILES: *c1ccccc1C(F)(F)F] |
| B-5 | 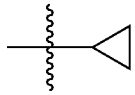 [SMILES: *C1CC1] |
| B-6 | 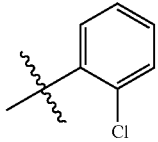 [SMILES: *c1ccccc1Cl] |
| B-7 | 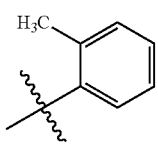 [SMILES: *c1ccccc1C] |
| B-8 | 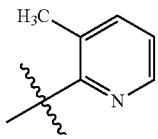 [SMILES: *c1ncccc1C] |
| B-9 | 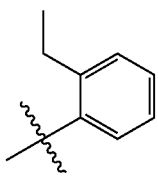 [SMILES: *c1ccccc1CC] |

TABLE 1-continued

Illustrative B moiethies of the compounds of Formula I.

| Sub-class # | B |
|---|---|
| B-10 | 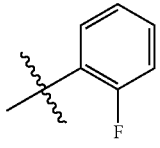 [SMILES: *c1ccccc1F] |
| B-11 | 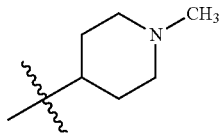 [SMILES: *C1CCN(C)CC1] |
| B-12 | 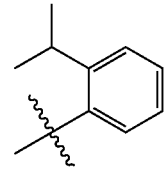 [SMILES: *c1ccccc1C(C)C] |
| B-13 | 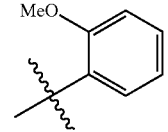 [SMILES: *c1ccccc1OC] |
| B-14 | 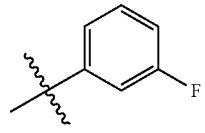 [SMILES: *c1cccc(F)c1] |
| B-15 | 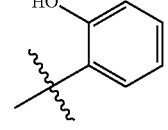 |
| B-16 | 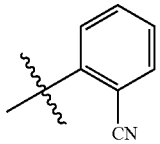 [SMILES: *c1ccccc1C#N] |
| B-17 | 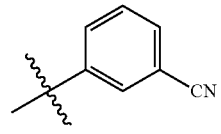 [SMILES: *c1cccc(C#N)c1] |
| B-18 | 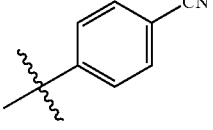 |

TABLE 1-continued
Illustrative B moieties of the compounds of Formula I.
| Sub-class # | B |
|---|---|
| B-19 | 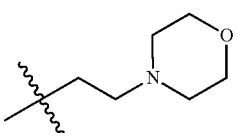 [SMILES: *CCN1CCOCC1] |
| B-20 | 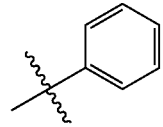 [SMILES: *c1ccccc1] |
| B-21 | 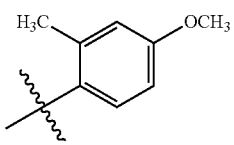 [SMILES: *c1ccc(OC)cc1C] |
| B-22 | 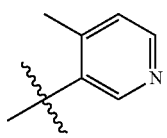 [SMILES: *c1cnccc1C] |
| B-23 | 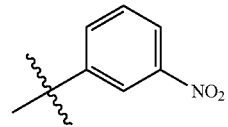 [SMILES: *c1cccc([N+](=O)[O-])c1] |
| B-24 | 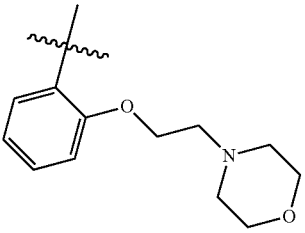 [SMILES: *c1ccccc1OCCN1CCOCC1] |
| B-25 | 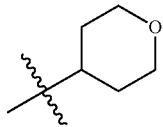 [SMILES: *C1CCOCC1] |
| B-26 | 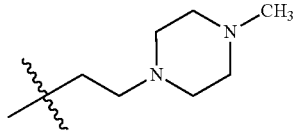 [SMILES: *CCN1CCN(C)CC1] |
| B-27 | 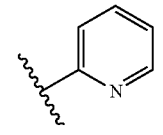 [SMILES: *c1ccccn1] |
| B-28 | 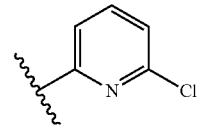 [SMILES: *c1cccc(Cl)n1] |
| B-29 | 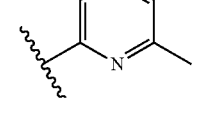 |
| B-30 | 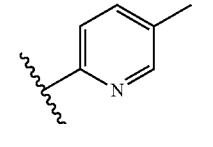 [SMILES: *c1ccc(C)cn1] |
| B-31 | 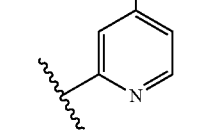 |
| B-32 | 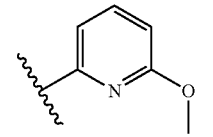 |
| B-33 | 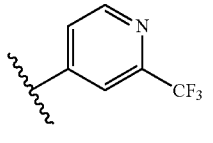 [SMILES: *c1ccnc(C(F)(F)F)c1] |
| B-34 | 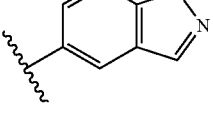 |
| B-35 | 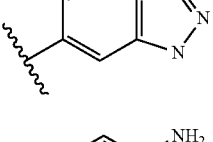 |
| B-36 | 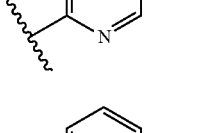 |
| B-37 | 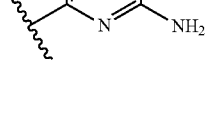 |

TABLE 1-continued
Illustrative B moieties of the compounds of Formula I.
| Sub-class # | B |
|---|---|
| B-38 | 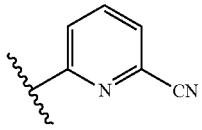 [SMILES: *c1cccc(C#N)n1] |
| B-39 | 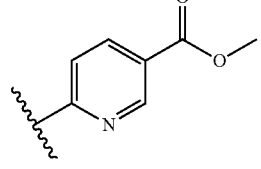 |
| B-40 | 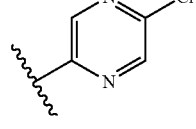 |
| B-41 | 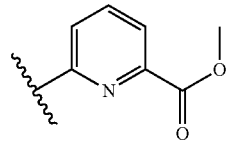 [SMILES: *c1cccc(C(=O)OC)n1] |
| B-42 | 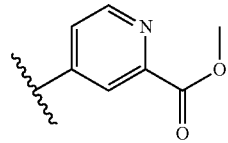 [SMILES: *c1ccnc(C(=O)OC)c1] |
| B-43 | 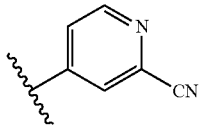 [SMILES: *c1ccnc(C#N)c1] |
| B-44 | 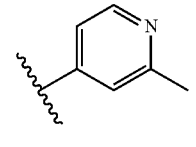 [SMILES: *c1ccnc(C)c1] |
| B-45 | 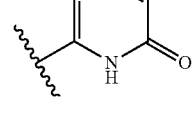 |
| B-46 | 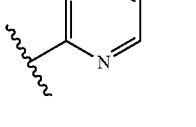 |
| B-47 | 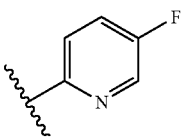 [SMILES: *c1ccc(F)cn1] |
| B-48 | 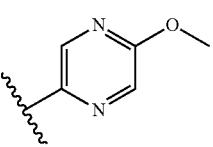 [SMILES: *c1cnc(OC)cn1] |
| B-49 | 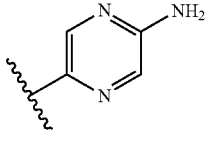 [SMILES: *c1cnc(N)cn1] |
| B-50 | 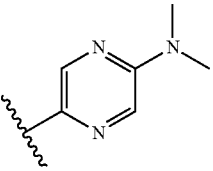 [SMILES: *c1cnc(N(C)C)cn1] |
| B-51 | 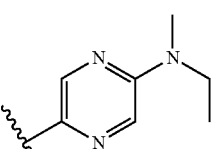 |
| B-52 | 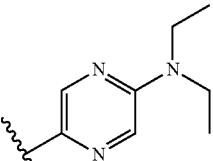 |
| B-53 | |
| B-54 | |

TABLE 1-continued

Illustrative B moieties of the compounds of Formula I.

| Sub-class # | B |
|---|---|
| B-55 | [structure: pyrazine linked to 4-methylpiperazin-1-yl] |
| B-56 | [structure: pyrazine linked to pyrrolidin-1-yl] |
| B-57 | [structure: pyrazine linked to piperidin-1-yl] |
| B-58 | [structure: pyrazine linked to morpholin-4-yl] |
| B-59 | [structure: pyrazine linked to 4-methylpiperidin-1-yl] |
| B-60 | [structure: pyrazine linked to 2-methylpiperidin-1-yl] |
| B-61 | [structure: pyrazine linked to pyrrol-1-yl] |
| B-62 | [structure: pyrazine linked to imidazol-1-yl] |
| B-63 | [structure: pyrazine linked to 2-methylimidazol-1-yl] |
| B-64 | [structure: pyrazine linked to 4-methylimidazol-1-yl] |
| B-65 | [structure: pyrazine linked to pyrazol-1-yl] |
| B-66 | [structure: pyrazine linked to 4-methylpyrazol-1-yl] |
| B-67 | [structure: pyrazine linked to 3-methylpyrazol-1-yl] |
| B-68 | [structure: pyrazine linked to 2-oxopyridin-1-yl] |

TABLE 1-continued

Illustrative B moiethies of the compounds of Formula I.

| Sub-class # | B |
|---|---|
| B-69 | (pyrazine with CN) |
| B-70 | (pyrazine with OMe) |
| B-71 | (pyrazine with NMe2) |
| B-72 | (pyrazine with NEt2) |
| B-73 | (pyrazine with morpholine) |
| B-74 | (pyrazine with Cl) |
| B-75 | (pyrazine with imidazole) |
| B-76 | (pyrazine with pyridinone) |
| B-77 | (pyrazine with pyrrolidine) |
| B-78 | (pyrazine) |
| B-79 | (thiazole) |
| B-80 | (2-methylthiazole) |
| B-81 | (2-tert-butylthiazole) |
| B-82 | (thiazole with NMeEt) |
| B-83 | (thiazole with NEt2) |
| B-84 | (thiazole with pyridinone) |
| B-85 | (thiazole with imidazole) |
| B-86 | (cyclohexyl) |

TABLE 1-continued

Illustrative B moieties of the compounds of Formula I.

| Subclass # | B |
|---|---|
| B-87 | —CH₃ |
| B-88 | —CH₂CH₃ |
| B-89 | cyclobutyl |
| B-90 | 4-methylpyridin-3-yl |
| B-91 | 3-(pyrrolidin-1-yl)propyl |
| B-92 | 3,5-dimethylphenyl |
| B-93 | 2,6-difluorophenyl |
| B-94 | 2,6-dimethylphenyl |
| B-95 | 3,5-difluorophenyl |
| B-96 | 3-(4-ethylpiperazin-1-yl)propyl |
| B-97 | piperidin-4-yl (NH) |
| B-98 | 1-acetylpiperidin-4-yl |
| B-99 | 1-(2-hydroxyethyl)piperidin-4-yl |
| B-100 | 1-(2-methylsulfonylethyl)piperidin-4-yl |
| B-101 | 1-(2-cyanoethyl)piperidin-4-yl |
| B-102 | 4-fluorophenyl |

TABLE 2

Illustrative R¹² of compounds of Formula I.

| Subclass # | $R^{12}$ |
|---|---|
| 12-1 | —CN |
| 12-2 | —Br |
| 12-3 | —Cl |
| 12-4 | —CH₂CH₃ |
| 12-5 | —CH₃ |
| 12-6 | —CH(CH₃)₂ |
| 12-7 | cyclopropyl |
| 12-8 | tert-butyl |

TABLE 2-continued
Illustrative R¹² of compounds of Formula I.
| Sub-class # | R¹² |
|---|---|
| 12-9 | 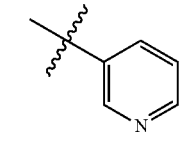 [SMILES: *c1cccnc1] |
| 12-10 | 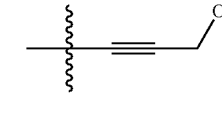 |
| 12-11 | 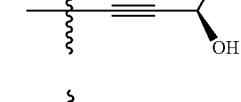 |
| 12-12 |  |
| 12-13 | 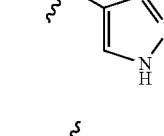 |
| 12-14 | 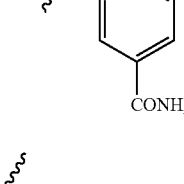 |
| 12-15 | 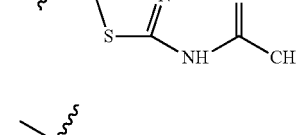 |
| 12-16 | 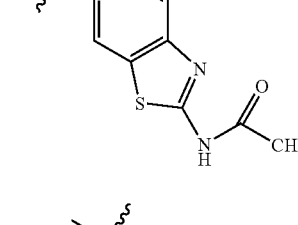 |
| 12-17 | 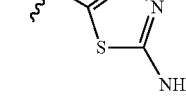 |
| 12-18 | 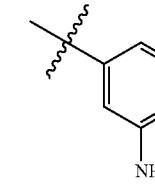 |
| 12-19 | 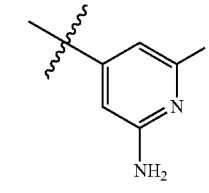 |
| 12-20 | 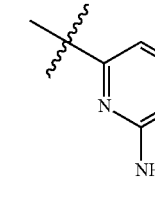 |
| 12-21 | 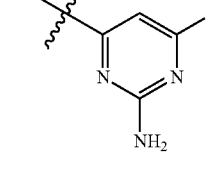 |
| 12-22 | 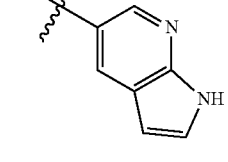 |
| 12-23 | 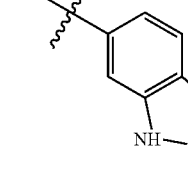 |
| 12-24 | 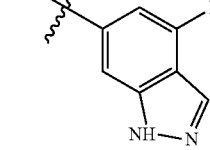 |

TABLE 2-continued

Illustrative R¹² of compounds of Formula I.

| Subclass # | R¹² |
|---|---|
| 12-25 | 1H-pyrrolo[2,3-b]pyridin-4-yl |
| 12-26 | 3-methoxyphenyl |
| 12-27 | 6-fluoro-1H-pyrrolo[2,3-b]pyridin-4-yl |
| 12-28 | -C≡C-C(CH₃)₂OH |
| 12-29 | -C≡C-C(CH₃)₃ |
| 12-30 | 4-ethylpyridin-2-yl |
| 12-31 | 4-chloro-3-methoxyphenyl |
| 12-32 | 4-chloro-3-hydroxyphenyl |
| 12-33 | 4-fluorophenyl |
| 12-34 | 3-fluoro-4-hydroxyphenyl |
| 12-35 | —H |
| 12-36 | 4-hydroxyphenyl |
| 12-37 | 4-fluorophenyl |
| 12-38 | 3-fluoro-4-hydroxyphenyl |
| 12-39 | 4-hydroxyphenyl |
| 12-40 | 3-chlorophenyl |
| 12-41 | 3-fluorophenyl |
| 12-42 | 3,4-dimethoxyphenyl |
| 12-43 | 4-methoxyphenyl |

TABLE 2-continued

Illustrative R¹² of compounds of Formula I.

| Sub-class # | R¹² |
|---|---|
| 12-44 | 4-fluoro-2-(aminomethyl)phenyl |
| 12-45 | 2-(aminomethyl)phenyl |
| 12-46 | 3-methoxyphenyl |
| 12-47 | 4-(aminomethyl)phenyl |
| 12-48 | 3-carboxyphenyl |
| 12-49 | 3-methoxy-5-fluorophenyl |
| 12-50 | 2-amino-benzothiazol-6-yl |
| 12-51 | 2-(3-methylureido)-benzothiazol-6-yl |
| 12-52 | 2-aminoquinolin-6-yl |
| 12-53 | 2-aminoquinazolin-6-yl |
| 12-54 | 2-aminobenzoxazol-5-yl |
| 12-55 | 2-aminobenzoxazol-6-yl |

TABLE 2-continued

Illustrative R$^{12}$ of compounds of Formula I.

| Sub-class # | R$^{12}$ |
|---|---|
| 12-56 | 4-aminoquinazolin-6-yl |
| 12-57 | 1-methyl-1H-pyrazol-4-yl |
| 12-58 | 1-(2-hydroxyethyl)-1H-pyrazol-4-yl |
| 12-59 | (2,4-dioxothiazolidin-5-ylidene)methyl |
| 12-60 | (2-oxopyrrolidin-3-ylidene)methyl |
| 12-61 | —I |
| 12-62 | 3-hydroxyphenyl |
| 12-63 | 3-fluoro-5-hydroxyphenyl |
| 12-64 | 2-fluoro-5-hydroxyphenyl (with OH and F substituents) |
| 12-65 | 4-methylpent-2-yn-1-yl (3,3-dimethylbut-1-ynyl) |
| 12-66 | 5-(diethylamino)pyridin-2-yl |
| 12-67 | 2-aminobenzo[d]thiazol-5-yl |
| 12-68 | 1H-pyrazol-3-yl |
| 12-69 | 2-methyl-1H-imidazol-4-yl |
| 12-70 | 5-methyl-1H-pyrazol-3-yl |
| 12-71 | 5-fluoro-1H-pyrazol-3-yl |

TABLE 2-continued

Illustrative R^{12} of compounds of Formula I.

| Sub-class # | R^{12} |
|---|---|
| 12-72 | 1H-1,2,4-triazol-3-yl |
| 12-73 | 5-oxo-2,5-dihydro-1H-pyrazol-3-yl |
| 12-74 | 1-methyl-5-oxo-2,5-dihydro-1H-pyrazol-3-yl |
| 12-75 | 3-oxo-2,3-dihydroisoxazol-5-yl |
| 12-76 | 3-oxo-2,3-dihydroisothiazol-5-yl |
| 12-77 | —C(CH$_3$)$_2$CN |
| 12-78 | —C(CH$_3$)$_2$C(O)NH$_2$ |
| 12-79 | —C(CH$_3$)$_2$C(O)NHMe |
| 12-80 | —C(CH$_3$)$_2$CH=CHC(O)NHMe |
| 12-81 | —CH$_2$-morpholin-4-yl |
| 12-82 | —C(CH$_3$)$_2$C(O)OCH$_3$ |
| 12-83 | —C(O)OH |
| 12-84 | —C(CH$_3$)$_2$C(O)NHOH |
| 12-85 | 2-amino-1H-benzimidazol-5-yl |
| 12-86 | 2-acetamido-1H-benzimidazol-5-yl |
| 12-87 | —C(CH$_3$)=CF$_2$ |
| 12-88 | —C(CH$_3$)$_2$-(1H-pyrazol-3-yl) |
| 12-89 | —CH$_2$-(1-methyl-1H-pyrazol-5-yl) |

TABLE 2-continued

Illustrative R$^{12}$ of compounds of Formula I.

| Subclass # | R$^{12}$ |
|---|---|
| 12-90 | 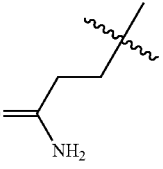 |
| 12-91 | 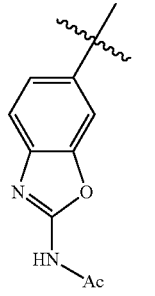 [SMILES: *c1ccc2nc(NC(C)=O)oc2c1] |
| 12-92 | 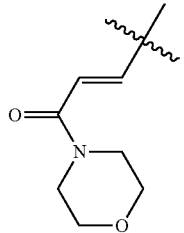 [SMILES: */C=C/C(=O)N1CCOCC1] |
| 12-93 | 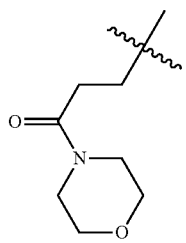 [SMILES: *CCC(=O)N1CCOCC1] |
| 12-94 | 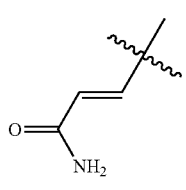 |
| 12-95 | 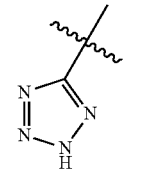 |
| 12-96 | 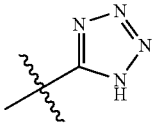 [SMILES: *c1nnn[nH]1] |
| 12-97 | —F |
| 12-98 | 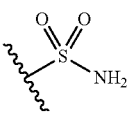 |
| 12-99 | 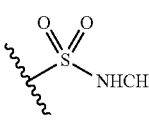 |
| 12-100 | 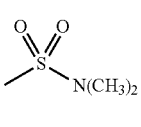 |
| 12-101 | 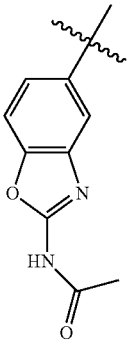 [SMILES: *c1ccc2oc(NC(C)=O)nc2c1] |
| 12-102 | 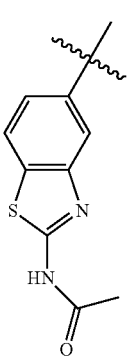 [SMILES: *c1ccc2sc(NC(C)=O)nc2c1] |

Other illustrative compounds of the present invention have a structure of Formula V-A, V-A1, or V-A2, wherein B is a moiety described in Table 1, in combination with R$^3$, which is —H, —Cl, —F, or CH$_3$, and R$^9$, which is —H, —CH$_3$, or —CH$_2$CH$_3$. A compound of Formula V-A, V-A1, or V-A2 includes any combination of R$^3$, B, and R$^9$.

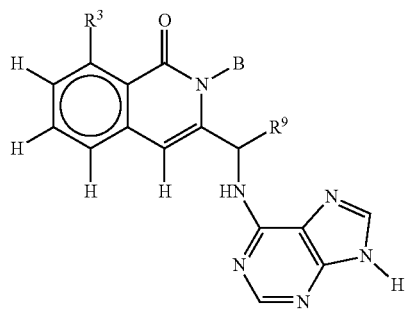

Formula V-A

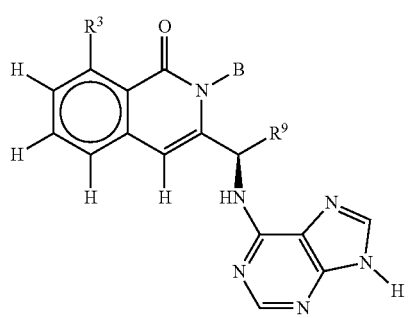

Formula V-A1

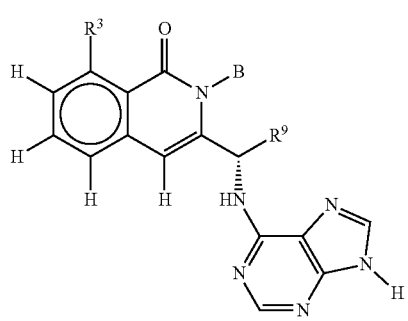

Formula V-A2

Yet other illustrative compounds of the present invention have a structure of Formula V-B, wherein B is a moiety described in Table 1, in combination with $R^3$, which is —H, —Cl, —F, or $CH_3$, and $R^9$, which is —H, —$CH_3$, or —$CH_2CH_3$. A compound of Formula V-B includes any combination of $R^3$, B, and $R^9$.

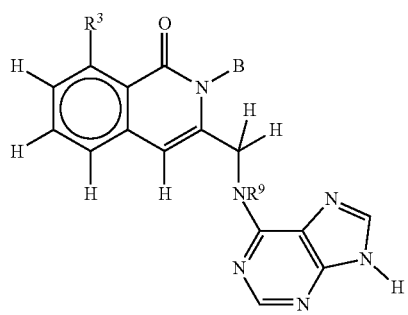

Formula V-B

Some other illustrative compounds of the present invention have a structure of Formula VI-A, wherein B is a moiety described in Table 1, in combination with $R^3$, which is —H, —Cl, —F, or $CH_3$, and $R^9$, which is —H, —$CH_3$, or —$CH_2CH_3$. A compound of Formula VI-A includes any combination of $R^3$, B, and $R^9$.

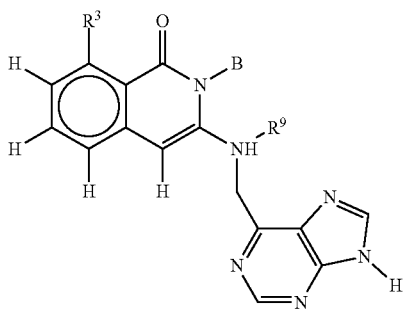

Formula VI-A

Further illustrative compounds that can be employed as described herein have a structure of one of Formulae VII-A1, VII-A2, VIII-A1, VIII-A2, IX-A1, IX-A2, X-A1, X-A2, XI-A1, X1-A2, XII-A, XII-A1, XII-A2, XIII-A, XIII-A1, XIII-A2, XIV-A, XIV-A1, or XIV-A2: wherein B is a moiety described in Table 1, any $R^{12}$ as described in Table 2, in combination with $R^3$, which is —H, —Cl, —F, or $CH_3$, $R^9$ which is —H, —$CH_3$, or —$CH_2CH_3$, and $R^{a'}$ which is —H, —Cl, —F, or —$NH_2$. A compound of Formulae VII-A1, VII-A2, VIII-A1, VIII-A2, IX-A1, IX-A2, X-A1, X-A2, XI-A1, X1-A2, XII-A, XII-A1, XII-A2, XIII-A, XIII-A1, XIII-A2, XIV-A, XIV-A1, or XIV-A2: includes any combination of $R^a$, $R^3$, B, $R^9$ and $R^{12}$.

Additional exemplary compounds include but are not limited to the following:

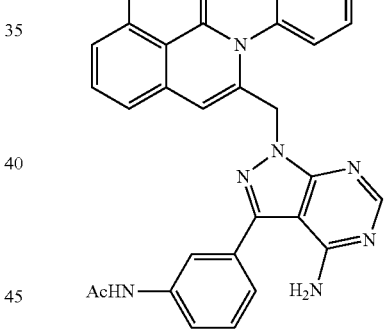

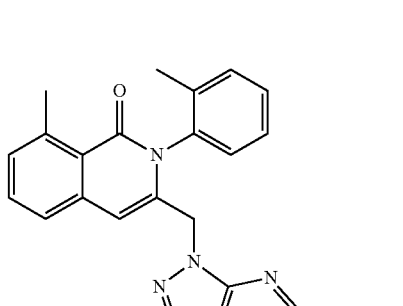

121
-continued
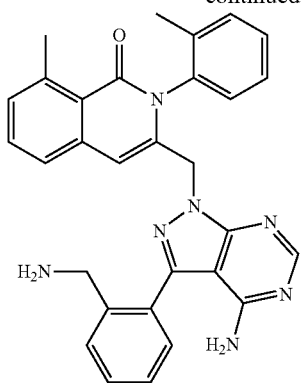
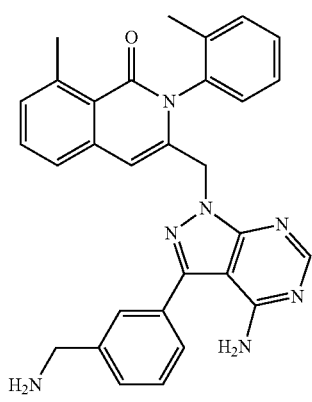
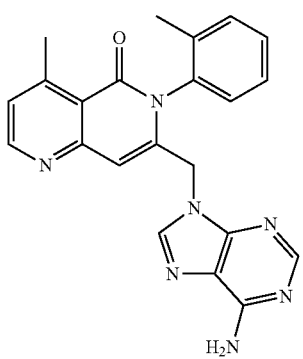
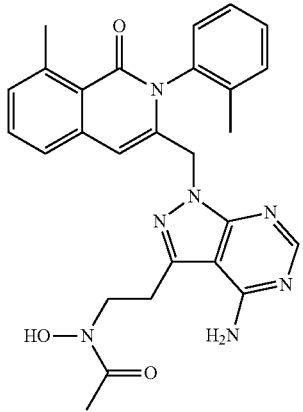
122
-continued
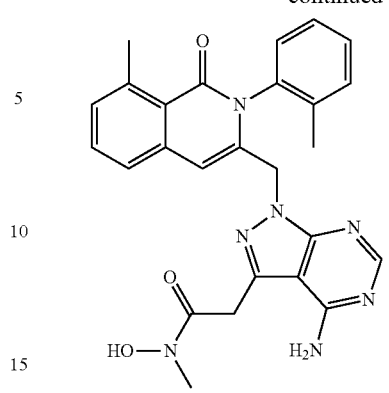
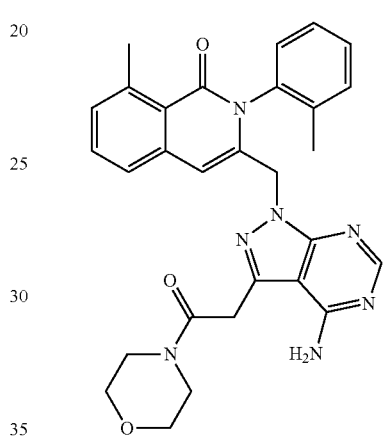
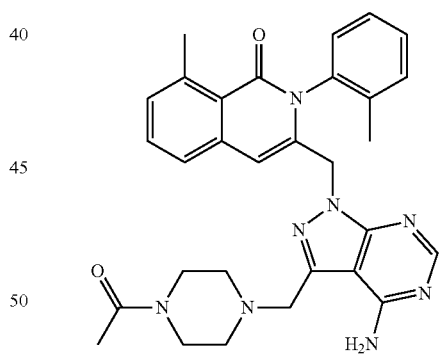
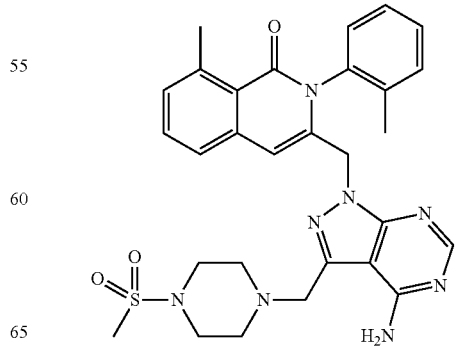

123
-continued
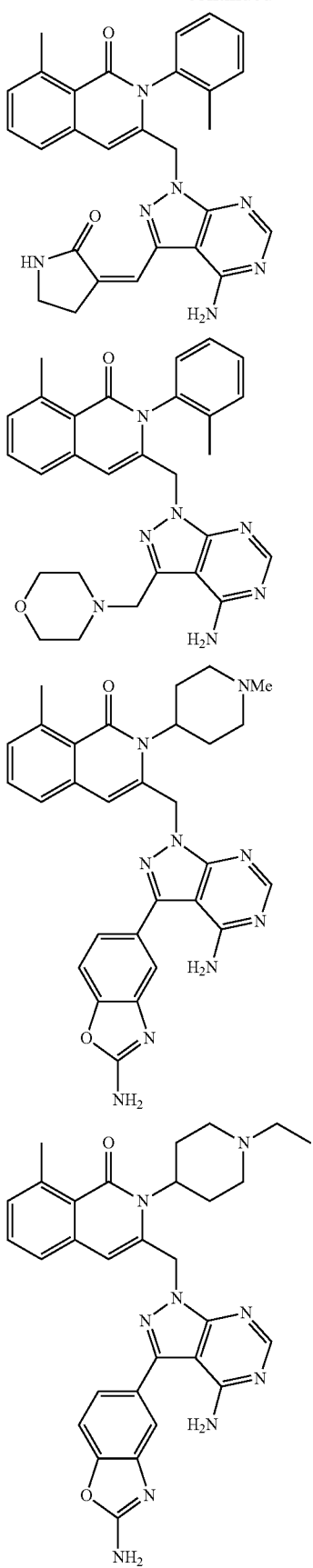
124
-continued
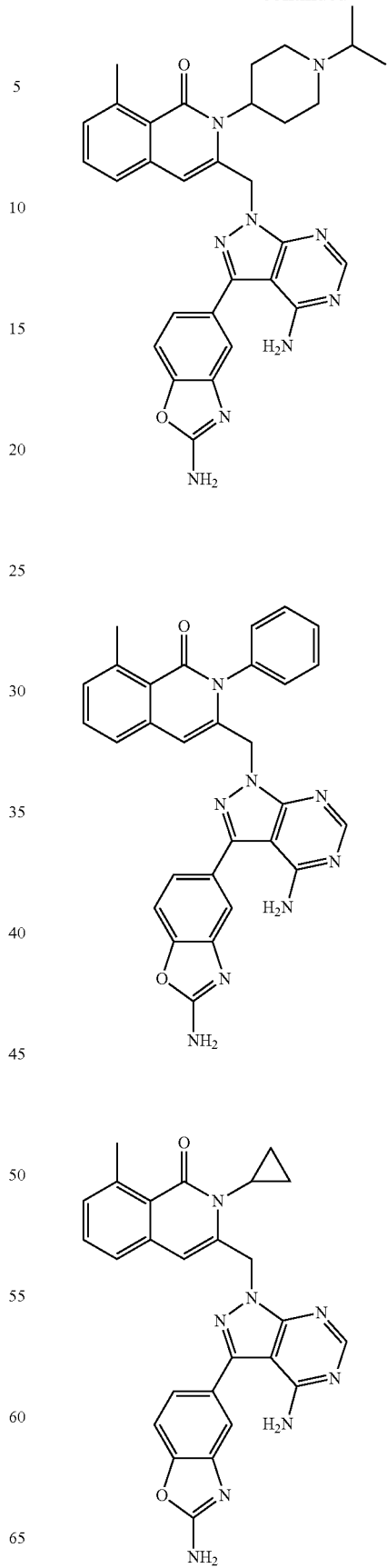

125
-continued
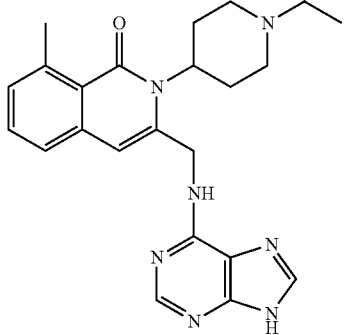
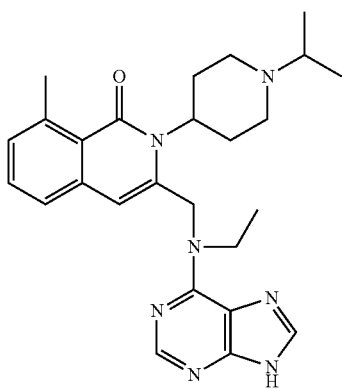
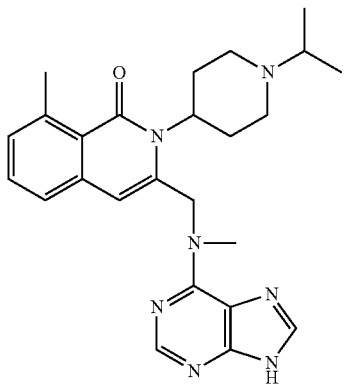
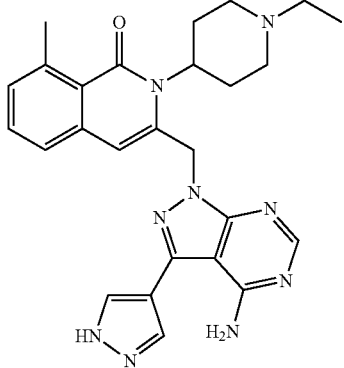
126
-continued
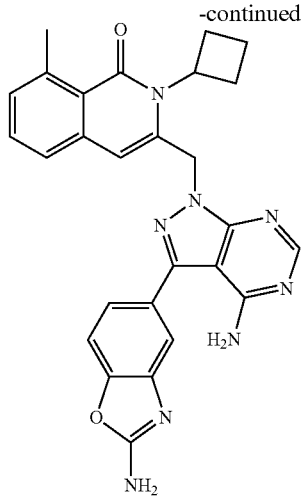
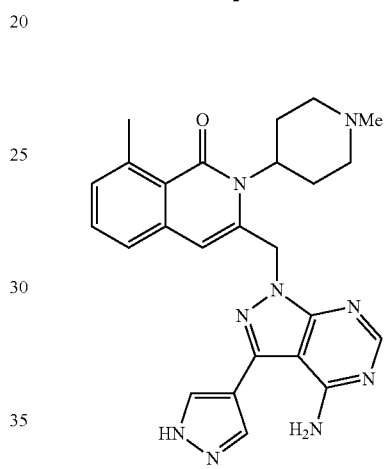
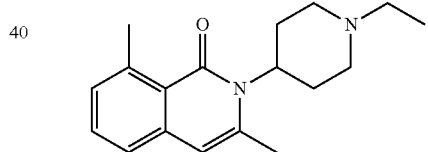
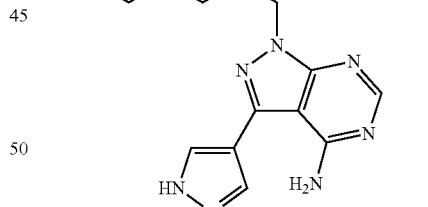
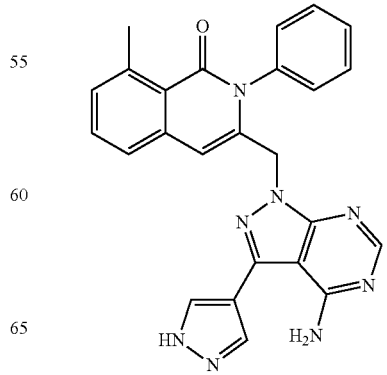

127
-continued
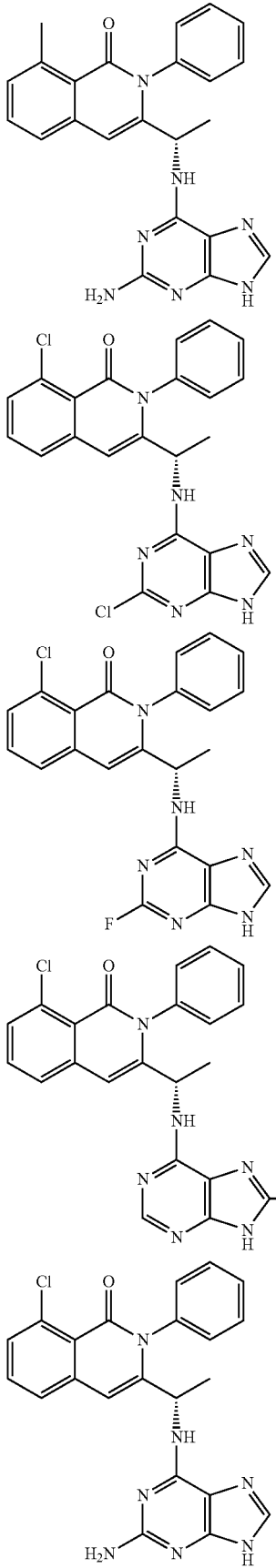
128
-continued
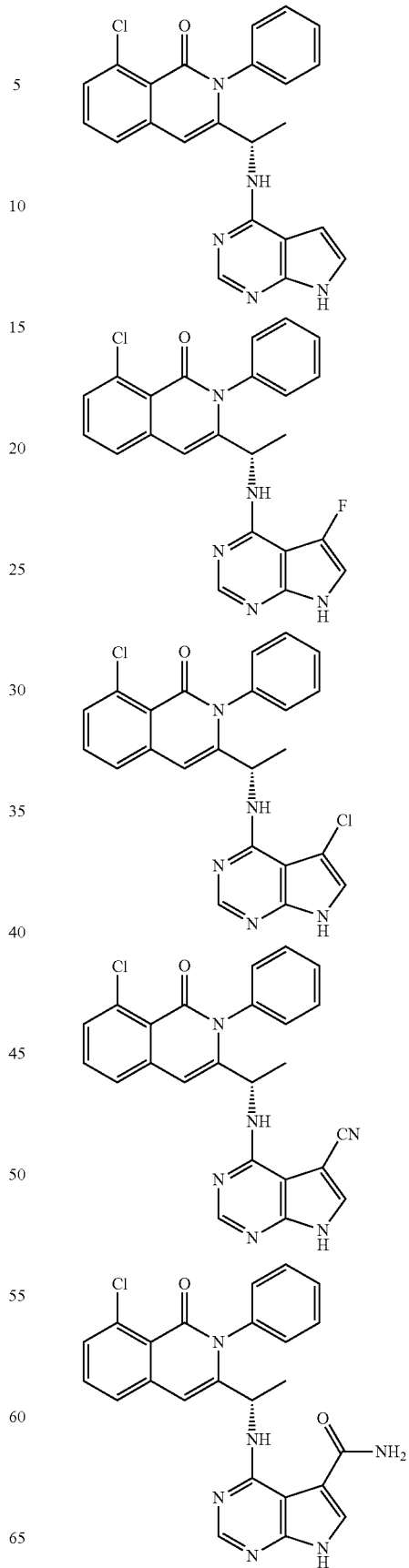

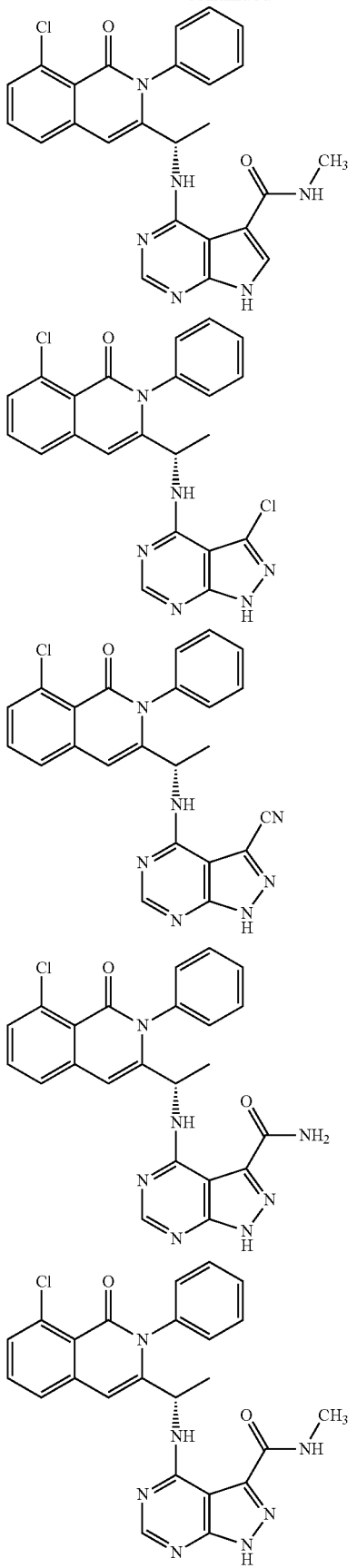
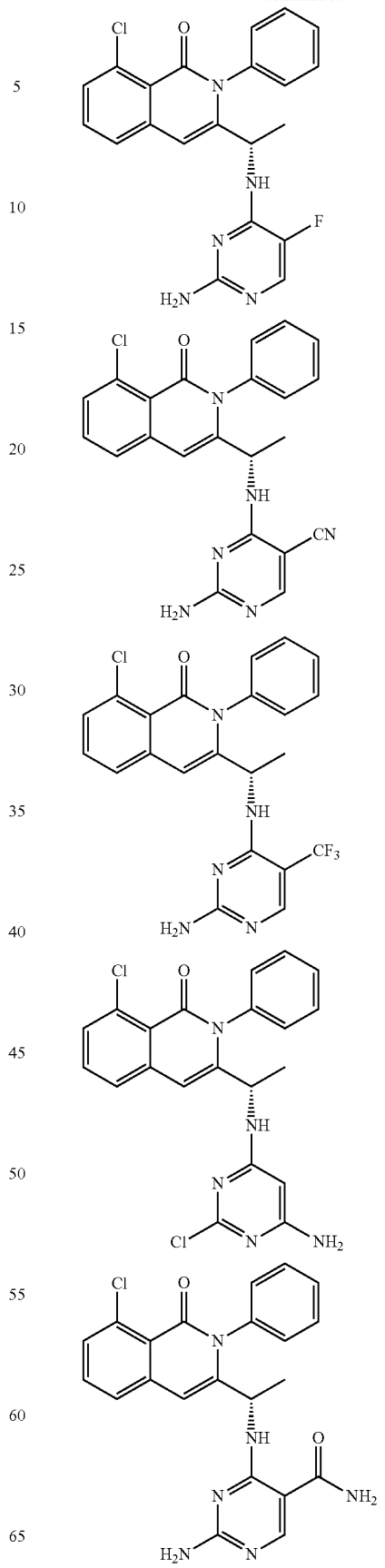

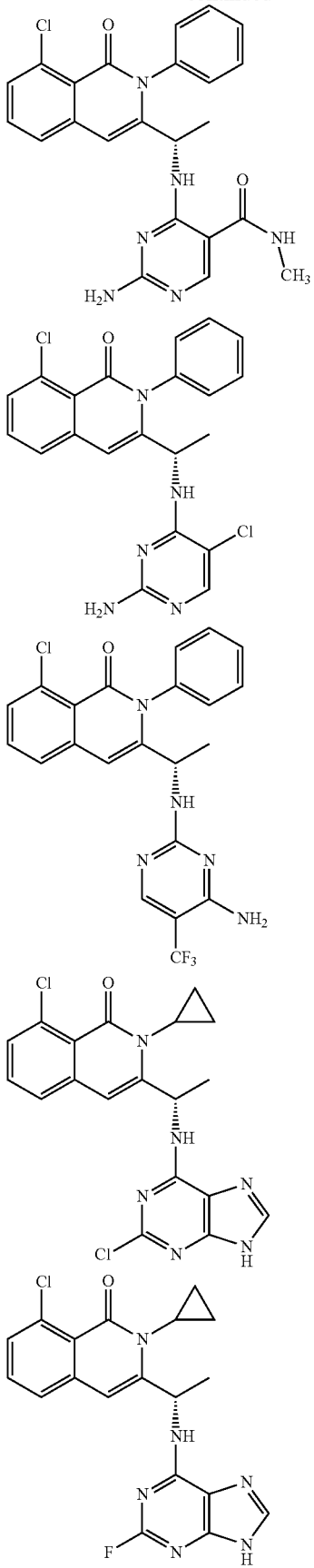
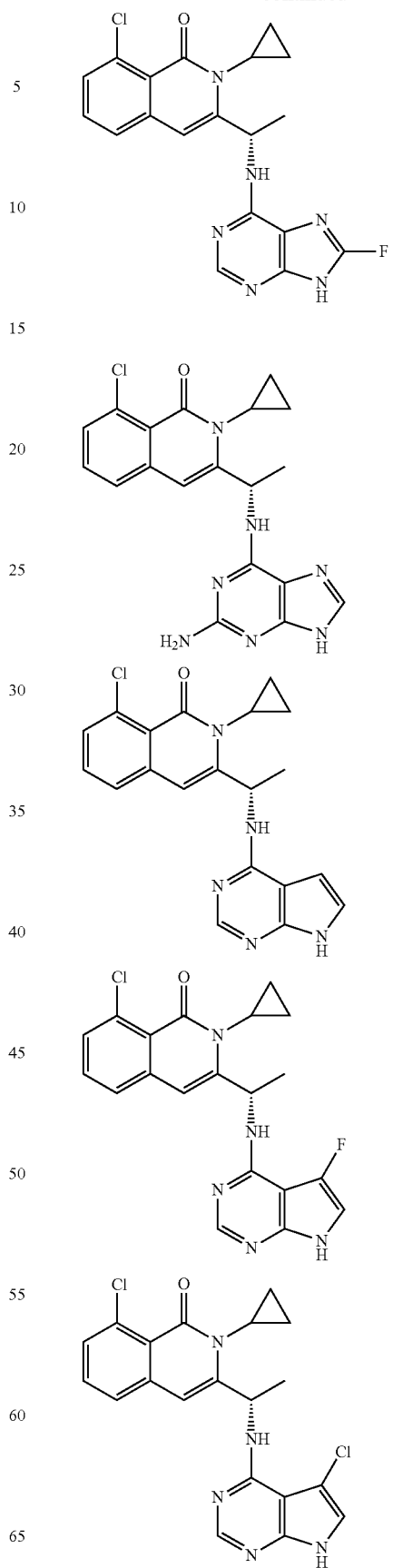

133
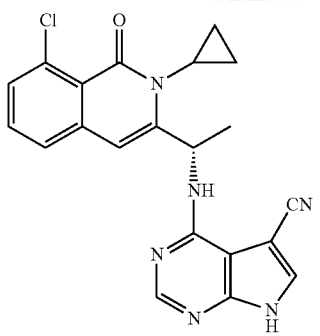
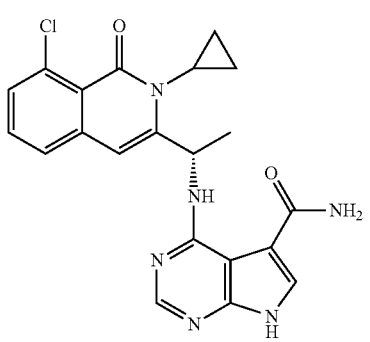
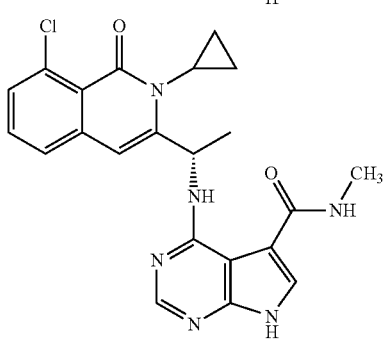
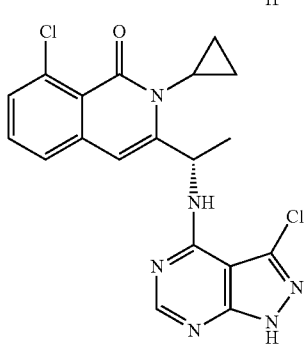
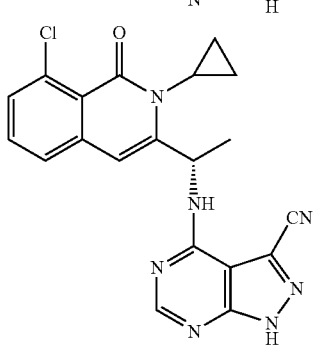
134
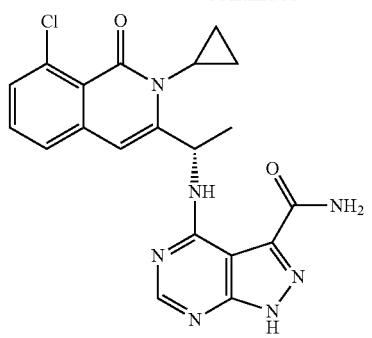
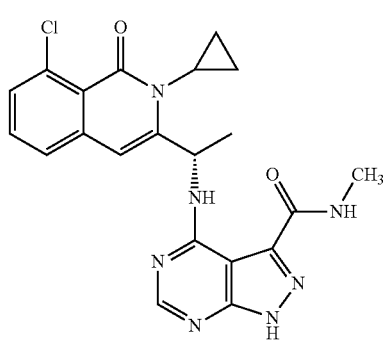
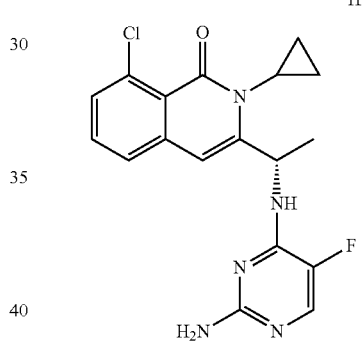
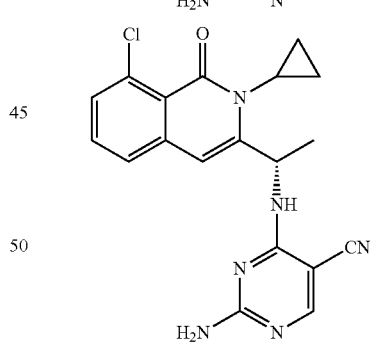
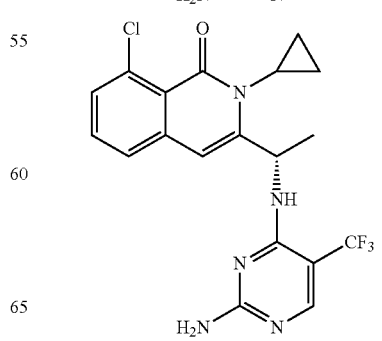

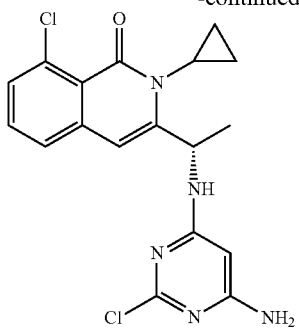

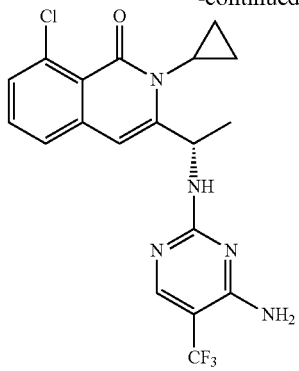

In some embodiments, the PI3K inhibitor is a compound of Formula I-1:

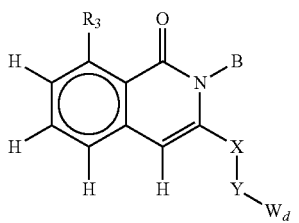

Formula I-1 or its pharmaceutically acceptable salt thereof, wherein B is a moiety of Formula II:

Formula II wherein $W_c$ is aryl, heteroaryl, heterocycloalkyl, or cycloalkyl, and
q is an integer of 0, 1, 2, 3, or 4;
X is a bond or —(CH($R^9$))$_z$—, and z is an integer of 1;
Y is —N($R^9$)—;
$W_d$ is:

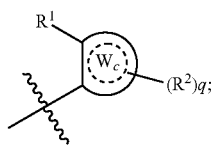

$R^1$ is hydrogen, alkyl, alkenyl, alkynyl, alkoxy, amido, alkoxycarbonyl, sulfonamido, halo, cyano, or nitro;
$R^2$ is alkyl, alkenyl, alkynyl, cycloalkyl, heterocycloalkyl, aryl, heteroaryl, heteroarylalkyl, alkoxy, amino, halo, cyano, hydroxy or nitro;
$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro; and each instance of $R^9$ is independently hydrogen, alkyl, or heterocycloalkyl.

In some embodiments, the compound is predominately in an (S)-stereochemical configuration In some embodiments, X is —(CH(R⁹))$_z$—, and Y is —NH—.

In some embodiments, R³ is —H, —CH₃, —CH₂CH₃, —CF₃, —Cl or —F.

In some embodiments, B is a moiety of Formula II:

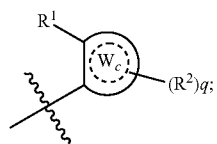

Formula II wherein W$_c$ is aryl, heteroaryl, heterocycloalkyl, or cycloalkyl;
q is an integer of 0 or 1;
R¹ is hydrogen, alkyl, or halo;
R² is alkyl or halo;
R³ is hydrogen, alkyl, or halo; and, optionally wherein the compound has one or more of the following features:
  (i) X is —CH(R⁹))$_z$—, wherein R⁹ is methyl and z=1; and W$_d$ is

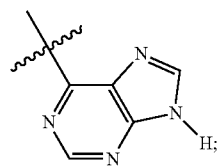

and/or
  (ii) R³ is methyl or chloro.

In some embodiments, the compound has a structure of Formula V-A2:

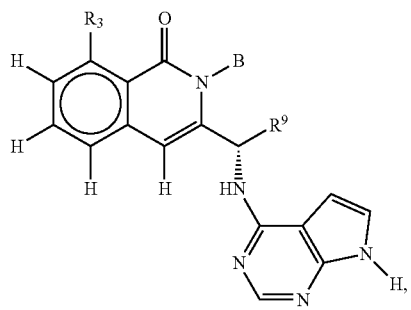

optionally wherein
(i) B is a moiety of Formula II:

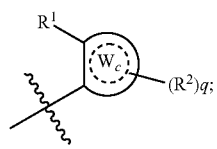

Formula II and W$_c$ is aryl or cycloalkyl, and/or (ii) R³ is methyl or chloro and further, optionally wherein one or more of the following also applies: (a) R⁹ is methyl or ethyl, (b) B is substituted or unsubstituted phenyl, (c) B is substituted or unsubstituted cycloalkyl. In some embodiments where B is substituted phenyl, B is substituted with fluoro. In some embodiments, B is phenyl that is substituted with one fluoro in the ortho or meta position of the phenyl ring.

In some embodiments, a compound used as described herein is selected from

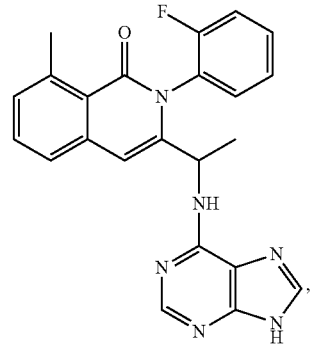

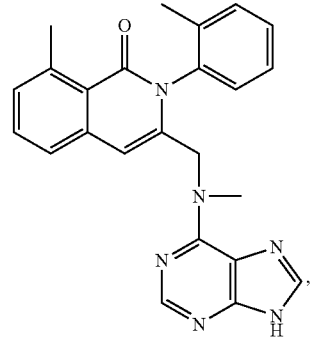

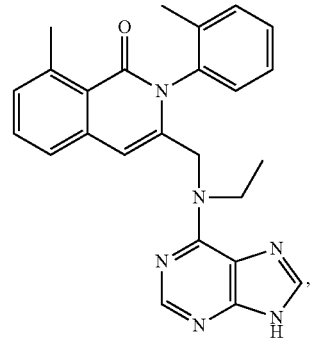

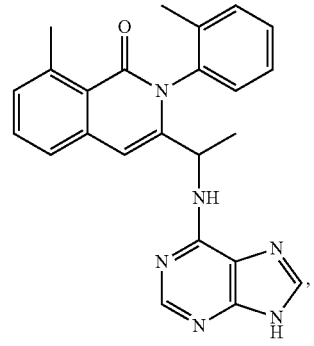

139
-continued
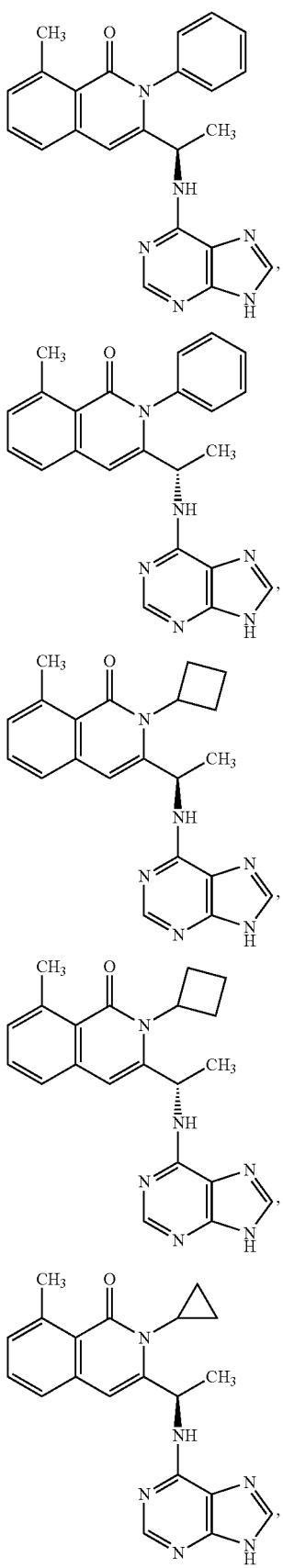
140
-continued
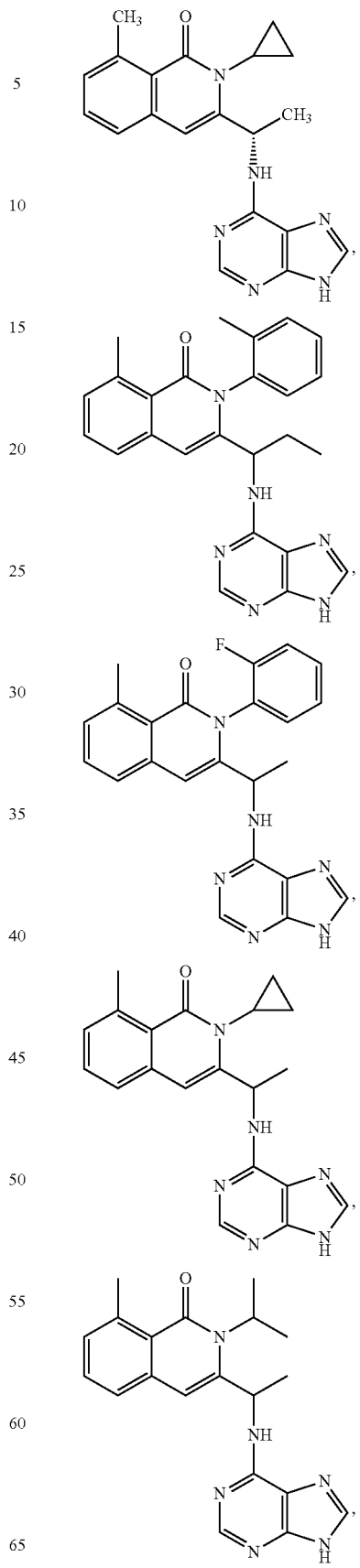

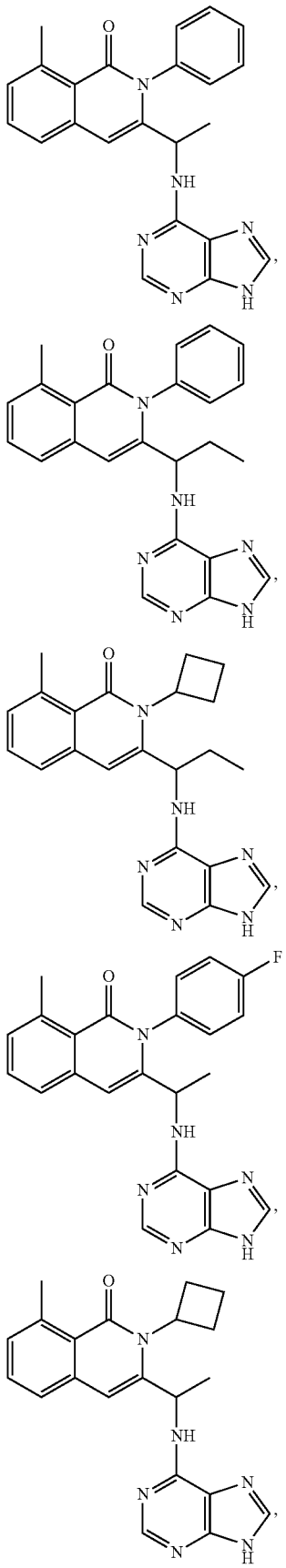

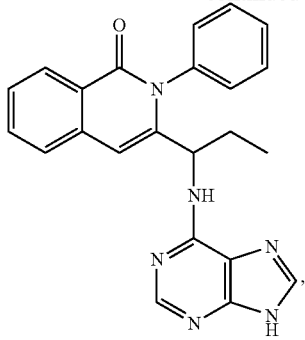
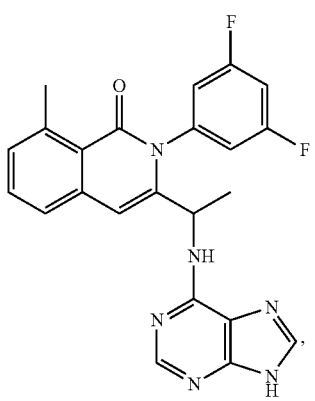
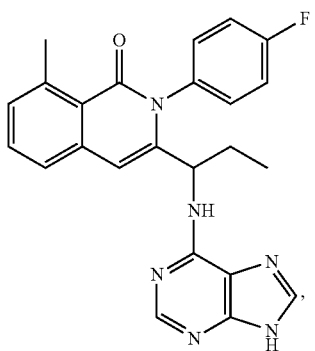
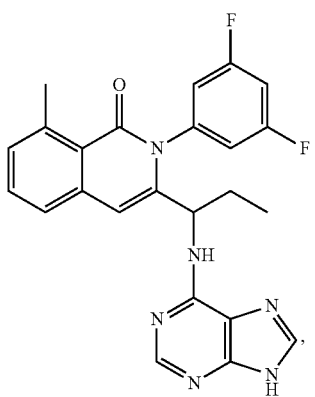
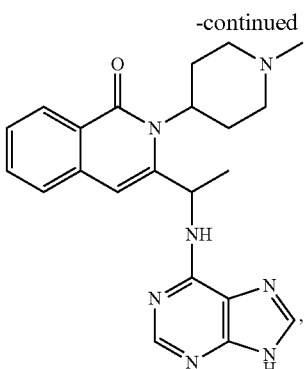
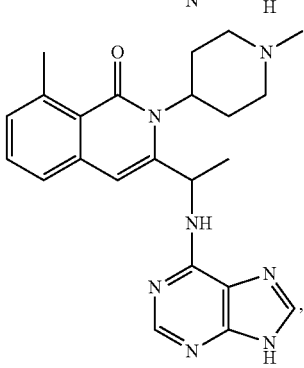
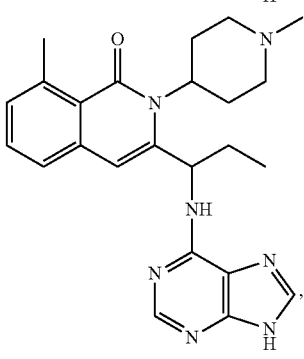
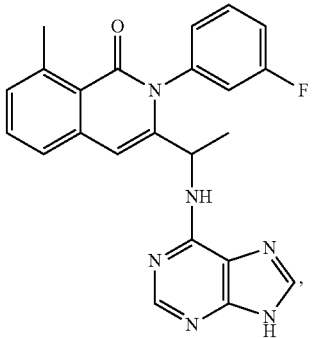
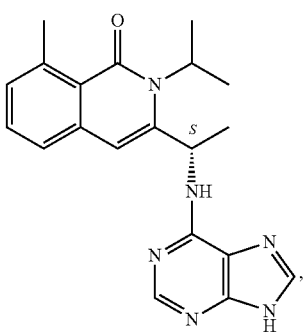

145
-continued
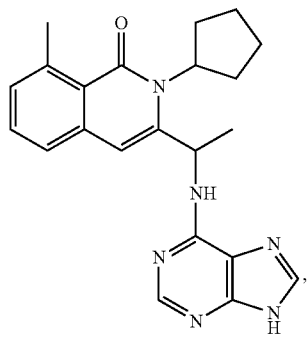
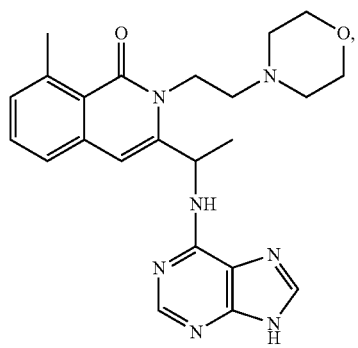
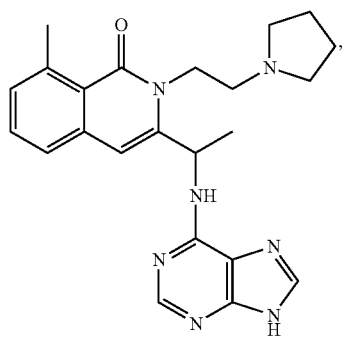
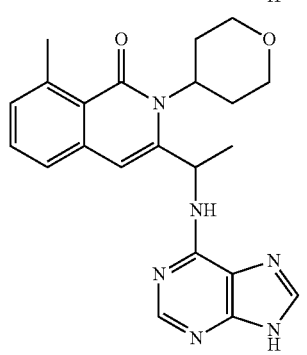
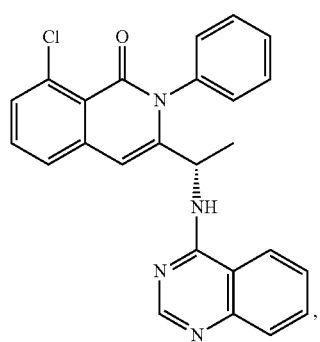
146
-continued
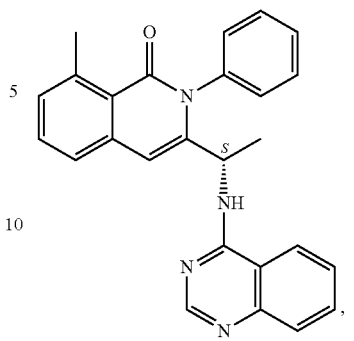
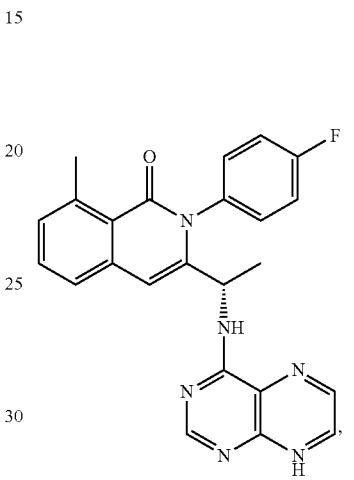
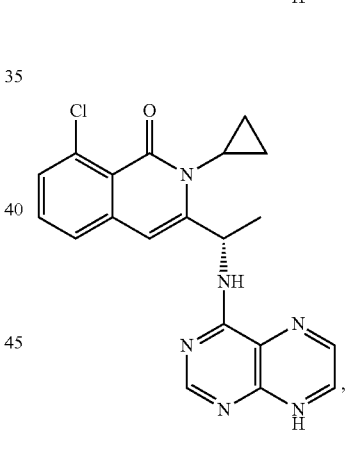
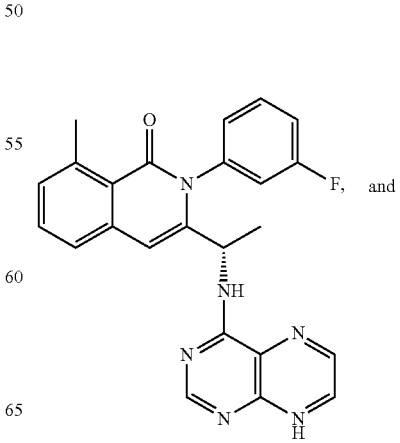
, and

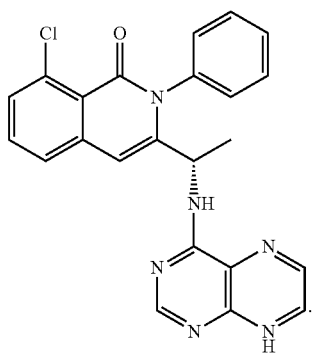 [SMILES: C[C@H](Nc1ncnc2nccnc12)c1cc2cccc(Cl)c2c(=O)n1-c1ccccc1]
In some embodiments, the compound is selected from
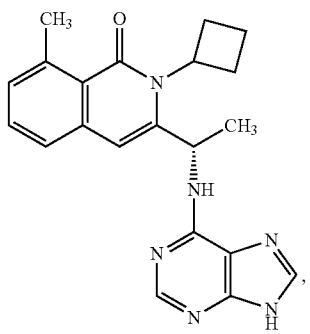
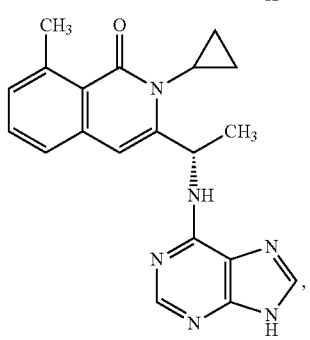
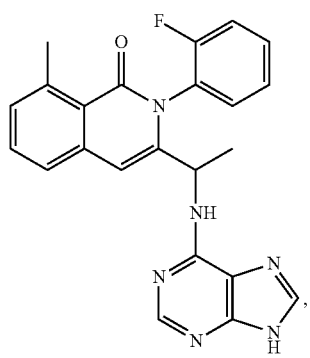
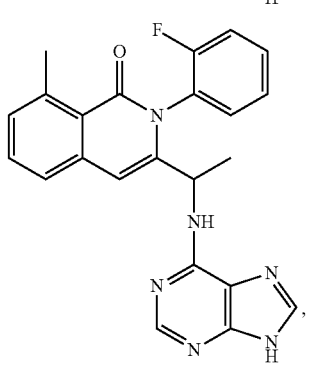
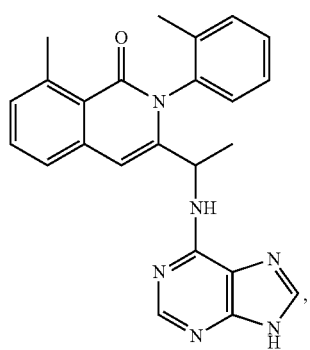
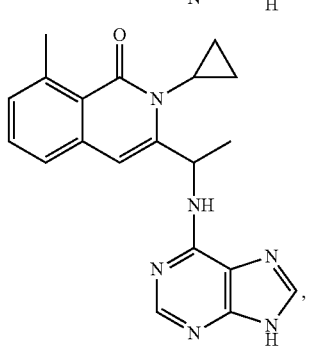
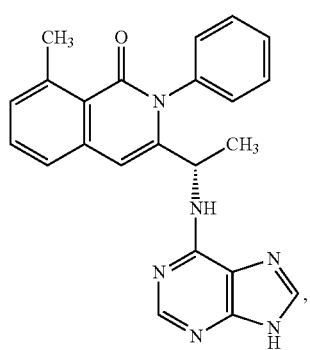
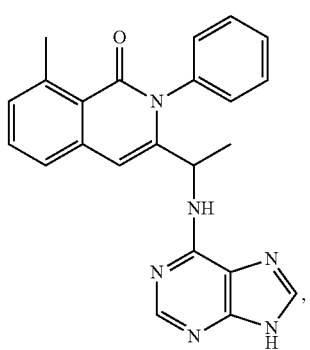

149
-continued
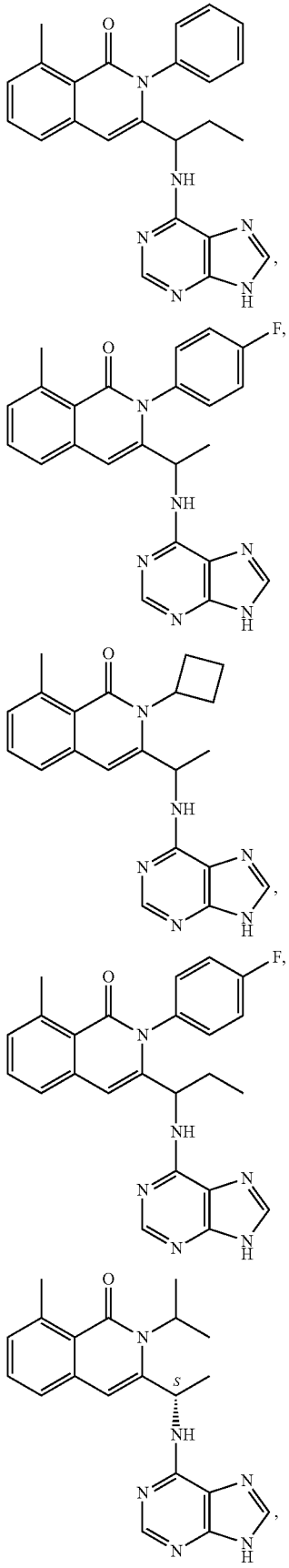
150
-continued
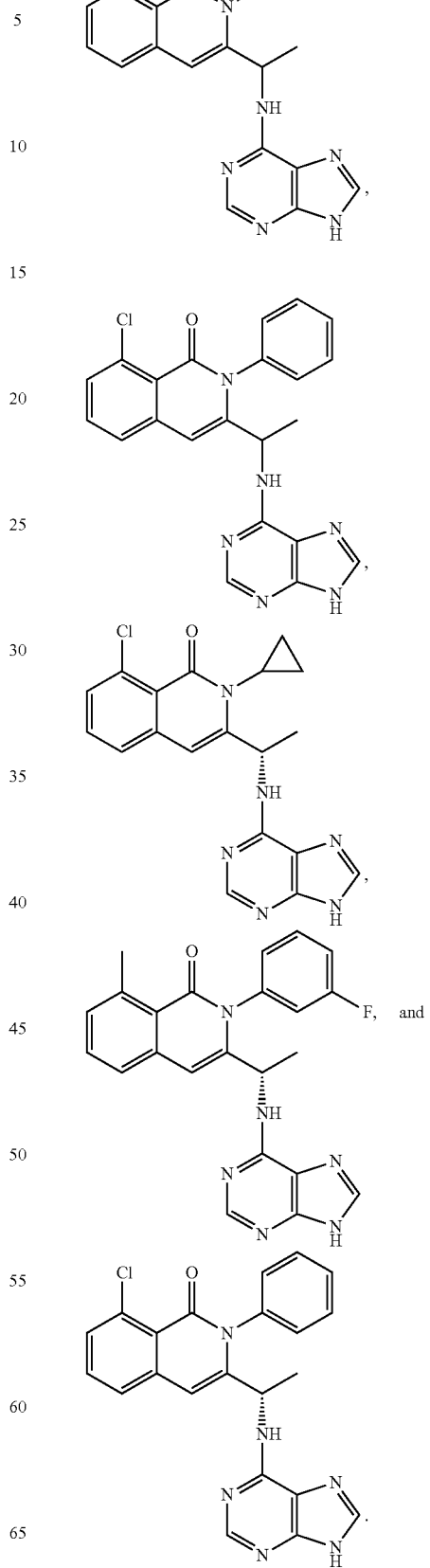

In some embodiments, the compound is selected from
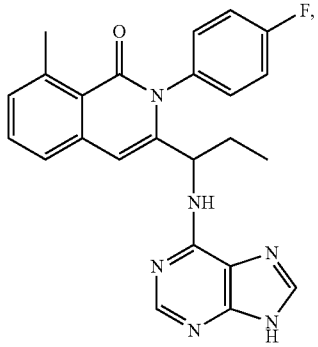
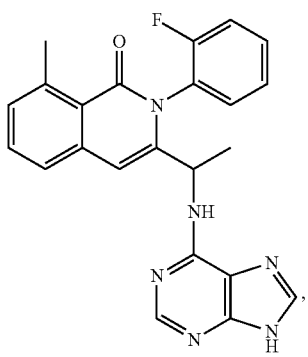
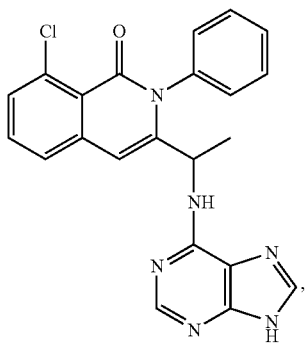
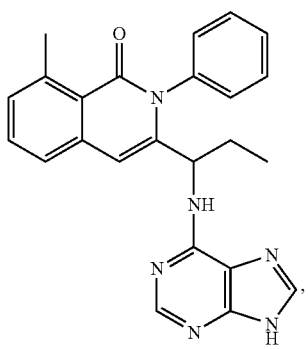
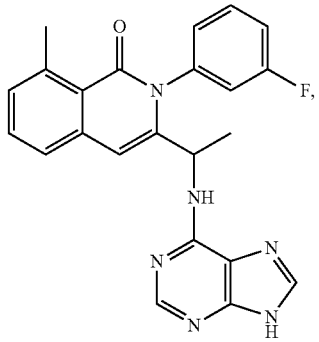
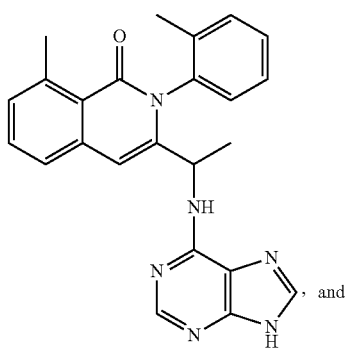, and
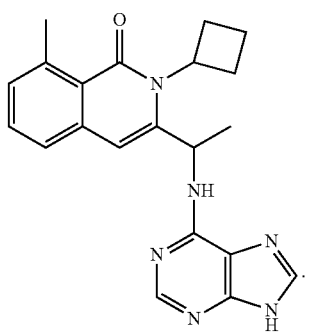
In some embodiments, the PI3K inhibitor has a formula selected from the group consisting of:
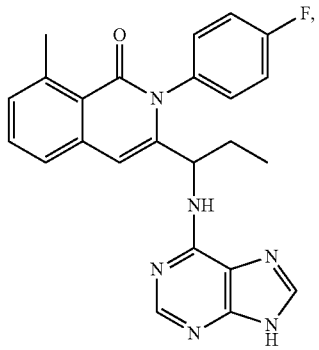

-continued
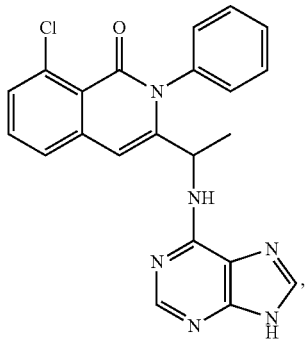
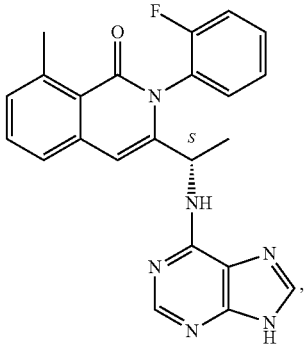
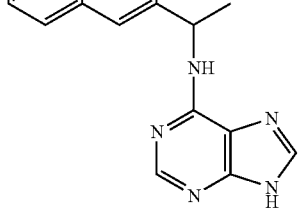, and
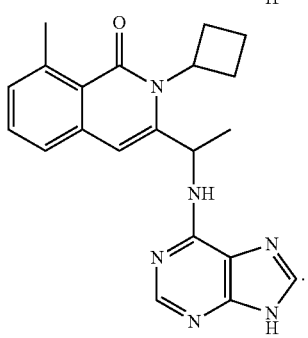
In some embodiments, the compound is the S-enantiomer having an enantiomeric purity selected from greater than about 55%, greater than about 80%, greater than about 90%, and greater than about 95%.
In some such embodiments, the compound is selected from:
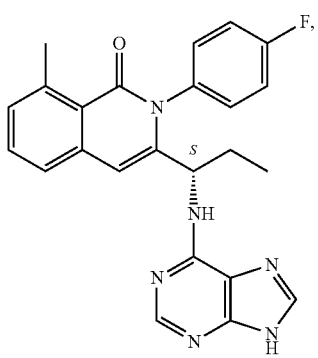

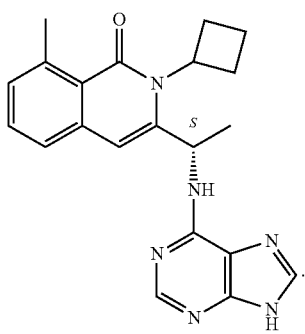
In some embodiments, the PI3K inhibitor has a formula selected from the group consisting of:
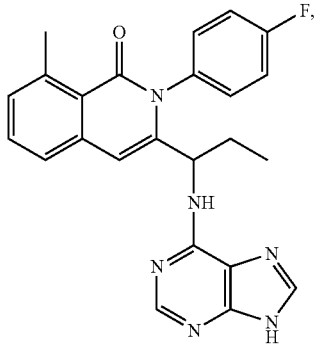
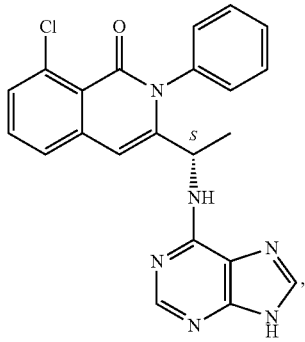 [SMILES: C[C@H](Nc1ncnc2[nH]cnc12)c1cc2cccc(Cl)c2c(=O)n1-c1ccccc1]
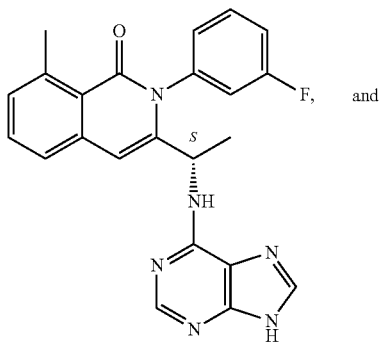
and
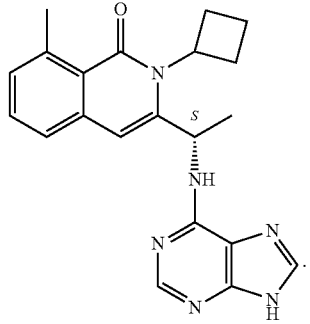
In certain such embodiments, the compound is
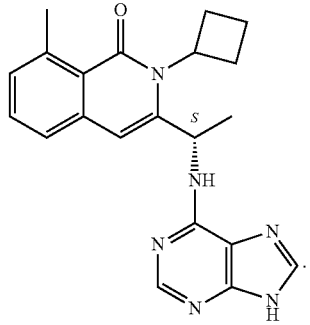
In other such embodiments, the compound is
In yet other such embodiments, the compound is In some embodiments, the compound has the following structure:

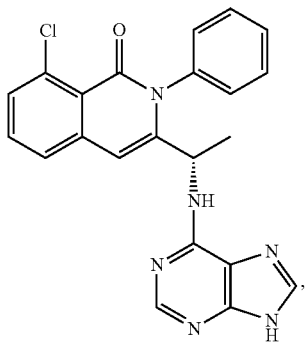

which is also referred to herein as Compound 292.

In some embodiments, a polymorph of a compound disclosed herein is used. Exemplary polymorphs are disclosed in U.S. Patent Publication No. 2012-0184568 ("the '568 publication"), which is hereby incorporated by reference in its entirety.

In one embodiment, the compound is Form A of Compound 292, as described in the '568 publication. In another embodiment, the compound is Form B of Compound 292, as described in the '568 publication. In yet another embodiment, the compound is Form C of Compound 292, as described in the '568 publication. In yet another embodiment, the compound is Form D of Compound 292, as described in the '568 publication. In yet another embodiment, the compound is Form E of Compound 292, as described in the '568 publication. In yet another embodiment, the compound is Form F of Compound 292, as described in the '568 publication. In yet another embodiment, the compound is Form G of Compound 292, as described in the '568 publication. In yet another embodiment, the compound is Form H of Compound 292, as described in the '568 publication. In yet another embodiment, the compound is Form I of Compound 292, as described in the '568 publication. In yet another embodiment, the compound is Form J of Compound 292, as described in the '568 publication.

Any of the compounds (PI3K inhibitors) disclosed herein can be in the form of pharmaceutically acceptable salts, hydrates, solvates, chelates, non-covalent complexes, isomers, prodrugs, isotopically labeled derivatives, or mixtures thereof.

Chemical entities described herein can be synthesized according to exemplary methods disclosed in U.S. Patent Publication No. US 2009/0312319, International Patent Publication No. WO 2011/008302A1, and U.S. Patent Publication No. 2012/0184568, each of which is hereby incorporated by reference in its entirety, and/or according to methods known in the art.

Pharmaceutical Compositions

The compounds disclosed herein can be formulated as pharmaceutical compositions.

In some embodiments, the pharmaceutical compositions comprise a compound disclosed herein, or a pharmaceutically acceptable salt thereof. In some embodiments, the pharmaceutical composition comprises two, three, four, or more compounds disclosed herein, or pharmaceutically acceptable salts thereof, as described herein. In some embodiments, the composition comprises a pharmaceutically acceptable excipient. In some embodiments, the composition comprises a plurality of pharmaceutically acceptable excipients.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other additional therapies (e.g., one or more additional agents, which are also typically administered in the form of pharmaceutical compositions). Where desired, the subject compounds and other agent(s) can be mixed into a preparation or both components can be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that can be used. An exemplary dosage is 10 to 30 mg per day. The exact dosage will depend upon the route of administration, the form in which the compound is administered, the subject to be treated, the body weight of the subject to be treated, and the preference and experience of the attending physician.

Described below are non-limiting exemplary pharmaceutical compositions and methods for preparing the same.

Pharmaceutical Compositions for Oral Administration.

In some embodiments, a pharmaceutical composition for oral administration is used, wherein the composition comprises a compound of the present invention, and a pharmaceutical excipient suitable for oral administration.

In some embodiments, a solid pharmaceutical composition for oral administration is used, wherein the composition comprises (i) an effective amount of a compound of the present invention; and optionally, (ii) an effective amount of a second agent; and (iii) a pharmaceutical excipient suitable for oral administration. In some embodiments, the composition further contains: (iv) an effective amount of a third agent.

In some embodiments, the pharmaceutical composition can be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The pharmaceutical compositions can be anhydrous pharmaceutical compositions and dosage forms comprising an active ingredient, since water can facilitate the degradation of some compounds. For example, water can be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the compositions to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyllaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein can be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition can include a solubilizer to ensure good solubilization and/or dissolution of the compound of the present invention and to minimize precipitation of the compound of the present invention. This can be especially important for compositions for non-oral use, e.g., compositions for injection. A solubilizer can also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, 6-valerolactone and isomers thereof, $\beta$-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer can also be used, such as 5%, 2%, 1% or even less. Typically, the solubilizer can be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base can be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the pharmaceutical composition is a composition for injection containing a compound as disclosed herein and a pharmaceutical excipient suitable for injection. Components and amounts of agents in the compositions are as described herein.

The forms in which the compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

In some embodiments, the pharmaceutical composition is a composition for transdermal delivery containing a compound of the present invention and a pharmaceutical excipient suitable for transdermal delivery.

Compositions can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such patches can be used to provide continuous or discontinuous infusion of a compound in controlled amounts, either with or without one or more additional agents.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. Preferably the compositions are administered by the oral or nasal respiratory route for local or systemic effect. Compositions in preferably pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can be administered, preferably orally or nasally, from devices that deliver the formulation in an appropriate manner Other Pharmaceutical Compositions.

Pharmaceutical compositions can also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also abe administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range can be more than adequate, while in other cases still larger doses can be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes can be used as appropriate. A single dose of a compound of the invention can also be used for treatment of an acute condition.

In some embodiments, a compound is administered in multiple doses. Dosing can be about once, twice, three times, four times, five times, six times, or more than six times per day. Dosing can be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compound can continue as long as necessary. In some embodiments, the compound is administered for more than 1, 2, 3, 4, 5, 6, 7, 14, or 28 days. In some embodiments, the compound is administered for less than 28, 14, 7, 6, 5, 4, 3, 2, or 1 day. In some embodiments, the compound is administered chronically on an ongoing basis, e.g., for the treatment of chronic effects.

An effective amount of a compound can be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions can also be delivered via an impregnated or coated device such as a stent, for example, or an artery-inserted cylindrical polymer. Such a method of administration can, for example, aid in the prevention or amelioration of restenosis following procedures such as balloon angioplasty. Without being bound by theory, compounds of the invention can slow or inhibit the migration and proliferation of smooth muscle cells in the arterial wall which contribute to restenosis. A compound can be administered, for example, by local delivery from the struts of a stent, from a stent graft, from grafts, or from the cover or sheath of a stent. In some embodiments, a compound of the invention is admixed with a matrix. Such a matrix can be a polymeric matrix, and can serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g. PEO-PLLA); polydimethylsiloxane, poly (ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices can be non-degrading or can degrade with time, releasing the compound or compounds. A compound can be applied to the surface of the stent by various methods such as dip/spin coating, spray coating, dip-coating, and/or brush-coating. A compound can be applied in a solvent and the solvent can be allowed to evaporate, thus forming a layer of compound onto the stent. Alternatively, a compound can be located in the body of the stent or graft, for example in microchannels or micropores. When implanted, the compound diffuses out of the body of the stent to contact the arterial wall. Such stents can be prepared by dipping a stent manufactured to contain such micropores or microchannels into a solution of the compound of the invention in a suitable solvent, followed by evaporation of the solvent. Excess drug on the surface of the stent can be removed via an additional brief solvent wash. In yet other embodiments, a compound can be covalently linked to a stent or graft. A covalent linker can be used which degrades in vivo, leading to the release of the compound. Any bio-labile linkage can be used for such a purpose, such as ester, amide or anhydride linkages. A Compound can additionally be administered intravascularly from a balloon used during angioplasty. Extravascular administration of a compounds via the pericard or via advential application of a formulation described herein can also be performed.

A variety of stent devices which can be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

The compounds of the invention can be administered in dosages. It is known in the art that due to intersubject variability in compound pharmacokinetics, individualization of dosing regimen is necessary for optimal therapy. Dosing for a compound of the invention can be found by routine experimentation in light of the instant disclosure.

When a compound of the invention, is administered in a composition that comprises one or more agents, and the agent has a shorter half-life than the compound of the invention unit dose forms of the agent and the compound of the invention can be adjusted accordingly.

The subject pharmaceutical composition can, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition can be in unit dosage forms suitable for single administration of precise dosages. The pharmaceutical composition will include a conventional pharmaceutical carrier or excipient and a compound according to the invention as an active ingredient. In addition, it can include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The activity of the compounds of the present invention may be determined using any method known in the art, or any method described herein. For example, the activity of the kinase may be assessed, e.g., by measuring the incorporation of $\gamma$-$^{33}$P-phosphate from $\gamma$-$^{33}$P-ATP onto N-terminal His tagged substrate, which is expressed in $E.$ $coli$ and is purified by conventional methods, in the presence of the kinase. The assay may be carried out in 96-well polypropylene plate. The incubation mixture (100, μL) may comprise 25 mM Hepes, pH 7.4, 10 mM $MgCl_2$, 5 mM β-glycerolphosphate, 100 μM Na-orthovanadate, 5 mM DTT, 5 nM kinase, and 1 μM substrate. Inhibitors may be suspended in DMSO, and all reactions, including controls may be performed at a final concentration of 1% DMSO. Reactions may be initiated by the addition of 10 μM ATP (with 0.5 μCi $\gamma$-$^{33}$P-ATP/well) and incubated at ambient temperature for a suitable time, e.g., for 45 minutes. Equal volume of 25% TCA may be added to stop the reaction and precipitate the proteins. Precipitated proteins may be trapped onto glass fiber B filterplates, and excess labeled ATP washed off using a Tomtec MACH III harvestor. Plates may be allowed to air-dry prior to adding 30 μL/well of Packard Microscint 20, and plates may be counted using a Packard TopCount®.

Methods

Treatments for Lupus

In one aspect, a method of reducing a lupus associated symptom in a biological sample is disclosed. The method includes contacting the biological sample with a PI3K inhibitor (e.g., as a single agent or in combination with another agent or therapeutic modality), in an amount sufficient to decrease or inhibit lupus (e.g., to decrease lupus associated symptoms). In one embodiment, the method is carried out in vivo, for example, in a mammalian subject, e.g., an animal model or as part of therapeutic protocol.

As used herein, "contacting" can be direct (e.g., by direct application of the PI3K inhibitor to a biological sample, e.g., in vitro) or indirect (e.g., by administering the PI3K inhibitor to a subject (e.g., by any known administration route, e.g., orally), such that the PI3K inhibitor reaches an affected biological sample within the body.

As used herein, a "biological sample" includes, for example, a cell or group of cells (e.g., PBMCs, or plasmacytoid dendritic cell(s)), a tissue, or a fluid (e.g., whole blood or serum) that comes into contact with the PI3K inhibitor, thereby resulting in a decrease or inhibition of lupus or lupus associated symptoms. In some embodiments, the biological sample is present within or derived from a subject who has lupus, or from a subject at risk for developing lupus. In some embodiments, the biological sample can be contacted with the PI3K inhibitor outside the body and then introduced into the body of a subject (e.g., into the body of the subject from whom the biological sample was derived or into the body of a different subject). In some embodiments, the biological sample includes cells that express Toll-like receptor 7 (TLR7) and/or Toll-like receptor 9 (TLR9).

In some embodiments, the cell is a plasmacytoid dendritic cell. In some embodiments, contacting the plasmacytoid dendritic cell with a PI3K inhibitor ameliorates or prevents development of a CLE skin lesion.

Also disclosed herein are methods of treating or preventing lupus in a subject. The methods include administering a PI3K inhibitor (e.g., as a single agent or in combination with another agent or therapeutic modality), to a subject in need thereof, in an amount sufficient to decrease lupus or a lupus associated symptom in the subject.

Type I interferons (IFNs), especially IFN-α, have been implicated in the pathogenesis of autoimmune diseases such as lupus. See, e.g., Ohl, K. and Tenbrock, K. (2011) $Journal$ $of$ $Biomedicine$ $and$ $Biotechnology$, Article ID 432595 (14 pages). In particular, SLE patients frequently show enhanced levels of serum IFN-α and the IFN levels have been found to correlate with anti-dsDNA production and disease activity. IFN-α therapy can lead to autoantibody production and an SLE-like syndrome. Furthermore, many of the symptoms of SLE resemble symptoms of patients with influenza or side effects of IFN-α therapy, for example, fever, fatigue, and leucopenia. Genetic association studies have most frequently identified genes that are components of the upstream or downstream pathways of type I interferon, e.g., STAT4 and IRF5, as being associated with SLE. Additionally, both adult and pediatric SLE PBMCs show significant upregulation of IFN-regulated gene transcripts (the "interferon signature"), which is considered a biomarker for disease activity. See, e.g., Id.

Although leucocytes produce IFN, plasmacytoid dendritic cells (PDCs or pDCs) are the main producers; they produce 100-200 times more IFN than any other cell type. It is thought that PDCs can produce such high amounts of IFN because they constitutively express Toll-like receptor 7 (TLR7) and Toll-like receptor 9 (TLR9).

The formation of immune complexes is a hallmark of SLE. Causes of immune complex formation include increased apoptosis and defective clearance of apoptotic material, as well as high occurrence of autoantibodies. Id. Immune complexes induce IFN-α production by pDCs Immune complexes are internalized after binding Fc gamma RIIa on the surface of pDCs and activate TLR9 and TLR7 in the endosomal compartment, which induces IFN-α secretion. Id. Overproduction of IFNs in lupus creates a vicious cycle, exerting wide effects that result in further enhanced synthesis of IFN. These effects are summarized in Ohl, K. and Tenbrock, K. (2011) $Journal$ $of$ $Biomedicine$ $and$ $Biotechnology$, Article ID 432595 (14 pages).

In human lupus (e.g., SLE and CLE), plasmacytoid dendritic cells (PDCs) actively produce IFN-α in response to endogenous TLR ligands derived from chronic inflammation. This results in a type 1 IFN gene signature. Type 1 IFNs (e.g., IFN-α) modulate autoimmunity by promoting CD maturation, T-cell survival, B-cell differentiation, immunoblogulin class switching and antibody production. See, e.g., Ghoreishi, M. and Dutz, J. P. (2009) *Lupus,* 19: 1029-1035.

In some embodiments, the subject is a mammal. In some embodiments, the subject is a human.

As used herein, a "symptom" associated with lupus includes, for example, any signs or symptoms of lupus as disclosed herein or as known in the art (e.g., joint pain and stiffness; muscle aches, pains, or weakness, fever; malaise; cutaneous manifestations (e.g., butterfly-shaped rash across the nose and cheeks; other skin rashes); unusual weight loss or weight gain; anemia; neurological or neuropsychiatric manifestations (e.g., trouble thinking, memory problems, confusion, depression, headache, seizures, strokes); kidney problems (e.g., nephritis, e.g., glomerulonephritis); chest pain; sun or light sensitivity; hair loss; Raynaud's phenomenon; vascular lesions or other vascular manifestations (e.g., Raynaud's phenomenon, nail fold telangiectasia and infarct, splinter haemorrhages, chilblain LE, acquired C1 esterase deficiency, vasculitis, urticarial vasculitis, purpura, thrombophlebitis, livedo reticularis, antiphospholipid syndrome, Degos syndrome and calcinosis)) as well as biological concomitants of lupus as disclosed herein or as known in the art (e.g., immune complexes, elevated levels of cytokines (e.g., interferons (e.g., Type I interferons, e.g., IFN-α and/or IFN-β); interleukins (e.g., IL-6, IL-8, IL-1, and IL-18) and TNF-α), elevated levels of anti-dsDNA autoantibodies, overexpression of IFN-α and/or IFN-β inducible genes, elevated levels of IP-10, elevated levels of sCD40L, reduced levels of C3-derived C3b, reduced peripheral iNKT cell frequencies, defective B cell-mediated stimulation of iNKT cells, altered CD1d expression on B cells, reduced numbers of natural regulatory T cells (Treg)). Symptoms can be assessed using assays and scales (e.g., Systemic Lupus Activity Measure-Revised (SLAM-R)) disclosed and/or exemplified herein and/or as known in the art. See, e.g., Willis, R. et al. (2012) *Lupus,* 21: 830-835; Yao, Y. et al. (2009) *Arthritis & Rheumatism,* 60(6): 1785-1796; Le Buanec, H. (2011) PNAS, 108(47):18995-19000; Bosma, A. et al. (2012) *Immunity,* 36, 477-490; Wenzel, J. et al. (2010) *Lupus,* 19: 1020-1028.

In some embodiments, the symptom is nephritis (e.g., glomerulonephritis), proteinuria, or spleen inflammation. In certain embodiments, the symptom is glomerulonephritis. In some embodiments, the symptom is an immune complex. In some embodiments, the symptom is a cutaneous manifestation of lupus. In some embodiments, the symptom is overexpression of IFN-α, TNF-α, IL-6, IL-8, or IL-1. In certain embodiments, the symptom is overexpression of IFN-α.

As used herein, to "decrease," "ameliorate," "reduce," "inhibit," "treat" (or the like) lupus or a symptom associated with lupus includes reducing (or preventing an increase in) the severity and/or frequency of one or more symptoms of lupus, as well as preventing lupus and/or one or more symptoms of lupus (e.g., by reducing (or preventing an increase in) the severity and/or frequency of flares of symptoms). In the context of biological molecules, to "decrease", "ameliorate," "reduce," "inhibit," or the like, includes decreasing the level (e.g., the level, e.g., of mRNA or protein, that can be measured in a biological sample) or the activity (e.g., the function) of the molecule.

In some embodiments, the symptom is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have lupus or the level in samples derived from subjects who do not have lupus). In some embodiments, the decrease is statistically significant, for example, as assessed using an appropriate parametric or non-parametric statistical comparison.

As used herein, "lupus" refers to all types and manifestations of lupus. Manifestations of lupus include, without limitation, systemic lupus erythematosus; lupus nephritis; cutaneous manifestations (e.g., manifestations seen in cutaneous lupus erythematosus, e.g., a skin lesion or rash); CNS lupus; cardiovascular, pulmonary, hepatic, haematological, gastrointestinal and musculoskeletal manifestations; neonatal lupus erythematosus; childhood systemic lupus erythematosus; drug-induced lupus erythematosus; anti-phospholipid syndrome; and complement deficiency syndromes resulting in lupus manifestations.

In some embodiments, the lupus is selected from systemic lupus erythematosus (SLE), cutaneous lupus erythematosus (CLE), drug-induced lupus, and neonatal lupus.

In some embodiments, the lupus is a CLE, e.g., acute cutaneous lupus erythematosus (ACLE), subacute cutaneous lupus erythematosus (SCLE), intermittent cutaneous lupus erythematosus (also known as lupus erythematosus tumidus (LET)), or chronic cutaneous lupus. In some embodiments, the intermittent CLE is selected from chronic discoid lupus erythematosus (CDLE) and lupus erythematosus profundus (LEP) (also known as lupus erythematosus panniculitis). Types, symptoms, and pathogenesis of CLE are described in Wenzel, J. et al. (2010), *Lupus,* 19, 1020-1028.

In certain embodiments, the subject is an animal model of lupus, a human with lupus, or a subject (e.g., a human) at risk for developing lupus. In some embodiments, the subject is a human who has a family history of lupus, who carries a gene associated with lupus, who is positive for a biomarker associated with lupus, or a combination thereof. In some embodiments, the subject has been diagnosed with lupus. In some embodiments, the subject has one or more signs or symptoms associated with lupus. In some embodiments, the subject is at risk for developing lupus (e.g., the subject carries a gene that, individually, or in combination with other genes or environmental factors, is associated with development of lupus).

In some embodiments, the subject exhibits elevated levels of antinuclear antibodies (e.g., anti-Smith antibodies, anti-double stranded DNA (dsDNA) antibodies, anti-U1 RNP, SS-a (or anti-Ro), SS-b (or anti-La)), antiphospholipid antibodies, anti-ss DNA antibodies, anti-histone antibodies, or anticardiolipin antibodies. In some embodiments, the subject exhibits elevated levels of anti-dsDNA antibodies. In some embodiments, the subject exhibits elevated levels of anti-Sm antibodies.

In some embodiments, the subject exhibits autoantibodies against one or more antigens that are known to be associated with lupus or with lupus subtypes. In some embodiments, the subject exhibits autoantibodies against Sm/anti-RNP or Ro/La autoantigens. See, e.g., Ching, K. H. et al. *PLoS ONE,* 7(2):e32001, doi:10/1271/journal.pone.0032001.

The levels of antibodies associated with lupus can be assessed using methods known in the art, e.g., indirect immunofluorescence. In some embodiments, the methods disclosed herein reduce or prevent an increase in the levels of one or more of the foregoing antibodies.

In some embodiments, the subject exhibits elevated levels of IFN-α, TNF-α, IL-6, IL-8, or IL-1. In certain embodiments, the subject exhibits elevated levels of IFN-α.

In some embodiments, the subject has a mutation (e.g., an SNP) in a gene associated with lupus. In one embodiment, the gene is selected from STAT4, IRF5, BANK1, ITGAM, PD1, FAM167A-BLK, IRF5-TNP03, KIAA1542, TNFAIP3, XKR6, 1q25.1, PXK, ATG5, ICA1, XKR6, LYN and SCUB2 or a combination thereof. See, e.g., Jarvinen, T. M. et al. (2012) *Rheumatology*, 51:87-92. In one embodiment, the subject is a non-European (e.g., an African American) who carries the disease risk allele of UBE2L3. See, e.g., Agik, S. et al. *Journal of Rheumatology* (2012), 39(1): 73-78.

In some embodiments, the subject carries the DR3 and DQ2 variants, or the DR2 and DQ6 variants of HLA class II genes.

In some embodiments, the subject has a deficiency in one or more complement proteins, e.g. a deficiency of a complement protein coded by the C4A or C2 genes on chromosome 6, or the C1r and C1s genes on chromosome 12.

In some embodiments, the subject is a subject who is suffering from an active lupus episode. In some embodiments, the subject has inactive lupus.

In some embodiments, the subject is an animal model of lupus Animal models of lupus are known in the art and include, e.g., the murine NZB/W F1 lupus model, which has many features of human lupus and is characterized by elevated levels of anti-nuclear and anti-dsDNA autoantibodies; an important role for plasmacytoid dendritic cells and IFN-α; T-cell, B-cell, macrophage involvement; pheymolytic anemia; progressive immune complex glomerulonephritis; proteinurea; severity and incidence more pronounced in females; and decreased survival. In some embodiments, lupus disease can be established at 23 weeks of age in the NZB/W F1 mouse model. In some embodiments, the mice can be administered daily treatments, e.g., daily treatments of Compound 292 over the following 20 weeks, at various concentrations, e.g., a concentration of 1 mg/kg, or 5 mg/kg, or 10 mg/kg. In some embodiments, blood and urine samples can be obtained throughout the testing period, and tested for antinuclear antibodies (in dilutions of serum) or protein concentration (in urine). In some embodiments, serum cam also tested for anti-ssDNA and anti-dsDNA antibodies by ELISA. In some some embodiments, glomerulonephritis can be assessed in kidney sections stained with H&E at the end of the study, or survival can also be an endpoint. For example, proteozome inhibitor Bortezimib is effective at blocking disease in the NZB/W model in both the prophylactic and therapeutic model with reductions in anto-antibody production, kidney damage, and improvements in survival (*Nature Medicine* 14: 748-755 (2008)). This established art model can be employed to demonstrate that the kinase inhibitors provided herein can suppress or delay the onset of lupus symptoms in lupus disease model mice.

Other animal models include, e.g., the MRL/1pr, NZB/W, and BSXB mouse strain, as well as transgenic forms of these. See, e.g., Ghoreishi, M. and Dutz, J. P. (2009) *Lupus*, 19: 1029-1035; Ohl, K. and Tenbrock, K. (2011) *Journal of Biomedicine and Biotechnology*, Article ID 432595 (14 pages). In some embodiments, the animal model is an animal (e.g., a mouse) that has been injected with *Trypanosoma equiperdum* (TE). See, e.g., Xia, Y. et al. (2011) *Rheumatology*, 50:2187-2196. Further animal models are described, e.g., in Pau, E. et al. (2012) *PLoS ONE*, 7(5):e36761 (15 pages); Mustafa, A. et al. (2011) *Toxicology*, 290:156-168; Ichikawa, H. T. et al. (2012) *Arthritis and Rheumatism*, 62(2): 493-503; Ouyang, S. et al. (2012) *J Mol Med*, DOI 10.1007/s00109-012-0866-3 (10 pages); Rankin, A. L. et al. (2012) *Journal of Immunology*, 188:1656-1667.

In some embodiments, the subject is female. In some embodiments, the subject is a female between the ages of 15 and 45. In some embodiments, the subject is not white (e.g., the subject is African-American, of African ancestry, of Latin American ancestry, of Asian ancestry, or of Native American ancestry). In some embodiments, the subject is a female who is not white. In some embodiments, the subject is of African ancestry. See, e.g., Ko, K. et al. (2012) *Journal of Rheumatology*, 39(1):73-78. In some embodiments, the subject is a female of African ancestry.

In some embodiments, the methods disclosed herein result in inhibition of immune complexes, cytokines (e.g., interferons (e.g., Type I interferons, e.g., IFN-α and/or IFN-β); interleukins (e.g., IL-6, IL-8, and IL-1) and TNF-α), anti-dsDNA autoantibodies, IFN-α and/or IFN-β inducible genes, IP-10, or sCD40L. See, e.g., Yao, Y. et al. *Arthritis & Rheumatism*, 60(6): 1785-1796.

In some embodiments, the methods disclosed herein result in inhibition of a Type I IFN (e.g., IFN-α).

In some embodiments, the methods disclosed herein result in modulation (e.g., inhibition) of a cytokine (e.g., a Type I IFN (e.g., IFN-α)) released as a result of TLR activation. In some embodiments, the TLR is TLR9. In some embodiments, the methods result in inhibition of IFN-α released as a result of TLR9 activation.

In some embodiments, the methods disclosed herein result in decreases in antinuclear antibodies (e.g., anti-Smith antibodies, anti-double stranded DNA (dsDNA) antibodies, or anti-histone antibodies.

In some embodiments, the method disclosed herein result in decreases in anticardiolipin antibodies.

In some embodiments, the lupus is systemic lupus erythematosus nephritis. Systemic lupus erythematosus nephritis is a prototypic antibody-mediated autoimmune disease where hyperactive helper T-cells drive polyclonal B-cell activation and secretion of pathogenic autoantibodies. The autoantibodies form immune complexes with their respective auto-antigens, depositing in sites such as the kidney initiating a destructive inflammatory process. This can result in lupus nephritis, in which circulating immune complexes deposit in the glomerular subendothelial space and in the mesangium, leading to deterioration of the glomerulus and eventual end-stage renal disease. The development of glomerular lesions involves multiple adhesion molecules cytokines, chemokines, growth factors, lipid mediators and Fc receptors. In some embodiments, the methods disclosed herein reduce nephritis (e.g., glomerulonephritis).

In some embodiments, the subject exhibits excessive PI3K activity or abnormal activity (e.g., excessive or reduced activity) of one or more components of the PI3K signaling pathway (e.g., Akt (PKB), mTOR, a Tec kinase (e.g., Btk, Itk, Tec), phospholipase C, PDK1, PKCs, NFκB, Rac GEF (e.g., Vav-1), or Rac).

Treatments for Fibrotic Conditions

The present invention provides methods of treating a fibrotic condition (e.g., a fibrosis) comprising administering a therapeutically effective amount of a PI3 kinase inhibitor, alone or in combination with one or more additional therapies (e.g., one or more additional therapeutic agents), to a subject in need thereof. In one embodiment, the PI3 kinase inhibitor is Compound 292. The invention also encompasses a composition for use, and use of, a PI3K inhibitor, alone or in combination with another agent, for preparation of one or more medicaments for use in treating a fibrotic condition.

The present invention also provides methods of reducing fibrosis in a cell or tissue. These methods include contacting a fibrotic cell or tissue with a PI3K inhibitor (e.g., as a single agent or in combination with another agent or therapeutic modality), in an amount sufficient to decrease or inhibit the fibrosis. These methods may be carried out in vitro or in vivo, for example, in a mammalian subject, e.g., an animal model or human. In one embodiment, the fibrosis is present in subject with a fibrotic condition.

As used herein, "fibrotic condition" refers to a disease or condition involving the formation and/or deposition of fibrous tissue, e.g., excessive connective tissue builds up in a tissue and/or spreads over or replaces normal organ tissue (reviewed in, e.g., Wynn, *Nature Reviews* 4:583-594 (2004) and Abdel-Wahab, O. et al. (2009) *Annu. Rev. Med.* 60:233-45, incorporated herein by reference). In certain embodiments, the fibrotic condition involves excessive collagen production and deposition. In certain embodiments, the fibrotic condition is caused, at least in part, by injury, e.g., chronic injury (e.g., an insult, a wound, a toxin, a disease). In further embodiments, the fibrotic condition is surgical-induced, burn-induced, or radiation-induced.

In some embodiments, the fibrotic condition is associated with excessive PI3K activity or abnormal activity (e.g., excessive or reduced activity) of one or more components of the PI3K signaling pathway (e.g., Akt (PKB), mTOR, a Tec kinase (e.g., Btk, Itk, Tec), phospholipase C, PDK1, PKCs, NFκB, Rac GEF (e.g., Vav-1), or Rac). In certain embodiments, the fibrotic condition is associated with an inflammatory, an autoimmune or a connective tissue disorder. For example, chronic inflammation in a tissue can lead to fibrosis in that tissue. Exemplary tissues in which fibrosis can develop include, but are not limited to, biliary tissue, liver tissue, lung tissue, heart tissue, vascular tissue, kidney tissue, skin tissue, gut tissue, peritoneal tissue, bone marrow, eye tissue, and the like. In certain embodiments, the tissue is epithelial tissue. In some embodiments, the fibrosis is systemic. In some embodiments, the fibrosis is associated with scleroderma.

Inhibition of a PI3K is useful for ameliorating fibrotic conditions and disorders, including reducing fibrosis, and/or having a protective effect by decreasing signs or symptoms of fibrosis. Such signs or symptoms may include decreased development of fibrotic lesions, a decrease in weight loss or other clinical symptoms, or altered expression of biological molecules (e.g., mRNA or protein expression) associated with development of a fibrotic condition.

Biological molecules associated with development of a fibrotic condition (e.g., systemic sclerosis) include, e.g., interferon-responsive genes (e.g., type I IFNs, e.g., IFNα and IFNβ), toll-like receptors (TLRs) and TLR ligands (e.g., autoantibodies (e.g., systemic sclerosis-associated autoantibodies) and TLR ligands generated from matrix molecules during tissue injury). See, e.g., Lafyatis, R. & York, M. (2009) *Current Opinion in Rheumatology*, 21:617-622. Other examples of biological molecules associated with development of a fibrotic condition include, e.g., PI3K, Akt, endothelin-1(ET-1), α-SMA, ezrin, paxillin, and moesin. See, e.g., Shi-Wen, X. et al. (2004) *Molecular Biology of the Cell*, 15: 2707-2719. Further examples of biological molecules associated with development of a fibrotic condition include, e.g., Akt, collagen, connective tissue growth factor (CCGF/CCN2), and protein phosphatase and tensin homolog (PTEN). See, e.g., Parapurman, S. K. et al. (1996) *Journal of Investigative Dermatology*, 131: 1996-2003. Yet other examples of biological molecules associated with development of a fibrotic condition include TGFβ, FAK, MEKK1, JNK, and α-SMA. See, e.g., Liu, S. et al. (2007) *Molecular Biology of the Cell*, 18: 2169-2178.

In some embodiments, biological molecules associated with development of a fibrotic condition are expressed and/or assessed in a fibroblast (e.g., a human lung fibroblast, e.g., an idiopathic pulmonary fibrosis fibroblast).

In some embodiments, a cell or tissue affected by the fibrotic condition (e.g., a fibroblast) expresses increased levels of a PI3 kinase (e.g., PI3K-β).

Exemplary fibrotic conditions that can be treated or prevented using the methods of the invention include, but are not limited to, a systemic fibrotic condition or a fibrotic condition of the lung, liver, heart, vasculature, kidney, skin, gastrointestinal tract, bone marrow, or a combination thereof. Each of these conditions is described in more detail herein.

Exemplary fibrotic conditions and disorders that can be treated with PI3K inhibitors include, but are not limited to, liver fibrosis, such as liver fibrosis associated with liver injury (e.g., liver injury caused by alcohol, viral infection (e.g., Hepatitis B and C infection); pulmonary fibrosis (e.g., lung fibrosis caused by smoking, drugs such as bleomycin); cardiac fibrosis; bone marrow fibrosis, kidney fibrosis, and ophthalmic fibrosis (e.g., glaucoma, age-related macular degeneration, diagetic macular edema, diabetic retinopathy, dry eye disease).

Opthalmic fibrosis or fibrosis of the eye can occur in response to injury, such as mechanical wound or various metabolic malfunctions (including, e.g., responses to inflammation, ischemia, and degenerative disease). Fibrotic conditions that affect the eye include anterior segment fibrotic diseases and posterior segment fibrotic diseases. See e.g., Friedlander, M. (2007) *Journal of Clinical Investigation*, 117 (3): 576-586. Anterior segment fibrotic diseases include, e.g., corneal opacification and glaucoma. Fibrosis in the context of posterior segment fibrotic disease may also be referred to as gliosis. Id. Examples of posterior segment fibrotic diseases include, e.g., retinopathies (e.g., diabetic retinopathy, proliferative vitreoretinopathy, retinopathy of prematurity), macular degeneration (e.g., age-related macular degeneration), and neovascular glaucoma.

In some embodiments, the fibrotic condition is an ophthalmic fibrotic disease or a fibrotic condition that affects the eye. In some embodiments, the fibrotic condition is an anterior segment fibrotic disease. In some embodiments, the fibrotic condition is selected from corneal opacification and glaucoma. In some embodiments, the fibrotic condition is a posterior segment fibrotic disease. In some embodiments, the fibrotic condition is a retinopathy. In some embodiments, the retinopathy is diabetic retinopathy. In some embodiments the fibrotic condition is macular degeneration. In some embodiments, the fibrotic condition is age-related macular degeneration.

Fibrosis of the lung (also referred to herein as "pulmonary fibrosis") is characterized by the formation of scar tissue within the lungs, which results in a decreased function. Pulmonary fibrosis is associated with shortness of breath, which progresses to discomfort in the chest weakness and fatigue, and ultimately to loss of appetite and rapid weight-loss. Approximately 500,000 people in the U.S. and 5 million worldwide suffer from pulmonary fibrosis, and 40,000 people in the U.S. die annually from the disease. Pulmonary fibrosis has a number of causes, including radiation therapy, but can also be due to smoking or hereditary factors (Meltzer, E B et al. (2008) *Orphanet J. Rare Dis.* 3:8).

Pulmonary fibrosis can occur as a secondary effect in disease processes such as asbestosis and silicosis, and is known to be more prevalent in certain occupations such as coal miner, ship workers and sand blasters where exposure to environmental pollutants is an occupational hazard (Green, F H et al. (2007) *Toxicol Pathol.* 35:136-47). Other factors that contribute to pulmonary fibrosis include cigarette smoking, and autoimmune connective tissue disorders, like rheumatoid arthritis, scleroderma and systemic lupus erythematosus (SLE) (Leslie, K O et al. (2007) *Semin Respir Crit. Care Med.* 28:369-78; Swigris, J J et al. (2008) *Chest.* 133:271-80; and Antoniou, K M et al. (2008) *Curr Opin Rheumatol.* 20:686-91). Other connective tissue disorders such as sarcoidosis can include pulmonary fibrosis as part of the disease (Paramothayan, S et al. (2008) *Respir Med.* 102:1-9), and infectious diseases of the lung can cause fibrosis as a long term consequence of infection, particularly chronic infections. Pulmonary fibrosis can also be a side effect of certain medical treatments, particularly radiation therapy to the chest and certain medicines like bleomycin, methotrexate, amiodarone, busulfan, and nitrofurantoin (Catane, R et al. (1979) *Int J Radiat Oncol Biol Phys.* 5:1513-8; Zisman, D A et al. (2001) *Sarcoidosis Vasc Diffuse Lung Dis.* 18:243-52; Rakita, L et al. (1983) Am Heart J. 106:906-16; Twohig, K J et al. (1990) *Clin Chest Med.* 11:31-54; and Witten C M. (1989) *Arch Phys Med. Rehabil.* 70:55-7). In other embodiments, idiopathic pulmonary fibrosis can occur where no clear causal agent or disease can be identified. Genetic factors can play a significant role in these cases of pulmonary fibrosis (Steele, M P et al. (2007) *Respiration* 74:601-8; Brass, D M et al. (2007) *Proc Am Thorac Soc.* 4:92-100 and du Bois R M. (2006) *Semin Respir Crit. Care Med.* 27:581-8).

In certain embodiments, the fibrotic condition is a fibrotic condition of the lung chosen from one or more of: pulmonary fibrosis, idiopathic pulmonary fibrosis (IPF), usual interstitial pneumonitis (UIP), interstitial lung disease, cryptogenic fibrosing alveolitis (CFA), or bronchiectasis.

In other embodiments, pulmonary fibrosis includes, but is not limited to, pulmonary fibrosis associated with chronic obstructive pulmonary disease (COPD), acute respiratory distress syndrome, scleroderma, pleural fibrosis, chronic asthma, acute lung syndrome, amyloidosis, bronchopulmonary dysplasia, Caplan's disease, Dressler's syndrome, histiocytosis X, idiopathic pulmonary haemosiderosis, lymphangiomyomatosis, mitral valve stenosis, polymyositis, pulmonary edema, pulmonary hypertension (e.g., idiopathic pulmonary hypertension (IPH)), pneumoconiosis, radiotherapy (e.g., radiation induced fibrosis), rheumatoid disease, Shaver's disease, systemic lupus erythematosus, systemic sclerosis, tropical pulmonary eosinophilia, tuberous sclerosis, Weber-Christian disease, Wegener's granulomatosis, Whipple's disease, or exposure to toxins or irritants (e.g., pharmaceutical drugs such as amiodarone, bleomycin, busulphan, carmustine, chloramphenicol, hexamethonium, methotrexate, methysergide, mitomycin C, nitrofurantoin, penicillamine, peplomycin, and practolol; inhalation of talc or dust, e.g., coal dust, silica). In certain embodiments, the pulmonary fibrosis is associated with an inflammatory disorder of the lung, e.g., asthma, and/or COPD.

In some embodiments, the fibrotic condition is a fibrotic condition of the liver or hepatic fibrosis, e.g., fatty liver disease, steatosis (e.g., nonalcoholic steatohepatitis (NASH), cholestatic liver disease, primary biliary cirrhosis (PBC), biliary fibrosis, cirrhosis, alcohol induced liver fibrosis, biliary duct injury, infection or viral induced liver fibrosis, congenital hepatic fibrosis, autoimmune hepatitis, or cholangiopathies (e.g., chronic cholangiopathies). Hepatic or liver fibrosis includes, e.g., hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins such as arsenic), alpha-1 antitrypsin deficiency, hemochromatosis, Wilson's disease, galactosemia, or glycogen storage disease. In certain embodiments, the hepatic fibrosis is associated with an inflammatory disorder of the liver.

In some embodiments, the fibrotic condition is a fibrotic condition of the heart or vasculature. A fibrotic condition of the heart or vasculature includes, but is not limited to, myocardial fibrosis (e.g., myocardial fibrosis associated with radiation myocarditis, a surgical procedure complication (e.g., myocardial post-operative fibrosis), vascular restenosis, atherosclerosis, cerebral disease, peripheral vascular disease, infectious diseases (e.g., Chagas disease, bacterial, trichinosis or fungal myocarditis)); granulomatous, metabolic storage disorders (e.g., cardiomyopathy, hemochromatosis); developmental disorders (e.g, endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis).

In one embodiment, the fibrotic condition is a fibrotic condition of the kidney or renal fibrosis (e.g., chronic kidney fibrosis). Renal fibrosis includes, e.g., nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic kidney fibrosis, nephrogenic systemic fibrosis, chronic progressive nephropathy (CPN), tubulointerstitial fibrosis, ureteral obstruction (e.g., fetal partial urethral obstruction), chronic uremia, chronic interstitial nephritis, radiation nephropathy, glomerulosclerosis (e.g., focal segmental glomerulosclerosis (FSGS)), progressive glomerulonephrosis (PGN), endothelial/thrombotic microangiopathy injury, scleroderma of the kidney, HIV-associated nephropathy (HIVVAN), or exposure to toxins, irritants, chemotherapeutic agents. In one embodiment, the kidney fibrosis is mediated by a bone morphogeneic protein (BMP). In certain embodiments, the renal fibrosis is a result of an inflammatory disorder of the kidney.

In certain embodiments, the fibrotic condition is a fibrotic condition of the bone marrow. In certain embodiments, the fibrotic condition of the bone marrow is myelofibrosis (e.g., primary myelofibrosis (PMF)), myeloid metaplasia, chronic idiopathic myelofibrosis, or primary myelofibrosis. In other embodiments, bone marrow fibrosis is associated with a hematologic disorder chosen from one or more of hairy cell leukemia, lymphoma, or multiple myeloma.

In other embodiments, the bone marrow fibrosis is associated with one or more myeloproliferative neoplasms (MPN) chosen from: essential thrombocythemia (ET), polycythemia vera (PV), mastocytosis, chronic eosinophilic leukemia, chronic neutrophilic leukemia, or other MPN.

In one embodiment, the fibrotic condition is primary myelofibrosis. Primary myelofibrosis (PMF) (also referred to in the literature as idiopathic myeloid metaplasia, and Agnogenic myeloid metaplasia) is a clonal disorder of multipotent hematopoietic progenitor cells (reviewed in Abdel-Wahab, O. et al. (2009) *Annu. Rev. Med.* 60:233-45; Varicchio, L. et al. (2009) *Expert Rev. Hematol.* 2(3):315-334; Agrawal, M. et al. (2010) *Cancer* 1-15). The disease is characterized by anemia, splenomegaly and extramedullary hematopoiesis, and is marked by progressive marrow fibrosis and atypical megakaryocytic hyperplasia. CD34+ stem/progenitor cells abnormally traffic in the peripheral blood and multi organ extramedullary erythropoiesis is a hallmark of the disease, especially in the spleen and liver. The bone marrow structure is altered due to progressive fibrosis, neoangiogenesis, and increased bone deposits. A significant percentage of patients with PMF have gain-of-function mutations in genes that regulate hematopoiesis, including Janus kinase 2 (JAK2) (~50%) (e.g., JAK2 V617F) or the thrombopoietin receptor (MPL) (5-10%), resulting in abnormal megakaryocyte growth and differentiation. Studies have suggested that the clonal hematopoietic disorder leads to secondary proliferation of fibroblasts and excessive collagen deposition. Decreased bone marrow fibrosis can improve clinical signs and symptoms, including anemia, abnormal leukocyte counts, and splenomegaly.

Bone marrow fibrosis can be observed in several other hematologic disorders including, but not limited to hairy cell leukemia, lymphoma, and multiple myeloma. However, each of these conditions is characterized by a constellation of clinical, pathologic, and molecular findings not characteristic of PMF (see Abdel-Wahab, O. et al. (2009) supra at page 235).

In other embodiments, the bone marrow fibrosis can be secondary to non-hematologic disorders, including but not limited to, solid tumor metastases to bone marrow, autoimmune disorders (systemic lupus erythematosus, scleroderma, mixed connective tissue disorder, polymyositis), and secondary hyperparathyroidism associated with vitamin D deficiency (see Abdel-Wahab, O. et al. (2009) supra at page 235). In most cases, it is possible to distinguish between these disorders and PMF, although in rare cases the presence of the JAK2V617F or MPLW515L/K mutation can be used to demonstrate the presence of a clonal MPN and to exclude the possibility of reactive fibrosis.

The effect of PI3K inhibitors in myelofibrosis can be characterized in mouse models available in the art, e.g., as described in Varicchio, L. (2009) supra.

Monitoring a clinical improvement in a subject with bone marrow fibrosis can be evaluated by one or more of: monitoring peripheral blood counts (e.g., red blood cells, white blood cells, platelets), wherein an increase in peripheral blood counts is indicative of an improved outcome. In some embodiments, clinical improvement in a subject with bone marrow fibrosis can be evaluated by monitoring one or more of: spleen size, liver size, and size of extramedullary hematopoiesis, wherein a decrease in one or more of these parameters is indicative of an improved outcome.

In some embodiments, the fibrotic condition is a fibrotic condition of the skin. In certain embodiments, the fibrotic condition is chosen from one or more of: skin fibrosis and/or scarring, scleroderma (e.g., systemic scleroderma), or keloid.

In some embodiments, the fibrotic condition is scleroderma. Scleroderma is a group of diseases that involve hardening and tightening of the skin and/or other connective tissues. Scleroderma is more common in women than in men and most commonly occurs between the ages of 30 and 50 years. Scleroderma may be localized (e.g., affecting only the skin) or systemic (e.g., affecting other systems such as, e.g., blood vessels and/or internal organs). Common symptoms of scleroderma include Raynaud's phenomenon, gastroesophageal reflux disease, and skin changes (e.g., swollen fingers and hands, or thickened patches of skin).

Localized scleroderma (localized cutaneous fibrosis) includes morphea and linear scleroderma. Morphea is typically characterized by oval-shaped thickened patches of skin that are white in the middle, with a purple border. Linear scleroderma is more common in children. Symptoms of linear scleroderma may appear mostly on one side of the body. In linear scleroderma, bands or streaks of hardened skin may develop on one or both arms or legs or on the forehead. En coup de sabre (frontal linear scleroderma or morphea en coup de sabre) is a type of localized scleroderma typically characterized by linear lesions of the scalp or face.

Systemic scleroderma (systemic sclerosis) includes, e.g., limited systemic sclerosis (also known as limited cutaneous systemic sclerosis, or CREST syndrome), diffuse systemic sclerosis (also known as diffuse cutaneous systemic sclerosis), and systemic sclerosis sine scleroderma. CREST stands for the following complications that may accompany limited scleroderma: calcinosis (e.g., of the digits), Raynaud's phenomenon, esophageal dysfunction, sclerodactyl), and telangiectasias. Typically, limited scleroderma involves cutaneous manifestations that mainly affect the hands, arms, and face. Limited and diffuse subtypes are distinguished based on the extent of skin involvement, with sparing of the proximal limbs and trunk in limited disease. See, e.g., Denton, C. P. et al. (2006), *Nature Clinical Practice Rheumatology,* 2(3):134-143. The limited subtype also typically involves a long previous history of Raynaud's phenomenon, whereas in the diffuse subtype, onset of Raynaud's phenomenon can be simultaneous with other manifestations or might occur later. Both limited and diffuse subtypes may involve internal organs. Typical visceral manifestations of limited systemic sclerosis include isolated pulmonary hypertension, severe bowel involvement, and pulmonary fibrosis. Typical visceral manifestations of diffuse systemic sclerosis include renal crisis, lung fibrosis, and cardiac disease. Diffuse systemic sclerosis typically progresses rapidly and affects a large area of the skin and one or more internal organs (e.g., kidneys, esophagus, heart, or lungs). Systemic sclerosis sine scleroderma is a rare disorder in which patients develop vascular and fibrotic damage to internal organs in the absence of cutaneous sclerosis.

In some embodiments, the fibrotic condition is scleroderma. In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

In certain embodiments, the fibrotic condition is a fibrotic condition of the gastrointestinal tract. A fibrotic condition of the gastrointestinal tract may be associated with an inflammatory disorder of the gastrointestinal tract, e.g., fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis or Crohn's disease. In certain embodiments, the fibrotic condition is diffuse scleroderma.

In certain embodiments, the fibrotic condition is selected from pulmonary fibrosis, bronchiectasis, interstitial lung disease; fatty liver disease; cholestatic liver disease, biliary fibrosis, hepatic fibrosis; myocardial fibrosis; and renal fibrosis.

In certain embodiments, the fibrotic condition is selected from biliary fibrosis, hepatic fibrosis, pulmonary fibrosis, myocardial fibrosis and renal fibrosis Other fibrotic conditions that can be treated with the methods and compositions of the invention include cystic fibrosis, endomyocardial fibrosis, mediastinal fibrosis, sarcoidosis, scleroderma, spinal cord injury/fibrosis.

Evaluating the effect of PI3K inhibitors, such as Compound 292, in several fibrotic conditions in vivo can be performed, for example, using animal models. A number of models in which fibrosis is induced are available in the art.

Administration of PI3K inhibitors, such as Compound 292, can be readily used to evaluate whether fibrosis is ameliorated in such models. Examples of such models, include but are not limited to, the unilateral ureteral obstruction model of renal fibrosis (see Chevalier et al., "Ureteral Obstruction as a Model of Renal Interstitial Fibrosis and Obstructive Nephropathy" *Kidney International* (2009) 75:1145-1152), the bleomycin induced model of pulmonary fibrosis (see Moore and Hogaboam "Murine Models of Pulmonary Fibrosis" *Am. J. Physiol. Lung. Cell. Mol. Physiol.* (2008) 294:L152-L160), a variety of liver/biliary fibrosis models (see Chuang et al., "Animal Models of Primary Biliary Cirrhosis" *Clin Liver Dis* (2008) 12:333-347; Omenetti, A. et al. (2007) *Laboratory Investigation* 87:499-514 (biliary duct-ligated model); a number of myelofibrosis mouse models as described in Varicchio, L. (2009) supra.; and the locally-injected bleomycin induced model of scleroderma (see, e.g., Yamamoto et al., "Animal Model of Sclerotic skin I: Local Injection of Bleomycin Induce Sclerotic Skin Mimicking Scleroderma, *Invest Dermatol* 112: 456-462 (1999). Regardless of the model, a PI3K inhibitor (e.g., Compound 292) can be evaluated using at least three general types of paradigms: 1) test whether the inhibitor can inhibit the fibrotic state; 2) test whether the inhibitor can stop fibrotic progression once initiated; and/or 3) test whether the inhibitor can reverse the fibrotic state once initiated.

Treatments for Inflammatory Myopathy

Disclosed herein are methods of treating inflammatory myopathies and skin conditions. The methods include administering a PI3K inhibitor (e.g., as a single agent or in combination with one or more additional agents or therapeutic modalities), to a subject in need thereof, thereby treating the inflammatory myopathy or the skin condition (e.g., by ameliorating one or more symptoms associated with the inflammatory myopathy or the skin condition). The PI3K inhibitor is administered in an amount sufficient to treat the inflammatory myopathy or the skin condition in the subject. An "amount sufficient," as used herein, includes a therapeutically effective amount and/or a prophylactically effective amount.

Interferons (IFNs) (e.g., Type I interferons, e.g., IFN-α) have been implicated in the pathogenesis of inflammatory myopathy (e.g., dermatomyositis) as well as other autoimmune diseases. See, e.g., Wong, D. et al. (2012) PLoS ONE, 7(1):e29161 doi:10.1371/journal.pone.0029161; Higgs, B. W. et al. (2012) *International Journal of Rhematic Diseases*, 15:25-35. Furthermore, various cytokines and chemokines (e.g., IFN-α, TNF-α, IL-6, IL-8, IL-1, IL-10, TGFβ, IL-17, IL-18, and IL-15) play a role in pathogenesis of inflammatory myopathy (e.g., dermatomyositis). See, e.g., Kao et al. (2011) *Curr Rhematol Rep* 13:225-232. For example, the bood, muscle, and skin of patients with dermatomyositis is characterized by the presence of an "IFN signature" involving upregulation of IFN-inducible genes. See, e.g., Wong, D. et al. (2012) *PLoS ONE*, 7(1):e29161; Higgs, B. W. et al. (2012) *International Journal of Rhematic Diseases*, 15:25-35. Type I IFN is the major contributor to the overexpression of IFN inducible genes in peripheral blood. Higgs, B. W. et al. Although leucocytes produce IFN, plasmacytoid dendritic cells (PDCs or pDCs) are the main producers; they produce 100-200 times more IFN than any other cell type. It is thought that PDCs can produce such high amounts of IFN because they constitutively express Toll-like receptor 7 (TLR7) and Toll-like receptor 9 (TLR9). Plasmacytoid dendritic cells (PDCs) actively produce IFN-α in response to endogenous TLR ligands derived from chronic inflammation, which can result in a type 1 IFN gene signature.

Experiments disclosed herein reveal, in part, that PI3 kinase inhibitors (e.g., Compound 292) can effectively modulate (e.g., inhibit or enhance) production of cytokines/chemokines (e.g., IFN-α, IL-1, IL-6, IL-8, and/or TNF-α) that are induced by various TLR ligands and are involved in the pathogenesis of inflammatory myopathies (e.g., dermatomyositis). At least in part for this reason, it is expected that PI3 kinase inhibitors (e.g., PI3Kδ inhibitors) are effective in the treatment of inflammatory myopathies.

As used herein, the term "inflammatory myopathy" (or "inflammatory myopathies") encompasses acute and chronic inflammatory muscle diseases and includes idiopathic inflammatory myopathies (e.g., polymyositis, dermatomyositis, inclusion body myositis, giant cell myositis, eosinophilic myositis, focal/localized myositis, granulomatous myositis, macrophagic myofasciitis, pipestem capillary disease) as well as inflammatory myopathies caused by or associated with allergic reactions, other diseases (e.g., cancer, connective tissue disease), exposure to a drug or toxin (e.g., cocaine, heroin, cimetidine, penicillamine, adulterated rapeseed oil, amiodarone, L-tryptophan, colchicines, statins, quinidine, or phenylbutazone), or exposure to an infectious agent (e.g., a virus, bacterium, fungus, protozoan, cestode, or nematode). There is evidence that some inflammatory myopathies are autoimmune myopathies (e.g., dermatomyositis, polymyositis, inclusion body myositis and immune-mediated necrotizing myopathies). As used herein, "dermatomyositis" includes all forms of dermatomyositis, including amyopathic dermatomyositis (dermatomyositis without muscle symptoms or without overt muscle symptoms).

In some embodiments, the subject is a mammal. In some embodiments, the subject is a human.

The inflammatory myopathy can be an acute inflammatory myopathy or a chronic inflammatory myopathy.

In some embodiments, the inflammatory myopathy is a chronic inflammatory myopathy (e.g., a myositis, e.g., dermatomyositis, polymyositis, or inclusion body myositis).

In some embodiments, the inflammatory myopathy is caused by an allergic reaction, another disease (e.g., cancer or a connective tissue disease), exposure to a toxic substance, a medicine, or an infectious agent (e.g., a virus). In some embodiments, the inflammatory myopathy is associated with lupus, rheumatoid arthritis, or systemic sclerosis. In some embodiments, the inflammatory myopathy is idiopathic.

In some embodiments, the inflammatory myopathy is selected from polymyositis, dermatomyositis, and inclusion body myositis.

In some embodiments, the inflammatory myopathy is dermatomyositis.

As used herein, a "symptom" associated with an inflammatory myopathy or a skin condition includes, for example, any sign, symptom, or complication of an inflammatory myopathy or a skin condition as disclosed herein or as known in the art.

Symptoms associated with inflammatory myopathies can include, for example, muscle weakness (e.g. proximal muscle weakness), skin rash (e.g., heliotrope rash, Gottron's papules, V-sign, shawl sign, utricaria), hyperpigmentation, fatigue (e.g., after walking or standing), tripping and/or falling, dysphagia, dysphonia, dyspnea, muscle pain, tender muscles, muscle atrophy, weight loss, low-grade fever, light sensitivity, calcium deposits (calcinosis) under the skin or in the muscle, lung problems (e.g., inflamed lungs, interstitial lung disease, e.g., diffuse interstitial pneumonitis/fibrosis), heart problems (e.g., myocarditis, arrhythmias, congestive heart failure), arthritis, arthralgia, Raynaud's phenomenon, ulcers, ocular complications and/or visual changes, abdominal pain, as well as biological concomitants of inflammatory myopathies as disclosed herein or as known in the art. Other symptoms or complications can include infections, aspiration pneumonia, and increased risk of cancer.

Dermatomyositis (DM) is typically characterized by a heliotrope rash that typically appears as a patchy, bluish-purple to dusky discoloration that on the face, particularly around both eyes, and/or on the neck, shoulders, upper chest, elbows, knees, knuckles, and back. The "shawl sign" is a splotchy rash, which may develop over the neck and upper chest and back in the pattern of a shawl. The rash in DM can be accompanied by calcium deposits that occur as hard lumps beneath the skin known as Gottron papules, which are frequently found on bony prominenences (e.g., those on the knuckles, elbow, knees, toes, and feet). The rash in DM can be itchy (e.g., a pruritic rash, e.g., utricaria). The rash may appear scaly, appear as white plaques on the insides of the cheeks, and/or as thickening on the palms of the hands (mechanic's hands). Initially, symptoms of DM may be limited to cutaneous manifestations. Muscle weakness typically begins in the proximal muscles (those closest to the trunk of the body) and may progress to distal muscles as the disease progresses.

Biological concomitants of inflammatory myopathies (e.g., dermatomyositis) include, e.g., altered (e.g., increased) levels of cytokines (e.g., Type I interferons (e.g., IFN-α and/or IFN-β), interleukins (e.g., IL-6, IL-10, IL-15, IL-17 and IL-18), and TNF-α), TGF-β, B-cell activating factor (BAFF), and overexpression of IFN inducible genes (e.g., Type I IFN inducible genes).

In certain embodiments, the symptom associated with inflammatory myopathy is an elevated level or increased biological activity of one or more of the following: IFN-α, TNF-α, IL-6, IL-8, IL-1, IL-10, TGFβ, IL-17, IL-18, and IL-15.

In some embodiments, decreasing or inhibiting the inflammatory myopathy comprises inhibiting (e.g., decreasing a level of, or decreasing a biological activity of) one or more of IFN-α, TNF-α, IL-6, IL-8, IL-1, IL-10, TGFβ, IL-17, IL-18, and IL-15 in the subject or in a sample derived from the subject.

Other biological concomitants of inflammatory myopathies can include, e.g., an increased erythrocyte sedimentation rate (ESR), an elevated level of muscle enzymes (e.g., creatine kinase, aldolase, aspartate aminotransferase (AST), lactate dehydrogenase (LDH)), electromyographic abnormalities, elevated rheumatoid factor, and/or presence of autoantibodies, e.g., anti-synthetase autoantibodies (e.g., anti-Job, anti-PL-7, anti-PL-12, anti-EJ, anti-OJ, anti-JS, anti-KS, anti-ZO, anti-YRS), anti-signal recognition particle antibodies (anti-SRP), anti-RNP antibodies, anti-nuclear autoantigen antibodies (e.g., Mi-2 antibodies), anti-p155 antibodies, anti-PM/Sci antibodies, anti-CADM-140, anti-SAE (small ubiquitin-like modifier activating enzyme), anti-p155/140 and anti-p140. These and other autoantibodies associated with inflammatory myopathies are known in the art; see, e.g., Sibilia, J. et al. (2010) *Presse Med,* 39(10) 1010-1025; Betteridge, Z. E. et al. (2009) *Curr Opin Rheumatol,* 21(6): 604-609; Gunawardena, H. et al. (2009) *Rheumatology,* 48 (6): 607-612; Koler, R. A. et al. (2001) *American Family Physician,* 64(9): 1565-1572; Ceribelli, A. et al. (2012) *Arthritis Res Ther.* 2012 Apr. 30; 14(2):R97; Dalakas, M. C. (2003) *Lancet,* 362:971-982.

In some embodiments, the methods disclosed herein result in decreases in autoantibodies, e.g., one or more autoantibodies associated with inflammatory myopathy.

As used herein, the term "skin condition" includes any inflammatory condition of the skin (e.g., eczema or dermatitis, e.g., contact dermatitis, atopic dermatitis, dermatitis herpetiformis, seborrheic dermatitis, nummular dermatitis, stasis dermatitis, perioral dermatitis), as well as accompanying symptoms (e.g., skin rash, itchiness (pruritis), swelling (edema), hay fever, anaphalaxis). Frequently, such skin conditions are caused by an allergen. As used herein, a "skin condition" also includes, e.g., skin rashes (e.g., allergic rashes, e.g., rashes resulting from exposure to allergens such as poison ivy, poison oak, or poison sumac, or rashes caused by other diseases or conditions), insect bites, minor burns, sunburn, minor cuts, and scrapes.

In some embodiments, the symptom associated with inflammatory myopathy, or the skin condition or symptom associated with the skin condition, is a skin rash or itchiness (pruritis) caused by a skin rash.

In some embodiments, the methods of the invention treat a skin condition (e.g., a skin rash) or symptoms associated with a skin condition (e.g., itchiness, inflammation, hay fever). In some such embodiments, the PI3K inhibitor is administered topically (e.g., as a topical cream, eyedrop, nose drop or nasal spray). In some such embodiments, the PI3K inhibitor is a PI3K delta inhibitor (e.g., a PI3K inhibitor that demonstrates greater inhibition of PI3K delta than of other PI3K isoforms). In some embodiments, the PI3K delta inhibitor prevents mast cell degranulation.

The skin condition (e.g., the skin rash) may be spontaneous, or it may be induced, e.g., by exposure to an allergen (e.g., poison ivy, poison oak, or poison sumac), drugs, food, insect bite, inhalants, emotional stress, exposure to heat, exposure to cold, or exercise. In some embodiments, the skin condition is a skin rash (e.g., a pruritic rash, e.g., utricaria). In some embodiments, the skin condition is an insect bite. In some embodiments, the skin condition is associated with another disease (e.g., an inflammatory myopathy, e.g., dermatomyositis).

In some embodiments, the subject (e.g., the subject in need of treatment for an inflammatory myopathy and/or a skin condition) exhibits an elevated level or elevated activity of IFN-α, TNF-α, IL-6, IL-8, IL-1, or a combination thereof. In certain embodiments, the subject exhibits an elevated level of IFN-α.

In some embodiments, treating (e.g., decreasing or inhibiting) the inflammatory myopathy, or the skin condition, comprises inhibiting (e.g., decreasing a level of, or decreasing a biological activity of) one or more of IFN-α, TNF-α, IL-6, IL-8, or IL-1 in the subject or in a sample derived from the subject. In some embodiments, the method decreases a level of IFN-α, TNF-α, IL-6, IL-8, or IL-1 in the subject or in a sample derived from the subject. In some embodiments, the method decreases a level of IFN-α in the subject or in a sample derived from the subject. In some embodiments, the level of IFN-α, TNF-α, IL-6, IL-8, or IL-1 is the level assessed in a sample of whole blood or PBMCs. In some embodiments, the level of IFN-α, TNF-α, IL-6, IL-8, or IL-1 is the level assessed in a sample obtained by a skin biopsy or a muscle biopsy. In some embodiments, the sample is obtained by a skin biopsy.

As used herein, a "sample" or a "biological sample" includes any cells, fluid, tissue, or the like that is present within or removed from a subject. For example, the sample can be whole blood, plasma, muscle, or skin (e.g., a muscle or skin sample obtained by a biopsy). In some embodiments, the sample comprises plasmacytoid dendritic cells (PDCs or pDCs). In some embodiments, the sample comprises peripheral blood mononuclear cells (PBMCs). In some embodiments, the biological sample includes cells that express Toll-like receptor 7 (TLR7) and/or Toll-like receptor 9 (TLR9).

As used herein, to "decrease", "ameliorate," "reduce," "treat" "inhibit" (or the like) includes preventing or reducing the severity and/or frequency of the condition to be treated (e.g., the inflammatory myopathy or the skin condition), as well as reducing (or preventing an increase in) the severity and/or frequency of one or more symptoms of the condition to be treated. In some embodiments, the severity or frequency of the symptom is reduced by at least 10%, at least 20%, at least 30%, at least 40%, at least 50%, at least 60%, at least 70%, at least 80%, at least 90%, or at least 95% relative to a control level. The control level includes any appropriate control as known in the art. For example, the control level can be the pre-treatment level in the sample or subject treated, or it can be the level in a control population (e.g., the level in subjects who do not have the condition to be treated or the level in samples derived from subjects who do not have the condition to be treated). In some embodiments, the decrease is statistically significant, for example, as assessed using an appropriate parametric or non-parametric statistical comparison.

In the context of biological molecules, to "decrease", "ameliorate," "reduce," "inhibit," or the like, includes decreasing the level (e.g., the level, e.g., of mRNA or protein, that can be measured in a biological sample) or the activity (e.g., the function) of the molecule. In some embodiments, the level or activity is reduced by at least 10%, at least 20%, at least 30%, at least 40%, at least 50%, at least 60%, at least 70%, at least 80%, at least 90%, or at least 95% relative to a control level.

In certain embodiments, the subject is an animal model of an inflammatory myopathy or a skin condition, a human with an inflammatory myopathy or a skin condition, or a subject (e.g., a human) at risk for developing an inflammatory myopathy or a skin condition. In some embodiments, the subject is a human who has a family history of an inflammatory myopathy or a skin condition, who carries a gene associated with an inflammatory myopathy or a skin condition, who is positive for a biomarker associated with an inflammatory myopathy or a skin condition, or a combination thereof. In some embodiments, the subject has been diagnosed with an inflammatory myopathy or a skin condition, e.g., as described herein. In some embodiments, the subject has one or more signs or symptoms associated with an inflammatory myopathy or a skin condition. In some embodiments, the subject is at risk for developing an inflammatory myopathy or a skin condition (e.g., the subject carries a gene that, individually, or in combination with other genes or environmental factors, is associated with development of an inflammatory myopathy or a skin condition). In some embodiments, the subject carries a gene associated with the development of an inflammatory myopathy, e.g., a human leukocyte antigen (HLA) type associated with development of an inflammatory myopathy (e.g., dermatomyositis) (e.g., DR3, DR5, or DR7) or a polymorphism of tumor necrosis factor (e.g., the −308A allele)).

In some embodiments, the subject is an animal model of inflammatory myopathy. Evaluating the effect of PI3K inhibitors, such as Compound 292, in ameliorating symptoms of inflammatory myopathy in vivo can be performed, for example, using animal models. A number of models of inflammatory myopathy are available in the art and can be used to evaluate whether administration of PI3K inhibitors, such as Compound 292, decrease or inhibit inflammatory myopathy in such models Animal models include spontaneous, induced, and transgenic models. See, e.g., Nagaraju, K. & Plotz, P. H. (2002) *Rheum Dis Clin North Am,* 28(4):917-933. Familial canine dermatomyositis in collies, as well as a similar disorder in Shetland sheepdogs, is an example of an animal model. See, e.g., Hargis, A. M. et al. (1985) *Am J Pathol.* 120(2):323-5. Other examples of animal models of inflammatory myopathy are known in the art. See, e.g., Paciello, O. et al. (2010) *Muscle Nerve,* 41(3):355-61; Katsumata, Y. & Ascherman, D. P. (2008) *Curr Opin Rheumatol,* 20(6):681-685; Hargis, A. M. & Prieur, D. J. (1988) *Clin Dermatol,* 6(2):120-129, 52-54; Nagaraju, K. & Plotz, P. H. (2002) *Rheum Dis Clin North Am,* 28(4):917-933.

In some embodiments, the subject is an animal model of a skin condition (e.g., an inflammatory skin condition, e.g., an allergic skin condition). Evaluating the effect of PI3K inhibitors, such as Compound 292, in ameliorating symptoms of a skin condition in vivo can be performed, for example, using animal models Animal models of skin conditions, e.g., allergic skin conditions, are known in the art and include animal models of atopic dermatitis (see, e.g., Jin, H. (2009) *J Invest Dermatol.,* 129(1):31-40) and cutaneous anaphylaxis (see, e.g., Fish, S. C. (2005) *Journal of Immunology,* 174:7716-7724).

In some embodiments, the methods disclosed herein result in inhibition of IFN inducible genes. In some embodiments, the methods result in inhibition of Type I IFN inducible genes.

In some embodiments, the methods disclosed herein result in inhibition of a Type I IFN (e.g., IFN-α).

In some embodiments, the methods disclosed herein result in modulation (e.g., inhibition) of a cytokine (e.g., a Type I IFN (e.g., IFN-α)) released as a result of TLR activation. In some embodiments, the TLR is TLR9. In some embodiments, the methods result in inhibition of IFN-α released as a result of TLR9 activation.

In some embodiments, the subject exhibits excessive PI3K activity or abnormal activity (e.g., excessive or reduced activity) of one or more components of the PI3K signaling pathway (e.g., Akt (PKB), mTOR, a Tec kinase (e.g., Btk, Itk, Tec), phospholipase C, PDK1, PKCs, NFκB, Rac GEF (e.g., Vav-1), or Rac).

Combination Treatments

In some embodiments, the PI3K inhibitor is administered in combination with one or more other therapies. Such therapies include therapeutic agents as well as other medical interventions, behavioral therapies (e.g., avoidance of sunlight), and the like. Exemplary therapeutic agents include, but are not limited to, anti-SDI-fibrotics, corticosteroids, anti-inflammatories, immunosuppressants, chemotherapeutic agents, anti-metabolites, and immunomodulators.

By "in combination with," it is not intended to imply that the other therapeutic agent and the PI3K inhibitor must be administered at the same time and/or formulated for delivery together, although these methods of delivery are within the scope of the invention. The PI3K inhibitor can be administered concurrently with, prior to, or subsequent to, one or more other additional agents. In general, each therapeutic agent will be administered at a dose and/or on a time schedule determined for that particular agent. The other therapeutic agent can be administered with the PI3K inhibitor in a single composition or separately in a different composition.

In general, it is expected that additional therapeutic agents employed in combination be utilized at levels that do not exceed the levels at which they are utilized individually. In some embodiments, the levels utilized in combination will be lower than those utilized individually.

In some embodiments, the PI3K inhibitor is a first line treatment for lupus, a fibrotic condition, or an inflammatory myopathy, i.e., it is used in a subject who has not been previously administered another drug intended to treat lupus, a fibrotic condition, an inflammatory myopathy, or one or more symptoms of lupus, a fibrotic condition, or an inflammatory myopathy.

In other embodiments, the PI3K inhibitor is a second line treatment for lupus, a fibrotic condition, or an inflammatory myopathy, i.e., it is used in a subject who has been previously administered another drug intended to treat lupus, a fibrotic condition, an inflammatory myopathy, or one or more symptoms of lupus, a fibrotic condition, or an inflammatory myopathy.

In other embodiments, the PI3K inhibitor is a third or fourth line treatment for lupus, a fibrotic condition, or an inflammatory myopathy, i.e., it is used in a subject who has been previously administered two or three other drugs intended to treat lupus, a fibrotic condition, an inflammatory myopathy, or one or more symptoms of lupus, a fibrotic condition, or an inflammatory myopathy.

In some embodiments, a PI3K inhibitor is administered to a subject following surgical excision/removal.

In some embodiments, a PI3K inhibitor is administered to a subject before, during, and/or after radiation treatment.

In embodiments where two agents are administered, the agents can be administered in any order. For example, the two agents can be administered concurrently (i.e., essentially at the same time, or within the same treatment) or sequentially (i.e., one immediately following the other, or alternatively, with a gap in between administration of the two). In some embodiments, the PI3K inhibitor is administered sequentially (i.e., after the first therapeutic).

In some embodiments, the PI3K inhibitor can be administered in combination with one or more additional therapies, e.g., additional therapies for the treatment of lupus or for the treatment of symptoms of lupus. Some examples of therapies for the treatment of lupus are disclosed, for example, in Chugh, P. K. (2012) European Journal of Internal Medicine, 23, 212-218. In some embodiments, the other therapy is Belimumab (Benlysta). In some embodiments, the other therapy is an anti-interferon therapy, e.g., AGS-009, Rontalizumab (rhuMAb IFN alpha), Vitamin D3, Sifalimumab (MEDI-545), AMG 811, IFNα Kinoid, or CEP33457. In some embodiments, the other therapy is an IFN-α therapy, e.g., AGS-009, Rontalizumab, Vitamin D3, Sifalimumab (MEDI-545) or IFNα Kinoid. In some embodiments, the other therapy is an anti B-cell therapy, e.g., Epratuzumab, LY2127399, Ocrelizumab, Atacicept, A-623, or SBI-087. In some embodiments, the other therapy is an anti T-cell therapy, e.g. AMG557. In some embodiments, the other therapy is an immunomodulatory or immunosuppressant therapy (e.g., laquinimod, rapamycin, cyclophosphamide (Cytoxan), azathioprine (Imuran, Azasan), mycophenolate (Cellcept), leflunomide (Arava) or methotrexate (Trexall)). In some embodiments, the other therapy is an anti-interleukin therapy, e.g., CNTO 136. In some embodiments, the other therapy is Tamibarotene, N-acetylcysteine, or CDP7657. In some embodiments, the other therapy is hydroxychloroquine treatment. See, e.g., Willis, R. et al. (2012) *Lupus*, 21: 830-835. In some embodiments, the other therapy is a B cell depletion therapy or anti-CD20 therapy (e.g., rituximab). In some embodiments, the other therapy is a vaccine (e.g., an iDC vaccine as described, e.g., in Xia, Y. et al. (2011) Rheumatology, 50:2187-2196, or an IFN-α vaccine, e.g., IFNα Kinoid). In some embodiments, the other therapy is a proteasome inhibitor (e.g., carfilzomib or bortezomib) or an immunoproteasome inhibitor (e.g., ONX 0914). See, e.g., Ichikawa, H. T. et al. (2012) Arthritis and Rheumatism, 62(2): 493-503. In some embodiments, the other therapy inhibits a Toll-like receptor (e.g., hydroxychloroquine, IMO-3100 (inhibits TLR7 and TLR9), or DV 1179 (inhibits TLR7 and TLR9)). In some embodiments, the other therapy is a nonsteroidal anti-inflammatory drug (NSAID). In some embodiments, the other therapy is an anti-malarial medication (e.g., hydroxychloroquine). In some embodiments, the other therapy is a corticosteroid.

In embodiments where a scleroderma (e.g., a localized scleroderma or systemic sclerosis) is treated, the PI3K inhibitor may be administered in combination with one or more additional therapies, including, e.g., an immunosuppressant (e.g., methotrexate, azathioprine (Imuran®), cyclosporine, mycophenolate mofetil (Cellcept®), and cyclophosphamide (Cytoxan®)), T-cell-directed therapy (e.g., halofuginone, basiliximab, alemtuzumab, abatacept, rapamycin), B-cell directed therapy (e.g., rituximab), autologous hematopoietic stem cell transplantation, a chemokine ligand receptor antagonist (e.g., an agent that targets the CXCL12/CSCR4 axis (e.g., AMD3100)), a DNA methylation inhibitor (5-azacytidine), a histone dactylase inhibitor (e.g., trichostatin A), a statin (e.g., atorvastatin, simvastatin, pravastatin), an endothelin receptor antagonist (e.g., Bosentan®), a phosphodiesterase type V inhibitor (e.g., Sildenafil®), a prostacyclin analog (e.g., trepostinil), an inhibitor of cytokine synthesis and/or signaling (e.g., Imatinib mesylate, Rosiglitazone, rapamycin, antitransforming growth factor β1 (anti-TGFβ1) antibody, mycophenolate mofetil, an anti-IL-6 antibody (e.g., tocilizumab)), corticosteroids, nonsteroidal anti-inflammatory drugs, light therapy, and blood pressure medications (e.g., ACE inhibitors). See, e.g., Ong, V. H. et al. (2010) *Current Opinion in Rheumatology*, 22:264-272.

In embodiments where a fibrotic condition of the bone marrow is treated, the PI3K inhibitor can be administered in combination with an agent chosen from a Jak2 inhibitor (including, but not limited to, INCB018424, XL019, TG101348, or TG101209), an immunomodulator, e.g., an IMID (including, but not limited to thalidomide, lenalidomide, or panolinomide), hydroxyurea, an androgen, erythropoietic stimulating agents, prednisone, danazol, HDAC inhibitors, or other agents or therapeutic modalities (e.g., stem cell transplants, or radiation).

An example of suitable therapeutics for use in combination with the PI3K inhibitor for treatment of heart fibrosis includes, but is not limited to, eplerenone, furosemide, pycnogenol, spironolactone, TcNC100692, torasemide (e.g., prolonged release form of torasemide), and combinations thereof.

An example of suitable therapeutics for use in combination with the PI3K inhibitor for treatment of kidney fibrosis includes, but is not limited to, cyclosporine, cyclosporine A, daclizumab, everolimus, gadofoveset trisodium (ABLAVAR®), imatinib mesylate (GLEEVEC®), matinib mesylate, methotrexate, mycophenolate mofetil, prednisone, sirolimus, spironolactone, STX-100, tamoxifen, TheraCLEC™, and combinations thereof.

An example of suitable therapeutics for use in combination with the PI3K inhibitor for treatment of skin fibrosis includes, but is not limited to, Bosentan (Tracleer), p144, pentoxifylline; pirfenidone; pravastatin, STI571, Vitamin E, and combinations thereof.

An example of suitable therapeutics for use in combination with the PI3K inhibitor for treatment of gastrointestinal fibrosis includes, but is not limited to, ALTU-135, bucelipase alfa (INN), DCI1020, EUR-1008 (ZENPEP™), ibuprofen, Lym-X-Sorb powder, pancrease MT, pancrelipase (e.g., pancrelipase delayed release), pentade canoic acid (PA), repaglinide, TheraCLEC™, triheptadecanoin (THA), ULTRASE MT20, ursodiol, and combinations thereof.

An example of suitable therapeutics for use in combination with the PI3K inhibitor for treatment of lung fibrosis includes, but is not limited to, 18-FDG, AB0024, ACT-064992 (macitentan), aerosol interferon-gamma, aerosolized human plasma-derived alpha-1 antitrypsin, alpha1-proteinase inhibitor, ambrisentan, amikacin, amiloride, amitriptyline, anti-pseudomonas IgY gargle, ARIKACE™, AUREXIS® (tefibazumab), AZAPRED, azathioprine, azithromycin, azithromycin, AZLI, aztreonam lysine, BIBF1120, Bio-25 probiotic, bosentan, Bramitob®, calfactant aerosol, captopril, CC-930, ceftazidime, ceftazidime, cholecalciferol (Vitamin D3), ciprofloxacin (CIPRO®, BAYQ3939), CNTO 888, colistin CF, combined Plasma Exchange (PEX), rituximab, and corticosteroids, cyclophosphamide, dapsone, dasatinib, denufosol tetrasodium (INS37217), dornase alfa (PULMOZYME®), EPI-bNE4, erythromycin, etanercept, FG-3019, fluticasone, FTI, GC1008, GS-9411, hypertonic saline, ibuprofen, iloprost inhalation, imatinib mesylate (GLEEVEC®), inhaled sodium bicarbonate, inhaled sodium pyruvate, interferon gamma-1b, interferon-alpha lozenges, isotonic saline, IW001, KB001, losartan, lucinactant, mannitol, meropenem, meropenem infusion, miglustat, minocycline, Moli1901, MP-376 (levofloxacin solution for inhalation), mucoid exopolysaccharide P. aeruginosa immune globulin IV, mycophenolate mofetil, n-acetylcysteine, N-acetylcysteine (NAC), NaC16%, nitric oxide for inhalation, obramycin, octreotide, oligoG CF-5/20, Omalizumab, pioglitazone, piperacillin-tazobactam, pirfenidone, pomalidomide (CC-4047), prednisone, prevastatin, PRM-151, QAX576, rhDNAse, SB656933, SB-656933-AAA, sildenafil, tamoxifen, technetium [Tc-99 m]sulfur colloid and Indium [In-111] DTPA, tetrathiomolybdate, thalidomide, ticarcillin-clavulanate, tiotropium bromide, tiotropium RESPIMAT® inhaler, tobramycin (GERNEBCIN®), treprostinil, uridine, valganciclovir (VALCYTE®), vardenafil, vitamin D3, xylitol, zileuton, and combinations thereof.

An example of suitable therapeutics for use in combination with the PI3K inhibitor for treatment of liver fibrosis includes, but is not limited to, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride), interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, and combinations thereof.

An example of other suitable therapeutics for use in combination with the PI3K inhibitor for treatment of cystic fibrosis includes, but is not limited to, 552-02, 5-methyltetrahydrofolate and vitamin B12, Ad5-CB-CFTR, Adeno-associated virus-CFTR vector, albuterol, alendronate, alpha tocopherol plus ascorbic acid, amiloride HCl, aquADEK™, ataluren (PTC124), AZD1236, AZD9668, azithromycin, bevacizumab, biaxin (clarithromycin), BIIL 283 BS (amelubent), buprofen, calcium carbonate, ceftazidime, cholecalciferol, choline supplementation, CPX, cystic fibrosis transmembrane conductance regulator, DHA-rich supplement, digitoxin, cocosahexaenoic acid (DHA), doxycycline, ECGC, ecombinant human IGF-1, educed glutathione sodium salt, ergocalciferol (vitamin D2), fluorometholone, gadobutrol (GADOVIST®, BAY86-4875), gentamicin, ghrelin, glargine, glutamine, growth hormone, GS-9411, H5.001CBCFTR, human recombinant growth hormone, hydroxychloroquine, hyperbaric oxygen, hypertonic saline, IH636 grape seed proanthocyanidin extract, insulin, interferon gamma-1b, IoGen (molecular iodine), iosartan potassium, isotonic saline, itraconazole, IV gallium nitrate (GANITE®) infusion, ketorolac acetate, lansoprazole, L-arginine, linezolid, lubiprostone, meropenem, miglustat, MP-376 (levofloxacin solution for inhalation), normal saline IV, Nutropin AQ, omega-3 triglycerides, pGM169/GL67A, pGT-1 gene lipid complex, pioglitazone, PTC124, QAU145, salmeterol, SB656933, SB656933, simvastatin, sitagliptin, sodium 4-phenylbutyrate, standardized turmeric root extract, tgAAVCF, TNF blocker, TOBI, tobramycin, tocotrienol, unconjugated Isoflavones 100, vitamin: choline bitartrate (2-hydroxyethyl)trimethylammonium salt 1:1, VX-770, VX-809, Zinc acetate, and combinations thereof.

In some embodiments, the PI3K inhibitor can be administered in combination with one or more additional therapies, e.g., additional therapies (e.g., additional agents) for the treatment of an inflammatory myopathy or a skin condition.

Additional therapies that may be used in the methods described herein (e.g., methods of treating inflammatory myopathies (e.g., dermatomyositis) or skin conditions) include, e.g., topical creams or ointments (e.g., topical corticosteroids, tacrolimus, pimecrolimus).

Additional therapies that may be used in the methods described herein (e.g., methods of treating inflammatory myopathies (e.g., dermatomyositis) or skin conditions) also include, e.g., cyclosporine (e.g., topical cyclosporine).

In some embodiments, the other therapy is an anti-interferon therapy, e.g., AGS-009, Rontalizumab (rhuMAb IFN alpha), Vitamin D3, Sifalimumab (MEDI-545), AMG 811, IFNα Kinoid, or CEP33457. In some embodiments, the other therapy is an IFN-α therapy, e.g., AGS-009, Rontalizumab, Vitamin D3, Sifalimumab (MEDI-545) or IFNα Kinoid.

Examples of additional therapies that may be used for the treatment of an inflammatory myopathy include additional agents, e.g., prednisone (e.g., oral prednisone)), methotrexate (Trexall, Methotrexate, Rheumatrex), azathioprine (Azasan, Imuran), intravenous immunoglobulin, tacrolimus (Prograf), pimecrolimus, cyclophosphamide (Cytoxan), cyclosporine (Gengraf, Neoral, Sandimmune), hydroxychloroquine (Plaquenil), chloroquine (Aralen), total body irradiation, rituximab (Rituxan), TNF inhibitors (e.g., etanercept (Enbrel), infliximab (Remicade)), AGS-009, Rontalizumab (rhuMAb IFN alpha), Vitamin D3, Sifalimumab (MEDI-545), AMG 811, IFNα Kinoid, or CEP33457.

Examples of other therapies that may be used for the treatment of an inflammatory myopathy include, e.g., physical therapy, exercise, rest, speech therapy, sun avoidance, heat therapy, surgery (e.g., to remove calcium deposits).

In some embodiments, the additional therapy is a corticosteroid (e.g., prednisone). The corticosteroid may be administered orally or intravenously.

In some embodiments, the additional therapy is an immunisuppressive therapy (e.g., methotrexate (Trexall, Methotrexate, Rheumatrex), azathioprine (Azasan, Imuran), intravenous immunoglobulin, tacrolimus (Prograf), cyclophosphamide (Cytoxan), cyclosporine (Gengraf, Neoral, Sandimmune)).

In some embodiments, the additional therapy is an anti-malarial medication (e.g., hydroxychloroquine (Plaquenil) or chloroquine (Aralen)).

In some embodiments, the PI3K inhibitor (e.g., PI3Kδ inhibitor) is administered in combination with an agent that inhibits IgE production or activity. In some embodiments, the PI3K inhibitor (e.g., PI3Kδ inhibitor) is administered in combination with an inhibitor of mTOR. Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC 1 and mTORC2. Agents that inhibit IgE activity include, for example, anti-IgE antibodies such as for example Omalizumab and TNX-901.

In some embodiments, the other therapy is selected from any one or more of the aforementioned therapies.

Kits

Kits are also provided herein. The kits include a PI3K inhibitor or composition comprising a PI3K inhibitor as described herein, in suitable packaging, and written material. The written material can include any of the following information: instructions for use, discussion of clinical studies, listing of side effects, scientific literature references, package insert materials, clinical trial results, and/or summaries of these and the like. The written material can indicate or establish the activities and/or advantages of the composition, and/or describe dosing, administration, side effects, drug interactions, or other information useful to the health care provider. Such information can be based on the results of various studies, for example, studies using experimental animals involving in vivo models and/or studies based on human clinical trials. The kit can further contain another therapy (e.g., another agent) and/or written material such as that described above that serves to provide information regarding the other therapy (e.g., the other agent). In some embodiments, the PI3K inhibitor and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

TLR9 Induced Biomarkers for Patient Selection

A subset of TLRs (e.g., TLR7, TLR8, and TLR9) induce an immune response characterized by induction of IFN-α. As shown in FIGS. 8-12, PI3K inhibition by Compound 292 inhibits induction of IFN-α via TLR9. TLR9 is a nucleotide-sensing TLR; and functions as a receptor for viral and bacterial nucleic acids, as well as cellular danger or stress signals, e.g., acute phase reactants. In addition to the recognition of foreign nucleic acids, TLR9 has been shown to recognize self nucleic acid complexes in inflammatory myopathies, such as lupus. As stated above, biological concomitants of inflammatory myopathies (e.g., lupus) can include increased levels of TLR 9 signaling induced cytokines such as IFN-α. The potent inhibition of the TLR9-induced IFN-α signaling pathway by Compound 292 indicates Compound 292 can be used to prevent or treat disorders where the IFN-α or a TLR (e.g., TLR9) signaling pathway is altered, (e.g., increased). Examples of such disorders include, but are not limited to, inflammatory myopathies, lupus, cutaneous lupus, rheumatoid arthritis, scleroderma, and dermatomyositis.

In other embodiments, an altered level (e.g., increased) of TLR 9-induced cytokines, such as IFN-α, can be used as a biomarker to select patients for treatment with Compound 292. For example, a subject, e.g., a patient suffering from an inflammatory myopathy, e.g., lupus, cutaneous lupus, rheumatoid arthritis, scleroderma, systemic scleroderma, or dermatomyositis, can be screened for expression of TLR 9 induced cytokine expression, and/or IFN-α; based on the cytokine expression profile, the subject selected or not selected for treatment with Compound 292. Other embodiments include, screening a subject, e.g., a patient diagnosed with lupus, for expression of IFN-α, if the subject expresses an increased level of IFN-α as compared to a reference value (e.g., a reference standard), the subject is then selected for treatment with Compound 292.

A gene signature characteristic of a type I interferon response commonly activated in rheumatic diseases can also be evaluated. Rheumatic diseases that can be evaluated can include, but are not limited to, systemic lupus erythematosus, dermatomyositis, polymyositis, rheumatoid arthritis, and systemic scleroderma (e.g., as described in Higgs et al. *Ann Rheum Dis* (2011) 70: 2029-2036). The gene signature can include analysis of the level (e.g., expression) of one or more genes involved in a type I interferon induced response, e.g., IF16, RSAD2, STAT2, IFI44, LIPA, IFI44L and IFI27 (e.g., as described in Higgs et al 2011, supra).

In an embodiment, the gene signature can include analysis of the level (e.g., expression) of one or more of: type I IFNs, TNF-α, IL-1β, IL-10, IL-13, IL-17, or GM-CSF (e.g., as described in Higgs et al. *International Journal of Rheumatic Diseases* (2012) 15: 25-35). In one embodiment, the gene signature can include analysis of the level (e.g., expression) of one or more of the following: IFN-α serum levels of high-mobility group box protein 1 (HMGB1), C3a, or dsDNA (e.g., as described in Ruan et al. *The Journal of Immunology* (2010) 185: 4213-4222). In an embodiment, the gene signature can include analysis of the level (e.g., expression) of one or more of: inflammatory cytokines, e.g., type I IFNs, type II IFNs, IL-6, IL-1, TNF-α; immunomodulatory cytokines, e.g., IL-10 and TGF-β; IL-21, IL-17, or IL-2 (e.g., as described in Ohl et al. *Journal of Biomedicine and Biotechnology* (2011) Article ID: 432595).

Any combination of the aforementioned genes can be used to evaluate a subject. In one embodiment, the levels, e.g., expression, of one, two, three, four, five, six, seven, eight, nine, ten, eleven, twelve, thirteen, fourteen, fifteen or more than fifteen of: IFN-α, type I IFNs, type II IFNs, TNF-α, IL-1β, IL-6, IL-1, IL-2, IL-8, IL-10, IL-13, IL-17, IL-21, GM-CSF, TGF-β, IF16, RSAD2, STAT2, IFI44, LIPA, IFI44L or IFI27 can be evaluated. In another embodiment, the levels, e.g., expression, of one or more of: IFN-α, TNF-α, IL-6, or IL-8. In one embodiment, the gene signature can include analysis of level (e.g., expression) of IL-17; for example, one or more of: IFN-α, TNF-α, IL-6, IL-8, or IL-17 can be evaluated.

EXAMPLES

Example 1

IC50 Values for Selected PI3K Inhibitors

The $IC_{50}$ values for selected compounds were determined and are provided in Table 3. These data demonstrate that these compounds can serve as PI3K δ inhibitors.

TABLE 3

In Vitro IC$_{50}$ data for selected compounds.

| IC50(nM) | + (greater than 10 microMolar) | ++ (less than 10 microMolar) | +++ (less than 1 microMolar | ++++ (less than 100 nM) |
|---|---|---|---|---|
| PI3K δ | Compound No. 197, 199, 241, 259, 261, 263, 280, 282, 283, 314, 315, 318, 321, 322 | Compound No. 1, 5, 22, 27, 38, 39, 40, 41, 46, 92, 117, 118, 120, 129, 132, 164, 165, 172, 188, 186, 193, 194, 195, 217, 242, 246, 281, 284, 305, 317, 325 | Compound No. 4, 14, 15, 17, 18, 21, 26, 29, 31, 32, 34, 35, 36, 42, 43, 44, 45, 47, 49, 57, 69, 71, 85, 87, 94, 106, 107, 143, 175, 179, 181, 182, 183, 187, 189, 192, 225, 226, 228, 235, 236, 239, 248, 250, 258, 269, 274, 275, 285, 286, 297, 298, 299, 300, 307, 309, 313, 319, | Compound No. 2, 3, 6, 7, 8, 9, 10, 11, 12, 13, 16, 19, 20, 23, 24, 25, 28, 30, 33, 37, 48, 50, 51, 52, 53, 54, 55, 56, 58, 59, 60, 61, 62, 63, 64, 65, 66, 67, 68, 70, 72, 73, 74, 75, 76, 77, 78, 79, 80, 81, 82, 83, 84, 86, 88, 89, 90, 91, 93, 95, 96, 97, 98, 99, 100, 101, 102, 103, 104, 105, 108, 109, 110, 111, 112, 113, 114, 115, 119, 123, 124, 125, 126, 128, 134, 135, 136, 137, 138, 139, 141, 142, 144, 145, 146, 147, 148, 149, 150, 151. 152, 153, 154, 155, 156, 157, 158, 159, 160, 161, 162, 166, 167, 168, 169, 170, 171, 173, 174, 176, 177, 178, 180, 185, 188, 190, 191, 196, 198, 200, 201, 202, 203, 204, 205, 206, 207, 208, 209, 210, 211, 212, 213, 214, 215, 216, 218, 219, 220, 221, 222, 223, 224, 227, 229, 230, 231, 232, 233, 234, 237, 238, 240, 243, 244, 245, 247, 249, 251, 252, 253, 254, 255, 256, 257, 260, 262, 264, 265, 266, 267, 268, 270, 271, 272, 273, 276, 277, 278, 279, 287, 288, 289, 290, 291, 292, 293, 294, 295, 296, 301, 302, 303, 306, 308, 310, 311, 312, 316, 320, 323, 324 |
| PI3K γ | Compound No. 1, 4, 5, 18, 38, 43, 60, 69, 169, 172, 192, 193, 194, 199, 227, 228, 233, 259, 263, 280, 281, 282, 283, 314, 315, 317, 318, 321, 322, 325 | Compound No. 17, 34, 35, 37, 38, 40, 42, 57, 61, 65, 91, 92, 94, 105, 107, 164, 170, 175, 179, 181, 183, 184, 186, 187, 189, 195, 197, 219, 221, 224, 232, 239, 241, 242, 246, 248, 258, 261, 274, 284, 285, 294, 299, 303, 305, 307, 309, 312, 313, 319 | Compound No. 2, 8, 9, 10, 11, 14, 15, 20, 22, 27, 28, 39, 41, 46, 47, 49, 51, 55, 58, 66, 70, 71, 73, 76, 78, 80, 93, 98, 99, 100, 103, 104, 106, 108, 109, 161, 162, 163, 165, 166, 180, 188, 202, 206, 209, 212, 214, 216, 218, 220, 222, 229, 234, 236, 238, 250, 267, 268, 269, 271, 275, 279, 286, 293, 298, 300, 301, 308, 316 | Compound No. 3, 6, 7, 12, 13, 16, 19, 21, 23, 24, 25, 26, 29, 30, 31, 33, 36, 44, 45, 48, 50, 52, 53, 54, 56, 59, 62, 63, 64, 67, 68, 72, 74, 75, 77, 79, 81, 82, 83, 84, 86, 87, 88, 89, 90, 95, 96, 97, 101, 102, 142, 145, 146, 147, 148, 149, 150, 151, 152, 160, 167, 168, 171, 173, 174, 176, 177, 178. 182, 185, 190, 191, 196, 198, 200, 201, 203, 204, 205, 207, 208, 210, 211, 213, 215, 223, 230, 231, 235, 237, 240, 243, 244, 245, 247, 249, 251, 252, 253, 254, 255, 256, 257, 260, 262, 264, 265, 266, 270, 272, 273, 276, 277, 278, 287, 288, |

TABLE 3-continued

In Vitro IC$_{50}$ data for selected compounds.

| IC50(nM) | + (greater than 10 microMolar) | ++ (less than 10 microMolar) | +++ (less than 1 microMolar) | ++++ (less than 100 nM) |
|---|---|---|---|---|
| | | | | 289, 290, 291, 292, 295, 296, 302, 304, 306, 310, 311, 320, 323, 324 |
| PI3K α | Compound No. 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 54, 55, 56, 57, 58, 59, 60, 61, 62, 64, 65, 67, 68, 69, 70, 71, 72, 73, 74, 79, 80, 81, 82, 83, 85, 87, 88, 91, 93, 96, 98, 99, 100, 103, 104, 105, 106, 107, 109, 110, 111, 112, 114, 146, 160, 161, 162, 163, 164, 165, 166, 167, 169, 170, 172, 174, 175, 179, 180, 181, 182, 183, 184, 186, 187, 188, 189, 191, 192, 193, 194, 197, 202, 211, 212, 214, 215, 216, 218, 219, 220, 221, 222, 224, 227, 228, 238, 239, 241, 242, 246, 247, 248, 249, 250, 258, 259, 261, 263, 265, 266, 267, 268, 271, 274, 275, 280, 281, 282, 283, 284, 285, 286, 290, 293, 294, 298, 299, 300, 304, 308, 309, 313, 314, 315, 316, 317, 318, 319, 321, 322, 324, 325 | Compound No. 3, 7, 63, 66, 84, 86, 89, 90, 97, 108, 113, 115, 152, 168, 171, 173, 185, 190, 198, 203, 204, 205, 206, 207, 209, 210, 213, 223, 235, 237, 240, 243, 244, 245, 251, 253, 254, 255, 256, 269, 273, 279, 291, 292, 295, 296 | Compound No. 53, 95, 101, 102, 145, 147, 149, 151, 177, 208, 257, 260, 262, 264, 270, 272, 276, 277, 278, 287, 288, 289, 320, 323 | Compound No. 142, 148, 150, 153, 154, 155, 156, 157, 158, 159, 176, 201, 252 |
| PI3K β | Compound No. 8, 9, 10, 11, 14, 21, 22, 24, 26, 27, 28, 29, 34, 35, 36, 37, 38, 39, 40, 41, 42, 43, 44, 46, 52, 54, 56, 57, 59, 60, 64, 68, 69, 70, 73, 76, 78, 79, 80, 87, 88, 91, 93, 98, 103, 104, 105, 107, 109, 112, 146, 152, 162, 163, 164, 165, 166, 169, 170, 172, 175, 179, 180, 181, 182, 183, 184, 186, 187, 188, 189, 192, 193, 194, 197, 216, 217, 218, 221, 222, 224, 238, 248, 259, 261, 263, 266, 271, 275, 280, 282, 283, 284, 285, 286, 294, 299, 304, 310, 311, 312, 315, 317, 321, 322, 325 | Compound No. 3, 12, 13, 23, 25, 53, 55, 58, 61, 63, 65, 67, 71, 72, 74, 75, 77, 81, 82, 83, 84, 85, 86, 96, 99, 106, 108, 110, 111, 113, 114, 115, 145, 147, 149, 151, 154, 158, 160, 161, 167, 168, 171, 173, 174, 177, 178, 190, 191, 198, 202, 203, 205, 206, 207, 209, 210, 211, 212, 214, 215, 219, 220, 223, 228, 235, 240, 243, 244, 247, 249, 265, 269, 274, 281, 295, 296, 298, 300, 308, 316, 324 | Compound No. 7, 62, 66, 82, 89, 90, 95, 97, 100, 102, 150, 153, 159, 176, 185, 201, 204, 208, 213, 227, 237, 251, 252, 267, 276, 277, 290, 292, 293 | Compound No. 101, 142, 155, 156, 157, 200, 253, 254, 255, 256, 257, 260, 262, 264, 268, 270, 272, 273, 278, 279, 287, 288, 289, 291, 320, 323, |
| B cell proliferation EC$_{50}$ (nM) | Compound No. 38, 162, 199 | Compound No. 1, 2, 5, 22, 26, 27, 39, 40, 43, 49, 57, 71, 87, 112, 197, 207, 235 | Compound No. 4, 8, 9, 10, 11, 14, 15, 18, 19, 20, 21, 24, 25, 28, 29, 30, 31, 32, 34, 35, 36, 41, 42, 45, 46, 47, 50, 51, 61, 69, 70, 76, 77, 78, 79, 80, 85, 86, 91, 98, 100, 103, | Compound No. 3, 6, 7, 12, 13, 16, 17, 23, 33, 37, 44, 48, 53, 54, 55, 62, 63, 66, 67, 68, 72, 73, 74, 75, 81, 82, 83, 84, 88, 89, 90, 93, 95, 96, 97, 99, 101, 102, 108, 109, |

TABLE 3-continued

In Vitro IC$_{50}$ data for selected compounds.

| IC50(nM) | + (greater than 10 microMolar) | ++ (less than 10 microMolar) | +++ (less than 1 microMolar | ++++ (less than 100 nM) |
|---|---|---|---|---|
| | | | 104, 105, 106, 107, 110, 111, 114, 119, 124, 133, 135, 145, 152, 161, 162, 163, 169, 195, 212, 243, 294, 312 | 113, 115, 123, 125, 126, 128, 134, 136, 137, 138, 139, 141, 142, 144, 146, 147, 148, 149, 150, 151, 153, 154, 155, 156, 157, 158, 159, 160, 166, 167, 168, 170, 171, 173, 174, 176, 177, 178, 180, 187, 185, 188, 190, 191. 196, 198, 200, 201, 202, 203, 204, 205, 206, 208, 209, 210, 211, 213, 214, 215, 216, 219, 220, 221, 222, 223, 224, 227, 228, 229, 230, 231, 232, 233, 234, 237, 244, 245, 247, 248, 249, 251, 252, 253, 254, 255, 256, 257, 270, 276, 277, 278, 289, 290, 292, 295, 296, 298, 300, 301, 302, 303, 306, 308, 310, 311 |

TABLE 4

Structures of the Compounds for the IC50 results described in Table 3.

Structure

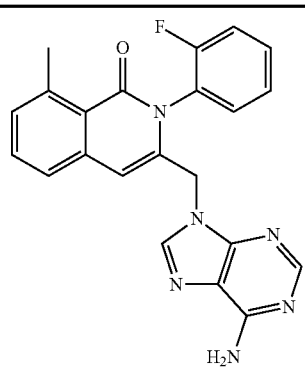

Compound 1

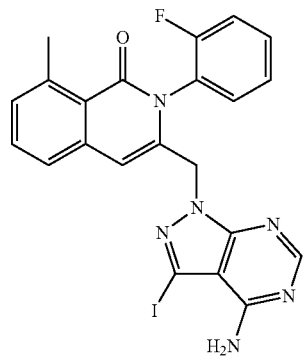 [SMILES: Cc1cccc2cc(Cn3nc(I)c4c(N)ncnc43)n(-c3ccccc3F)c(=O)c12]

Compound 2

TABLE 4-continued

Structures of the Compounds for the IC50 results described in Table 3.

Structure

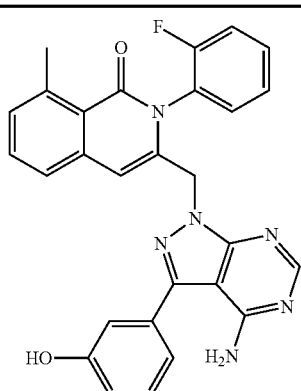

Compound 3

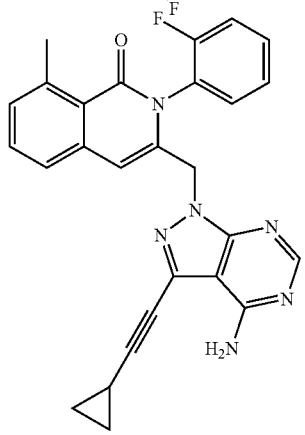

Compound 4

TABLE 4-continued
Structures of the Compounds for the IC50 results described in Table 3.
Structure
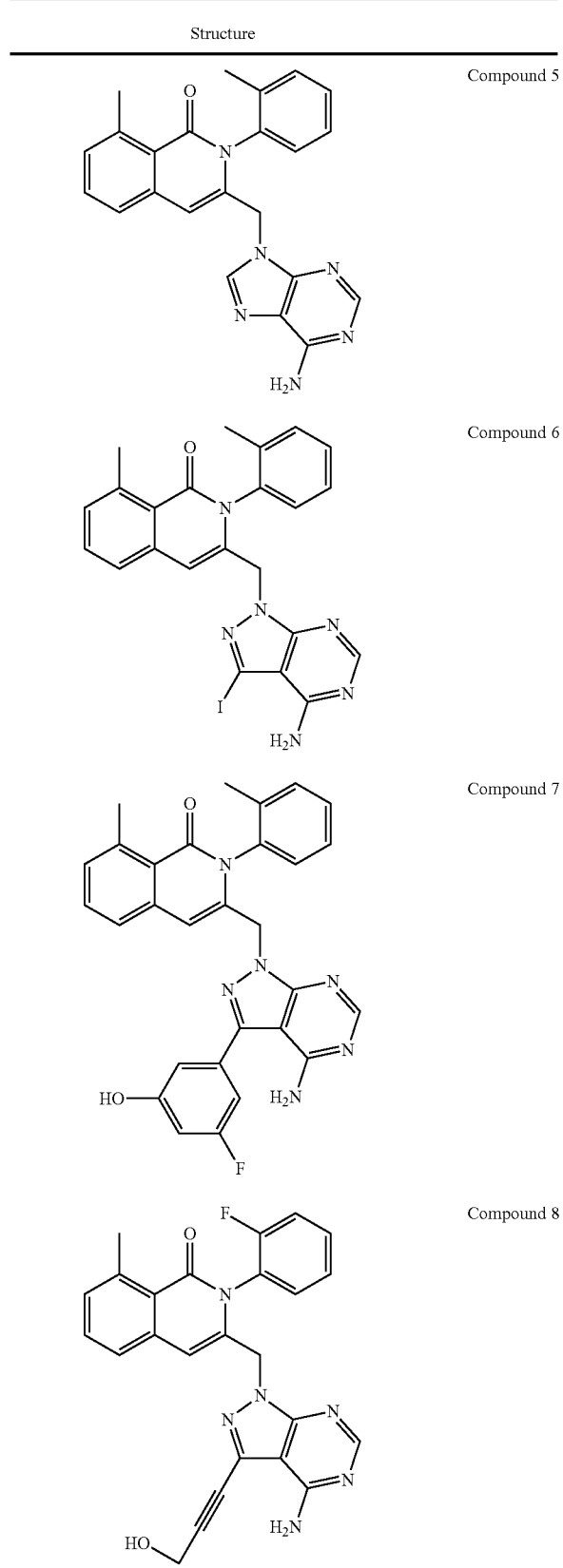
Compound 5
Compound 6
Compound 7
Compound 8
TABLE 4-continued
Structures of the Compounds for the IC50 results described in Table 3.
Structure
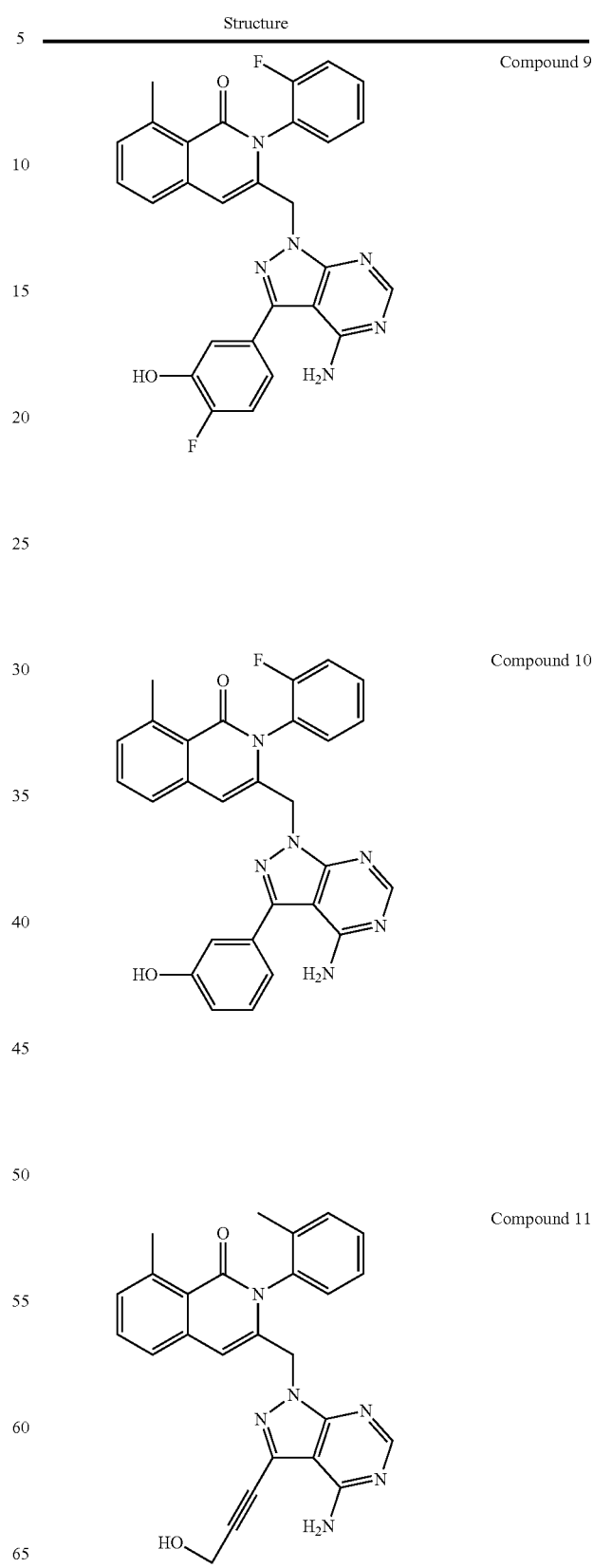
Compound 9
Compound 10
Compound 11

TABLE 4-continued

Structures of the Compounds for the IC50 results described in Table 3.

Structure

Compound 12

Compound 13

Compound 14

TABLE 4-continued

Structures of the Compounds for the IC50 results described in Table 3.

Structure

Compound 15

Compound 16

Compound 17

Compound 18

TABLE 4-continued
Structures of the Compounds for the IC50 results described in Table 3.
Structure
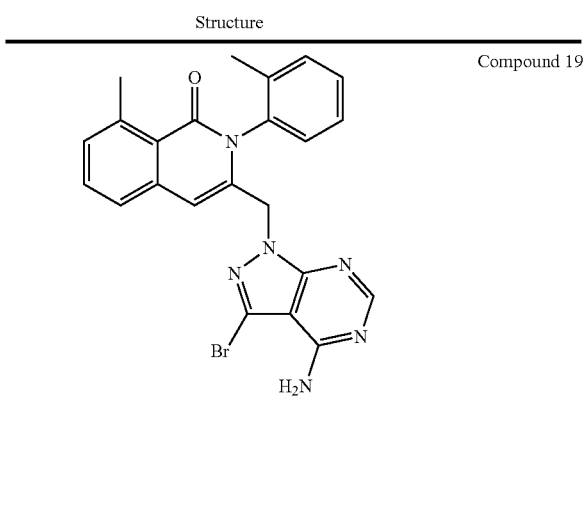
Compound 19
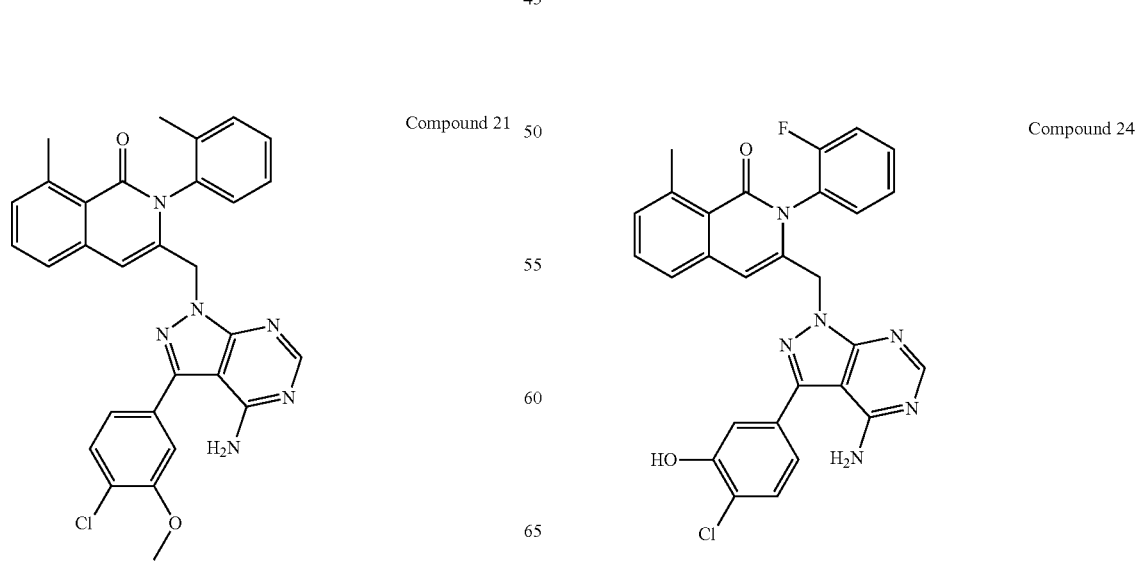
Compound 20
Compound 21
TABLE 4-continued
Structures of the Compounds for the IC50 results described in Table 3.
Structure
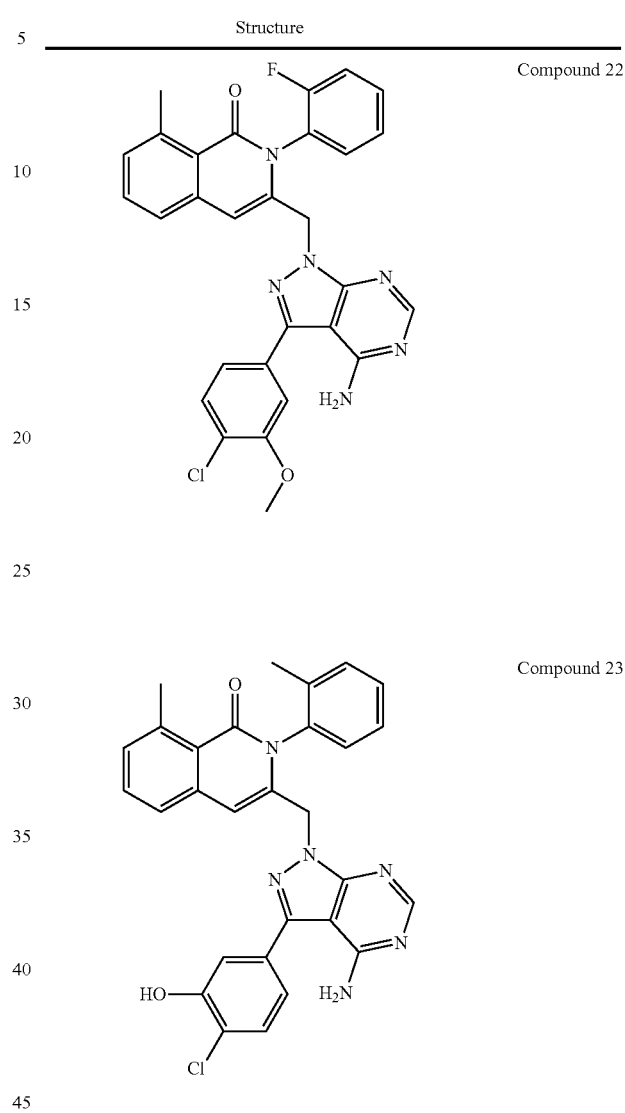
Compound 22
Compound 23
Compound 24

TABLE 4-continued

Structures of the Compounds for the IC50 results described in Table 3.

Structure

Compound 25

Compound 26

Compound 27

Compound 28

Compound 29

Compound 30

Compound 31

TABLE 4-continued

Structures of the Compounds for the IC50 results described in Table 3.

Structure

Compound 32

Compound 33

Compound 34

Compound 35

TABLE 4-continued

Structures of the Compounds for the IC50 results described in Table 3.

Structure

Compound 36

Compound 37

Compound 38

TABLE 4-continued
Structures of the Compounds for the IC50 results described in Table 3.
Structure
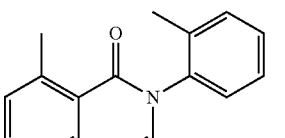

TABLE 4-continued
Structures of the Compounds for the IC50 results described in Table 3.
Structure
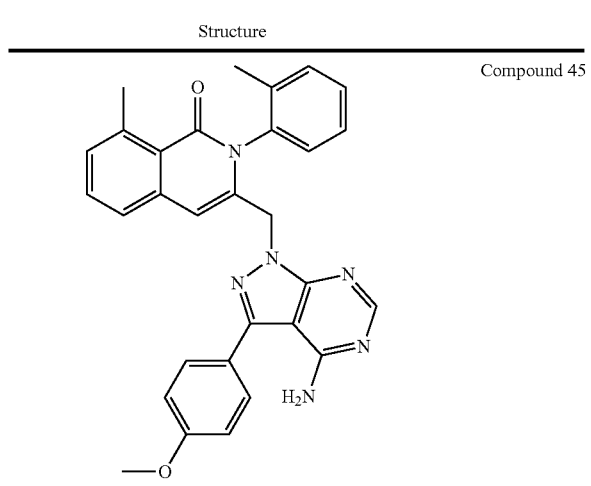
Compound 45
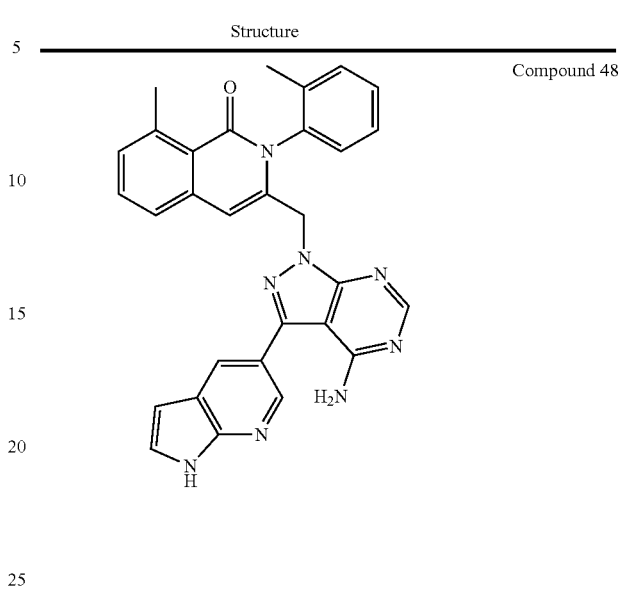
Compound 48
Compound 46
Compound 49
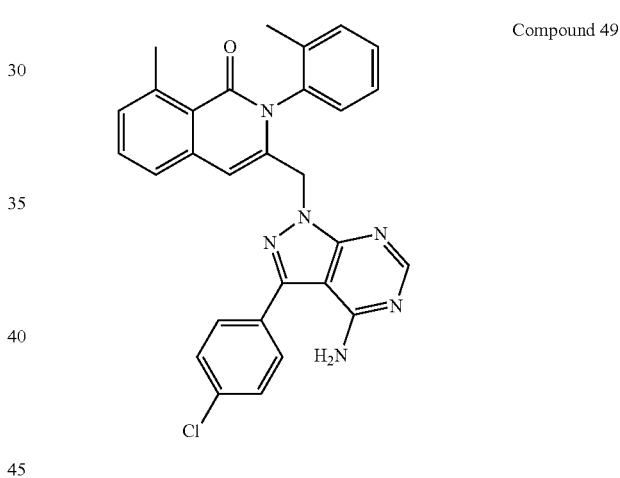
Compound 47
Compound 50
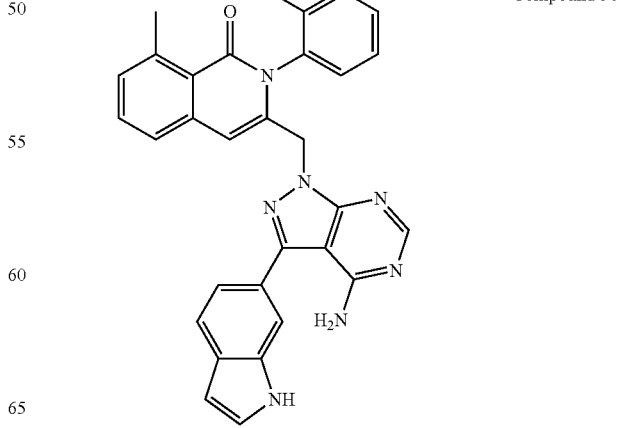

TABLE 4-continued
Structures of the Compounds for the IC50 results described in Table 3.
| Structure | |
|---|---|
| 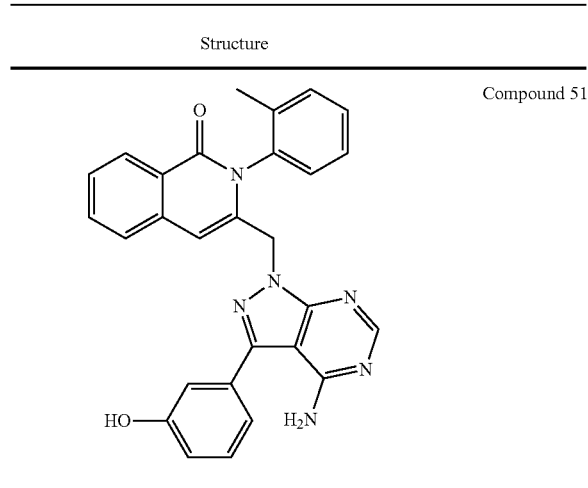 | Compound 51 |
| 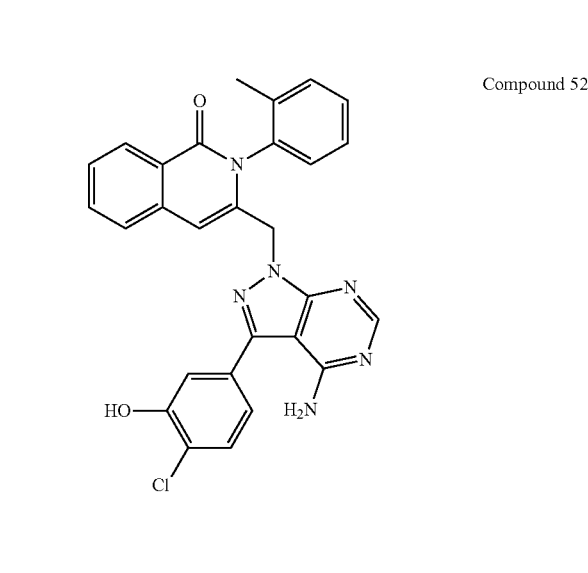 | Compound 52 |
| 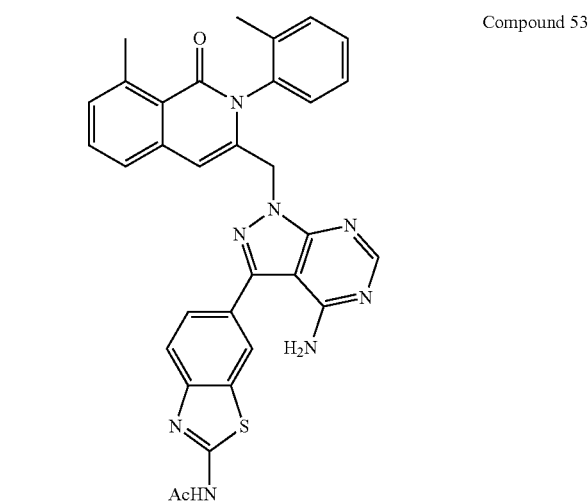 | Compound 53 |
TABLE 4-continued
Structures of the Compounds for the IC50 results described in Table 3.
| Structure | |
|---|---|
| 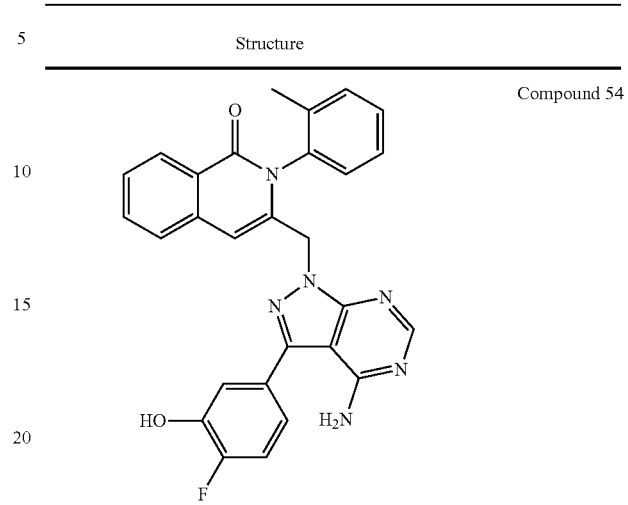 | Compound 54 |
| 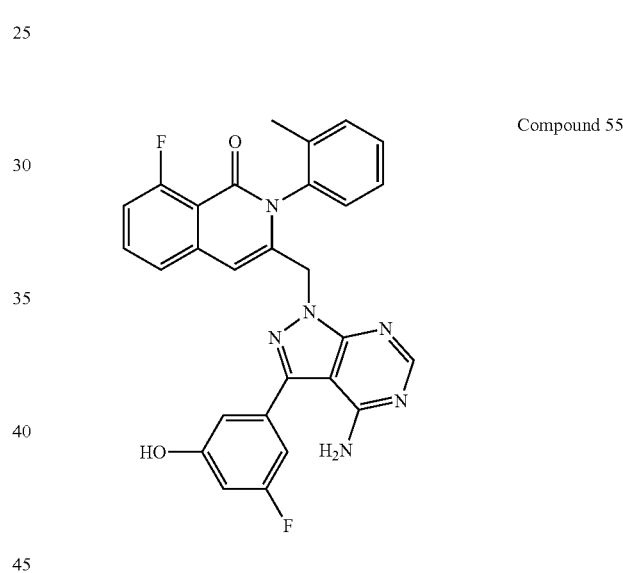 | Compound 55 |
| 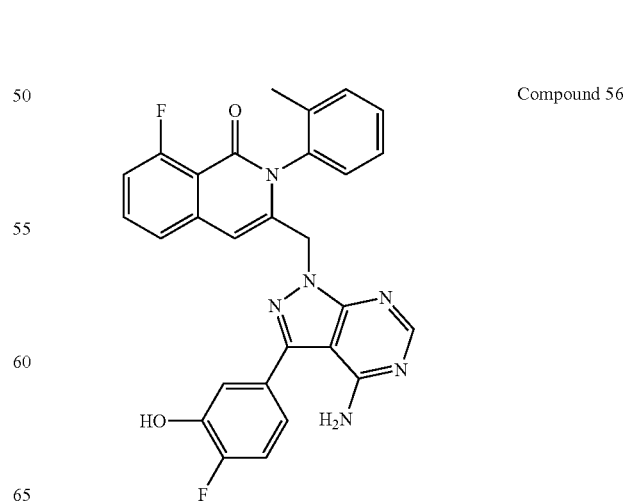 | Compound 56 |

TABLE 4-continued

Structures of the Compounds for the IC50 results described in Table 3.

| Structure | |
|---|---|
| (chemical structure) | Compound 57 |
| (chemical structure) | Compound 58 |
| (chemical structure) | Compound 59 |
| (chemical structure) | Compound 60 |
| (chemical structure) | Compound 61 |
| (chemical structure) | Compound 62 |
| (chemical structure) | Compound 63 |
| (chemical structure) | Compound 64 |

TABLE 4-continued
Structures of the Compounds for the IC50 results described in Table 3.
Structure
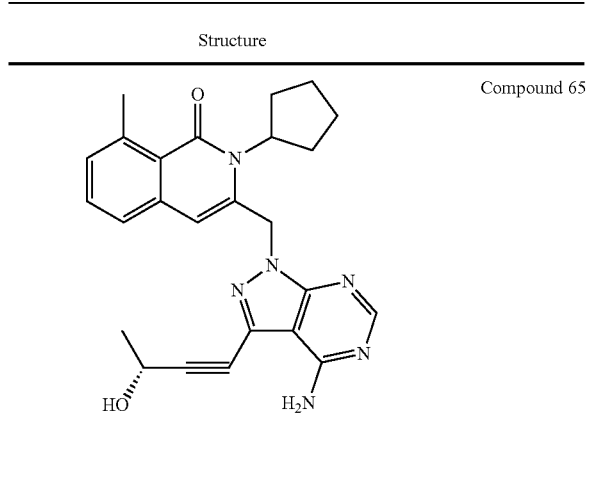
Compound 65
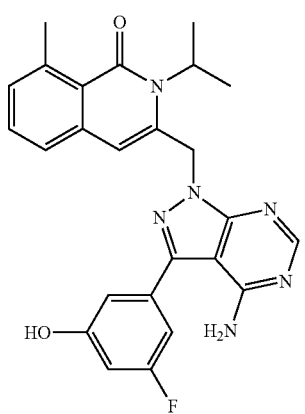 [SMILES: Cc1cccc2cc(Cn3nc(-c4cc(O)cc(F)c4)c4c(N)ncnc43)n(C(C)C)c(=O)c12]
Compound 66
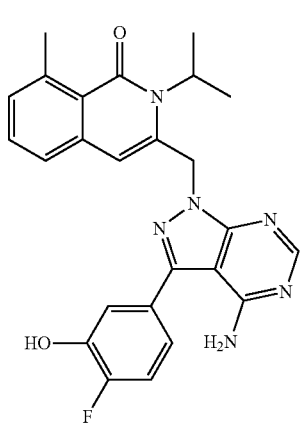
Compound 67
TABLE 4-continued
Structures of the Compounds for the IC50 results described in Table 3.
Structure
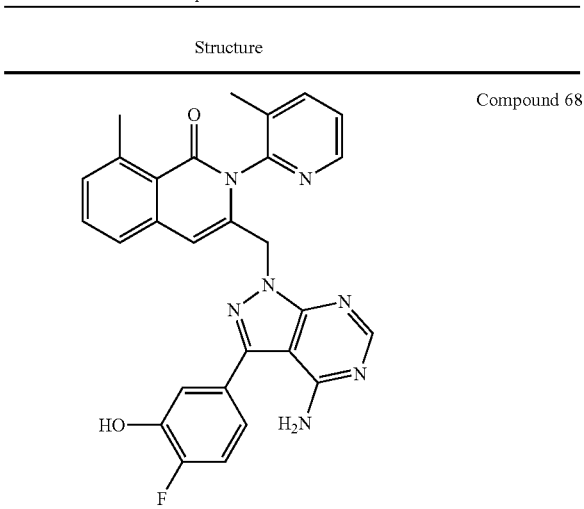
Compound 68
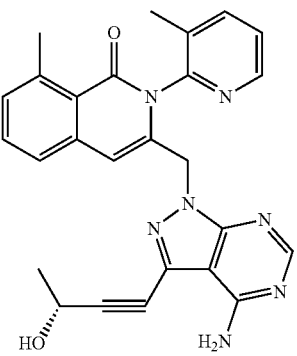 [SMILES: Cc1cccnc1-n1c(Cn2nc(C#C[C@@H](C)O)c3c(N)ncnc32)cc2cccc(C)c2c1=O]
Compound 69
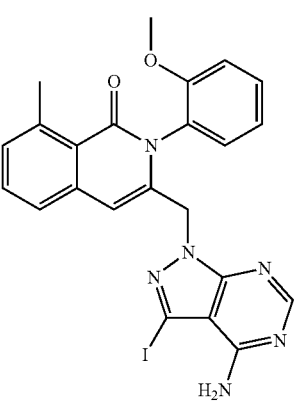 [SMILES: COc1ccccc1-n1c(Cn2nc(I)c3c(N)ncnc32)cc2cccc(C)c2c1=O]
Compound 70

TABLE 4-continued

Structures of the Compounds for the IC50 results described in Table 3.

Structure

Compound 71

Compound 72

Compound 73

TABLE 4-continued

Structures of the Compounds for the IC50 results described in Table 3.

Structure

Compound 74

Compound 75

Compound 76

Compound 77

TABLE 4-continued

Structures of the Compounds for the IC50 results described in Table 3.

Structure

Compound 78
Compound 79
Compound 80
Compound 81
Compound 82
Compound 83
Compound 84

TABLE 4-continued
Structures of the Compounds for the IC50 results described in Table 3.
| Structure | |
|---|---|
| 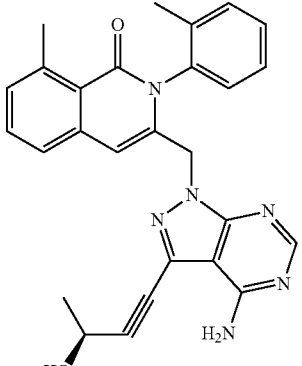 | Compound 85 |
| 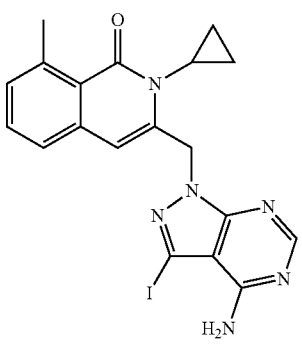 [SMILES: Cc1cccc2cc(Cn3nc(I)c4c(N)ncnc43)n(C3CC3)c(=O)c12] | Compound 86 |
| 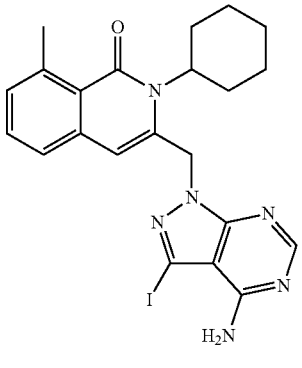 [SMILES: Cc1cccc2cc(Cn3nc(I)c4c(N)ncnc43)n(C3CCCCC3)c(=O)c12] | Compound 87 |
| 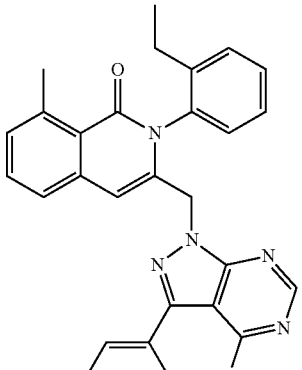 | Compound 88 |
TABLE 4-continued
Structures of the Compounds for the IC50 results described in Table 3.
| Structure | |
|---|---|
| 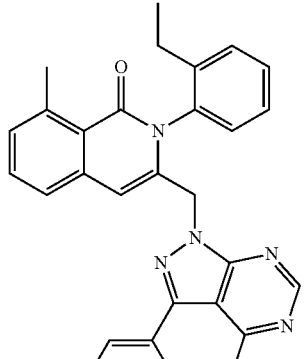 | Compound 89 |
| 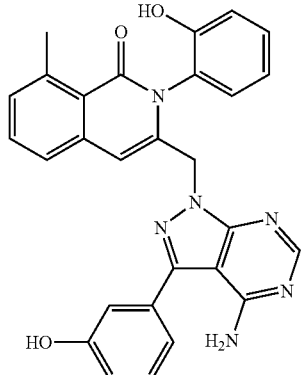 | Compound 90 |
| 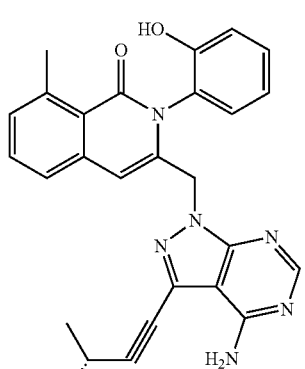 | Compound 91 |

TABLE 4-continued
Structures of the Compounds for the IC50 results described in Table 3.
Structure
Compound 92
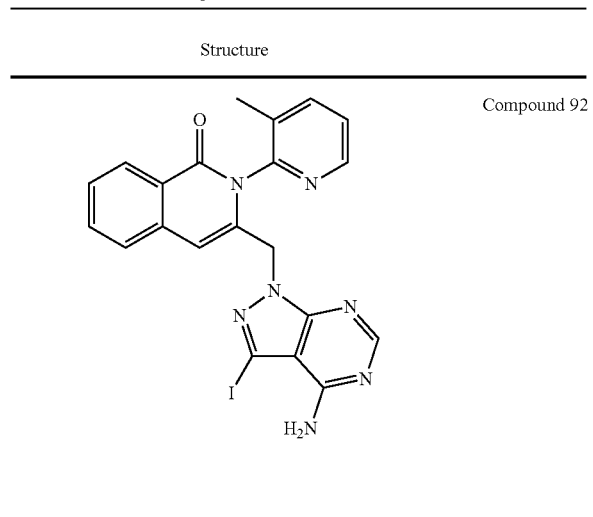
Compound 93
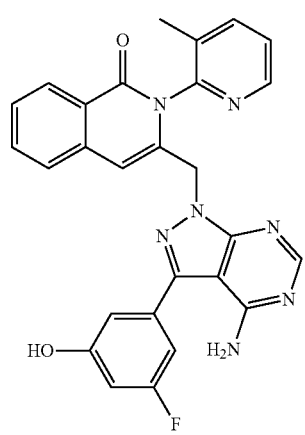 [SMILES: Cc1cccnc1-n1c(Cn2nc(-c3cc(O)cc(F)c3)c3c(N)ncnc32)cc2ccccc2c1=O]
Compound 94
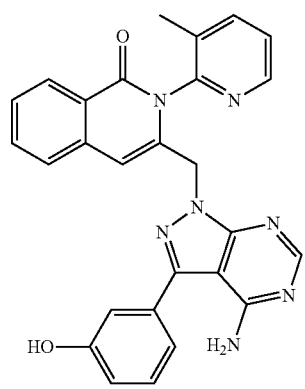 [SMILES: Cc1cccnc1-n1c(Cn2nc(-c3cccc(O)c3)c3c(N)ncnc32)cc2ccccc2c1=O]
TABLE 4-continued
Structures of the Compounds for the IC50 results described in Table 3.
Structure
Compound 95
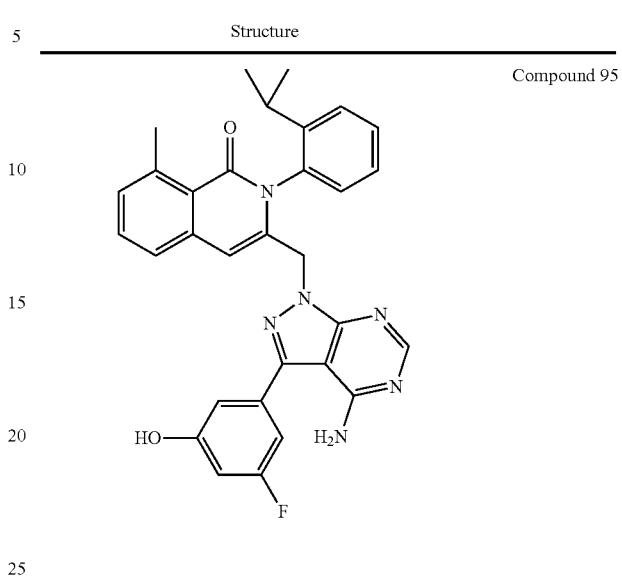
Compound 96
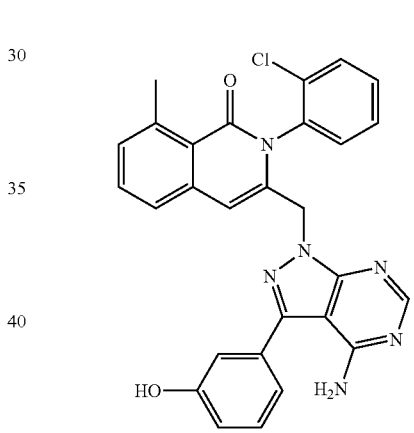
Compound 97
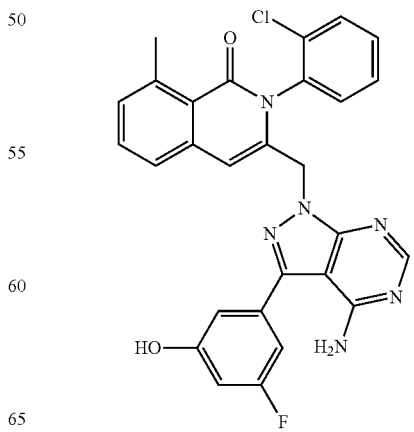

TABLE 4-continued
Structures of the Compounds for the IC50 results described in Table 3.
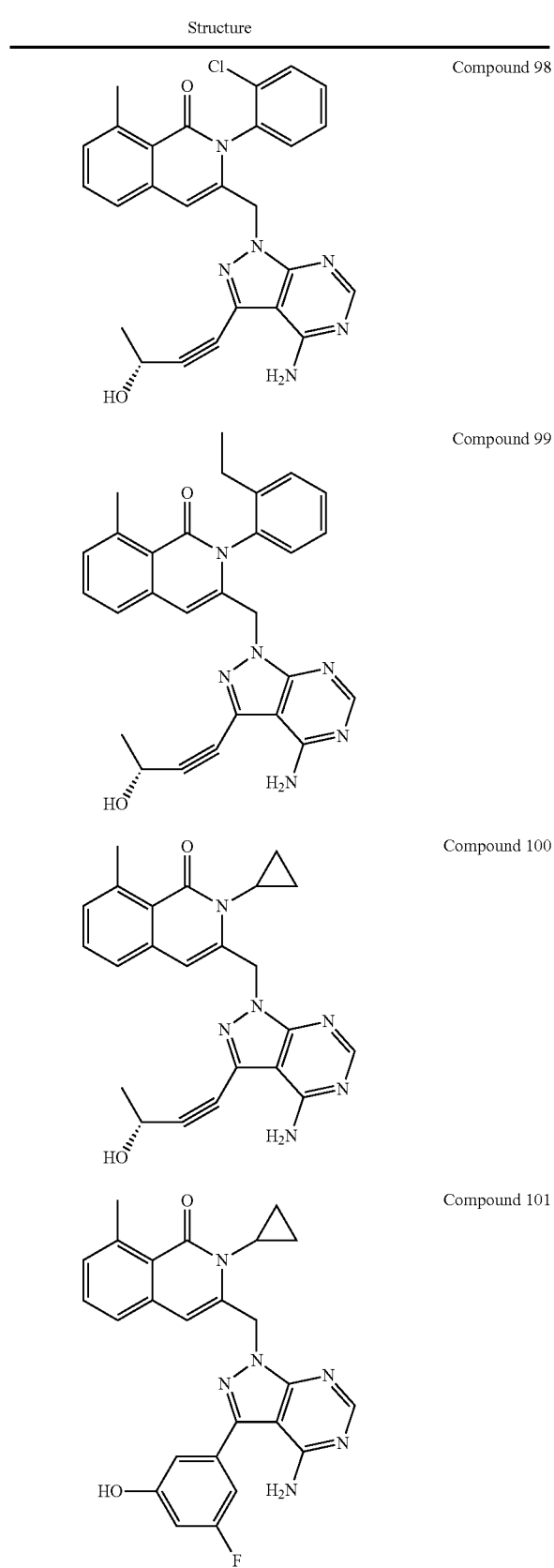
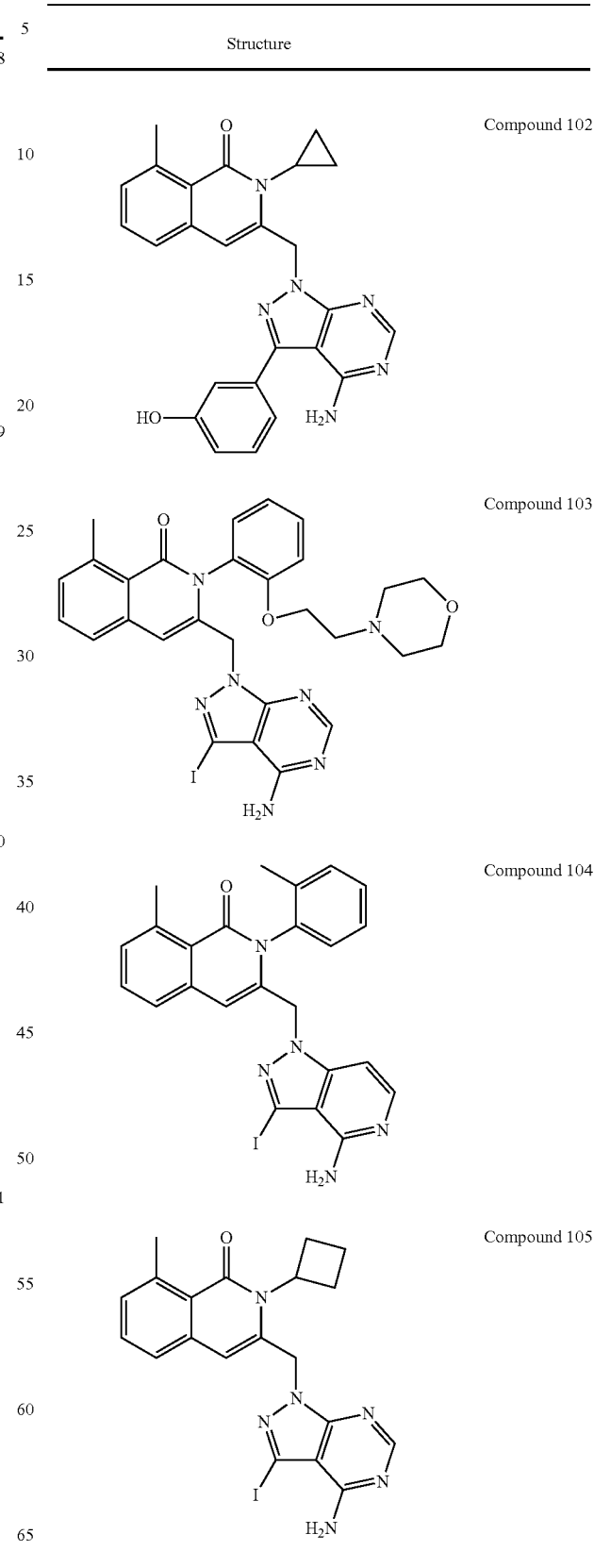

TABLE 4-continued

Structures of the Compounds for the IC50 results described in Table 3.

| Structure | |
|---|---|
| (structure) | Compound 106 |
| (structure) | Compound 107 |
| (structure) | Compound 108 |
| (structure) | Compound 109 |
| (structure) | Compound 110 |
| (structure) | Compound 111 |
| (structure) | Compound 112 |

TABLE 4-continued
Structures of the Compounds for the IC50 results described in Table 3.
| Structure | |
|---|---|
| 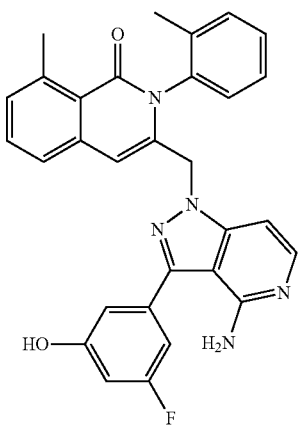 [SMILES: Cc1ccccc1-n1c(Cn2nc(-c3cc(O)cc(F)c3)c3c(N)nccc32)cc2cccc(C)c2c1=O] | Compound 113 |
| 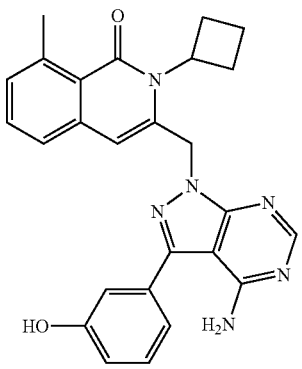 [SMILES: Cc1cccc2cc(Cn3nc(-c4cccc(O)c4)c4c(N)ncnc43)n(C3CCC3)c(=O)c12] | Compound 114 |
| 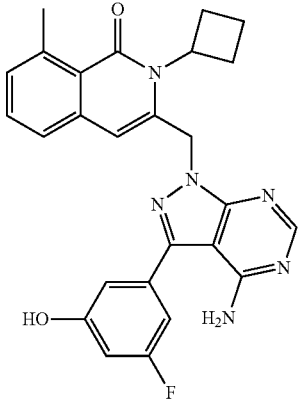 [SMILES: Cc1cccc2cc(Cn3nc(-c4cc(O)cc(F)c4)c4c(N)ncnc43)n(C3CCC3)c(=O)c12] | Compound 115 |
| 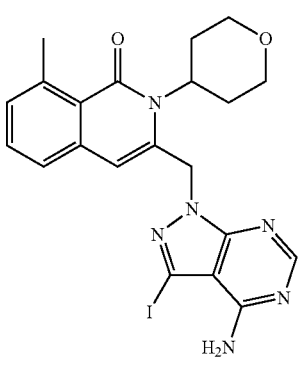 | Compound 116 |
| 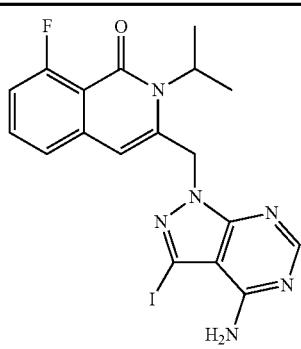 | Compound 117 |
| 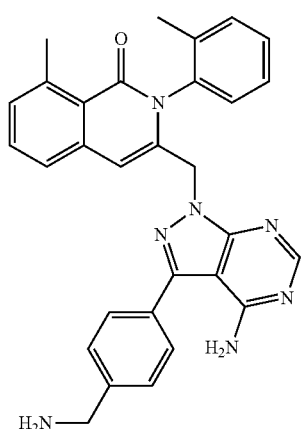 | Compound 118 |
| 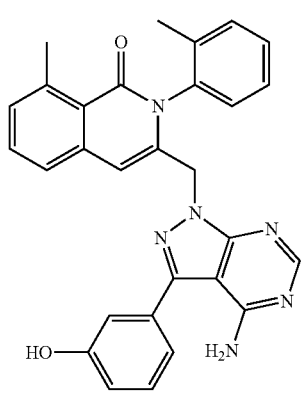 | Compound 119 |
| 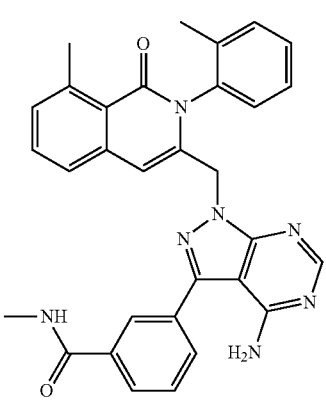 [SMILES: CNC(=O)c1cccc(-c2nn(Cc3cc4cccc(C)c4c(=O)n3-c3ccccc3C)c3ncnc(N)c23)c1] | Compound 120 |

TABLE 4-continued
Structures of the Compounds for the IC50 results described in Table 3.
Structure
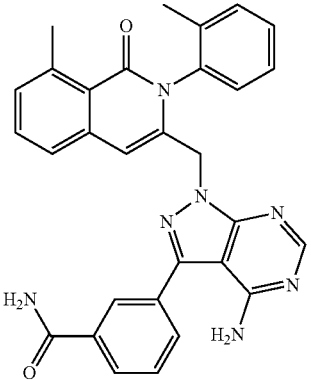 [SMILES: Cc1ccccc1-n1c(Cn2nc(-c3cccc(C(N)=O)c3)c3c(N)ncnc32)cc2cccc(C)c2c1=O]
Compound 121
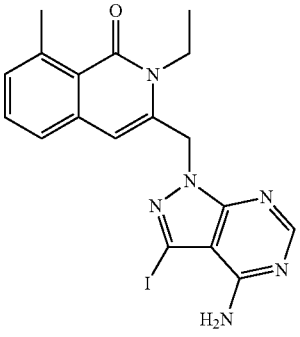 [SMILES: CCn1c(Cn2nc(I)c3c(N)ncnc32)cc2cccc(C)c2c1=O]
Compound 122
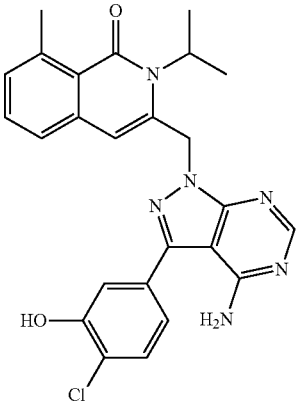 [SMILES: Cc1cccc2cc(Cn3nc(-c4ccc(Cl)c(O)c4)c4c(N)ncnc43)n(C(C)C)c(=O)c12]
Compound 123
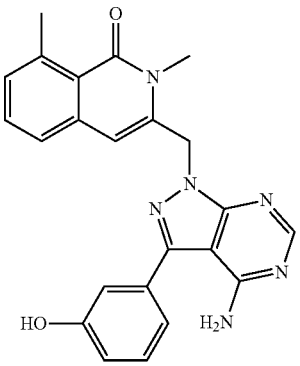 [SMILES: Cc1cccc2cc(Cn3nc(-c4cccc(O)c4)c4c(N)ncnc43)n(C)c(=O)c12]
Compound 124
TABLE 4-continued
Structures of the Compounds for the IC50 results described in Table 3.
Structure
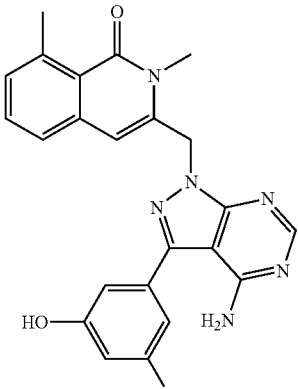
Compound 125
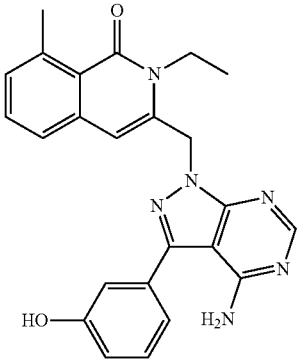 [SMILES: CCn1c(Cn2nc(-c3cccc(O)c3)c3c(N)ncnc32)cc2cccc(C)c2c1=O]
Compound 126
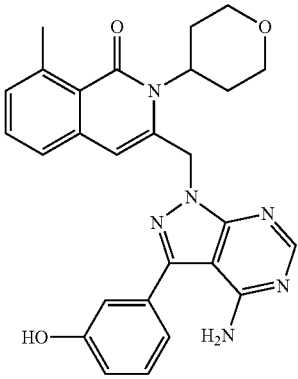 [SMILES: Cc1cccc2cc(Cn3nc(-c4cccc(O)c4)c4c(N)ncnc43)n(C3CCOCC3)c(=O)c12]
Compound 127

TABLE 4-continued
Structures of the Compounds for the IC50 results described in Table 3.
Structure
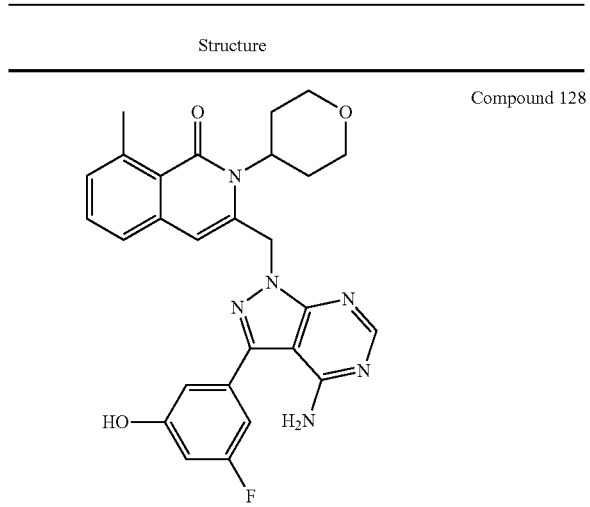
Compound 128
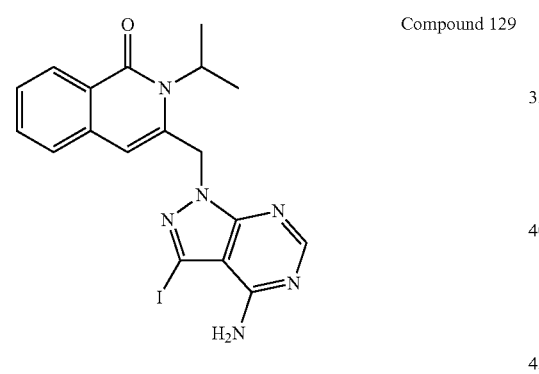
Compound 129
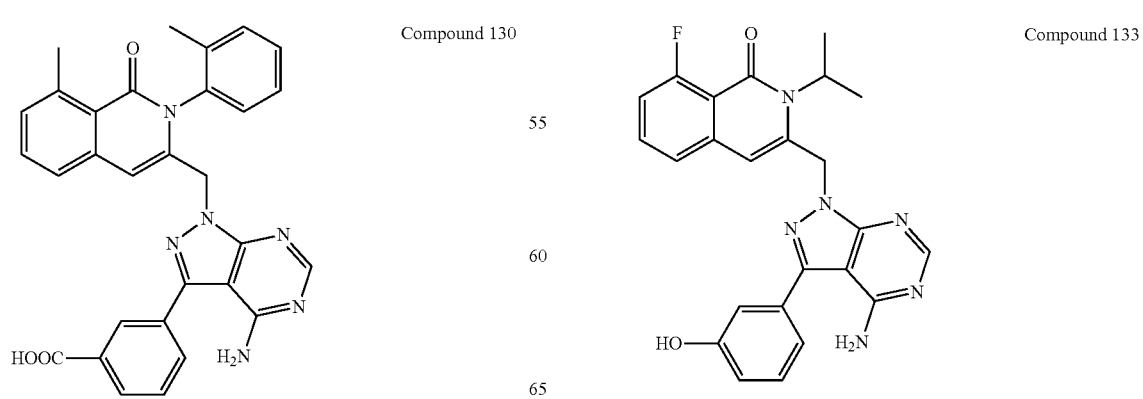
Compound 130
TABLE 4-continued
Structures of the Compounds for the IC50 results described in Table 3.
Structure
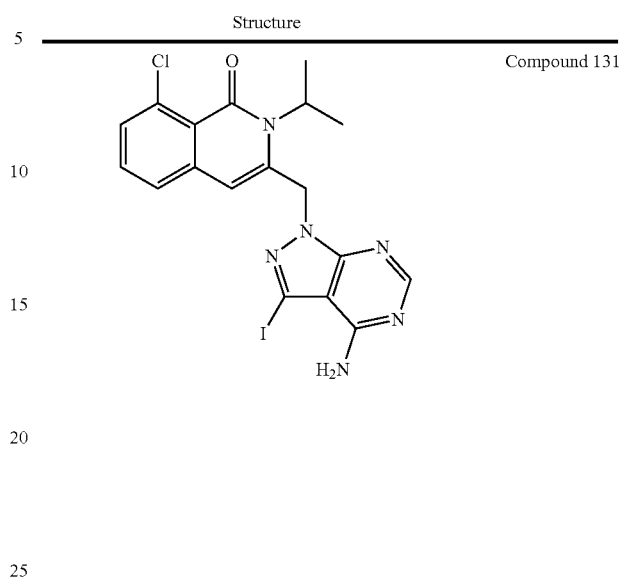
Compound 131
Compound 132
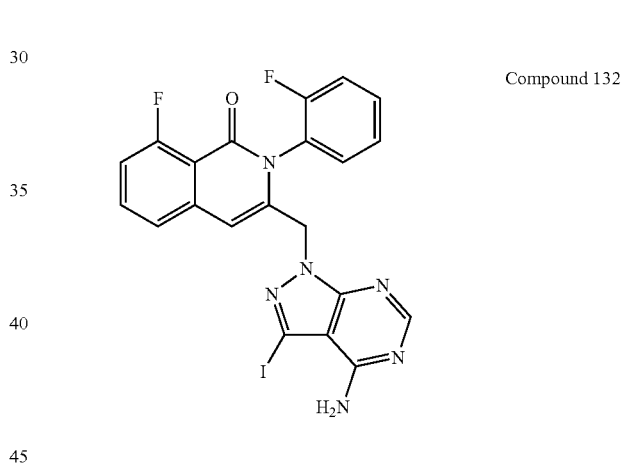
Compound 133

TABLE 4-continued

Structures of the Compounds for the IC50 results described in Table 3.

| Structure | |
|---|---|
| (structure) | Compound 134 |
| +Get,415 | Compound 135 |
| (structure) | Compound 136 |
| (structure) | Compound 137 |
| (structure) | Compound 138 |
| (structure) | Compound 139 |
| (structure) | Compound 141 |
| (structure) | Compound 142 |

TABLE 4-continued
Structures of the Compounds for the IC50 results described in Table 3.
Structure
Compound 143
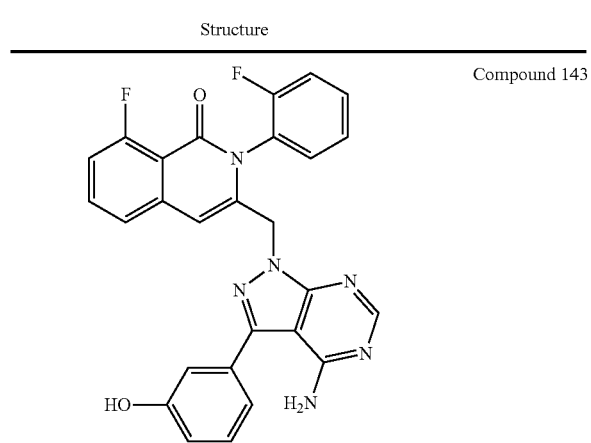
Compound 146
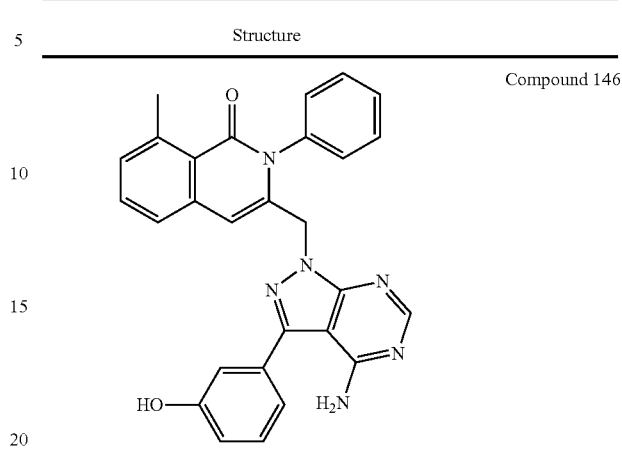
Compound 144
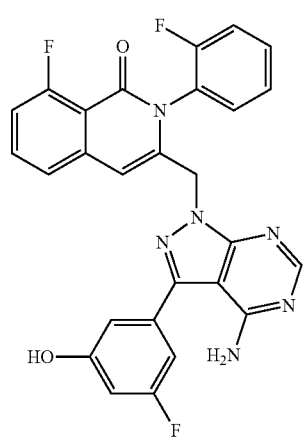
Compound 147
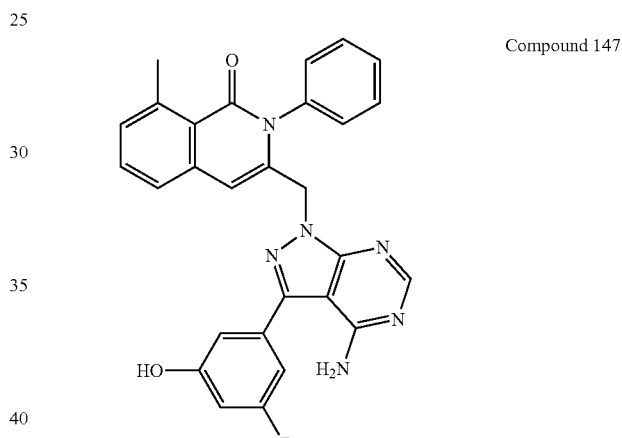
Compound 145
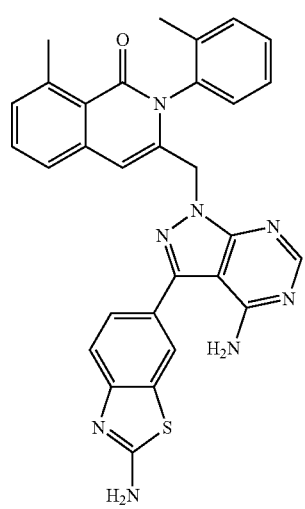 [SMILES: Cc1ccccc1-n1c(Cn2nc(-c3ccc4nc(N)sc4c3)c3c(N)ncnc32)cc2cccc(C)c2c1=O]
Compound 148
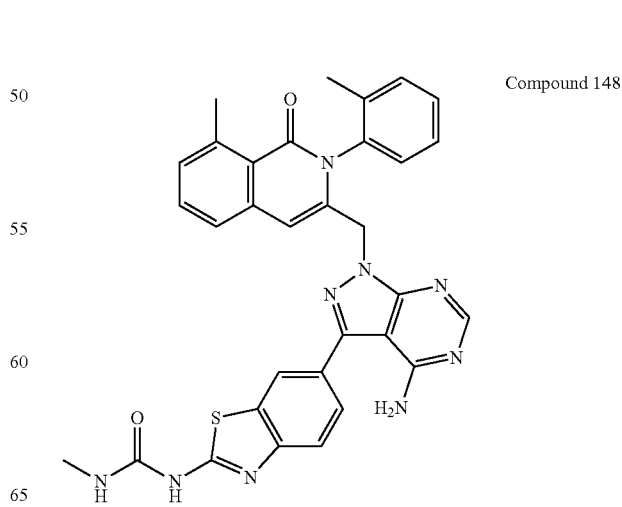

TABLE 4-continued

Structures of the Compounds for the IC50 results described in Table 3.

| Structure | |
|---|---|
| (structure) | Compound 149 |
| (structure) | Compound 150 |
| (structure) | Compound 151 |
| (structure) | Compound 152 |
| (structure) | Compound 153 |
| (structure) | Compound 154 |

TABLE 4-continued
Structures of the Compounds for the IC50 results described in Table 3.
Structure
Compound 155
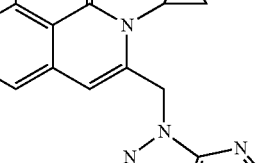
Compound 156
Compound 157
TABLE 4-continued
Structures of the Compounds for the IC50 results described in Table 3.
Structure
Compound 158
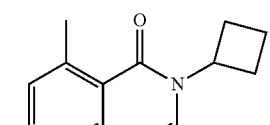
Compound 159
Compound 160

TABLE 4-continued

Structures of the Compounds for the IC50 results described in Table 3.

Structure

Compound 161

Compound 162

Compound 163

Compound 164

Compound 165

Compound 166

Compound 167

TABLE 4-continued
Structures of the Compounds for the IC50 results described in Table 3.
Structure
Compound 168
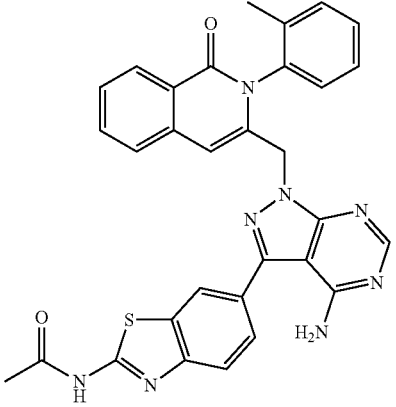 [SMILES: CC(=O)Nc1nc2ccc(-c3nn(Cc4cc5ccccc5c(=O)n4-c4ccccc4C)c4ncnc(N)c34)cc2s1]
Compound 169
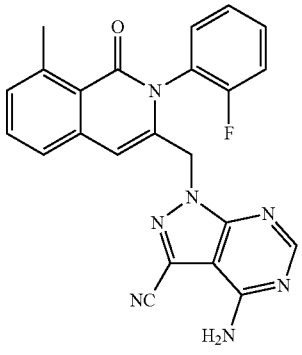 [SMILES: Cc1cccc2cc(Cn3nc(C#N)c4c(N)ncnc43)n(-c3ccccc3F)c(=O)c12]
Compound 170
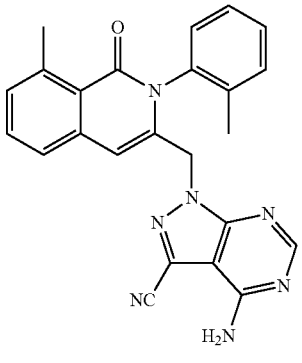 [SMILES: Cc1ccccc1-n1c(Cn2nc(C#N)c3c(N)ncnc32)cc2cccc(C)c2c1=O]
Compound 171
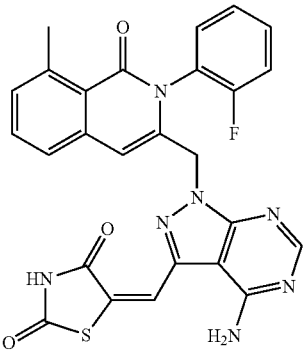
TABLE 4-continued
Structures of the Compounds for the IC50 results described in Table 3.
Structure
Compound 172
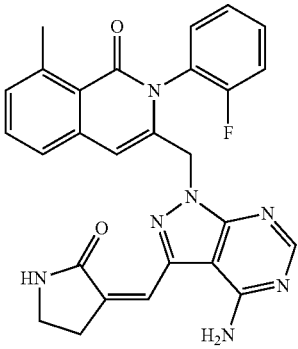 [SMILES: Cc1cccc2cc(Cn3nc(/C=C4/CCNC4=O)c4c(N)ncnc43)n(-c3ccccc3F)c(=O)c12]
Compound 173
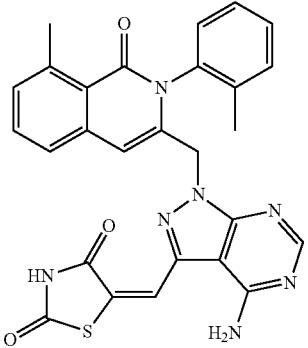 [SMILES: Cc1ccccc1-n1c(Cn2nc(/C=C3/SC(=O)NC3=O)c3c(N)ncnc32)cc2cccc(C)c2c1=O]
Compound 174
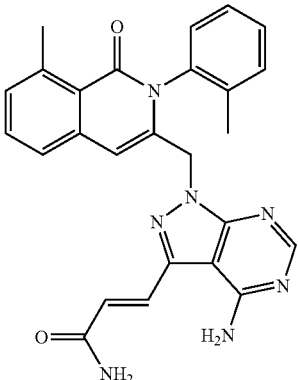
Compound 175
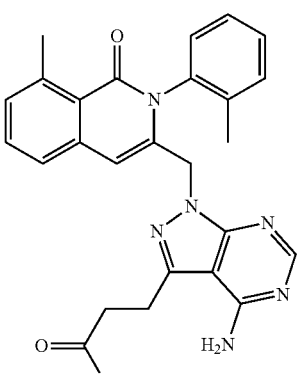

TABLE 4-continued

Structures of the Compounds for the IC50 results described in Table 3.

Structure

Compound 176

Compound 177

Compound 178

TABLE 4-continued

Structures of the Compounds for the IC50 results described in Table 3.

Structure

Compound 179

Compound 180

Compound 181

Compound 182

TABLE 4-continued

Structures of the Compounds for the IC50 results described in Table 3.

| Structure | |
|---|---|
| (structure) | Compound 183 |
| (structure) | Compound 184 |
| (structure) | Compound 185 |
| (structure) | Compound 186 |
| (structure) | Compound 187 |
| (structure) | Compound 188 |
| (structure) | Compound 189 |
| (structure) | Compound 190 |

TABLE 4-continued
Structures of the Compounds for the IC50 results described in Table 3.
| Structure | |
|---|---|
| 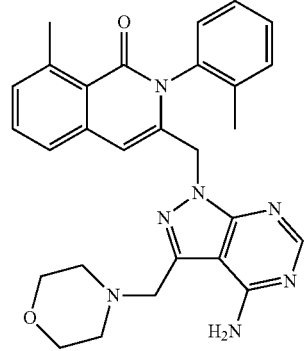 [SMILES: Cc1ccccc1-n1c(Cn2nc(CN3CCOCC3)c3c(N)ncnc32)cc2cccc(C)c2c1=O] | Compound 191 |
| | Compound 192 |
| | Compound 193 |
| 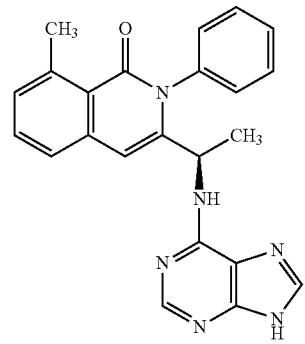 [SMILES: Cc1cccc2cc([C@@H](C)Nc3ncnc4[nH]cnc34)n(-c3ccccc3)c(=O)c12] | Compound 194 |
| | Compound 195 |
| | Compound 196 |
| | Compound 197 |

TABLE 4-continued

Structures of the Compounds for the IC50 results described in Table 3.

| Structure | |
|---|---|
| (structure) | Compound 198 |
| (structure) | Compound 199 |
| (structure) | Compound 200 |
| (structure) | Compound 201 |
| (structure) | Compound 202 |
| (structure) | Compound 203 |
| (structure) | Compound 204 |
| (structure) | Compound 205 |

TABLE 4-continued

Structures of the Compounds for the IC50 results described in Table 3.

Structure

Compound 206

Compound 207

Compound 208

Compound 209

TABLE 4-continued

Structures of the Compounds for the IC50 results described in Table 3.

Structure

Compound 210

Compound 211

Compound 212

Compound 213

TABLE 4-continued
Structures of the Compounds for the IC50 results described in Table 3.
| Structure | |
|---|---|
| 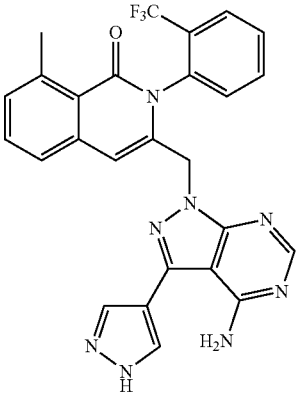 [SMILES: Cc1cccc2cc(Cn3nc(-c4cn[nH]c4)c4c(N)ncnc43)n(-c3ccccc3C(F)(F)F)c(=O)c12] | Compound 214 |
| 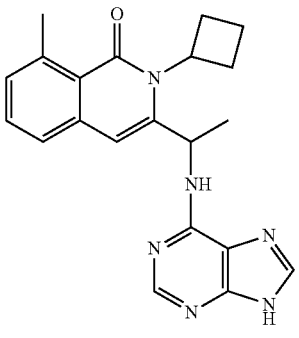 [SMILES: Cc1cccc2cc(C(C)Nc3ncnc4[nH]cnc34)n(C3CCC3)c(=O)c12] | Compound 215 |
| 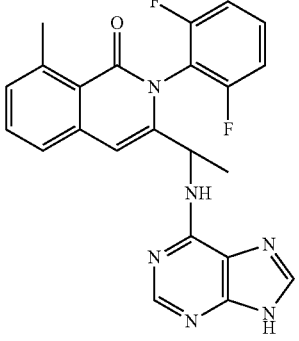 | Compound 216 |
| 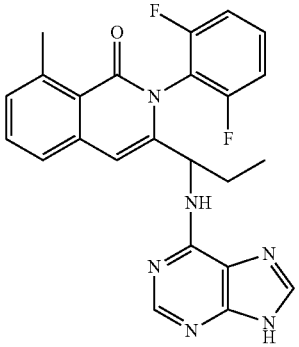 [SMILES: CCC(Nc1ncnc2[nH]cnc12)c1cc2cccc(C)c2c(=O)n1-c1c(F)cccc1F] | Compound 217 |
| 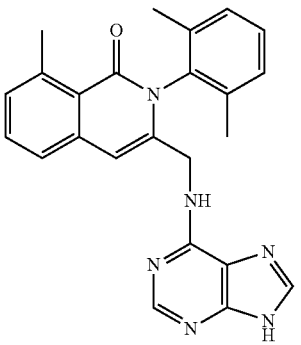 [SMILES: Cc1cccc(C)c1-n1c(CNc2ncnc3[nH]cnc23)cc2cccc(C)c2c1=O] | Compound 218 |
| 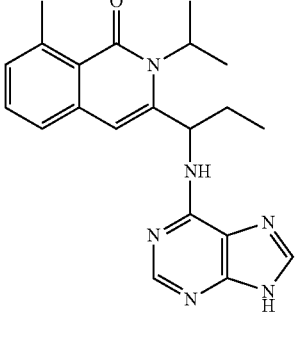 | Compound 219 |
| 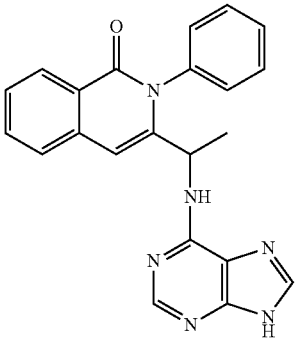 [SMILES: CC(Nc1ncnc2[nH]cnc12)c1cc2ccccc2c(=O)n1-c1ccccc1] | Compound 220 |
| 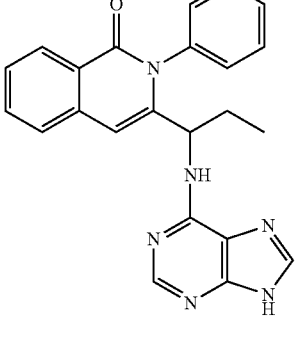 | Compound 221 |

TABLE 4-continued
Structures of the Compounds for the IC50 results described in Table 3.
| Structure | |
|---|---|
| 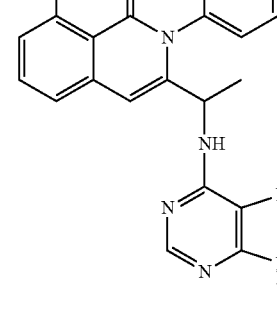 | Compound 222 |
| 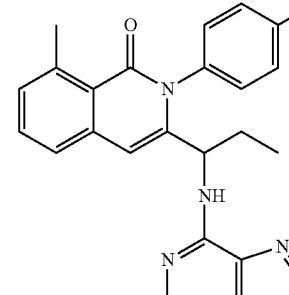 | Compound 223 |
| 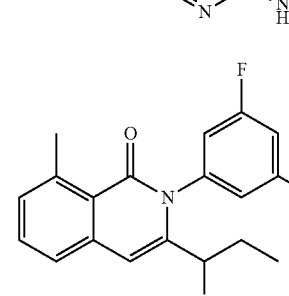 | Compound 224 |
| 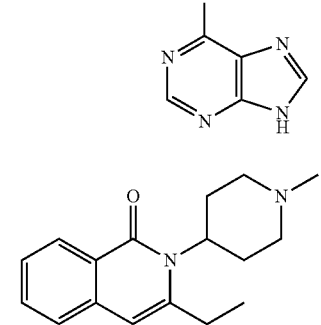 | Compound 225 |
TABLE 4-continued
Structures of the Compounds for the IC50 results described in Table 3.
| Structure | |
|---|---|
| 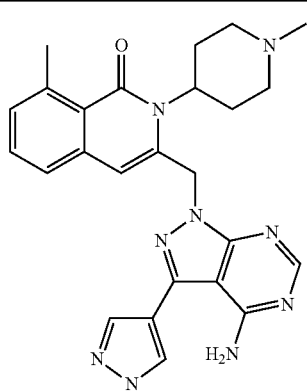 | Compound 226 |
| 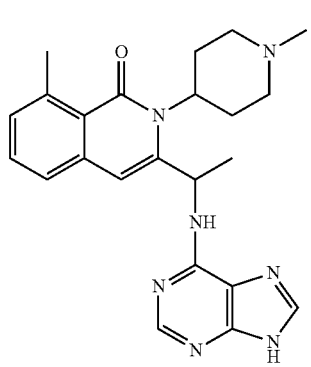 [SMILES: Cc1cccc2cc(C(C)Nc3ncnc4[nH]cnc34)n(C3CCN(C)CC3)c(=O)c12] | Compound 227 |
| 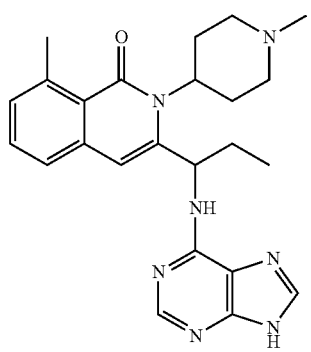 [SMILES: CCC(Nc1ncnc2[nH]cnc12)c1cc2cccc(C)c2c(=O)n1C1CCN(C)CC1] | Compound 228 |
| 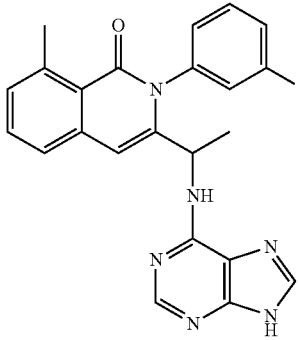 | Compound 229 |

TABLE 4-continued

Structures of the Compounds for the IC50 results described in Table 3.

Structure

Compound 230

Compound 231

Compound 232

Compound 233

TABLE 4-continued

Structures of the Compounds for the IC50 results described in Table 3.

Structure

Compound 234

Compound 235

Compound 236

Compound 237

TABLE 4-continued

Structures of the Compounds for the IC50 results described in Table 3.

Structure

Compound 238

Compound 239

Compound 240

Compound 241

TABLE 4-continued

Structures of the Compounds for the IC50 results described in Table 3.

Structure

Compound 242

Compound 243

Compound 244

Compound 245

TABLE 4-continued
Structures of the Compounds for the IC50 results described in Table 3.
Structure
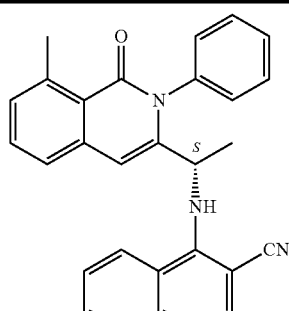
Compound 246
Compound 247
Compound 248
Compound 249
TABLE 4-continued
Structures of the Compounds for the IC50 results described in Table 3.
Structure
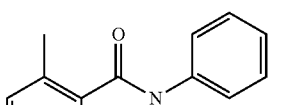
Compound 250
Compound 251
Compound 252

TABLE 4-continued

Structures of the Compounds for the IC50 results described in Table 3.

Structure

Compound 253

Compound 254

Compound 255

Compound 256

TABLE 4-continued

Structures of the Compounds for the IC50 results described in Table 3.

Structure

Compound 257

Compound 258

Compound 259

Compound 260

TABLE 4-continued

Structures of the Compounds for the IC50 results described in Table 3.

| Structure | |
|---|---|
| (chemical structure) | Compound 261 |
| (chemical structure) | Compound 262 |
| (chemical structure) | Compound 263 |
| (chemical structure) | Compound 264 |
| (chemical structure) | Compound 265 |
| (chemical structure) | Compound 266 |
| (chemical structure) | Compound 267 |
| (chemical structure) | Compound 268 |

TABLE 4-continued
Structures of the Compounds for the IC50 results described in Table 3.
Structure
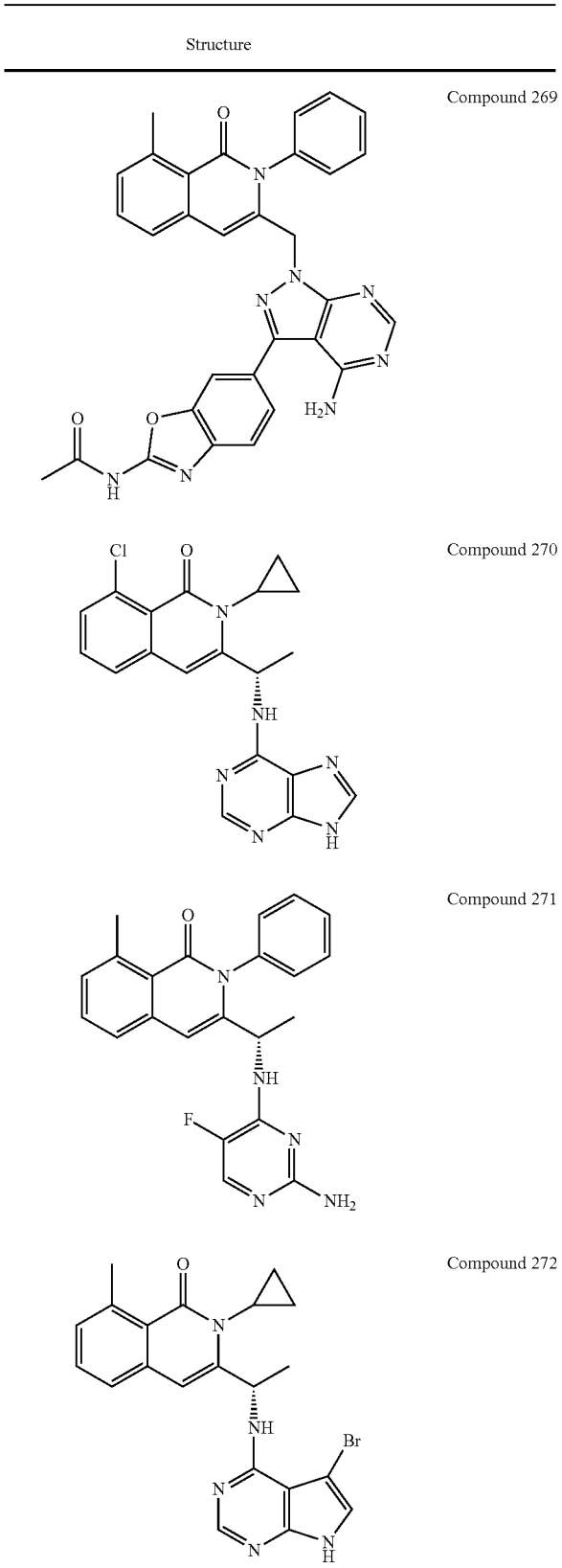
Compound 269
Compound 270
Compound 271
Compound 272
TABLE 4-continued
Structures of the Compounds for the IC50 results described in Table 3.
Structure
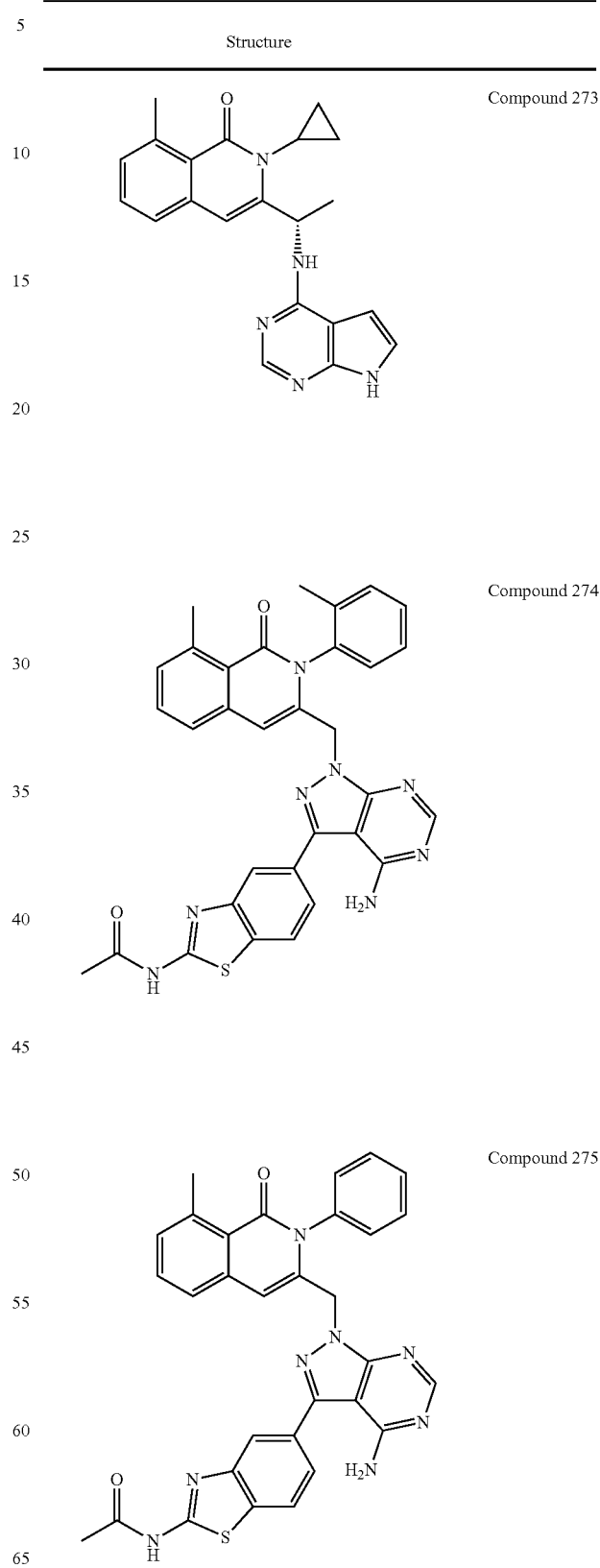
Compound 273
Compound 274
Compound 275

TABLE 4-continued

Structures of the Compounds for the IC50 results described in Table 3.

Structure

TABLE 4-continued
Structures of the Compounds for the IC50 results described in Table 3.
| Structure | |
|---|---|
| 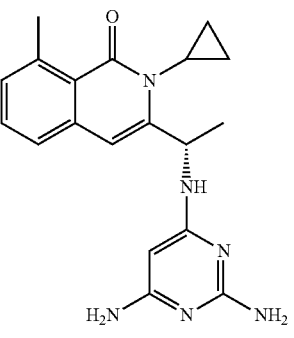 [SMILES: Cc1cccc2cc([C@H](C)Nc3cc(N)nc(N)n3)n(C3CC3)c(=O)c12] | Compound 284 |
| 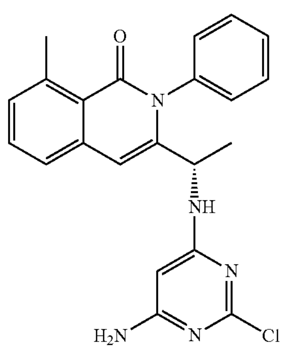 [SMILES: Cc1cccc2cc([C@H](C)Nc3cc(N)nc(Cl)n3)n(-c3ccccc3)c(=O)c12] | Compound 285 |
| 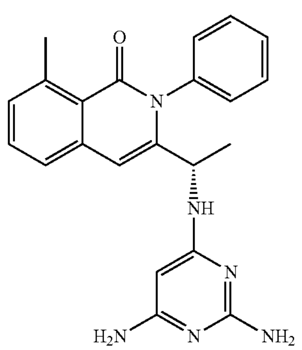 [SMILES: Cc1cccc2cc([C@H](C)Nc3cc(N)nc(N)n3)n(-c3ccccc3)c(=O)c12] | Compound 286 |
| 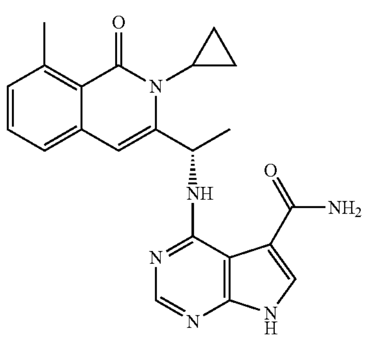 [SMILES: Cc1cccc2cc([C@H](C)Nc3ncnc4[nH]cc(C(N)=O)c34)n(C3CC3)c(=O)c12] | Compound 287 |
TABLE 4-continued
Structures of the Compounds for the IC50 results described in Table 3.
| Structure | |
|---|---|
| 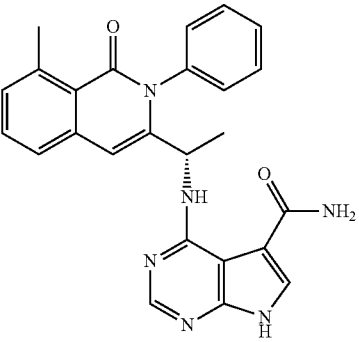 [SMILES: Cc1cccc2cc([C@H](C)Nc3ncnc4[nH]cc(C(N)=O)c34)n(-c3ccccc3)c(=O)c12] | Compound 288 |
| 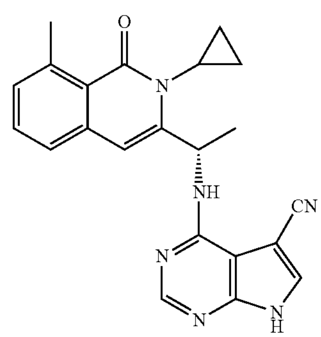 [SMILES: Cc1cccc2cc([C@H](C)Nc3ncnc4[nH]cc(C#N)c34)n(C3CC3)c(=O)c12] | Compound 289 |
| 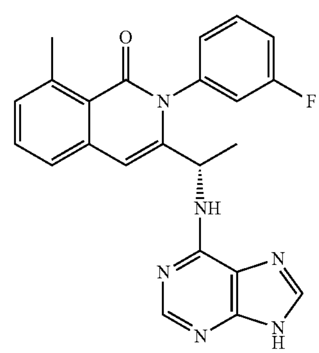 [SMILES: Cc1cccc2cc([C@H](C)Nc3ncnc4[nH]cnc34)n(-c3cccc(F)c3)c(=O)c12] | Compound 290 |
| 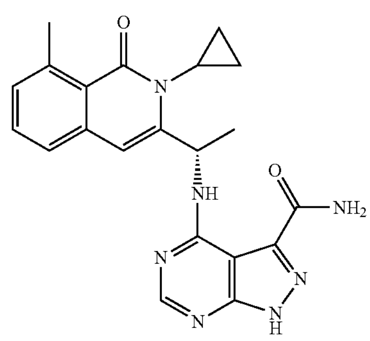 [SMILES: Cc1cccc2cc([C@H](C)Nc3ncnc4[nH]nc(C(N)=O)c34)n(C3CC3)c(=O)c12] | Compound 291 |

TABLE 4-continued
Structures of the Compounds for the IC50 results described in Table 3.
Structure
Compound 292
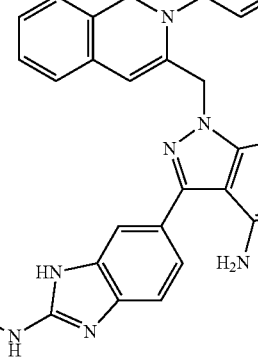
Compound 293
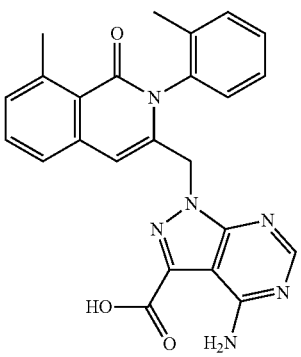 [SMILES: Cc1ccccc1-n1c(Cn2nc(C(=O)O)c3c(N)ncnc32)cc2cccc(C)c2c1=O]
Compound 294
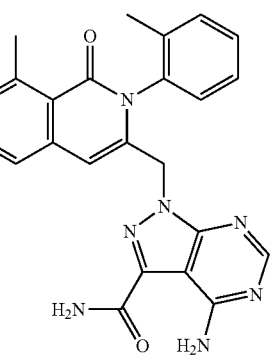
Compound 295
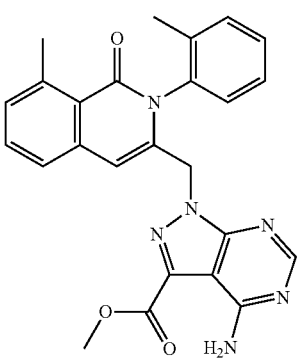 [SMILES: COC(=O)c1nn(Cc2cc3cccc(C)c3c(=O)n2-c2ccccc2C)c2ncnc(N)c12]
TABLE 4-continued
Structures of the Compounds for the IC50 results described in Table 3.
Structure
Compound 296
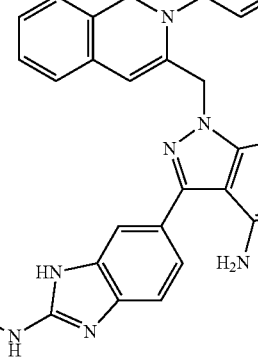
Compound 297
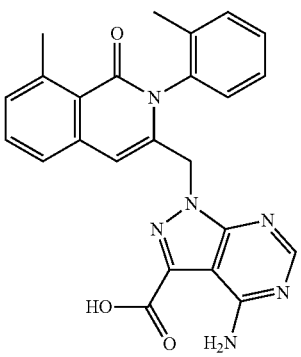 [SMILES: Cc1ccccc1-n1c(Cn2nc(C(=O)O)c3c(N)ncnc32)cc2cccc(C)c2c1=O]
Compound 298
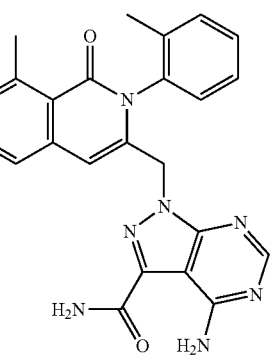
Compound 299
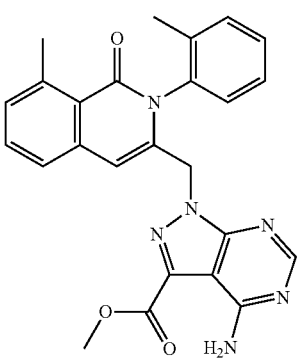 [SMILES: COC(=O)c1nn(Cc2cc3cccc(C)c3c(=O)n2-c2ccccc2C)c2ncnc(N)c12]

TABLE 4-continued

Structures of the Compounds for the IC50 results described in Table 3.

Structure

Compound 300

Compound 301

Compound 302

Compound 303

Compound 304

Compound 305

Compound 306

TABLE 4-continued

Structures of the Compounds for the IC50 results described in Table 3.

| Structure | |
|---|---|
| Compound 307 | Compound 311 |
| Compound 308 | Compound 312 |
| Compound 309 | Compound 313 |
| Compound 310 | Compound 314 |

TABLE 4-continued

Structures of the Compounds for the IC50 results described in Table 3.

Structure

Compound 315

Compound 316

Compound 317

Compound 318

TABLE 4-continued

Structures of the Compounds for the IC50 results described in Table 3.

Structure

Compound 319

Compound 320

Compound 321

Compound 322

TABLE 4-continued

Structures of the Compounds for the IC50 results described in Table 3.

Structure

Compound 323

Compound 324

Compound 325

Example 2

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgC12), and freshly sonicated phosphatidylinositol (100 μg/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1 N HCl followed by 160 μl CHCl$_3$:MeOH (1:1). The biphasic mixture is vortexed, briefly centrifuged, and the organic phase is transferred to a new tube using a gel loading pipette tip precoated with CHCl3. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC50 determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including but not limited to PI 3-Kinase α, β, δ, and γ. An exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism® 5.

Example 3

Compound 292 Inhibits PI3K-δ, PI3K-γ, PI3K-β, and PI3K-α

The PI3K inhibitory activity of Compound 292 was tested in several assays described herein. Overall, Compound 292 inhibits PI3K-δ activity at lower doses compared to other PI3Ks (e.g., at least 10-fold lower dose compared to PI3K-γ, PI3K-β or PI3K-α).

In one exemplary assay tested, Compound 292 inhibited PI3K-δ activity at lower doses, e.g., an IC$_{50}$ in the range of about 0.5 nM to 10 nM, typically about 1 nM to 5 nM. For example, Compound 292 inhibits PI3K-γ activity at higher doses, e.g., an IC$_{50}$ in the range of about 20 nM to 40 nM. Compound 292 inhibits PI3K-β activity at higher doses, e.g., an IC$_{50}$ in the range of about 70 nM to 90 nM. Compound 292 inhibits PI3K-β activity at higher doses, e.g., an IC$_{50}$ in the range of about 1500 nM to 2 μM.

In another exemplary assay tested, Compound 292 inhibited PI3K-δ activity at lower doses, e.g., an IC$_{50}$ in the range of about 50 nM to 100 nM. For example, Compound 292 inhibits PI3K-γ activity at higher doses, e.g., an IC$_{50}$ in the range of about 1 μM to 5 μM. Compound 292 inhibits PI3K-β activity at higher doses, e.g., an IC$_{50}$ in the range of about 2

μM to 10 μM. Compound 292 inhibits PI3K-β activity at higher doses, e.g., an $IC_{50}$ in the range of about 100 μM to 200 μM.

Example 4

Functional Cellular Activity of Compound 292

The functional cellular activities of Compound 292 were assessed. The results are shown in Table 5 below. Compound 292 suppressed murine B-cell proliferation and human B-cell proliferation at subnanomolar concentrations, with an $EC_{50}$ of 0.5 nM. Compound 292 suppressed human T-cell proliferation at nanomolar concentrations, with an $EC_{50}$ of 9.5 nM.

To determine PI3K-δ,γ isoform activity in vitro, Compound 292 was assessed in PI3K-δ and PI3K-γ selective cell-based assays. To assess the ability to inhibit the PI3K-δ isoform, AKT phosphorylation (T308) was measured by enzyme-linked immunosorbent assay (ELISA) in anti-IgM antibody-stimulated RAJI cells, a human Burkitt's lymphoma cell line, in the presence or absence of Compound 292. Compound 292 potently inhibited AKT phosphorylation with an $IC_{50}$ value of 2.0 nM. To assess the ability to inhibit the PI3K-γ isoform, the murine macrophage-like cell line, RAW 264.7, was stimulated with C5a, and the level of AKT phosphorylation (T308) was measured by ELISA. Compound 292 inhibited PI3K-γ in C5a activated RAW 264.7 cells with an $IC_{50}$ value of 44.0 nM. Compound 292 is a potent inhibitor of both PI3K-δ and PI3K-γ in isoform-selective cell-based assays.

TABLE 5

Compound 292 Functional Cellular Activity

| Functional Cellular Activity | $EC_{50}$ |
|---|---|
| Murine B-cell proliferation | 0.5 nM |
| Human B-cell proliferation | 0.5 nM |
| Human T-cell proliferation | 9.5 nM |
| PI3K-δ selective assay (RAJI cells, human lymphoma cell line) | 2 nM |
| PI3K-γ selective assay (RAW 264.7, murine macrophage-like cell line) | 44 nM |
| Anti-fCER1 BAT (delta) | 78 nM |

In one exemplary assay tested, Compound 292 potently inhibited PI3K-δ specific basophil activation in human whole blood with an $IC_{50}$ of 78 nM.

Example 5

Compound 292 Potently Inhibits Induction of IFN-α in Primary Human PBMCs

The role of PI3Ks in TLR signaling is not clear from the literature. For TLR-9 induced cytokines, PI3K inhibition has been called neutral, suppressive, and positive. Thus, the literature suggests that PI3K inhibition may not be effective in inhibiting IFN-α via TLR9. The present example demonstrates that PI3K inhibition by Compound 292 inhibits induction of IFN-α via TLR9.

Human PBMCs were stimulated with CPG-A. CPG-A selectively activates PDCs, inducing IFN-α production via TLR9. IFN-α is a PDC cell selective readout. Primary human PBMCs from two normal human donors were used as a source of PDC cells. 200 K cells per well were used. Cells were pretreated with the specified concentration of Compound 292 for 30 minutes. Then the cells were treated with the specified concentration of CPG-A for 16 hours. RPMI-5% serum was employed.

FIG. 1 shows that the extent of inhibition by Compound 292 depends on the extent of IFN-α induction, reflecting the positive feedback of IFN-α on itself. Compound 292 potently inhibited induction of IFN-α induction via TLR9, as demonstrated with 0.1 μM CPG-A induction and a 30 minute pre-incubation period and 0.2 μM CPG-A induction. These data show that PI3K delta and/or gamma are important in the induction of IFN-α in PDCs. Furthermore, PI3K inhibition with Compound 292 blocked the induction IFN-α in PDCs and can thus have therapeutic benefit in the treatment of lupus (e.g., cutaneous or systemic lupus), fibrotic conditions (e.g., fibrosis), or inflammatory myopathies (e.g., myositis, e.g., dermatomyositis).

Example 6

Effects of Compound 292 on Induced Cytokine Release

Using methods analogous to those presented in Example 7, the effects of Compound 292 were investigated using CPG-A and other TLR ligands, including LPS, PAM2CSK4, and R848 to induce release of cytokines, including IFN-α, IL-1, IL-6, IL-8, and TNF. These experiments were conducted using PBMCs.

CPGA Induced Cytokines

Consistent with the results provided in the previous example, Compound 292 blocked CPG-A induced IFN-α. See FIG. 2, which shows the results as percent inhibition (all samples combined). Compound 292 also inhibited CPG-A induced TNF-α (see FIG. 3), IL-6 (see FIG. 4), and IL-8 (see FIG. 5). CPG-A did not detectably induce IL-1.

PAM2CSK4 Induced Cytokines

PAM2CSK4 signals through TL2/TLR6, which plays a role in atherosclerosis, colitis, ischemic injury, e.g., cardiac events and stroke. Compound 292 inhibited PAM2CSK4 induced TNF-α (see FIG. 6), IL-6 (see FIG. 7), IL-8 (see FIG. 8), and IL-1 (see FIG. 9). PAM2CSK4 treatment did not detectably induce IFN-α production (data not shown).

R848 Induced Cytokines

Compound 292 did not detectably affect R848 induced IFN-α, TNF-α, IL-6, or IL-8. Compound 292 slightly inhibited R848 induced IL-1.

LPS Induced Cytokines

Compound 292 enhanced the production of LPS induced TNF-α, IL-6, and IL-1. Compound 292 did not detectably affect the production of LPS induced IL-8. LPS treatment did not detectably induce IFN-α production (data not shown).

The results described above are summarized in Table 6. These results show that CPGA induced cytokines, including IFN-α, IL-6, IL-8, and TNF-α were inhibited by Compound 292. Similarly, PAM2CSK4 induced cytokines, including TNF-α, IL-6, IL-8, and ILL were inhibited by Compound 292. R848 induced cytokines were not affected by Compound 292 to the extent that CPGA or PAM2CSK4 induced cytokines were. LPS induced IL-1, IL6, and TNF-α were increased by Compound 292, whereas LPS-induced IL-8 was not affected.

TABLE 6

Summary of observed effects of Compound 292 on
induced cytokine production

Figure 2:
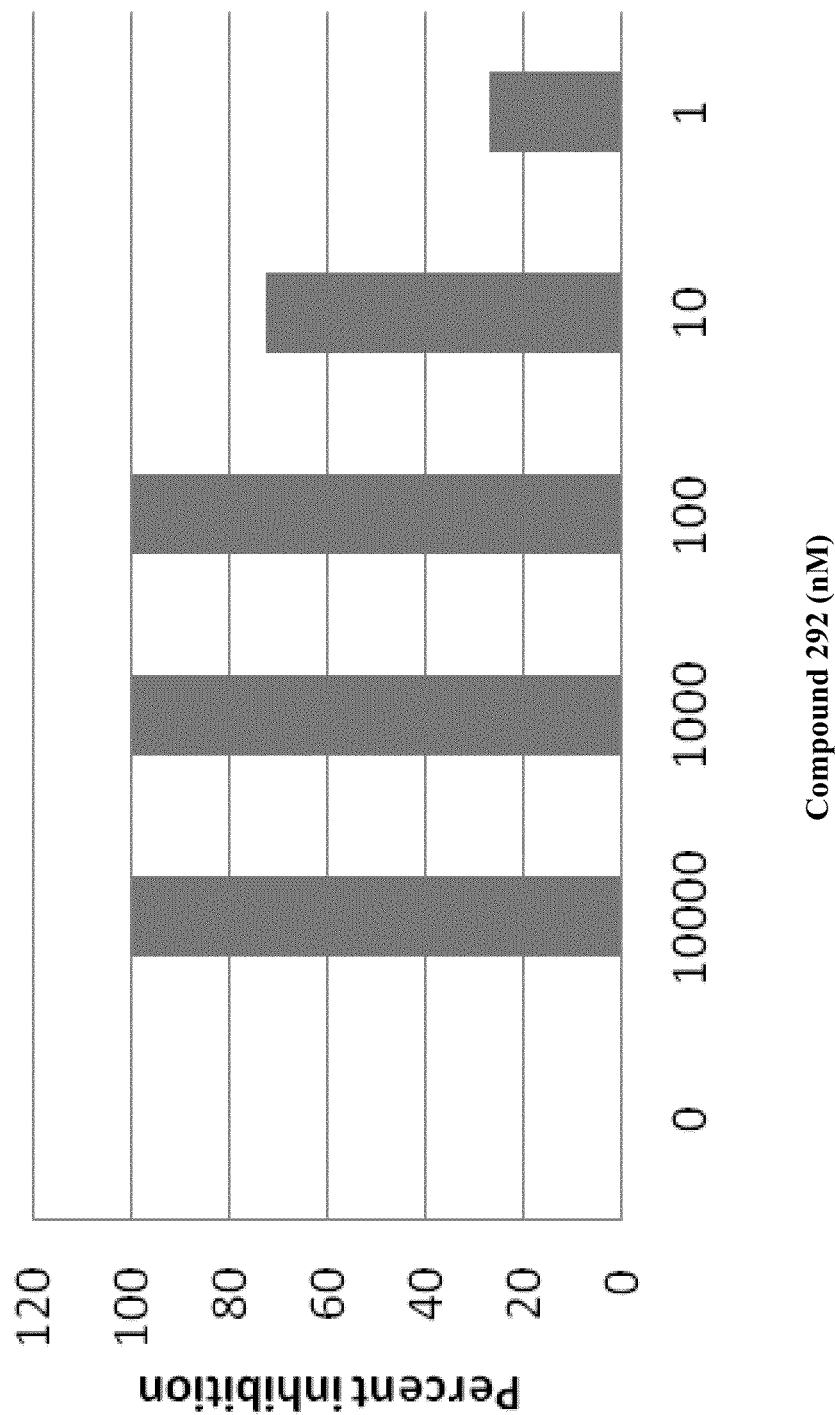
FIG. 2 depicts that Compound 292 inhibited CPG-A induced IFN-α production. The results are graphed as the percent inhibition (all samples combined).
Figure 3:
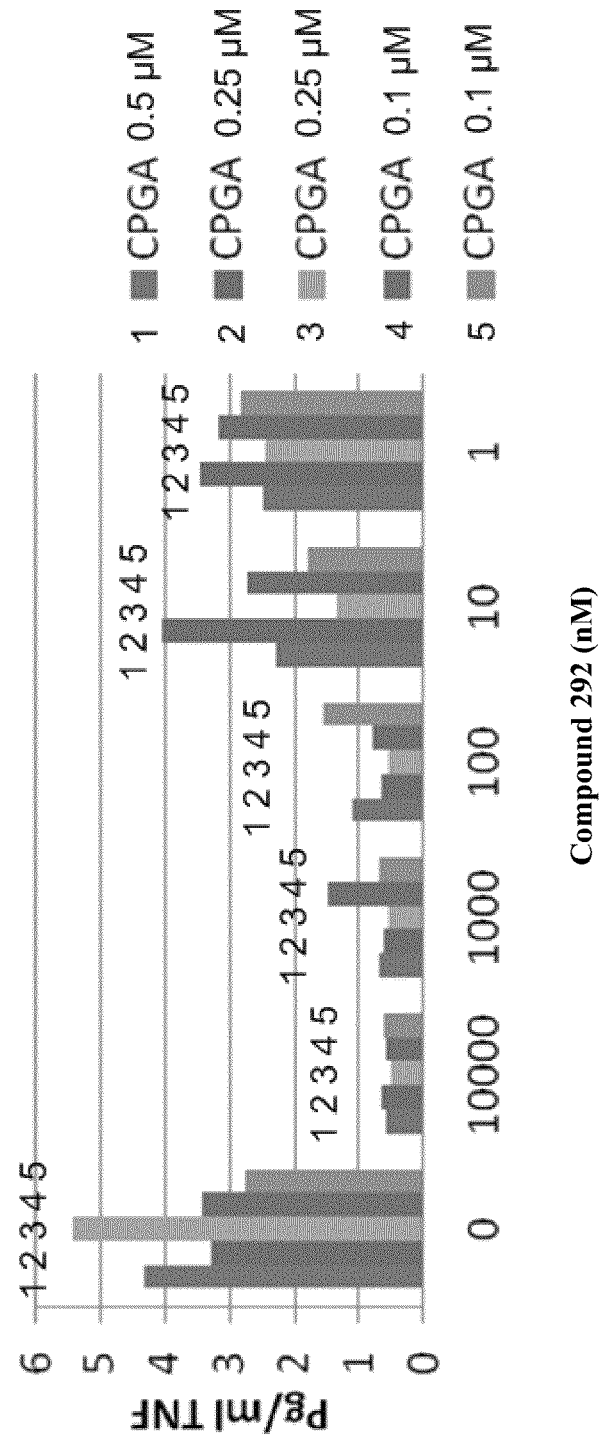
FIG. 3 depicts that Compound 292 inhibited CPG-A induced TNF-α production.
Figure 4:
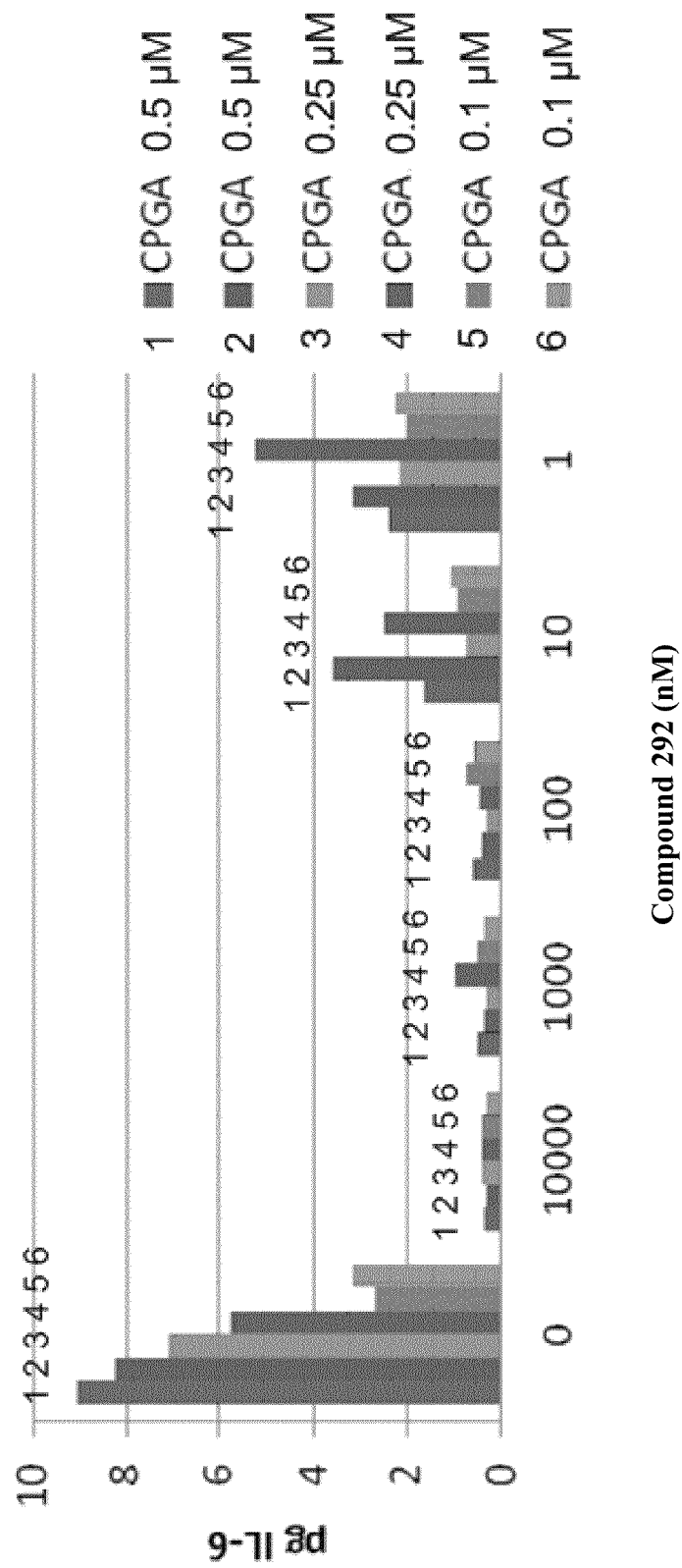
FIG. 4 depicts that Compound 292 inhibited CPG-A induced IL-6 production.
Figure 5:
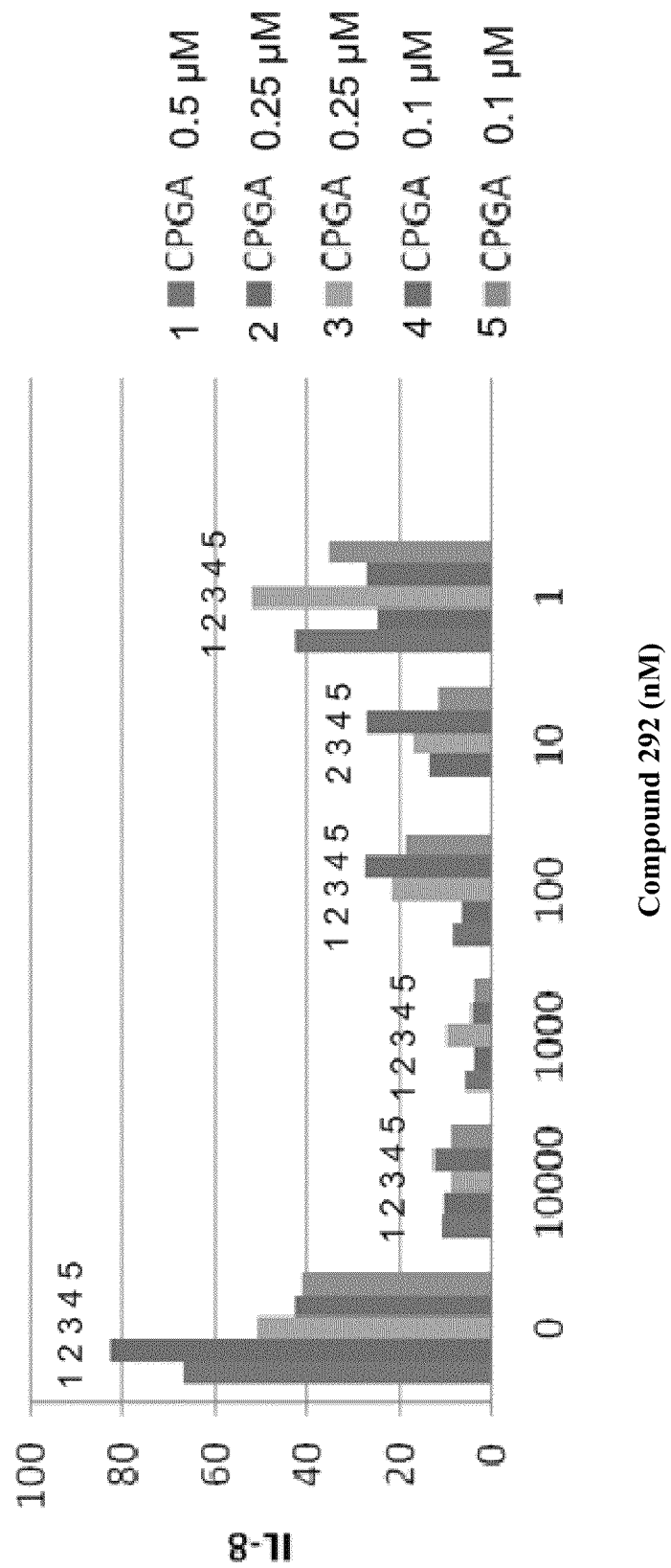
FIG. 5 depicts that Compound 292 inhibited CPG-A induced IL-8 production.
Figure 6:
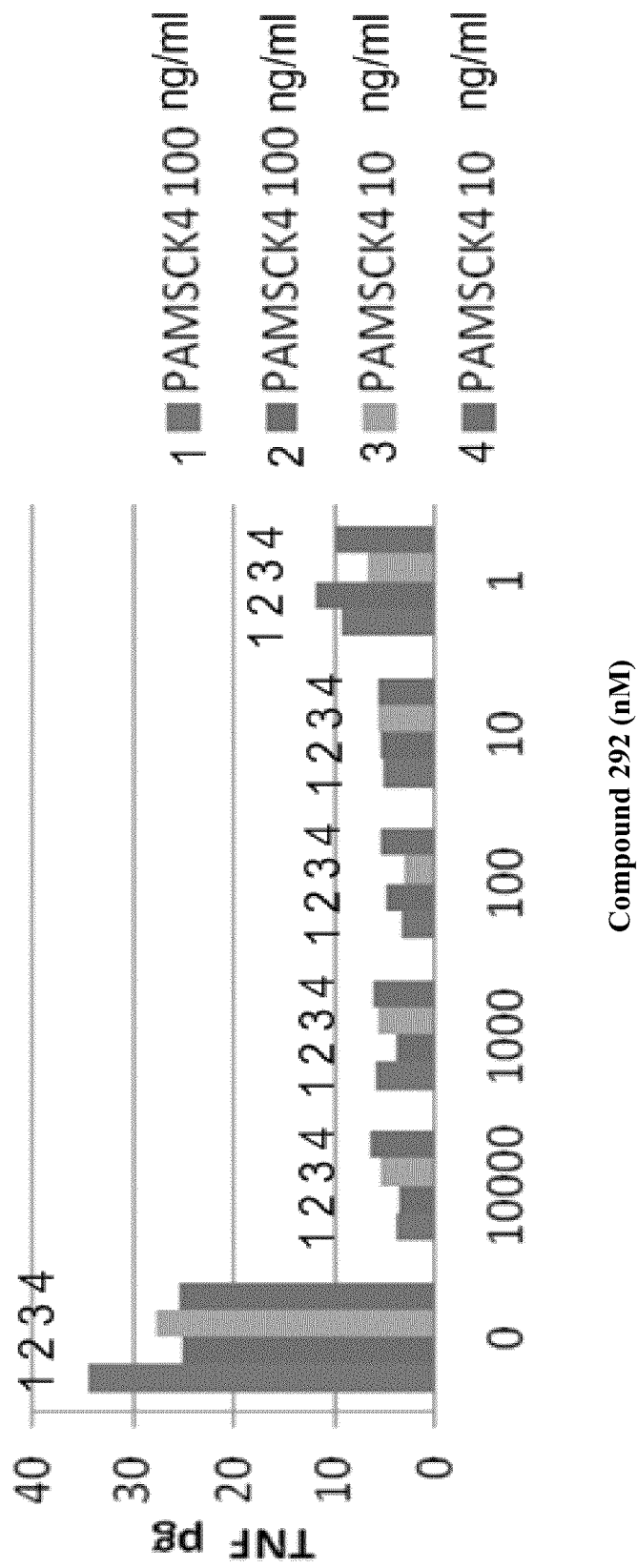
FIG. 6 depicts that Compound 292 inhibited PAMCSK induced TNF-α production.
Figure 7:
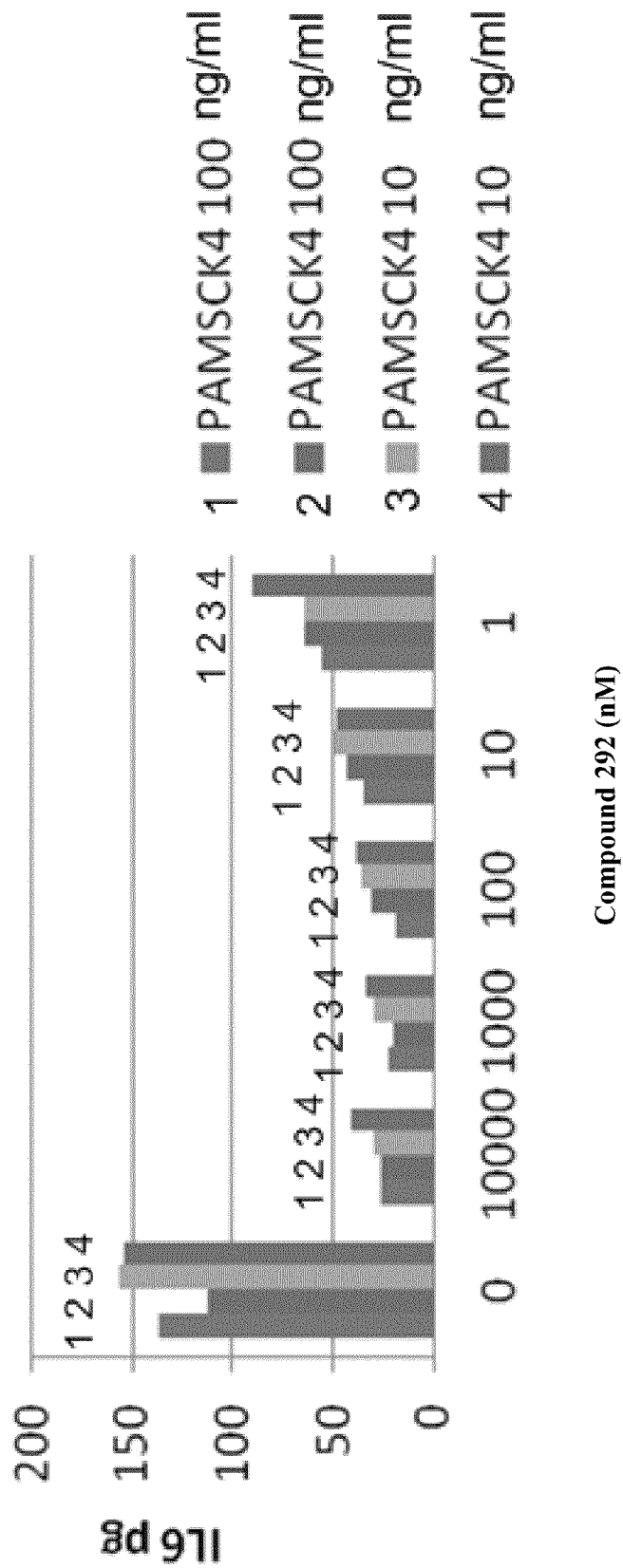
FIG. 7 depicts that Compound 292 inhibited PAMCSK induced IL-6 production.
Figure 8:
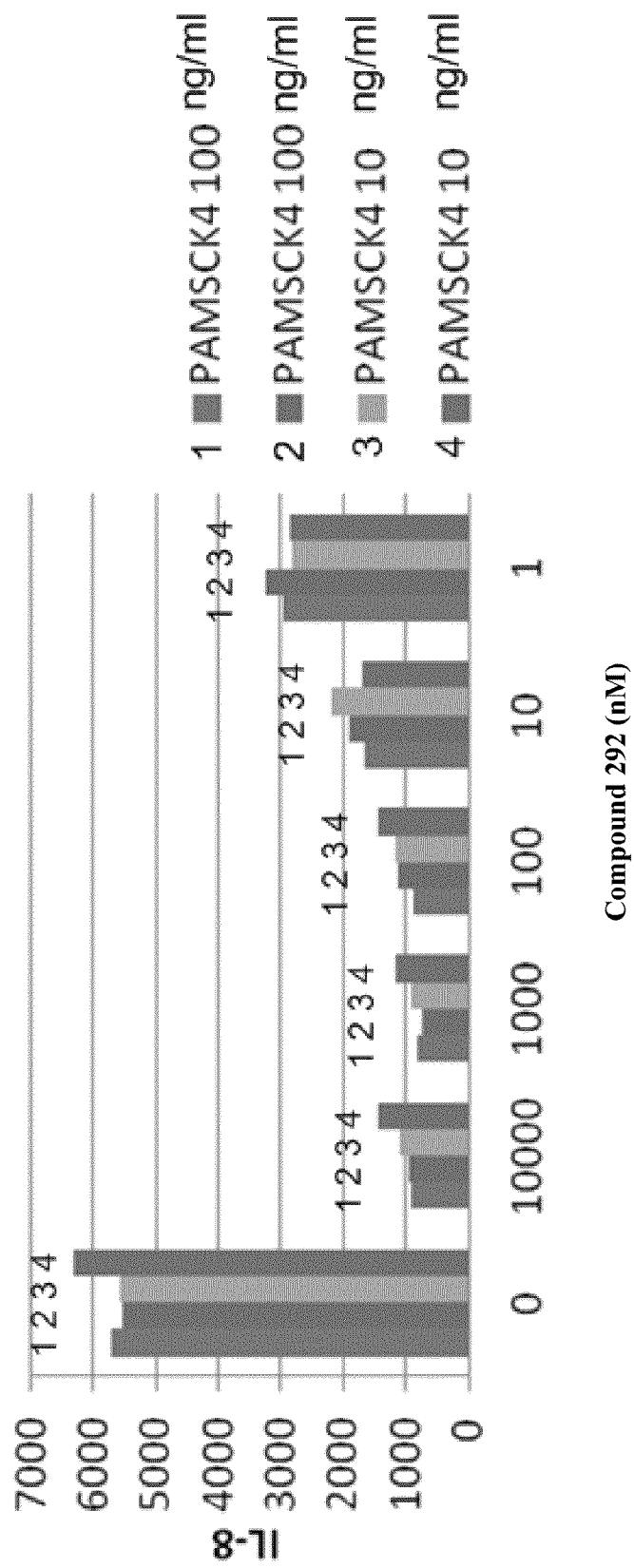
FIG. 8 depicts that Compound 292 inhibited PAMCSK induced IL-8 production.
Figure 9:
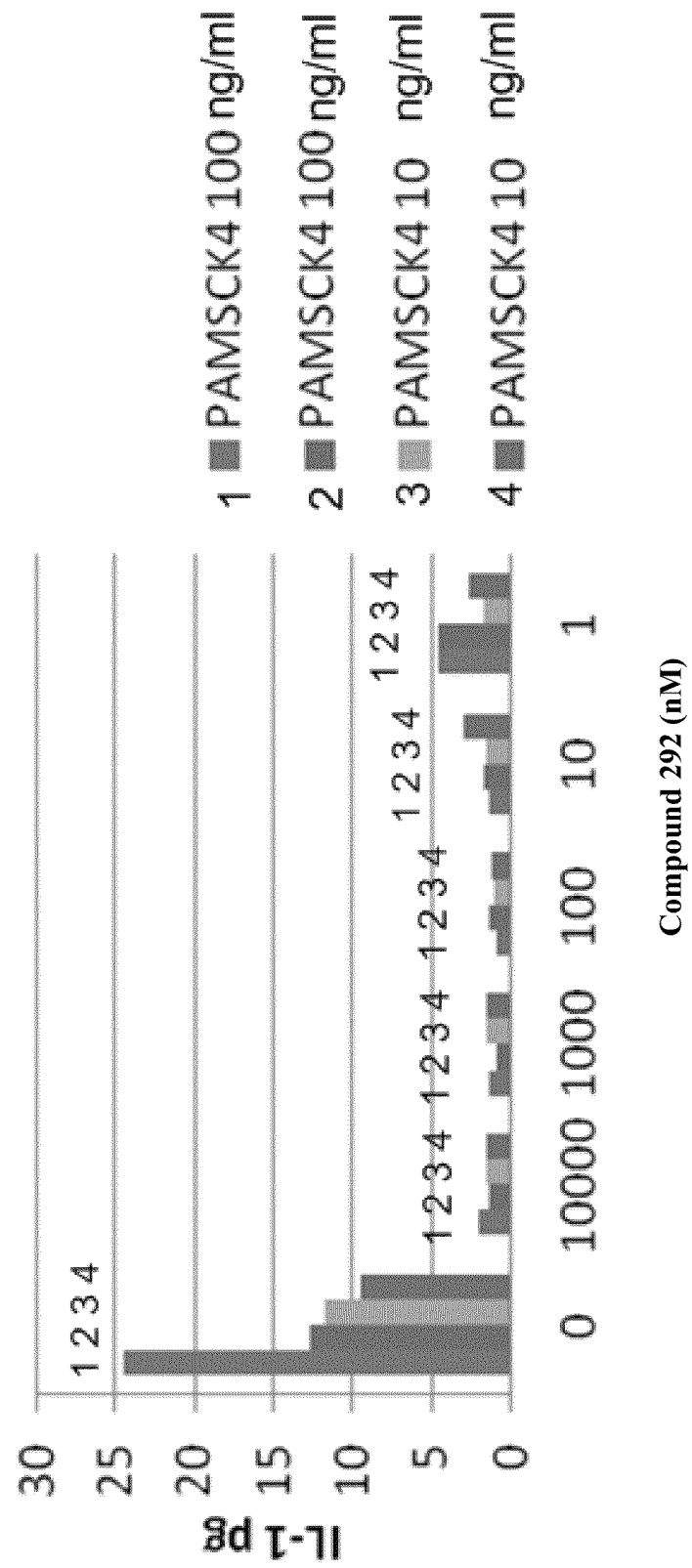
FIG. 9 depicts that Compound 292 inhibited PAMCSK induced IL-1 production.
Figure 10:
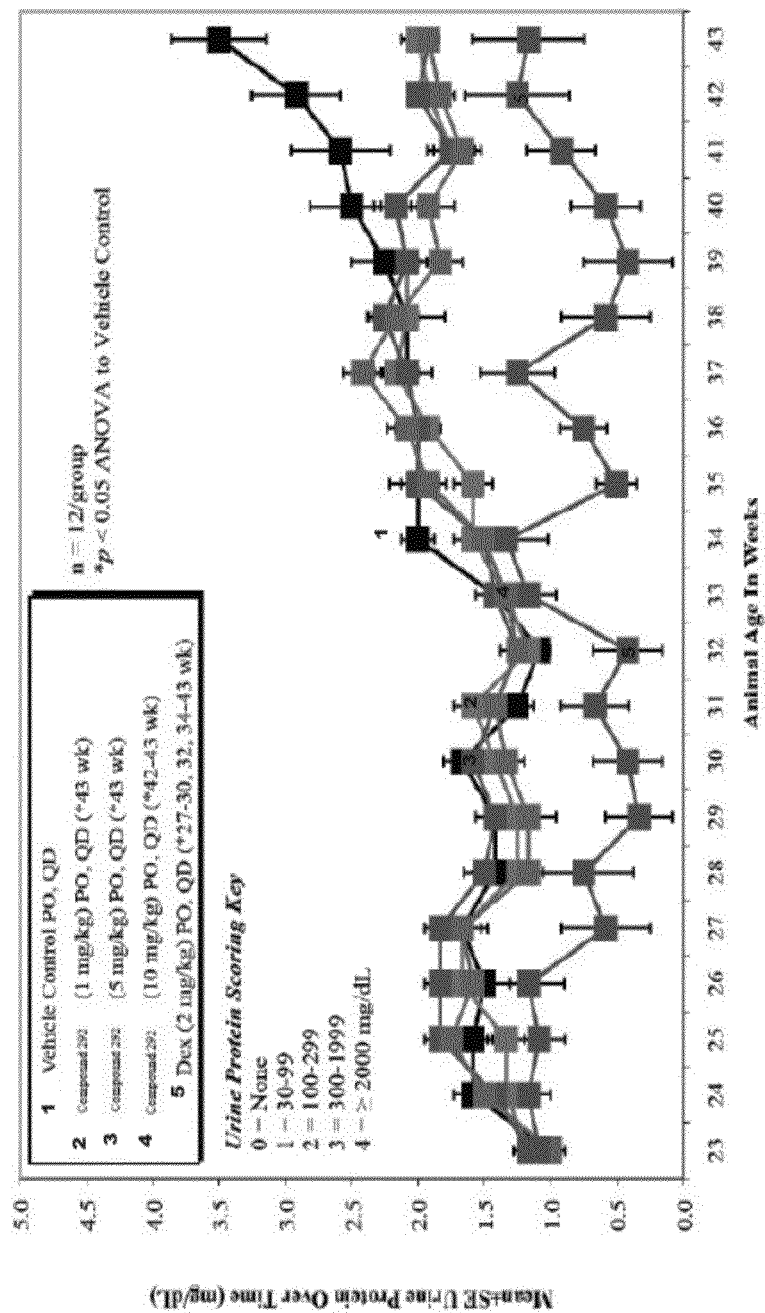
FIG. 10 depicts the means and standard errors of urine protein levels (in mg/dl) over time (from animal age 23-24 weeks) in each experimental group and shows that proteinuria was reduced by treatment with Compound 292.
Figure 11:
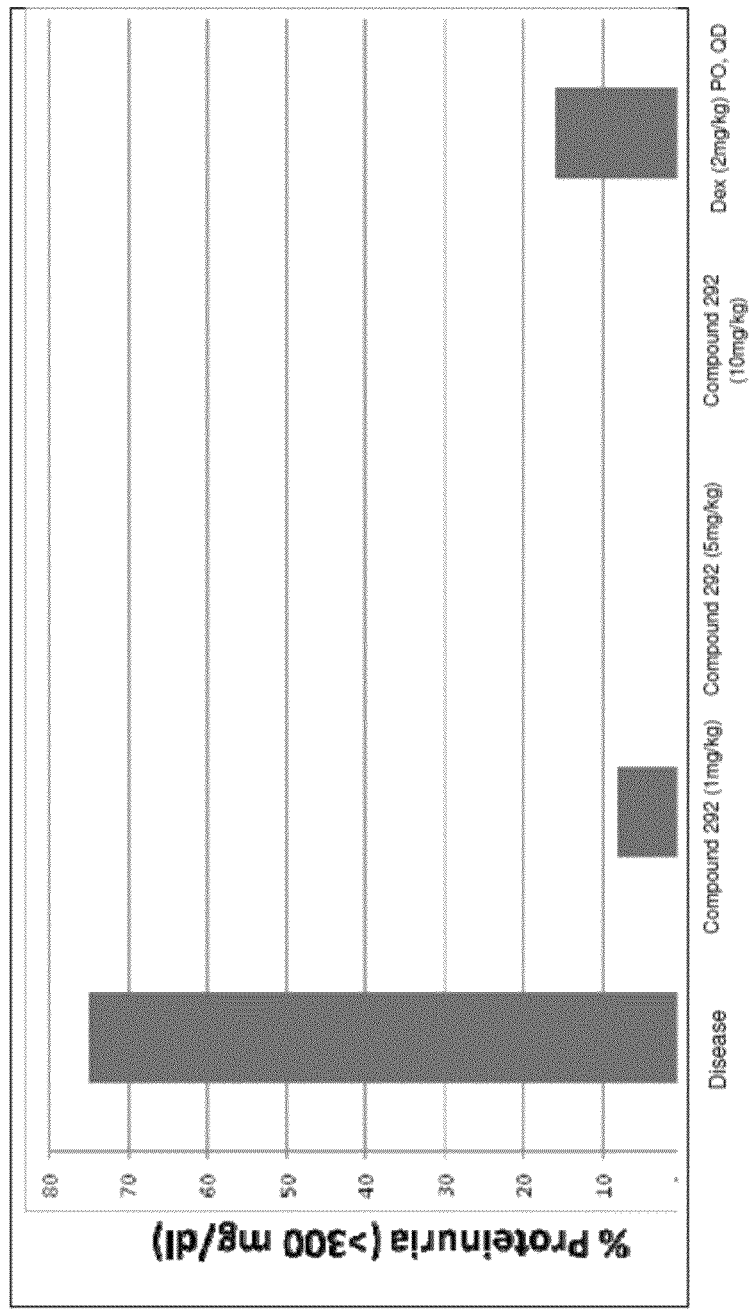
FIG. 11 depicts the % of animals with proteinuria (defined as urine protein levels >300 mg/dl) at animal age 43 weeks in each experimental group and shows that Compound 292 at all doses (1, 5, or 10 mg/kg) significantly reduced proteinuria compared with vehicle ("disease") treatment.
Figure 12:
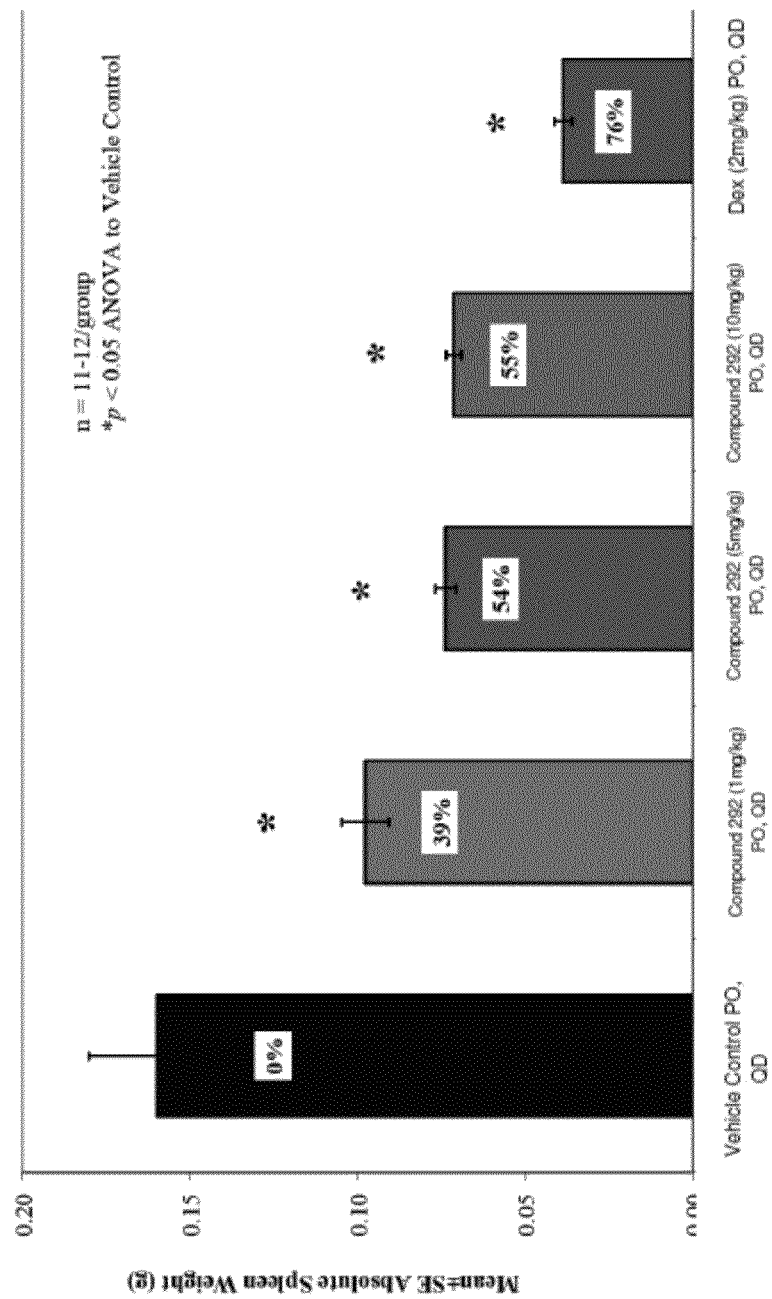
FIG. 12 depicts the means and standard errors of absolute spleen weight at 43 weeks in each experimental group and shows that Compound 292 at all doses (1, 5, or 10 mg/kg) significantly reduced spleen inflammation compared with vehicle control treatment.

| TLR ligand inducer | IFN-α | TNF-α | IL-6 | IL-8 | IL-1 |
|---|---|---|---|---|---|
| CPG-A | Inhibited FIGURE 2 | Inhibited FIGURE 3 | Inhibited FIGURE 4 | Inhibited FIGURE 5 | N/A: no induction |
| PAMCSK | N/A: no induction | Inhibited FIGURE 6 | Inhibited FIGURE 7 | Inhibited FIGURE 8 | Inhibited FIGURE 9 |

Example 7

TLR9 Induced Biomarkers for Patient Selection

A subset of TLRs (e.g., TLR7, TLR8, and TLR9) can induce an immune response characterized by induction of IFN-α. As shown in Example 6, PI3K inhibition by Compound 292 inhibits induction of IFN-α via TLR9. TLR9 is a nucleotide-sensing TLR; and functions as a receptor for viral and bacterial nucleic acids, as well as cellular danger or stress signals, e.g., acute phase reactants. In addition to the recognition of foreign nucleic acids, TLR9 has been shown to recognize self nucleic acid complexes in inflammatory myopathies, such as lupus. As stated above, biological concomitants of inflammatory myopathies (e.g., lupus) can include increased levels of TLR 9 signaling-induced cytokines, such as IFN-α. The potent inhibition of the TLR9-induced IFN-α signaling pathway by Compound 292 indicates that Compound 292 can be used to prevent or treat disorders where the IFN-α or a TLR (e.g., TLR9) signaling pathway is altered (e.g., increased). Examples of such disorders include, but are not limited to, inflammatory myopathies, lupus, cutaneous lupus, rheumatoid arthritis, scleroderma, and dermatomyositis.

In other embodiments, an altered level (e.g., increased) of TLR 9-induced cytokines, such as IFN-α, can be used as a biomarker to select a patient for treatment with Compound 292. For example, a subject, e.g., a patient suffering from an inflammatory myopathy (e.g., lupus, cutaneous lupus, rheumatoid arthritis, scleroderma, systemic scleroderma, or dermatomyositis), can be screened for the level (e.g., expression) of TLR 9-induced cytokine expression and/or IFN-α. Based on the cytokine expression profile, the subject can be selected or not selected for treatment with Compound 292. Other embodiments include, screening a subject, e.g., a patient diagnosed with lupus, for the level (e.g., expression) of IFN-α, if the subject expresses an increased level of IFN-α as compared to a reference value (e.g., a reference standard), the subject is then selected for treatment with Compound 292.

A gene signature characteristic of a type I interferon response commonly activated in rheumatic diseases can also be evaluated. Rheumatic diseases evaluated can include, but are not limited to, systemic lupus erythematosus, dermatomyositis, polymyositis, rheumatoid arthritis, and systemic scleroderma (e.g., as described in Higgs et al. *Ann Rheum Dis* (2011) 70: 2029-2036). The gene signature can include analysis of the level (e.g., expression) of one or more genes involved in a type I interferon induced response, e.g., one or more of IFI6, RSAD2, STAT2, IFI44, LIPA, IFI44L or IFI27 (e.g., as described in Higgs et al 2011, supra).

In one embodiment, the gene signature can include analysis of the level (e.g., expression) of one or more of: type I IFNs, TNF-α, IL-1β, IL-10, IL-13, IL-17, or GM-CSF (e.g., as described in Higgs et al. *International Journal of Rheumatic Diseases* (2012) 15: 25-35). In an embodiment, the gene signature can include analysis of the level (e.g., expression) of one or more of: IFN-α serum levels of high-mobility group box protein 1 (HMGB1), C3a, or dsDNA (e.g., as described in Ruan et al. *The Journal of Immunology* (2010) 185: 4213-4222). In an embodiment, the gene signature can include analysis of the level (e.g., expression) of one or more of: inflammatory cytokines, e.g., type I IFNs, type II IFNs, IL-6, IL-1, TNF-α; immunomodulatory cytokines, e.g., IL-10 and TGF-β; IL-21, IL-17, or IL-2 (e.g., as described in Ohl et al. *Journal of Biomedicine and Biotechnology* (2011) Article ID: 432595).

Any combination of the aforementioned genes can be used to evaluate a subject. In one exemplary embodiment, the level (e.g., expression) of one, two, three, four, five, six, seven, eight, nine, ten, eleven, twelve, thirteen, fourteen, fifteen or more than fifteen of the following genes: IFN-α, type I IFNs, type II IFNs, TNF-α, IL-1β, IL-6, IL-1, IL-2, IL-8, IL-10, IL-13, IL-17, IL-21, GM-CSF, TGF-β, IF16, RSAD2, STAT2, IFI44, LIPA, IFI44L or IFI27 can be evaluated. In another embodiment, the level (e.g., expression) of one or more of the following IFN-α, TNF-α, IL-6, or IL-8 can be evaluated. In yet another embodiment, the gene signature can further include analysis of IL-17; for example, the level (e.g., expression) of one or more of: IFN-α, TNF-α, IL-6, IL-8, or IL-17 can be evaluated.

Example 8

Effects of Compound 292 in the NZB/W F1 Lupus Model

The murine NZB/W F1 lupus model was used to investigate the efficacy of Compound 292 administered orally (PO) in the treatment of lupus. The murine NZB/W F1 lupus model has many features of human lupus, and is characterized by elevated levels of anti-nuclear and anti-dsDNA autoantibodies; a critical role for plasmacytoid dendritic cells and IFN-α; T-cell, B-cell, macrophage involvement; pheymolytic anemia; progressive immune complex glomerulonephritis; proteinurea; severity and incidence more pronounced in females; and decreased survival. Treatment with Compound 292 showed significant beneficial effect in the treatment of lupus in NZBWF1/J mice as determined by evaluation of urine protein scores, organ weights, plasma anti-dsDNA IgG levels, and histopathology of the kidneys.

Materials and Methods

Subjects

Female NZBWF1/J mice (n=60) that were 8 weeks old on arrival and weighed approximately 35-51 grams (mean 42 g) at enrollment (mouse age approx. 23 weeks) were obtained from The Jackson Laboratory, Bar Harbor, Me. (stock number 100008). Animals were identified by a distinct number of ink marks at the base of the tail delineating animal number. After enrollment, all cages were labeled with protocol number, group number, and animal numbers.

Upon arrival, animals were housed 4/cage in shoe-box polycarbonate cages with wire tops, wood chip bedding, and suspended food and water bottles. An attending veterinarian was on site or on call during the live phase of the study. No concurrent medications were given.

During the acclimation and study periods, animals were housed in a laboratory environment with temperatures ranging 67-76° F. and relative humidity of 30%-70%. Automatic timers provided 12 hours of light and 12 hours of dark Animals were allowed access ad libitum to Harlan Teklad Rodent Chow and fresh municipal tap water.

Animal care including room, cage, and equipment sanitation conformed to the guidelines cited in *Guide for the Care and Use of Laboratory Animals*. National Research Council, Institute of Laboratory Animal Resources Commission on Life Sciences. Washington, D.C.: National Academy Press; 1996.

Experimental Design

The experimental design is shown in Table 7 below. Female NZBWF1/J mice (12/group) were dosed daily (QD) for 20 weeks (mouse age 23 weeks to 42 weeks) by the PO route with vehicle (5% NMP, 10% Solutol HS-15, 85% PEG400, Compound 292 (1, 5, or 10 mg/kg), or the reference compound dexamethasone (Dex, 2 mg/kg). Starting at age 23 weeks and then every week thereafter, urine from each animal was tested for proteinuria using Clinitech Multistick test strips (Bayer) Animals were observed daily for significant clinical signs, moribundity, and mortality Animals were bled via orbital sinus on days 0, 49, 98, and 140 (mouse age 23, 30, 37, and 43 weeks) for Anti-dsDNA ELISA (Alpha Diagnostics). Mice were terminated at age 43 weeks (day 140).

TABLE 7

Experimental groups

| ID | N | Compound | Route | Regimen | Dose Level (mg/kg) | Dose Volume (ml/kg) |
|---|---|---|---|---|---|---|
| Group 1 | 12 | Vehicle | PO | QD | 0 | 10 |
| Group 2 | 12 | Compound 292 | PO | QD | 1 | 10 |
| Group 3 | 12 | Compound 292 | PO | QD | 5 | 10 |
| Group 4 | 12 | Compound 292 | PO | QD | 10 | 10 |

Dosing

All dose solutions were prepared to deliver in 10 ml/kg (0.3 ml/30 g mouse). The oral solutions of Compound 292 were formulated in 5% NMP, 10% Solutol HS-15, 85% PEG400.

Observations, Measurements, and Specimens

Body weights were measured and recorded prior to study initiation for randomization, on the first day of dosing prior to dosing, and weekly throughout the study. Body weights were also recorded at scheduled termination points and as needed if test subjects appeared to decrease in weight by visual inspection. The animals were observed daily for significant clinical signs, moribundity and mortality.

Urine from each animal was tested weekly (beginning at mouse age 23 weeks) for proteinuria using Clinitech Multistick test strips (Bayer).

Urine Protein Scoring Key
 0=None
 1=30-99 mg/dL
 2=100-299 mg/dL
 3=300-1999 mg/dL
 4=≥2000 mg/dL At necropsy, animals were anesthetized with isoflurane and bled via cardiac puncture for serum (for clinical chemistry analysis) and plasma (for Anti-dsDNA ELISA and PK). Terminal urine was collected and assessed. Spleens and kidneys (paired) were collected, weighed, and placed in 10% NBF. Serum obtained at necropsy was sent to Antech Diagnostics for analysis. Terminal plasma samples were split with half being used for Anti-dsDNA ELISA and the other half being shipped to the sponsor.

For animals found to be moribund or dead as an adverse affect of disease induction prior to the scheduled necropsy, the time of death or sacrifice was noted, and the terminal data were carried through to study termination.

Anti-dsDNA IgG analysis was performed on days 0, 49, 98, and 140 (mouse age 23, 30, 37, and 43 weeks). Anti-dsDNA IgG levels were determined using an Anti-dsDNA IgG ELISA Kit (Alpha Diagnostic, kit #5120, lot #90903K4) following manufacturer's instructions.

Clinical Chemistry Methods

Blood samples for clinical chemistry evaluation were collected at termination via cardiac puncture from Isoflurane anesthetized animals into serum separator microtainer tubes. Serum was sent to Antech Diagnostics for analysis.

The following parameters were measured: Albumin (ALB), Albumin:Globulin ratio (A/G), Alkaline phosphatase (ALK), Alanine aminotransferase (ALT), Aspartate aminotransferase (AST), Calcium (CA), Magnesium (Mg), Phosphorous (P), Globulin (GLOB), Electrolytes (Sodium (Na), Potassium (K), Chloride (Cl)), Gamma glutamyltransferase (GGT), Total bilirubin (TBILI), Amylase (AMY), Lipase (LIP), Osmolality, Triglycerides (TRIG), Total cholesterol (CHOL), Urea nitrogen (BUN), Creatinine (CREAT), Glucose (GLU), Total protein (TP), and Creatinine kinase (CPK).

Morphologic Pathology Methods

Histopathologic evaluation was performed on kidneys. Kidneys from all surviving animals were examined microscopically by a board certified veterinary pathologist and observations were entered into a computer-assisted data retrieval system. Kidney sections were stained with Masson's Trichrome, or Hematoxylin and Eosin. To maintain blinding of the analysis, slides were labeled with the animal number with no reference to treatment group.

Kidneys were scored according to the following system (developed by Chan O, Madaio M P, Shlomchik M J. The roles of B cells in MRL/lpr murine lupus. *Annals New York Academy of Sciences*, 1997; 815:75-82), modified to suit the lesion severity.

Glomerulonephritis
 0=Normal.
 1=Focal or multifocal, minimal to mild, early proliferative.
 2=Multifocal mild to moderate or mild diffuse proliferative.
 3=Diffuse moderate proliferative with or without multifocal severe areas.
 4=Marked diffuse proliferative, with crescents/sclerosis, multifocal protein casts present.
 5=Severe diffuse proliferative, with crescents/sclerosis, diffuse protein casts present.

Protein Cast Severity
 0=Normal.
 1=Focal or multifocal, minimal to mild, early proliferative.
 2=Multifocal mild to moderate or mild diffuse proliferative.
 3=Diffuse moderate proliferative with or without multifocal severe areas.
 4=Marked diffuse proliferative, with crescents/sclerosis, multifocal protein casts present.
 5=Severe diffuse proliferative, with crescents/sclerosis, diffuse protein casts present.

Interstitial Nephritis (Inflammation not Obviously Associated with Vessels)
 0=Normal
 0.5=Very Minimal=Small focal area of MNC in pelvis only.
 1=Minimal=Occasional small focal, accumulations of MNC affecting less than 10% of total interstitium and generally localized around pelvis.

2=Mild=Multifocal small to larger infiltrates distributed around pelvis and cortex affecting 10-25% of cortex area.

3=Moderate=Multifocal small to extensive infiltrates in pelvis and cortex affecting 26-50% of cortex area.

4=Marked=Multifocal to diffuse infiltration affecting 51-75% of pelvis and cortex area.

5=Severe=Diffuse infiltration affecting 76-100% of pelvis and cortex area.

Vessels

0=Normal 0.5=Very Minimal=One vessel with minimal perivascular infiltrate.

1=Minimal=Small but definite perivascular infiltrates (1-2).

2=Mild=Several (3-4) foci of perivascular infiltrate, no necrosis.

3=Moderate=Multifocal (5-6) foci of perivascular infiltrate, more extensive, may have some necrosis of vessel wall.

4=Marked=Multifocal (7-8) foci of perivascular infiltrate, extensive with necrosis.

5=Severe=Multifocal (>8) foci of perivascular infiltrate, extensive with necrosis.

These 4 scores were summed to obtain a total kidney score and then the summed score as well as each individual parameter was compared across groups to determine significant differences with p≤0.05.

Statistical Analysis

Clinical and histopathology data for each mouse were entered into Microsoft Excel and the means for each group were determined with percent change from disease controls calculated by comparing values for treated and control animals. For mice that died or were euthanized prior to study termination, terminal data were carried through to study termination for the purpose of analysis. One of 12 vehicle-treated disease control mice died prior to study termination. All other mice survived to study termination.

Data were analyzed using a one-way analysis of variance (1-way ANOVA) or Kruskal-Wallis test (non-parametric) along with the appropriate multiple comparison post-test. Significance for all tests was set at p≤0.05.

Percent inhibition was calculated using the following formula:

% Change=(Mean Treated−Mean Disease Control)/
(0−Mean Disease Control)×100.

Results

Body Weight

Body weight loss (measured as percent change from baseline) for vehicle-treated control mice was 15.32% at study termination. Body weight loss for mice treated with Compound 292 did not differ significantly from vehicle controls over time. Mice treated with Dex had significantly inhibited disease-induced body weight loss from mouse age 25 wk to 41 wk.

Urine Protein

Mean urine protein scores for vehicle controls increased over time from a low of 1.0 in week 23 to a high of 3.50 at study termination. Urine protein levels were significantly reduced for mice treated with 1 mg/kg Compound 292 (*p<0.05 at mouse age 43 wk), 5 mg/kg Compound 292 (*p<0.05 at mouse age 43 wk), 10 mg/kg Compound 292 (*p<0.05 at mouse age 42-43 wk), or Dex (*p<0.05 at mouse age 27-30, 32, 34-43 wk) as compared to vehicle controls (see FIG. 10 and FIG. 11).

Kidney Weight

Vehicle control mice had a mean kidney weight of 0.470 grams. Kidney weights were significantly increased for mice treated with Dex (20% increase) as compared to vehicle controls. Kidney weights for mice treated with Compound 292 did not differ significantly from vehicle controls.

Spleen Weight

Vehicle control mice had a mean spleen weight of 0.160 grams. Spleen weights were significantly reduced for mice treated with 1 mg/kg Compound 292 (39% reduction), 5 mg/kg Compound 292 (54%), 10 mg/kg Compound 292 (55%), or Dex (76% reduction) as compared to vehicle controls (see FIG. 12).

Anti-dsDNA IgG Level

Figure 13:
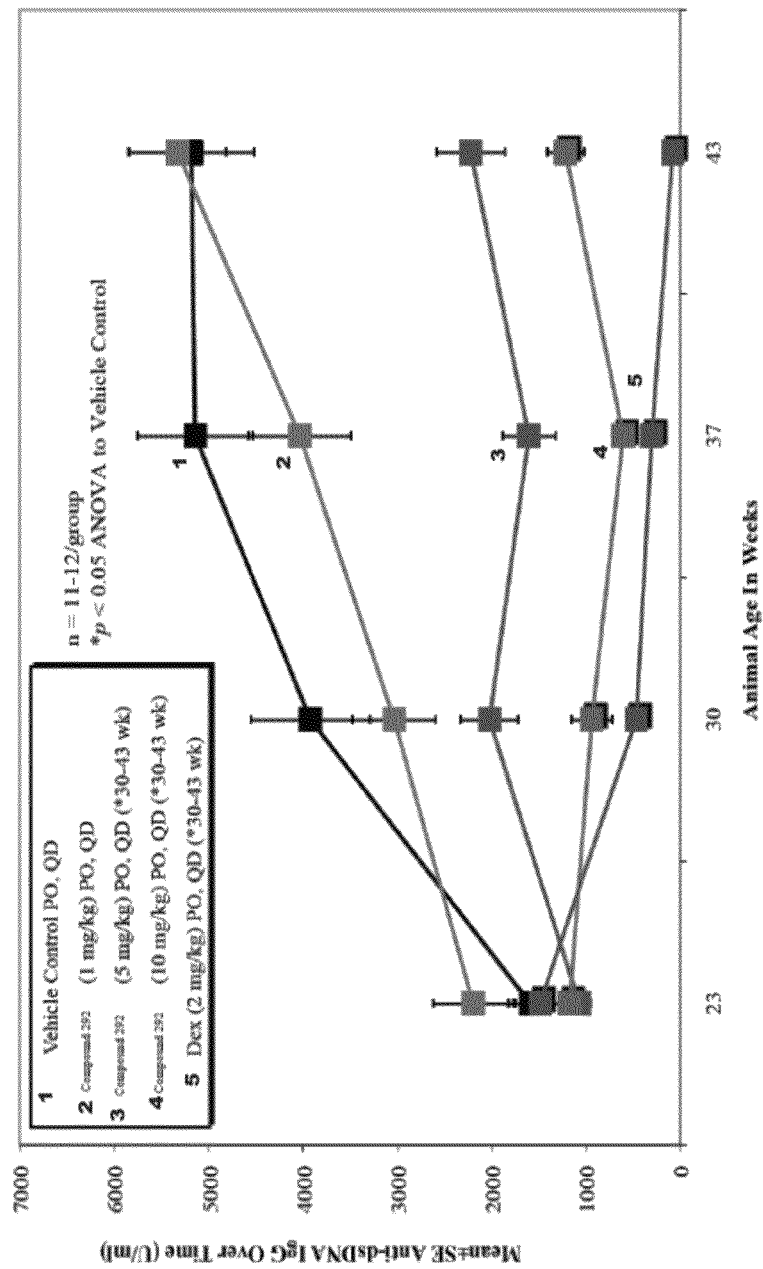
FIG. 13 depicts the means and standard errors of anti-dsDNA antibody levels (in U/ml) at animal ages 23, 30, 37, and 43 weeks in each experimental group and shows that at 30, 37, and 43 weeks, Compound 292 significantly reduced anti-dsDNA antibody levels in mice treated with 5 or 10 mg/kg Compound 292 or Dex compared with vehicle control treatment.

Plasma anti-dsDNA levels for vehicle controls increased over the course of the study from 1591.00 U/ml on day 0 to 5182.66 U/ml at termination. Plasma anti-dsDNA IgG levels were significantly reduced for mice treated with 5 or 10 mg/kg Compound 292 or Dex when measured on days 49, 98, and 140 (mouse age 30, 37, and 43 wk) (see FIG. 13).

Clinical Chemistry

Analysis of clinical chemistry revealed that mice treated with Compound 292 had significantly increased albumin (ALB), albumin/globulin ratio (A/G), and calcium (CA) and significantly reduced globulin (GLOB), aspartate aminotransferase (AST), blood urea nitrogen (BUN), BUN/creatinine ratio, triglycerides (TRIG), and creatine kinase (CPK) as compared to vehicle controls. Additionally, mice treated with 1 mg/kg Compound 292 had significantly increased sodium (Na) and chloride (Cl); mice treated with 5 mg/kg had significantly reduced amylase (AMY); and mice treated with 10 mg/kg Compound 292 had significantly increased phosphorus (P) and magnesium (Mg) as compared to vehicle controls. Mice treated with Dex had significantly increased ALB, A/G, alkaline phosphatase (ALK), P, glucose (GLU), CA, Mg, and sodium/potassium ratio (Na/K) and significantly reduced GLOB, BUN, BUN/creatinine ratio, potassium (K), TRIG, AMY, and CPK (data not shown).

Morphologic Pathology

Kidneys were evaluated using Hemotoxylin & Eosin (H&E) stained slides for characteristic histopathologic changes of lupus-induced nephritis including glomerular mesangiolysis, hypercellularity, matrix synthesis, interstitial fibrosis, and inflammation.

Vehicle control mice were found to have normal to marked histopathologic changes consistent with lupus nephritis. These changes included none to marked diffuse proliferative glomerulonephritis, none to moderate interstitial nephritis, and none to moderate perivascular inflammation.

Figure 14:
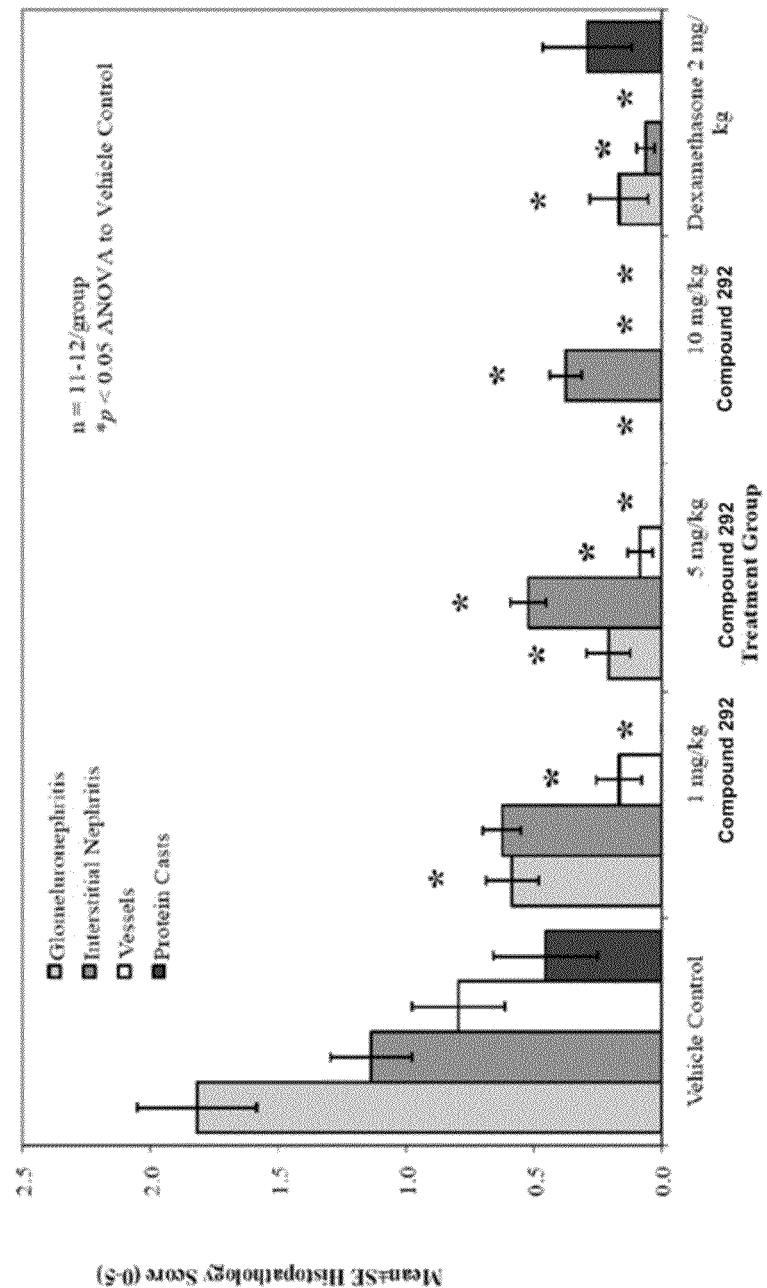
FIG. 14 depicts the means and standard errors of histopathology scores for each experimental group and shows that Compound 292 at all doses (1, 5, or 10 mg/kg) reduced glomerulonephritis, perivascular inflammation, and protein cast severity as compared to vehicle controls.
Figure 15:
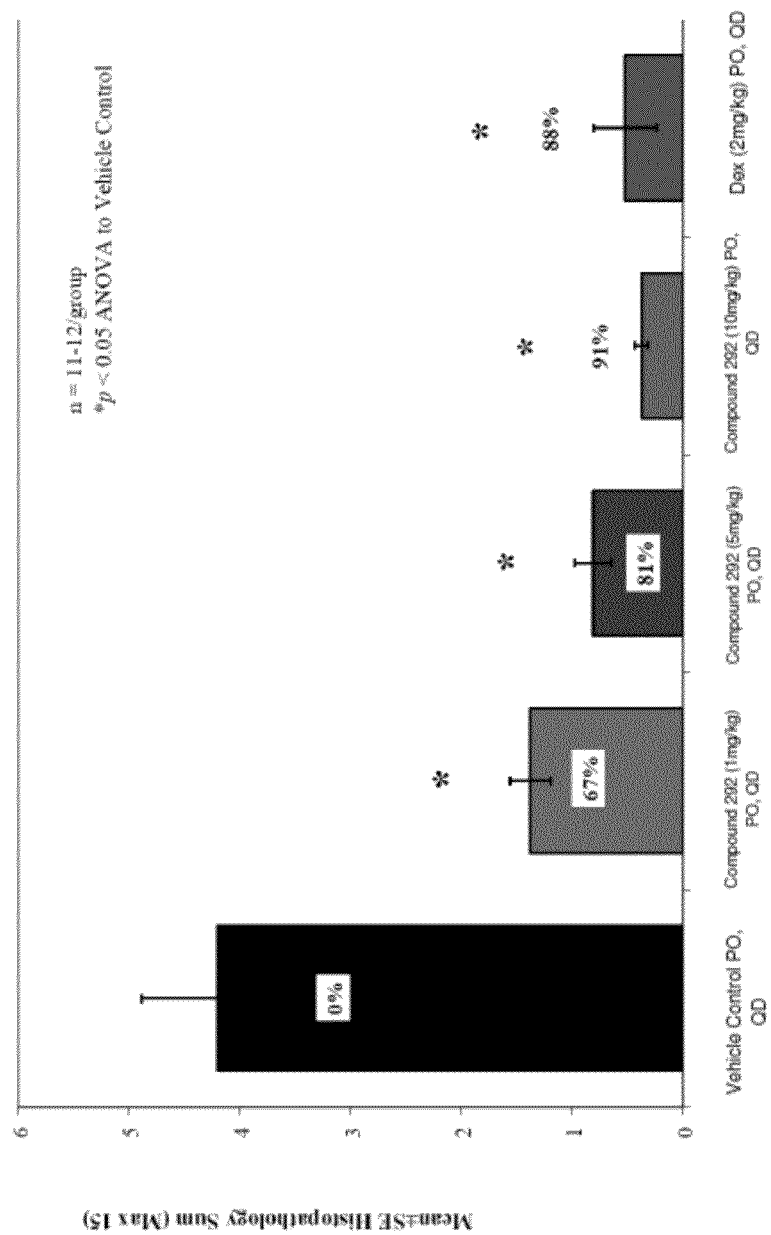
FIG. 15 depicts the means and standard errors of summed histopathology scores for each experimental group and shows that Compound 292 at all doses (1, 5, or 10 mg/kg) reduced summed histopathology scores as compared to vehicle controls.

Mice treated with 1 mg/kg Compound 292 had significantly reduced glomerulonephritis (68% reduction), perivascular inflammation (79%), protein cast severity (100%), and summed histopathology scores (67%) as compared to vehicle controls (see FIG. 14 and FIG. 15).

Mice treated with 5 mg/kg Compound 292 had significantly reduced glomerulonephritis (89% reduction), interstitial nephritis (54%), perivascular inflammation (90%), protein cast severity (100%), and summed histopathology scores (81%) as compared to vehicle controls (see FIG. 14 and FIG. 15).

Mice treated with 10 mg/kg Compound 292 had significantly reduced glomerulonephritis (100% reduction), interstitial nephritis (67%), perivascular inflammation (100%), protein cast severity (100%), and summed histopathology scores (91%) as compared to vehicle controls (see FIG. 14 and FIG. 15).

Mice treated with Dex had significantly reduced glomerulonephritis (91% reduction), interstitial nephritis (95%), perivascular inflammation (100%), and summed histopathology scores (88%) as compared to vehicle controls (see FIG. 14 and FIG. 15).

CONCLUSIONS

Treatment with Compound 292 showed significant beneficial effect in the treatment of lupus in NZBWF1/J mice as determined by evaluation of urine protein scores, organ weights, plasma anti-dsDNA IgG levels, and histopathology of the kidneys.

Compound 292 inhibits proteinurea associated with lupus. Urine protein scores were significantly reduced at study termination (mouse age 43 weeks) for mice treated with Compound 292 (1, 5, or 10 mg/kg) as compared to vehicle controls; the high dose (10 mg/kg) group also had significantly reduced urine protein during the previous week (mouse age 42 wk).

Compound 292 inhibits spleen inflammation associated with lupus. Absolute spleen weights were significantly reduced for mice treated with 1 mg/kg Compound 292 (39% reduction), 5 mg/kg Compound 292 (54%), or 10 mg/kg Compound 292 (55%) as compared to vehicle controls.

Compound 292 inhibits anti-dsDNA autoantibodies associated with lupus. Plasma anti-dsDNA IgG levels were significantly reduced for mice treated with 5 or 10 mg/kg Compound 292 when measured on days 49, 98, and 140 (mouse age 30, 37, and 43 wk).

Change in body weight over time (measured as percent change from baseline) and absolute kidney weight did not differ significantly from vehicle controls. Histopathologic evaluation confirmed the clinical observations; summed histopathology parameters were significantly reduced for mice treated with 1 mg/kg Compound 292 (67% reduction), 5 mg/kg Compound 292 (81%), or 10 mg/kg Compound 292 (91%) as compared to vehicle controls.

These results show that the administration of a PI3K inhibitor (e.g., a PI3K delta inhibitor, e.g., Compound 292) is efficacious in treating lupus in a murine model of lupus. Compound 292 is therefore expected to be efficiacious in treating human lupus, including, e.g., systemic lupus erythematosus and mitigating associated signs and symptoms of lupus, e.g., glomerulonephritis, proteinuria, anti-dsDNA autoantibodies, and spleen inflammation.

Example 9

Animal Model for Scleroderma

A compound's efficacy in treating scleroderma can be tested using animal models. An exemplary animal model is a mouse model for scleroderma induced by repeated local injections of bleomycin ("BLM") described, for example, in Yamamoto et al., "Animal Model of Sclerotic skin I: Local Injection of Bleomycin Induce Sclerotic Skin Mimicking Scleroderma, *J Invest Dermatol* 112: 456-462 (1999), the entirety of which is incorporated herein by reference. This mouse model provides dermal sclerosis that closely resembles systemic sclerosis both histologically and biochemically. The sclerotic changes observed in the model include, but are not limited to: thickened and homogenous collagen bundles and cellular filtrates; gradual increase in number of mast cells; degranulation of mast cells; elevated histamine release; increase in hydroxyproline in skin; presence of anti-nuclear antibody in serum; and strong expression of transforming growth factor β-2 mRNA. Therefore, efficacy of a compound in treating scleroderma can be assessed by monitoring the lessening of one or more of these changes.

Briefly, the following exemplary procedures can be used to generate the mouse model for scleroderma: Specific pathogen-free, female BALB/C mice and C3H mice of 6 weeks old, weighing about 20 g, are purchased and maintained with food and water ad libitum. BLM is dissolved in PBS at differing concentrations and sterilized with filtration. Aliquots of each concentration of BLM or PBS are injected subcutaneously into the shaved back of the mice daily for 1-4 weeks with a needle. Alternatively, mice are injected every other day.

Histolopathological and biochemical changes induced can be assessed using any methods commonly practiced in the field. For example, histopathological changes can be assessed using a standard avidine-biotin peroxidase technique with anti-L3T4 monoclonal antibody, anti-Lyt2 monoclonal antibody, anti-mouse pan-tissue-fixed macrophage antibody, anti-stem cell factor monoclonal antibody, anti-transforming growth factor-βpolyclonal antibody, and anti-decorin antibody. Cytokine expression of cellular infiltrates can be assessed by using several anti-cytokine antibodies. Hydroxyproline level can be assessed by hydrolyzing skin pieces with hydrochloric acid, neutralizing with sodium hydroxide, and colorimetrically assessing the hydrolates at 560 nm with p-dimethylaminobenzaldehyde. Pepsin-resistant collagen can be assessed by treating collagen sample extracted from biopsied tissues and analyzing by polyacrylamide stacking gel electrophoresis. Mast cells can be identified by toluidine blue, and cells containing matachromatic granules can be counted under high magnification of a light microscope. Serum levels of various cytokines can be assessed by enzyme-linked immunosorbent assay, and mRNA levels of the cytokines can be assessed by reverse-transcriptase polymerase chain reaction. Autoantibodies in serum can be detected using 3T3 fibroblasts as the substrate for the screening.

Example 10

Effects of Compound 292 in the Experimental Autoimmune Encephalomyelitis (EAE) Model Effects of Compound 292 on treating inflammation was investigated in a 28 day semi-therapeutic mouse EAE model.
EAE Induction EAE was induced in 60 mice using Hooke Kit™ $MOG_{35-55}$/CFA Emulsion PTX (Hooke Laboratories, Lawrence Mass.), catalog number EK-0110, lot number 0104, per manufacturer's recommended protocol, except that pertussis toxin was diluted with phosphate buffered saline to achieve 1.4× and 1.3× solution (starting from the 1.5× solution in the kit). This was done to optimize disease severity for this particular study.

Mice were injected subcutaneously, at two sites in the back, with the emulsion component of the kit (containing $MOG_{35-55}$). One site of injection was in the area of the upper back, approximately 1 cm caudal of the neck line. The second site was in the area of the lower back, approximately 2 cm cranial of the base of the tail. Injection volume was 0.1 mL at each site. Within 2 hours of the injection of emulsion, and then again 24 hours after the injection of emulsion, the pertussis toxin component of the kit was administered intraperitoneally. Volume of each injection was 0.1 mL.
Groups and Treatment EAE was induced in 60 mices, which were divided into six groups with 10 mice in each group: Group 1—Vehicle, p.o., QD, 5 mL/kg (negative control); Group 2—FTY720, 3 mg/kg, p.o., QD, 5 mL/kg (positive control); Group 3—Compound 292, 0.3 mg/kg, p.o., QD, 5 mL/kg; Group 4—Compound 292, 1 mg/kg, p.o., QD, 5 mL/kg; Group 5—Compound 292, 3 mg/kg, p.o., QD, 5 mL/kg; and Group 6—Compound 292, 10 mg/kg, p.o., QD, 5 mL/kg. Vehicle for Group 2 (FTY720) was water and 2% ethanol. Vehicle for all other groups was water, 0.5% CMC (low viscosity), and 0.05% Tween80. Mice were dosed at the same time every day, +/−1 hour. The last day of dosing was Day 27 after immunization.

Scoring and Readout

Readouts were EAE scores and changes in body weight. Mice were scored daily from Day 7 to Day 28, and body weights were measured three times/week (Monday, Wednesday and Friday), starting on Day-1.

EAE was scored on scale 0 to 5:
0 No obvious changes in motor functions of the mouse in comparison to non-immunized mice. When picked up by the tail, the tail has tension and is erect. Hind legs are usually spread apart. When the mouse is walking, there is no gait or head tilting.
1 Limp tail. When the mouse is picked up by the tail, instead of being erect, the whole tail drapes over finger.
2 Limp tail and weakness of hind legs. When mouse is picked up by tail, legs are not spread apart, but held closer together. When the mouse is observed walking, it has a clearly apparent wobbly walk.
3 Limp tail and complete paralysis of hind legs (most common); or limp tail with paralysis of one front and one hind leg; or all of: severe head tilting, walking only along the edges of the cage, pushing against the cage wall, and spinning when picked up by the tail.
4 Limp tail, complete hind leg and partial front leg paralysis. Mouse is minimally moving around the cage but appears alert and feeding. Usually, euthanasia is recommended after the mouse scores level 4 for 2 days. When the mouse is euthanized because of severe paralysis, score of 5 is entered for that mouse for the rest of the experiment.
5 Complete hind and complete front leg paralysis, no movement around the cage; or mouse is spontaneously rolling in the cage; or mouse is found dead due to paralysis.

In-between scores were assigned when the clinical signs fell between two above defined scores.

Tissue Collection

At the end of the study, the following tissues were collected:

Collection of Plasma for PK:

On Day 27, plasma was isolated from mice in Groups 3 through 6. Three mice from each group were bled at 30 minutes and 1 hour after the last dose of Compound 292. Plasma was isolated from another 3 in these groups at 4 hours, and from another 3 mice in these groups at 6 hours after the last dose of Compound 292. On Day 28, plasma was isolated from three mice in each of Groups 3 through 6 at trough. Blood was collected into EDTA tubes. The blood was placed at 4° C. after collection and then centrifuged within 20 minutes of collection to separate plasma. Approximately 100 μL of plasma was collected from each sample and stored at −80 C immediately after collection.

Collection of Serum:

On Day 28, serum was isolated from all the mice in the study and from the naïve mice. Blood was collected into Gel Clot Activator tubes, left at room temperature for 15-30 minutes, and then centrifuged for 5 minutes to separate serum. At least 100 μL of serum was collected from each sample and stored at −80° C. immediately after collection.

Collection of Spines for Histological Analysis:

After the last collection of blood on Day 28, mice in Groups 1, 2, 3, and 6 and the 3 naïve mice were sacrificed and immediately perfused with PBS. Spines were collected in buffered formalin for histological analysis.

Histological Analysis of Spines:

At the end of the study 3 luxol fast blue (LFB) stained sections and 3 H&E sections, from lumbar, thoracic, and cervical spinal cord of all mice in Groups 1, 2, 3, and 6 and the 3 naïve mice were prepared and analyzed.

Count of Inflammatory Foci:

Inflammatory foci were counted in each H&E stained section. Each group of approximately 20 cells was counted as one focus. Foci larger than 20 cells were counted based on an estimate of how many foci of 20 cells were present.

Estimation of demyelination area: The demyelination score represents an estimate of demyelinated area for each section as follows. For LFB stained slides, the demyelinated area was estimated based on intensity of blue staining of myelin. For H&E stained sections, demyelinated area was estimated by looking for interruption of normal structure—pallor and vacuolation consistent with edema and demyelination, and dilated axons.

0—no demyelination (less than 5% demyelinated area)
1—5 to 20% demyelinated area
2—20 to 40% demyelinated area
3—40 to 60% demyelinated area
4—60 to 80% demyelinated area
5—80 to 100% demyelinated area.

Count of Apoptotic Cells:

The number of apoptotic cells in each of the three H&E sections was determined.

Results

Figure 16:
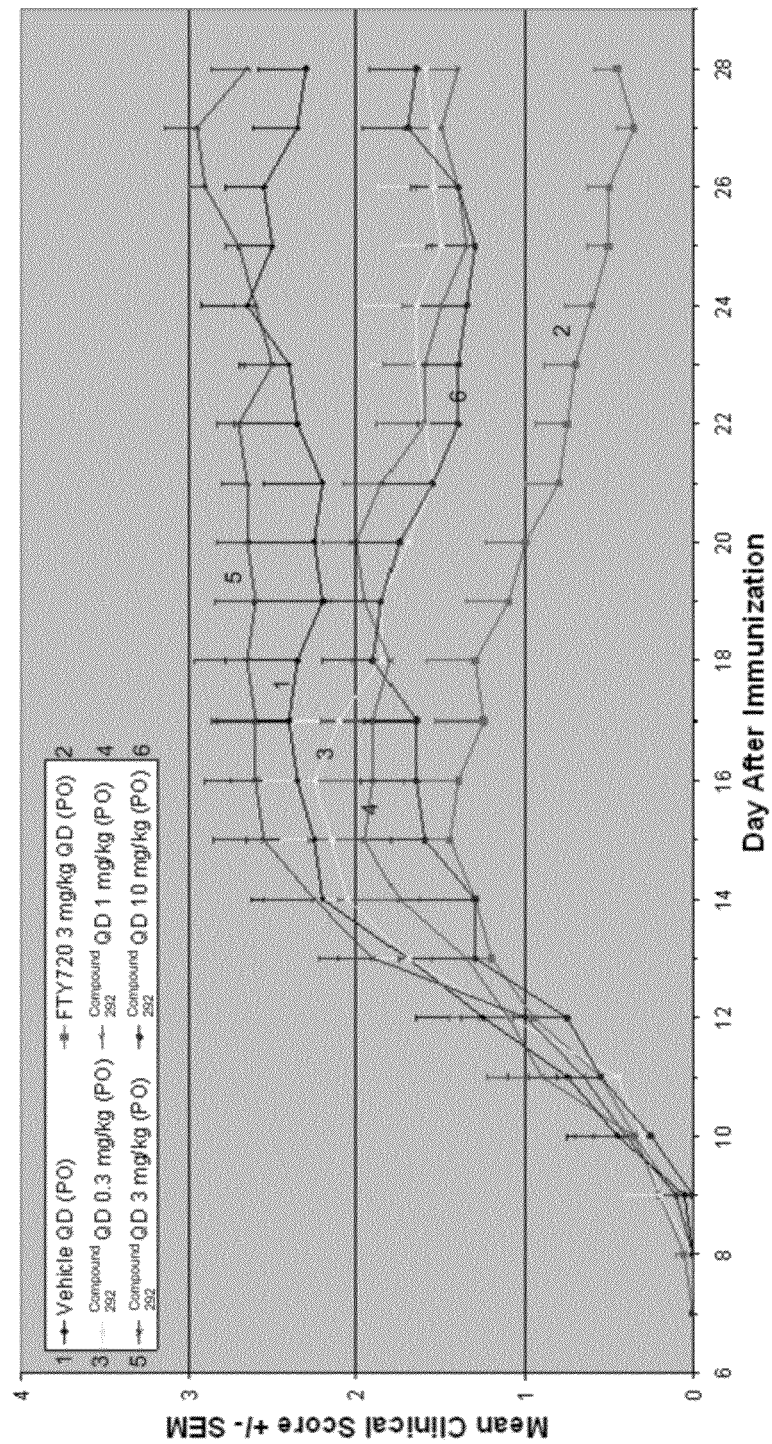
FIG. 16 depicts the effects over time of Compound 292 on Experimental Autoimmune Encephalomyelitis (EAE) severity (mean clinical score) in murine EAE model.
Figure 17:
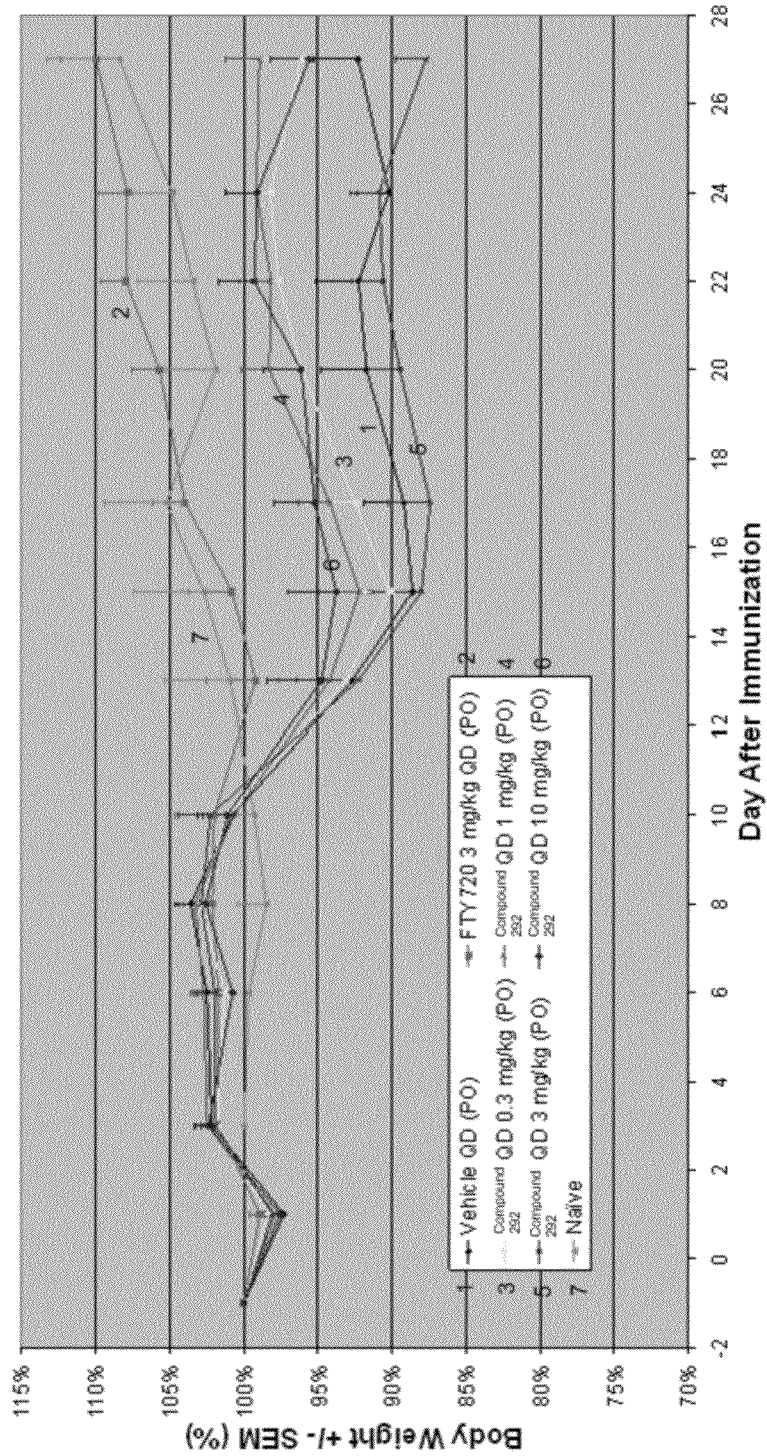
FIG. 17 depicts the effects over time of Compound 292 on body weight in murine EAE model.
Figure 18A:
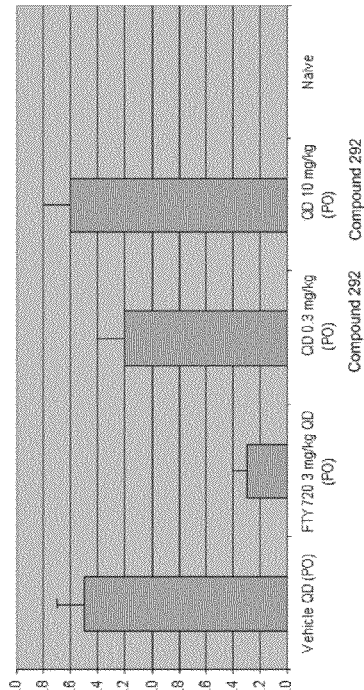
FIG. 18A depicts the effects of Compound 292 on number of inflammatory foci in murine EAE model.
Figure 18B:
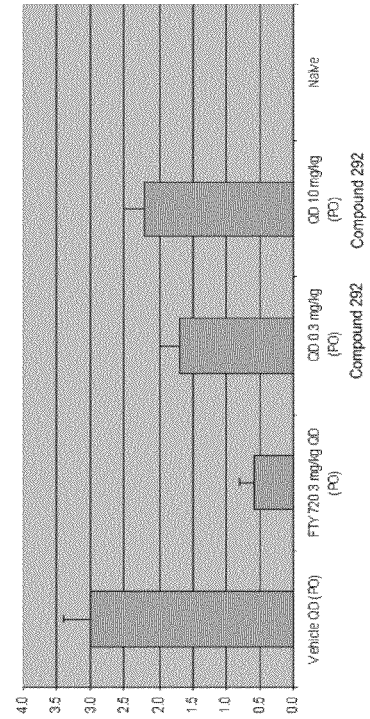
FIG. 18B depicts the demyelination scores (based on LFB histological sections) of Compound 292 in murine EAE model.
Figure 18C:
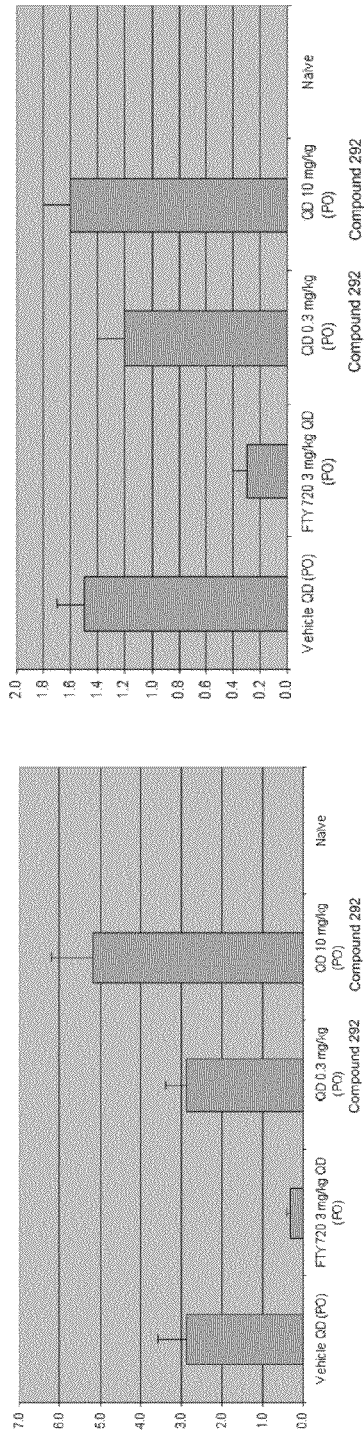
FIG. 18C depicts the demyelination scores (based on H&E histological sections) of Compound 292 in murine EAE model.
Figure 18D:
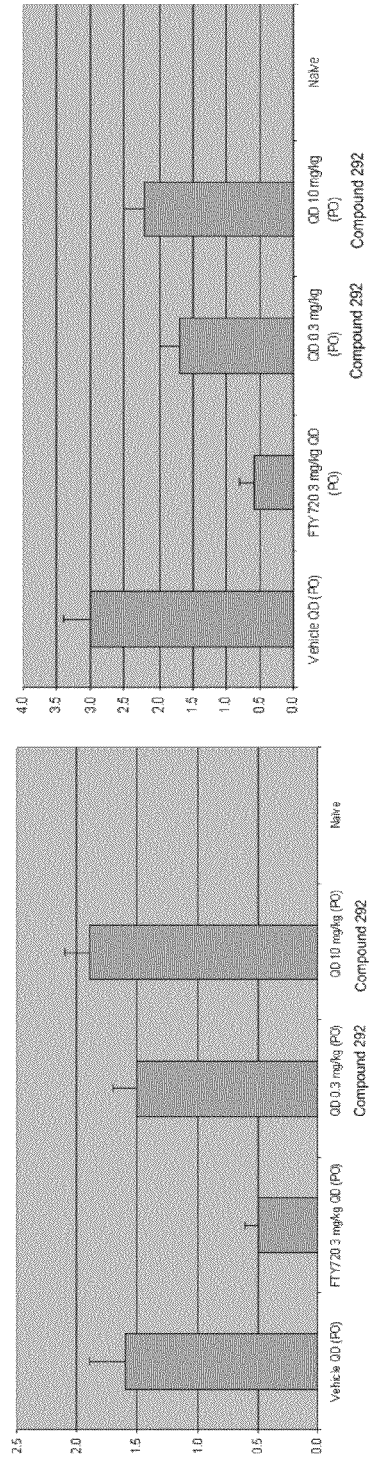
FIG. 18D depicts the effects of Compound 292 on number of apoptotic cells in murine EAE model.

EAE development was evaluated by comparing incidence, time to EAE onset, MMS, and EAE scores at the end of the study between the compound-treated groups and the vehicle-treated group (negative control) (Table 8, FIG. 16). Change in body weight at the end of the study was also compared between the compound-treated groups and the vehicle-treated group (Table 8, FIG. 17). Histological scores were compared between the compound-treated group and the vehicle-treated group (Tables 8, FIGS. 18A, 18B, 18C, and 18D).

TABLE 8

Summary of EAE Results

| Treatment | Median Day of Onset | MMS +/−SD | End score +/−SD | End % body weight +/−SD | Inflammatory foci +/−SD | Demyelination (LFB) +/−SD |
| --- | --- | --- | --- | --- | --- | --- |
| Vehicle QD (p.o.) | 11.5 | 3.10 +/− 0.52 | 2.30 +/− 0.89 | 92.3 +/− 9.3 | 2.9 +/− 2.3 | 1.5 +/− 0.6 |
| FTY720 3 mg/kg QD (p.o.) | 11.5 | 1.65 +/− 1.23 | 0.45 +/− 0.44 | 110.0 +/− 7.4 | 0.3 +/− 0.4 | 0.3 +/− 0.3 |

TABLE 8-continued

Summary of EAE Results

| Treatment | Median Day of Onset | MMS +/−SD | End score +/−SD | End % body weight +/−SD | Inflammatory foci +/−SD | Demyelination (LFB) +/−SD |
|---|---|---|---|---|---|---|
| Compound 292 0.3 mg/kg QD (p.o.) | 11.5 | 2.50 +/− 0.85 | 1.60 +/− 1.02 | 96.1 +/− 11.8 | 2.9 +/− 1.5 | 1.2 +/− 0.7 |
| Compound 292 1 mg/kg QD (p.o.) | 11.0 | 2.70 +/− 0.72 | 1.40 +/− 0.81 | 99.0 +/− 7.4 | not measured | not measured |
| Compound 292 3 mg/kg QD (p.o.) | 12.0 | 3.40 +/− 0.21 | 2.65 +/− 0.67 | 87.7 +/− 6.4 | not measured | not measured |
| Compound 292 10 mg/kg QD (p.o.) | 14.0 | 2.55 +/− 0.76 | 1.65 +/− 0.85 | 95.6 +/− 8.5 | 5.2 +/− 3.2 | 1.6 +/− 0.8 |
| Naive | N/A | 0.00 +/− 0.00 | 0.00 +/− 0.00 | 108.4 +/− 8.4 | 0.0 +/− 0.0 | 0.0 +/− 0.0 |

Compound 292 was administered at 4 doses: 0.3, 1, 3, and 10 mg/kg, p.o., QD.

The mean day of EAE onset was 11.3+/−0.4, 12.5+/−1.0, 12.1+/−0.7, and 14.4+/−1.5 days after immunization for the mice which developed EAE for the 0.3, 1, 3, and 10 mg/kg groups, respectively. The time to disease onset was not significantly different than the vehicle group for any of the Compound 292-treated groups. The median day of EAE onset was 11.5, 11, 12, and 14 days after immunization for the 0.3, 1, 3, and 10 mg/kg groups, respectively.

Compound 292-treated mice developed moderately severe to severe EAE with MMSs of 2.50+/−0.85, 2.70+/−0.72, 3.40+/−0.21, and 2.55+/−0.76 for the 0.3, 1, 3, and 10 mg/kg groups, respectively. All the MMSs, with the exception of the 3 mg/kg group, were lower than the MMS of the vehicle-treated mice, but none of the differences reached statistical significance (p=0.0542, p=0.1165, p=0.1276, and p=0.0616 for the 0.3, 1, 3, and 10 mg/kg groups, respectively).

The average EAE scores on Day 28 (end of study) were 1.60+/−1.02, 1.40+/−0.81, 2.65+/−0.67, and 1.65+/−0.85 for the 0.3, 1, 3, and 10 mg/kg groups, respectively. This was significantly lower for the 1 mg/kg group compared to the vehicle group (p=0.0291). The end scores were lower in the 0.1 and 10 mg/kg groups compared to the vehicle group, but the differences did not reach statistical significance (p=0.1349 and p=0.1250 for the 0.3 and 10 mg/kg groups, respectively). The end score was higher in the 3 mg/kg group compared to the vehicle group, but the difference did not reach statistical significance (p=0.3957).

The average body weights on Day 27 were 96.1+/−11.8%, 99.0+/−7.4%, 87.7+/−6.4%, and 95.6+/−8.5% of their weights on Day-1 for the 0.3, 1, 3, and 10 mg/kg groups, respectively. This was significantly higher in the 1 mg/kg group compared to the vehicle group (p=0.0477). The body weights of the 0.1 and 10 mg/kg groups were higher than the average relative body weights of the vehicle group, but the difference did not reach statistical significance (p=0.2153 and p=0.2109 for the 0.1 and 10 mg/kg groups, respectively). The body weight of the mice treated with 3 mg/kg of Compound 292 was lower than for the vehicle-treated group, but the difference did not reach statistical significance (p=0.1076).

Histological analysis was performed on mice treated with 0.3 and 10 mg/kg. Inflammation was found in the spinal cords of the mice treated with Compound 292. There were 2.9+/−1.5 and 5.2+/−3.2 (average+/−SD) inflammatory foci per section in the groups treated with 0.3 and 10 mg/kg, respectively. The 10 mg/kg group had significantly more inflammatory foci than the vehicle group (p=0.0396). The group treated with 0.3 mg/kg was not significantly different from the vehicle group (p=0.5000). Demyelination was found in most sections in both 0.3 and 10 mg/kg treated groups.

In the LFB sections demyelination scores were 1.2+/−0.7 and 1.6+/−0.8 (average per section+/−SD) for the 0.3 and 10 mg/kg treated mice, respectively. These were not significantly different from the vehicle-treated mice (p=0.3931 and 0.8466, respectively).

In the H&E sections demyelination scores were 1.5+/−0.5 and 1.9+/−0.8 (average per section+/−SD) in the 0.3 and 10 mg/kg treated mice, respectively. These were not significantly different from the vehicle-treated mice (p=1.000 and 0.4443, respectively).

The number of apoptotic cells was lower in the Compound 292-treated groups than in the vehicle-treated group. There were 1.7+/−0.9 and 2.2+/−1.0 (average per section+/−SD) apoptotic cells in the 0.3 and 10 mg/kg treated groups, respectively. This was significantly less than in the vehicle group for the 0.3 mg/kg-treated group (p=0.0076) and close to significantly less for the 10 mg/kg-treated group (p=0.0699). The number of apoptotic cells found in histological sections is a sensitive measure of damage in the spinal cords and it suggests that there may be some reduction in overall EAE pathology in the Compound 292-treated mice. This is consistent with a small reduction in the severity of the clinical scores at the end of the study compared to the vehicle-treated mice.

Collectively, these results indicate that in this study Compound 292 was efficacious in reducing EAE when dosed semi-therapeutically at 1 mg/kg, p.o., QD. There was a trend toward disease inhibition for 0.1 and 10 mg/kg treatment groups, but this inhibition did not reach statistical significance. Mice dosed with 3 mg/kg developed somewhat more severe EAE compared to the vehicle-treated mice, but this difference did not reach statistical significance.

Example 11

Effects of Compound 292 in the Inflammatory Bowel Disease (IBD) Model

A study was conducted to evaluate the potential efficacy of Compound 292 (1, 3, or 10 mg/kg) administered daily (QD) by the oral (PO) route for 21 days (d21-41) in female SCID mice with $CD4^+$ inflammatory bowel disease. In this murine model, female C.B-17 SCID mice are injected intraperitoneally (IP) with $CD45RB^{high}$ cells, a subset of $CD4^+$ T cells obtained from normal BALB/c mice, to induce spontaneous chronic inflammation in the large intestine. Gross and histopathologic changes resulting from this treatment resemble those occurring in Crohn's disease and ulcerative colitis in humans. See Leach et al., Inflammatory Bowel Disease in C.B-17 scid Mice Reconstituted with the CD45RB$^{high}$ Subset of CD4$^+$ T Cells, *American Journal of Pathology*, 1996, 148 (5), 1503-1515.

On study day 0, Balb/C mice were terminated, and spleens were obtained for CD45RB$^{high}$ cell isolation per the SCID IBD cell separation protocol. SCID mice were weighed and received intraperitoneal (IP) injections of the sorted cells (approx. 4×10$^6$ cells/ml, 100 µl/mouse injections). On study day 21, mice were weighed and randomized by body weight loss into treatment groups, and daily (QD), oral (PO) dosing was initiated. Dosing continued through study day 41, and mice were terminated on day 42. Group 1, N=4, normal control; group 2, N=10, vehicle control (0.5% CMC, 0.05% Tween80 in H$_2$O); group 3, N=10, Compound 292 (10 mg/kg); group 4, N=10, Compound 292 (3 mg/kg); group 5, N=10, Compound 292 (1 mg/kg); group 6, N=10, CSA (50 mg/kg in 1% CMC).

For each animal, the entire colon (proximal and distal) was trimmed into 8 equally spaced pieces for processing and embedding. Sections were stained with hemotoxylin and eosin (H&E). For each H&E stained section, submucosal edema was quantitated by measuring the distance from the muscularis mucosa to the internal border of the outer muscle layer in a non tangential area thought to most represent the severity of this change. Mucosal thickness was also measured in a non-tangential area of the section that best represented the overall mucosal thickness. This parameter is indicative of gland elongation and mucosal hyperplasia. In order to incorporate this parameter into the summed score, a hyperplasia score was derived from the measurement as follows:

0=<250 µm
1=250-349 µm
2=350-449 µm
3=450-599 µm
4=600-699 µm
5=≥700 µm

The extent of inflammation (foamy macrophage, lymphocyte and PMN infiltrate) was assigned severity scores according to the following criteria:

Normal=0
Minimal=1 (generally focal affecting 1-10% of mucosa or if diffuse then minimal)
Mild=2 (generally focal affecting 11-25% of mucosa or if diffuse then mild)
Moderate=3 (26-50% of mucosa affected with areas of gland loss replaced by inflammatory cell infiltrate, milder in remaining areas of mucosa)
Marked=4 (51-75% of mucosa affected with areas of gland loss replaced by inflammatory cell infiltrate, milder in remaining areas of mucosa)
Severe=5 (76-100% of mucosa affected with areas of gland loss replaced by inflammatory cell infiltrate, milder in remaining areas of mucosa)

The parameters reflecting epithelial cell loss/damage were scored individually using a percent area involved scoring method:

None=0
1-10% of the mucosa affected=1
11-25% of the mucosa affected=2
26-50% of the mucosa affected=3
51-75% of the mucosa affected=4
76-100% of the mucosa affected=5

Parameters that were scored using percent involvement included: (1) Colon glandular epithelial loss—this includes crypt epithelial as well as remaining gland epithelial loss; and (2) Colon Erosion—this reflects loss of surface epithelium and generally is associated with mucosal hemorrhage (reflective of the bleeding seen clinically and at necropsy).

The 4 important scored parameters (inflammation, glandular epithelial loss, erosion, hyperplasia) were ultimately summed to arrive at a sum of histopathology scores, which indicates the overall damage and would have a maximum score of 20.

Inflammatory cell infiltrates in the colonic mucosa were evaluated for approximate % of neutrophils in the total infiltrate using the criteria below. The approximate % of total was then multiplied by the 0-5 inflammation score in an attempt to semiquantify relative PMN infiltration across sections and animals.

0=approx 0%
10=approx 10%
25=approx 25%
50=approx 50%
75=75% or greater

This value was then multiplied by the inflammation score in an attempt to semiquantify relative PMN infiltration across sections and animals.

Results

Vehicle treated control mice (DSS control) had moderate weight loss and clinical changes consistent with CD4$^+$ inflammatory bowel disease in mice. Vehicle control mice had mean colon lengths of 9.58 cm, mean colon weight of 0.725 g, and weight/length ratio of 0.076 g/cm (FIGS. 19-22).

Figure 19:
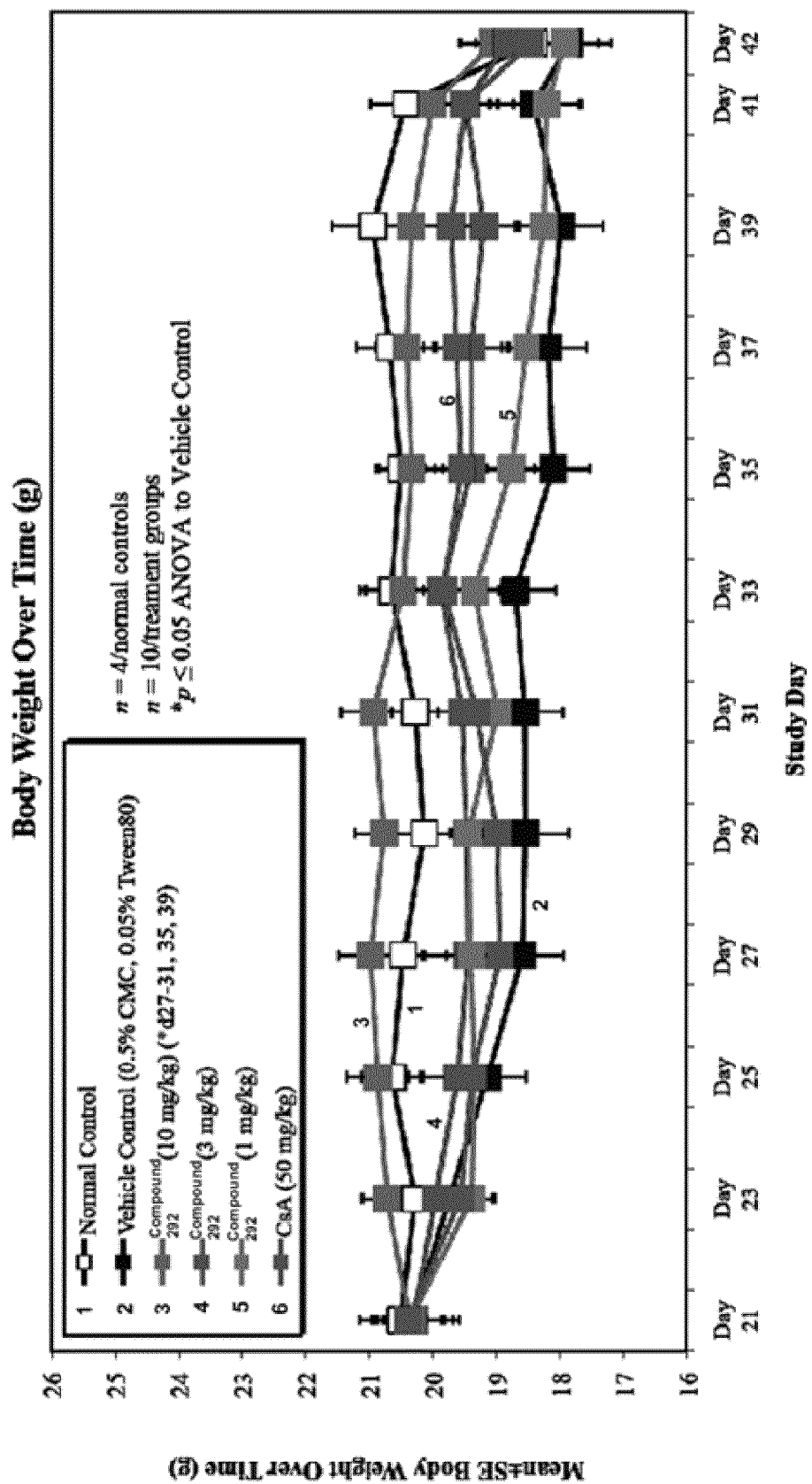
FIG. 19 depicts the effects over time of Compound 292 on body weight in Inflammatory Bowel Disease (IBD) Model.

Absolute body weight measurements were significantly (by ANOVA) increased for mice treated with 10 mg/kg Compound 292 (*significant days 27-31, 35, 39) as compared to vehicle treated disease control mice. When compared to vehicle controls using a Student's t-test, absolute body weight measurements for this group were also significantly increased on days 25 and 37. Body weight loss was not significantly affected for mice in any treatment group as compared to vehicle controls (FIG. 19).

Figure 20:
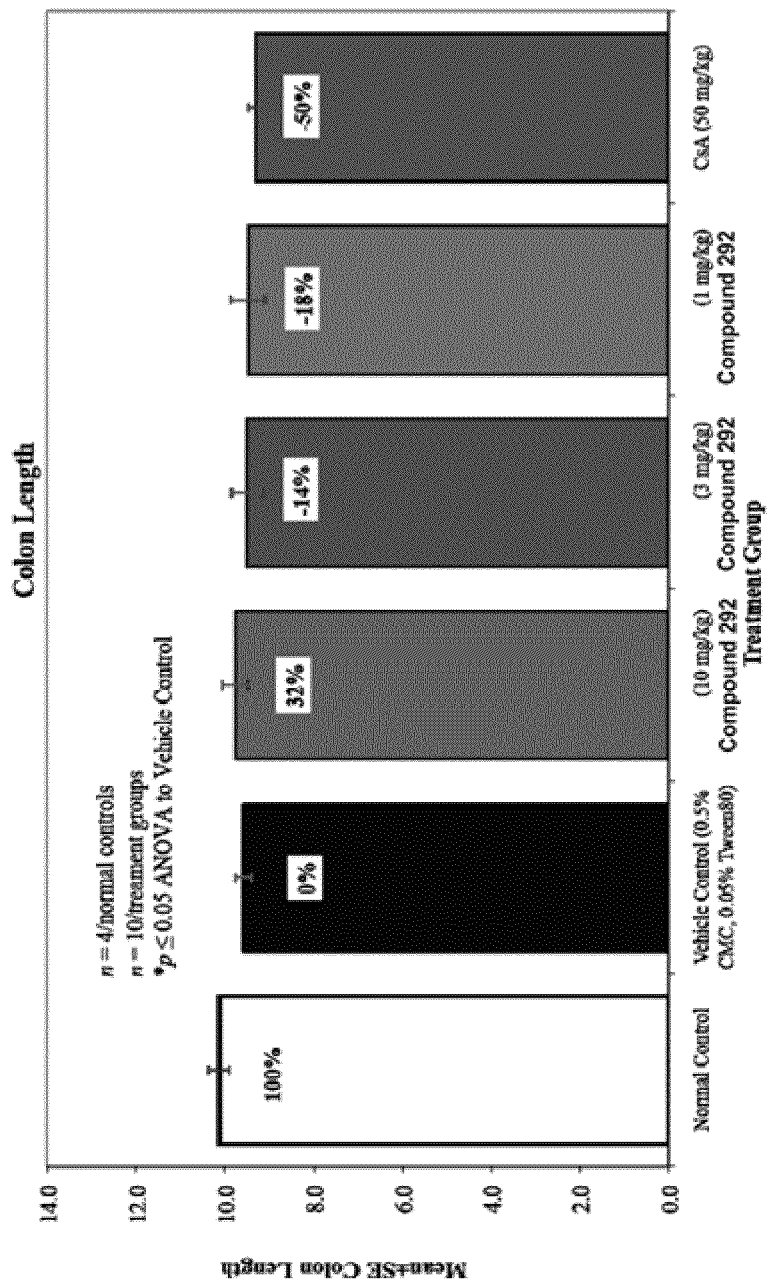
FIG. 20 depicts the effects of Compound 292 on colon length in IBD Model.
Figure 21:
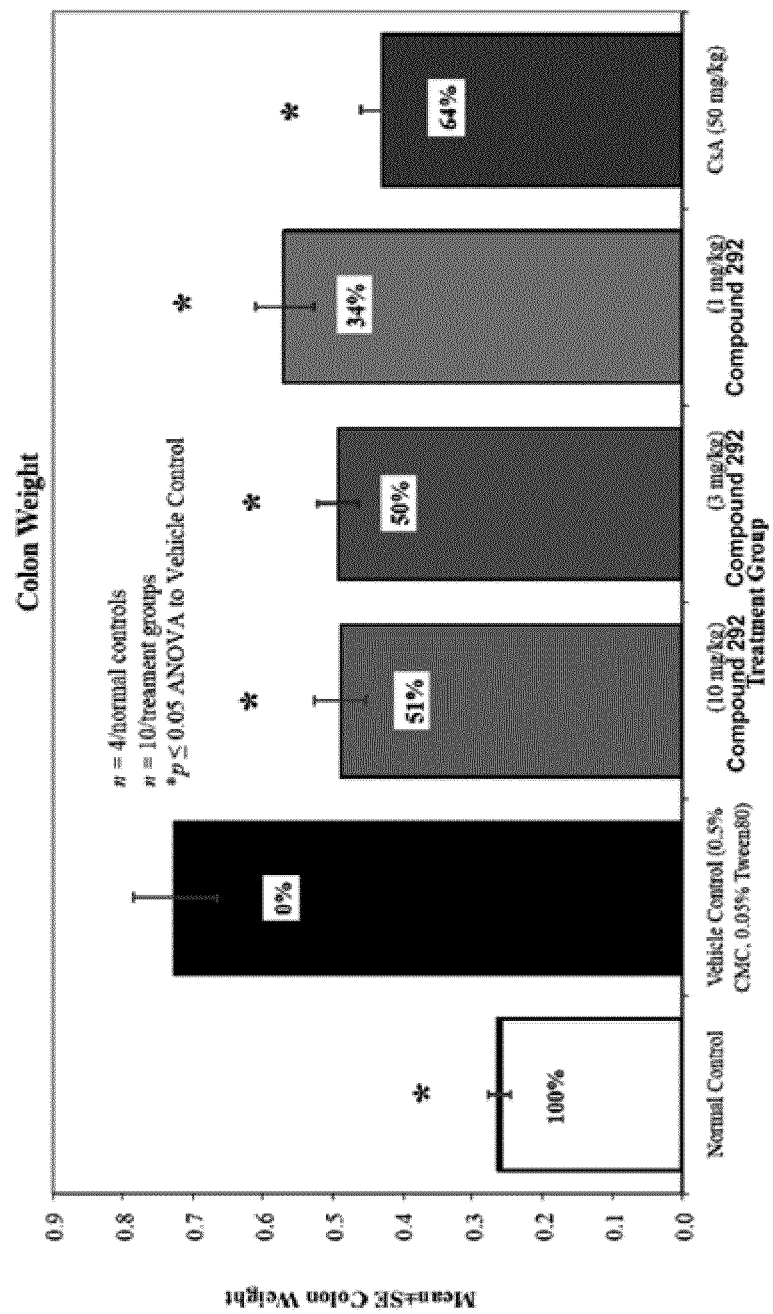
FIG. 21 depicts the effects of Compound 292 on colon weight in IBD Model.
Figure 22:
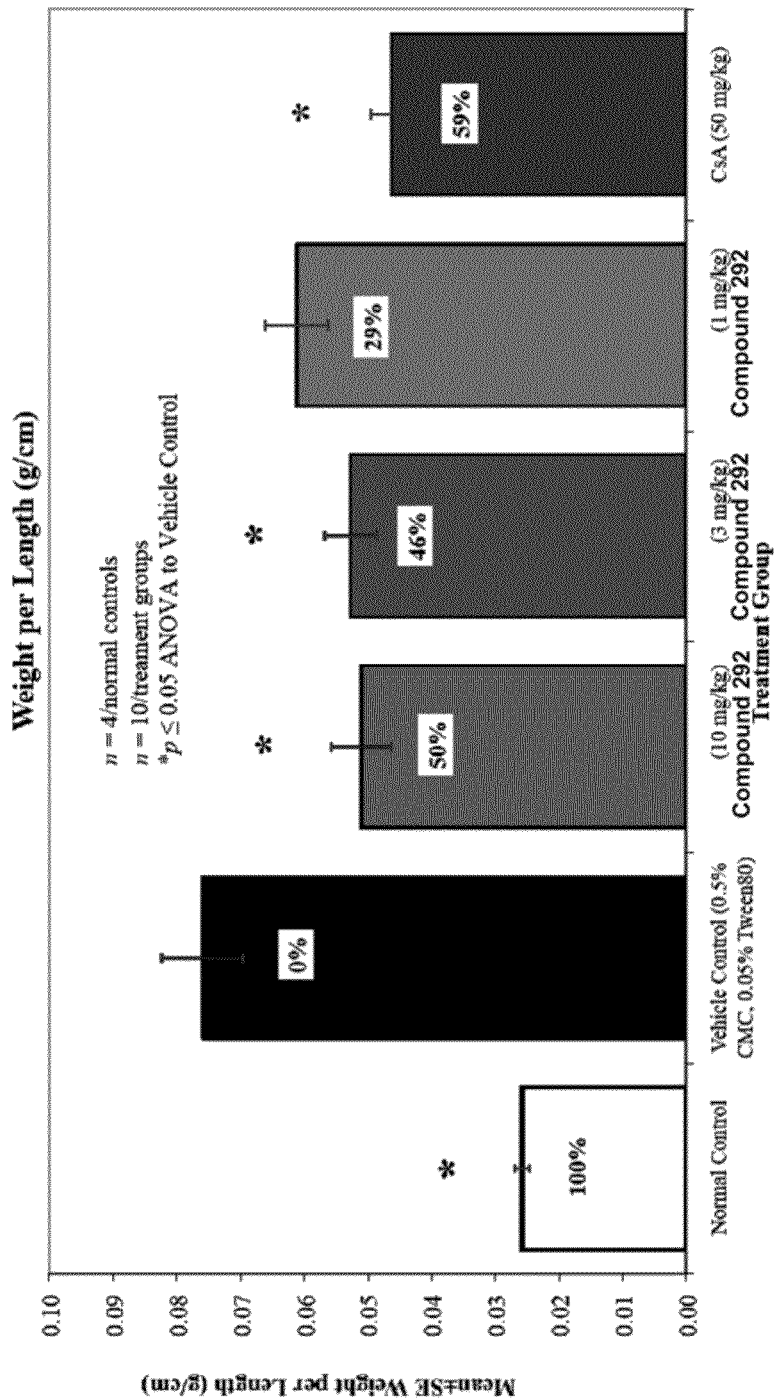
FIG. 22 depicts the effects of Compound 292 on colon weight per length in IBD Model.

Colon length was not significantly affected for mice in any treatment group as compared to vehicle controls (FIG. 20). Colon weights were significantly (by ANOVA) reduced toward normal for mice treated with 10 mg/kg Compound 292 (51% reduction), 3 mg/kg Compound 292 (50%), 1 mg/kg Compound 292 (34%), or CsA (64%) as compared to vehicle controls (FIG. 21). Colon weight/length ratio was significantly reduced toward normal for mice treated with 10 mg/kg Compound 292 (50% reduction), 3 mg/kg Compound 292 (46%), or CsA (59%) as compared to vehicle controls (FIG. 22).

Vehicle control mice had colonic inflammation that ranged from moderate to severe, with minimal to marked gland loss, none to moderate erosion, and minimal to severe hyperplasia. Vehicle controls had mean edema of 39.6 µm, mean PMN percent of 50%, mean neutrophil score of 2.0, and mean mucosal thickness of 484.8 µm. Disease severity was slightly increased in the distal colon (mean histopathology summed score=9.9) as compared to the proximal colon (score=9.5) (FIGS. 23-27).

Figure 23:
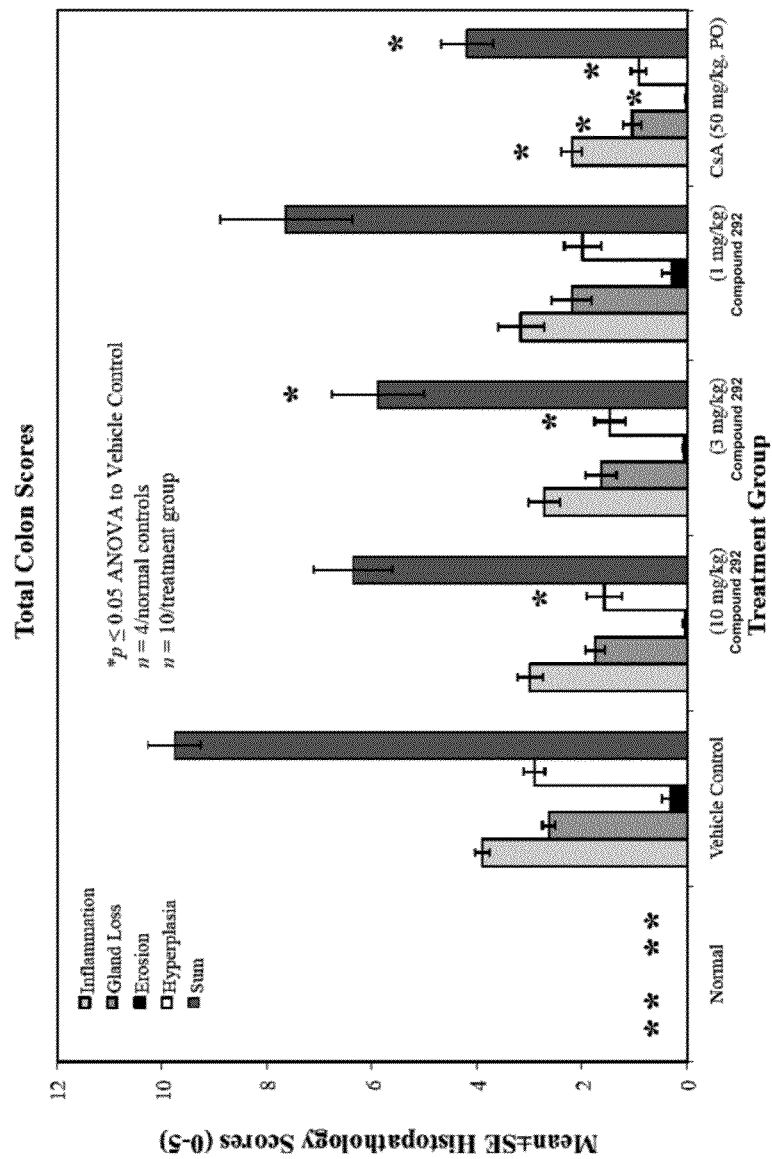
FIG. 23 depicts the total colon scores of Compound 292 in IBD Model.
Figure 26:
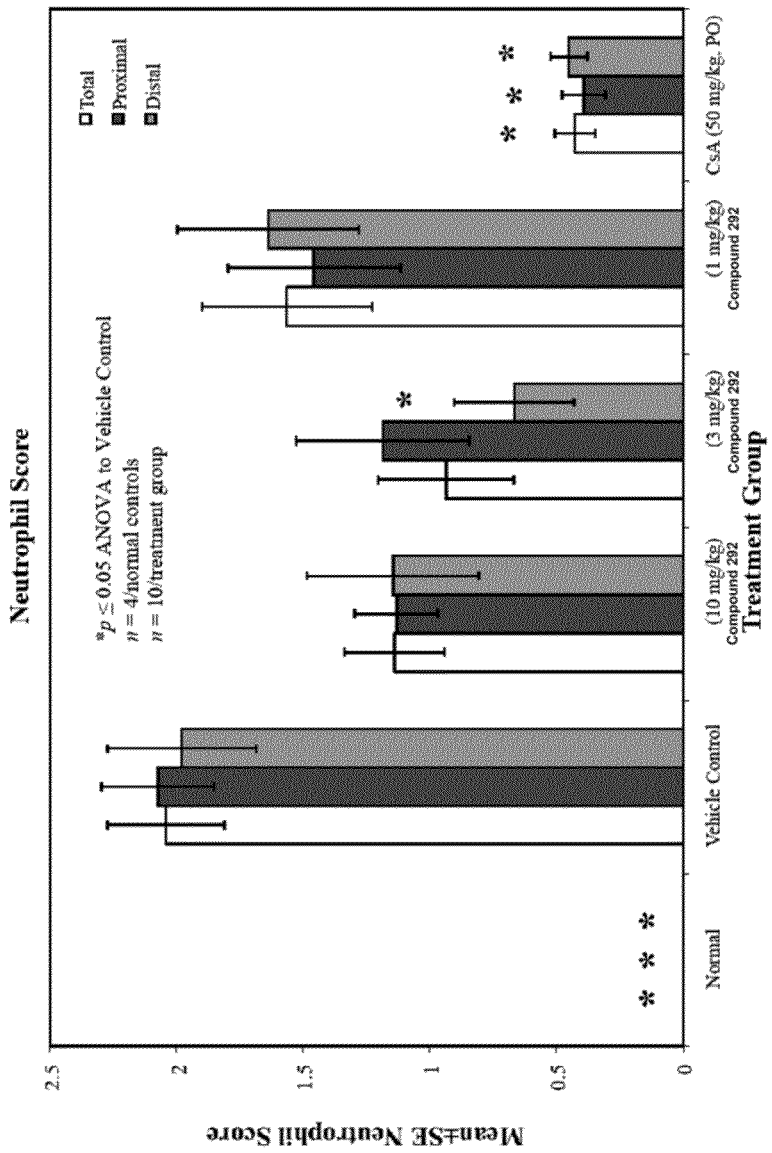
FIG. 26 depicts the neutrophil scores of Compound 292 in IBD Model.
Figure 27:
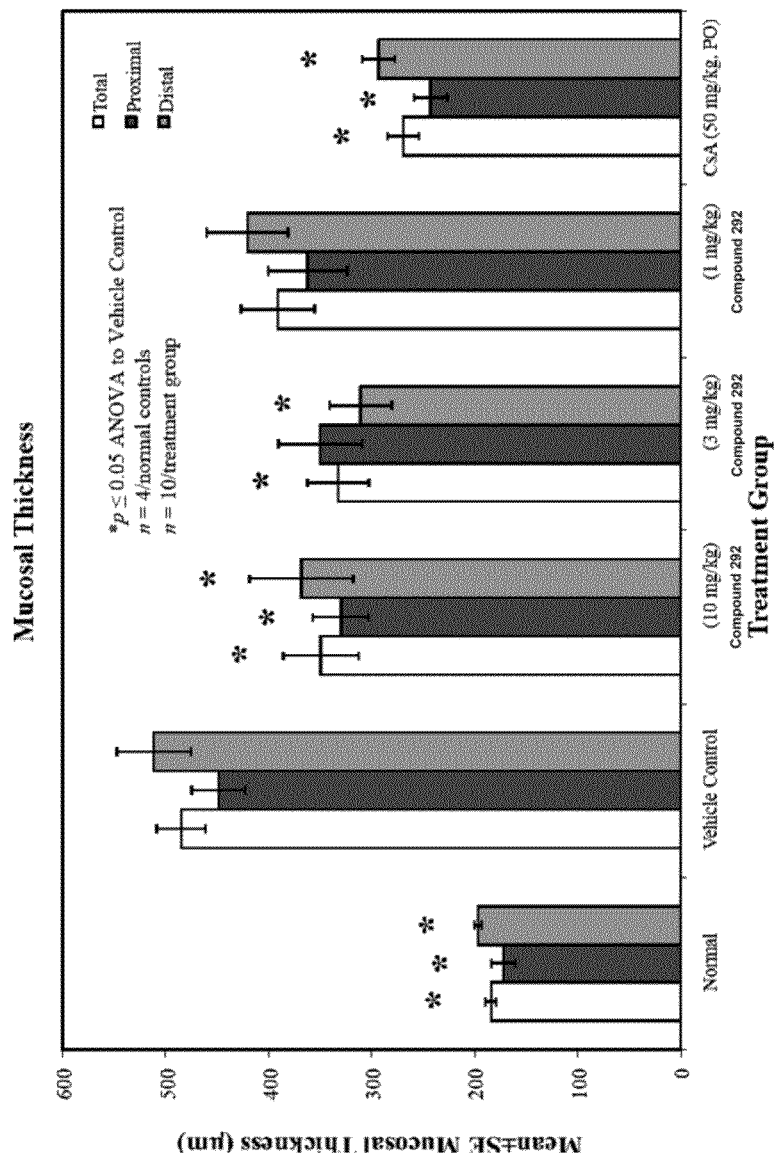
FIG. 27 depicts the mucosal thickness of Compound 292 in IBD Model.

Mice treated with 10 mg/kg Compound 292 had significantly (by ANOVA) reduced colon hyperplasia (46% reduction), PMN percent (37%), and mucosal thickness (45%) as compared to vehicle controls. Mice treated with 3 mg/kg Compound 292 had significantly reduced colon hyperplasia (49%), summed histopathology score (40%), PMN percent (47%), and mucosal thickness (51%). Mice treated with CsA had significantly reduced colon inflammation (44%), gland loss (60%), erosion (96%), hyperplasia (68%), summed histopathology score (57%), PMN percent (68%), neutrophil score (79%), and mucosal thickness (72%). When compared to vehicle controls using a Student's t-test or Mann-Whitney U test (non-parametric), mice treated with 10 mg/kg Compound 292 also had significantly reduced colon edema (60% reduction, p=0.030), inflammation (24%, p=0.010), gland loss (33%, p=0.005), summed histopathology score (35%, p=0.005), and neutrophil score (44%, p=0.021); mice treated with 3 mg/kg Compound 292 had significantly reduced colon inflammation (30%, p=0.007), gland loss (38%, p=0.018), and neutrophil score (54%, p=0.007); and mice treated with 1 mg/kg Compound 292 had significantly reduced colon hyperplasia (32%, p=0.031) and mucosal thickness (31%, p=0.043) (FIGS. 23, 26, and 27).

Figure 24:
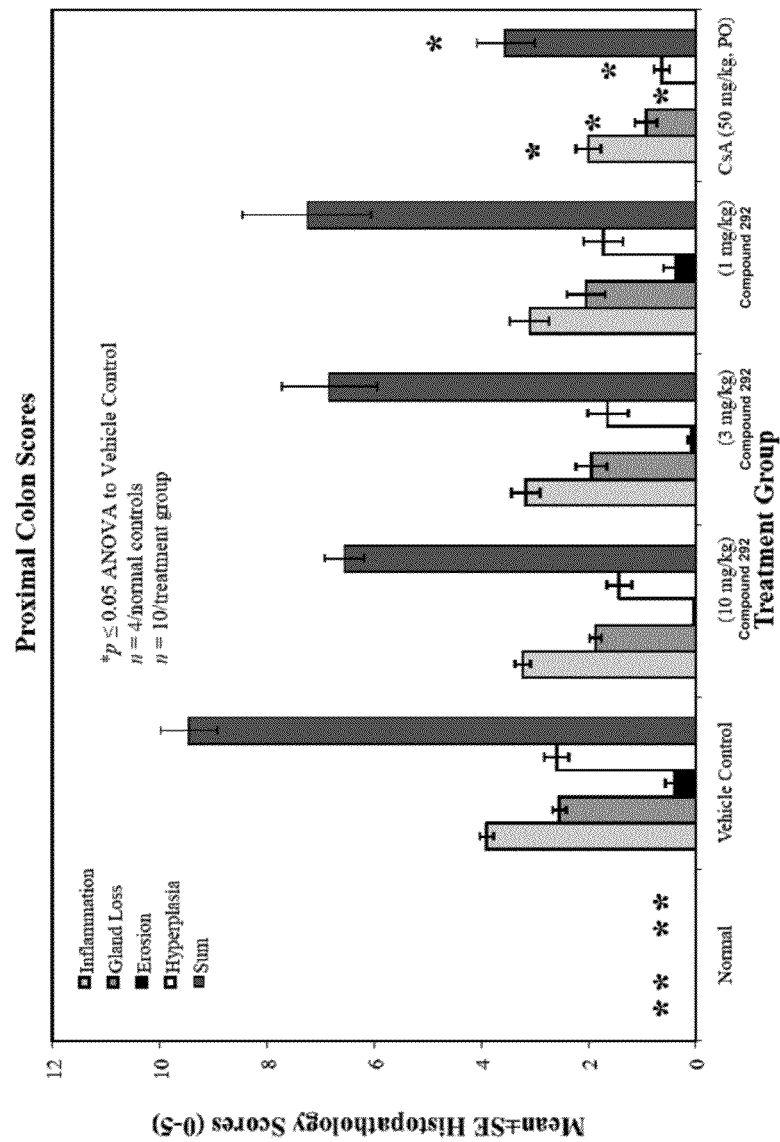
FIG. 24 depicts the proximal colon scores of Compound 292 in IBD Model.
Figure 25:
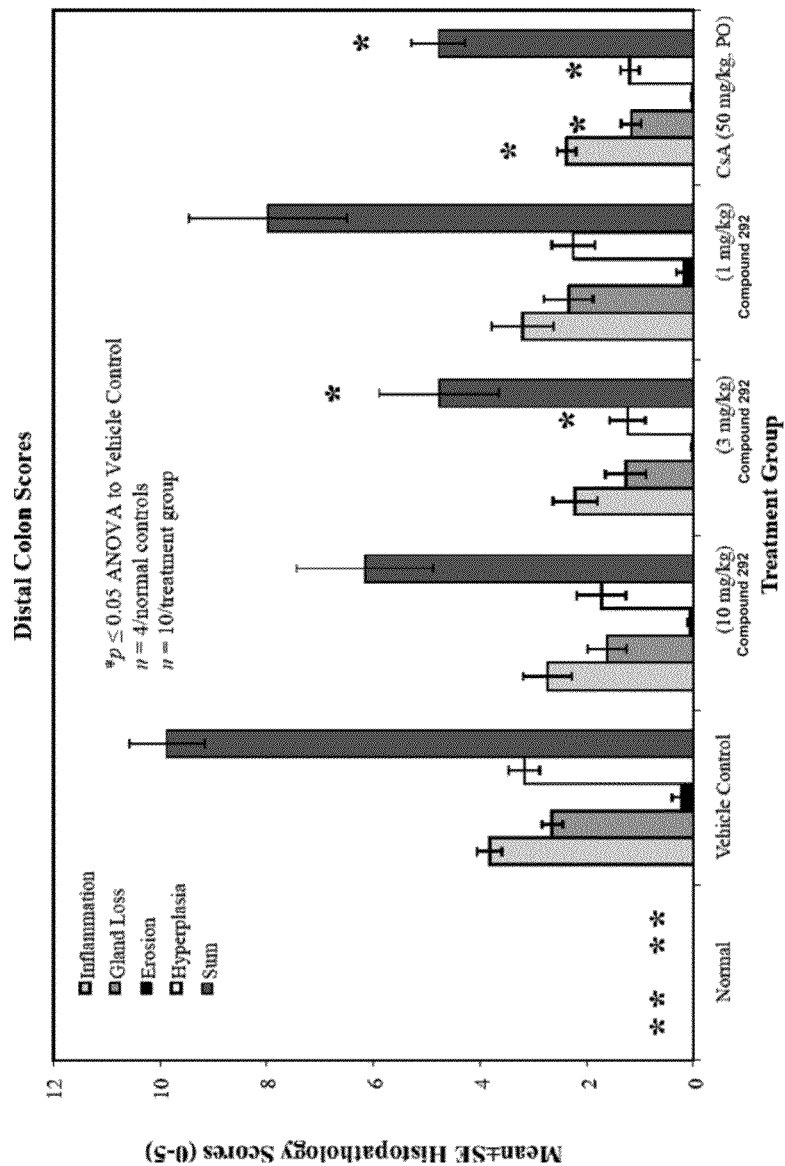
FIG. 25 depicts the distal colon scores of Compound 292 in IBD Model.

When considering only proximal colon sections, mice treated with 10 mg/kg Compound 292 had significantly (by ANOVA) reduced colon edema (68% reduction), PMN percent (37%), and mucosal thickness (43%) as compared to vehicle controls. Mice treated with 3 mg/kg Compound 292 had significantly reduced PMN percent (39%). Mice treated with CsA had significantly reduced colon edema (78%), inflammation (49%), gland loss (64%), erosion (100%), hyperplasia (76%), summed histopathology score (62%), PMN percent (70%), neutrophil score (81%), and mucosal thickness (74%). When compared to vehicle controls using a Student's t-test or Mann-Whitney U test (non-parametric), mice treated with 10 mg/kg Compound 292 also had significantly reduced colon inflammation (17% reduction, p=0.005), gland loss (26%, p=0.004), erosion (94%, p=0.045), hyperplasia (45%, p=0.006), summed histopathology score (31%, p=0.001), and neutrophil score (45%, p=0.005); and mice treated with 3 mg/kg Compound 292 had significantly reduced colon inflammation (19%, p=0.007), gland loss (24%, p=0.019), hyperplasia (37%, p=0.036), summed histopathology score (28%, p=0.013), neutrophils score (43%, p=0.013), and mucosal thickness (36%, p=0.051) (FIGS. 24, 26, and 27).

When considering only distal colon sections, mice treated with 10 mg/kg Compound 292 had significantly (by ANOVA) reduced colon mucosal thickness (46%) as compared to vehicle controls. Mice treated with 3 mg/kg Compound 292 had significantly reduced hyperplasia (61%), summed histopathology score (52%), PMN percent (56%), neutrophil score (66%), and mucosal thickness (64%). Mice treated with CsA had significantly reduced colon inflammation (38%), gland loss (56%), hyperplasia (62%), summed histopathology score (52%), PMN percent (65%), neutrophil score (77%), and mucosal thickness (69%). When compared to vehicle controls using a Mann-Whitney U test, mice treated with 10 mg/kg Compound 292 also had significantly reduced colon inflammation (28% reduction, p=0.032), gland loss (39%, p=0.025), hyperplasia (46%, p=0.044), and summed histopathology score (38%, p=0.031); and mice treated with 3 mg/kg Compound 292 had significantly reduced colon inflammation (42%, p=0.004) and gland loss (52%, p=0.010) (FIGS. 24, 26, and 27).

Results of this study indicate that daily, oral dosing of mice with Compound 292 (3 or 10 mg/kg) had significant beneficial effect on the clinical and histopathology parameters associated with CD4+ inflammatory bowel disease. Treatment with 1 mg/kg Compound 292 significantly reduced colon weight.

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method for reducing a lupus-associated symptom in a subject, comprising administering to the subject a phosphoinositide 3-kinase (PI3K) inhibitor, in an amount sufficient to decrease one or more symptoms, wherein the symptom comprises one or more of an elevated level of IFN-α, TNF-α, IL-6, IL-8, or IL-1.

2. The method of claim 1, wherein the symptom comprises an elevated level of an anti-dsDNA autoantibody.

3. The method of claim 1, wherein the symptom is chosen from one or more of nephritis, proteinuria, or spleen inflammation.

4. The method of claim 1, wherein the symptom comprises an increased level of immune complexes.

5. The method of claim 1, wherein the symptom comprises a vascular lesion.

6. The method of claim 1, wherein the symptom comprises a cutaneous manifestation of lupus.

7. The method of claim 1, wherein the symptom affects one or more of the skin, kidney, heart, lung, blood, or nervous system.

8. The method of claim 1, wherein the PI3K inhibitor is a compound of Formula I-1:

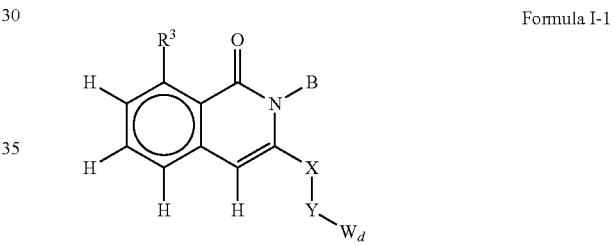

Formula I-1 or a pharmaceutically acceptable salt thereof, wherein
B is a moiety of Formula II:

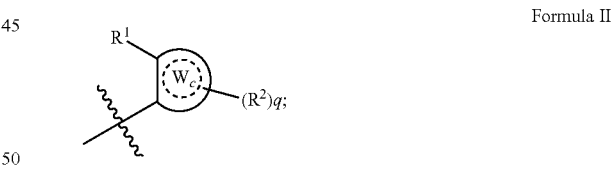

Formula II wherein $W_c$ is aryl, heteroaryl, heterocycloalkyl, or cycloalkyl, and
q is an integer of 0, 1, 2, 3, or 4;
X is a bond or —(CH($R^9$))$_z$—, and z is an integer of 1;
Y is —N($R^9$)—;
$W_d$ is:

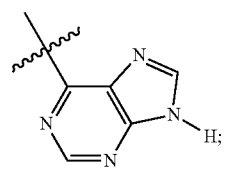

R[1] is hydrogen, alkyl, alkenyl, alkynyl, alkoxy, amido, alkoxycarbonyl, sulfonamido, halo, cyano, or nitro;

R[2] is alkyl, alkenyl, alkynyl, cycloalkyl, heterocycloalkyl, aryl, heteroaryl, heteroarylalkyl, alkoxy, amino, halo, cyano, hydroxy or nitro;

R[3] is hydrogen, alkyl, alkenyl, alkynyl, cycloalkyl, heterocycloalkyl, alkoxy, amido, amino, alkoxycarbonyl sulfonamido, halo, cyano, hydroxy or nitro; and each instance of R[9] is independently hydrogen, alkyl, or heterocycloalkyl.

9. The method of claim 8, wherein B is a moiety of Formula II:

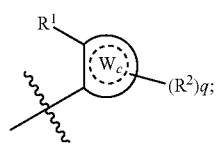

Formula II wherein $W_c$ is aryl, heteroaryl, heterocycloalkyl, or cycloalkyl;

q is an integer of 0 or 1;

R[1] is hydrogen, alkyl, or halo;

R[2] is alkyl or halo; and

R[3] is hydrogen, alkyl, or halo.

10. The method of claim 8, wherein X is —(CH(R[9]))$_z$—, and Y is —NH—.

11. The method of claim 8, wherein R[3] is —H, —CH$_3$, —CH$_2$CH$_3$, —CF$_3$, —Cl or —F.

12. The method of claim 9, wherein X is —(CH(R[9]))$_z$—, wherein R[9] is methyl and z=1; and $W_d$ is

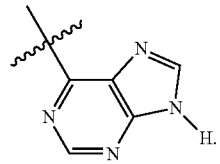

13. The method of claim 8, wherein the compound is predominately in an (S)-stereochemical configuration.

14. The method of claim 8, wherein the compound has a structure of Formula V-A2:

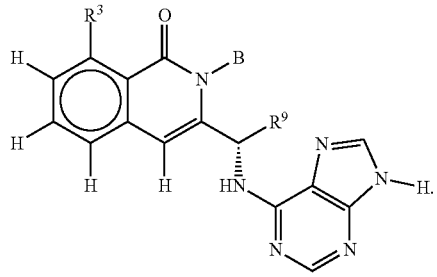

Formula V-A2

15. The method of claim 1, wherein the PI3K inhibitor is a compound selected from the group consisting of

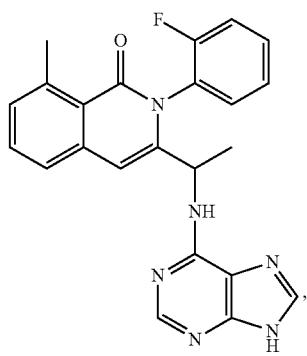

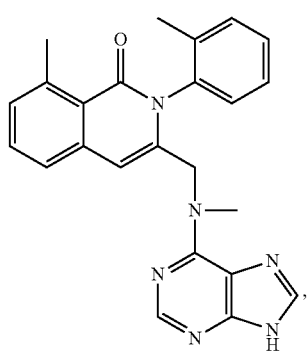

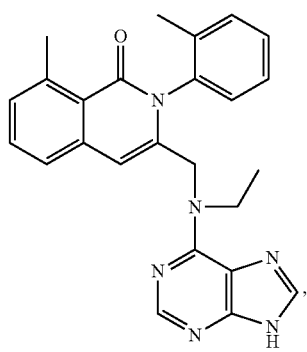

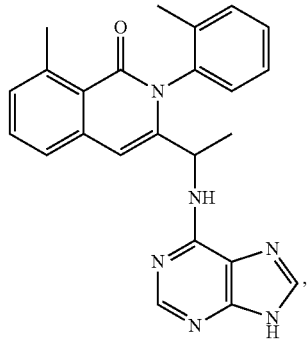

309
-continued
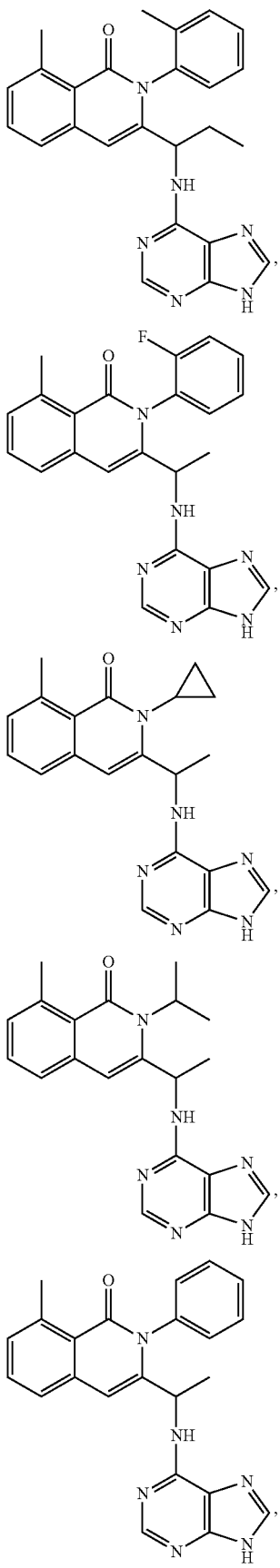
310
-continued
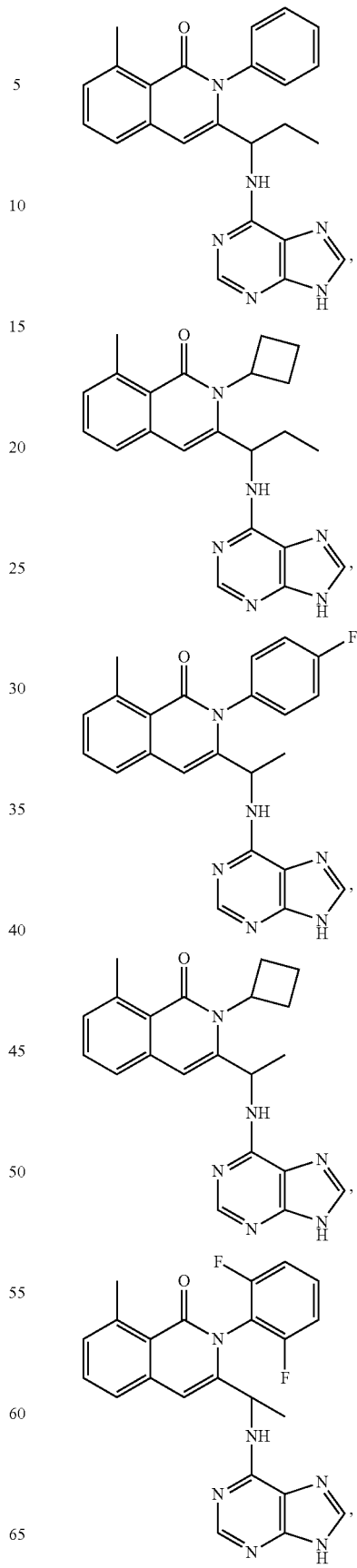

311
-continued
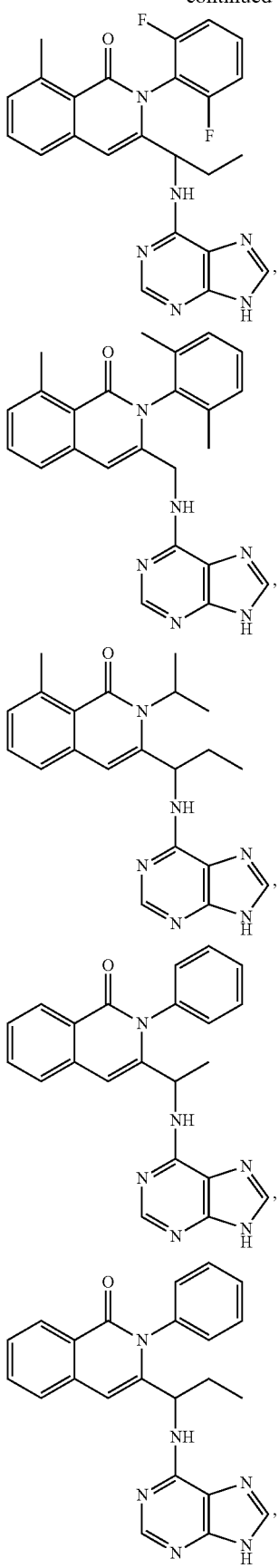
312
-continued
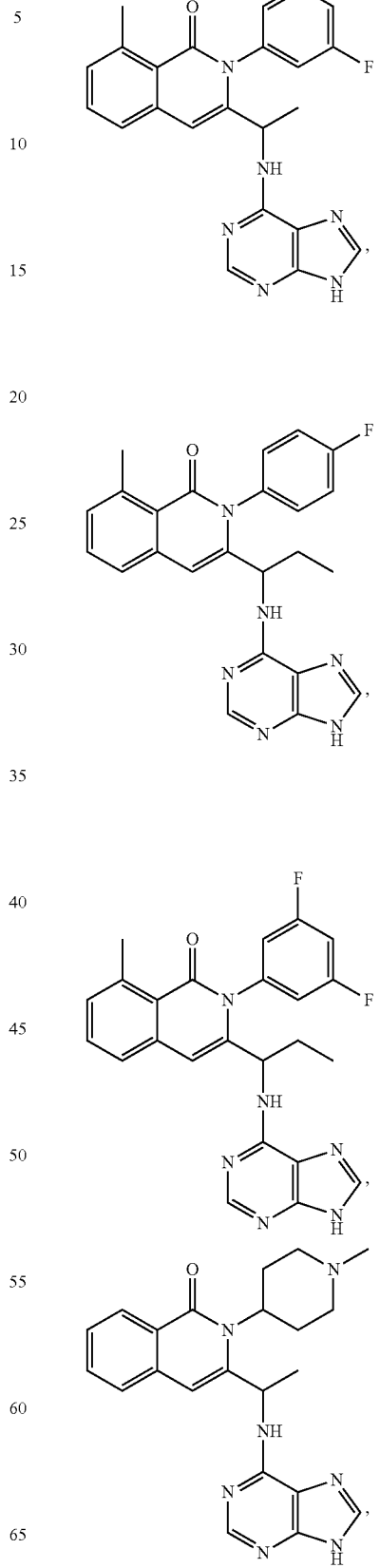

313
-continued
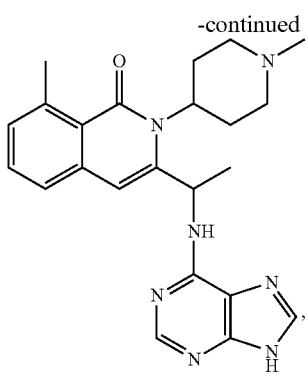
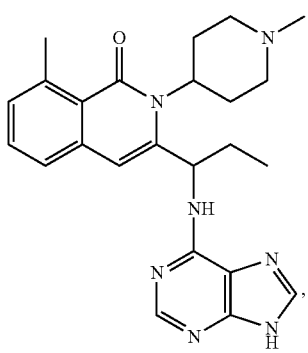
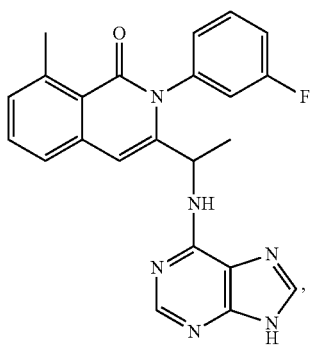
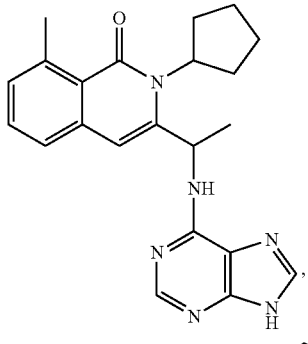
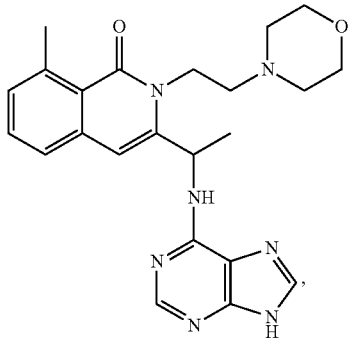
314
-continued
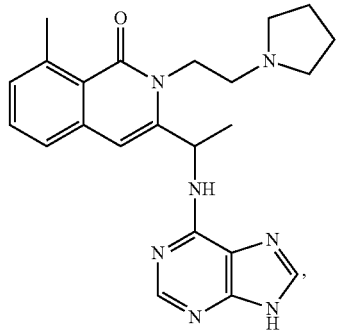
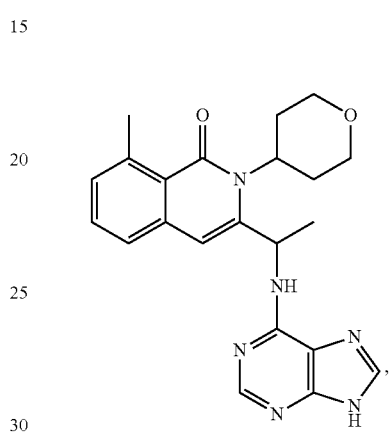
and
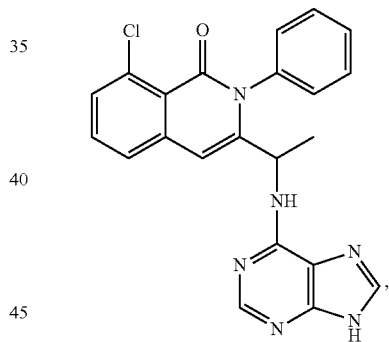
or a pharmaceutically acceptable salt thereof.
16. The method of claim 1, wherein the PI3K inhibitor is a compound selected from the group consisting of:
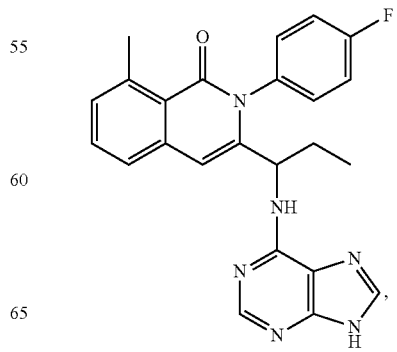

-continued
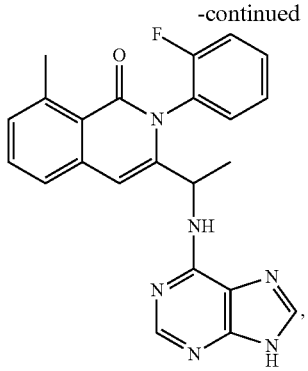
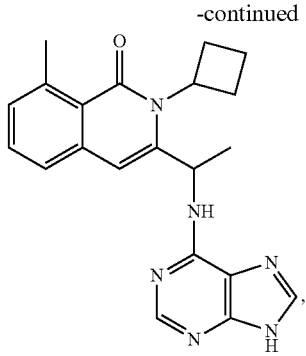
or a pharmaceutically acceptable salt thereof.
17. The method of claim 1, wherein the PI3K inhibitor is a compound selected from the group consisting of:
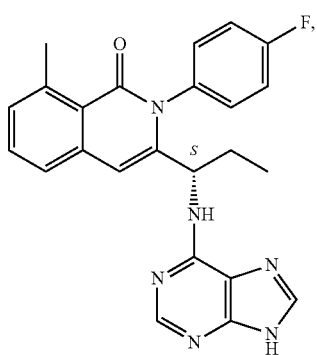
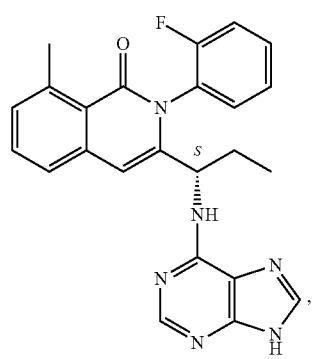
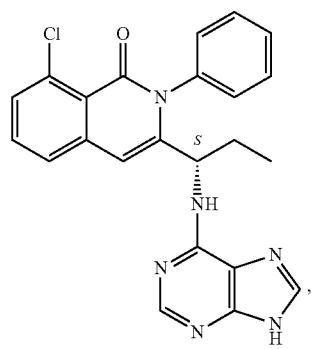

317
-continued
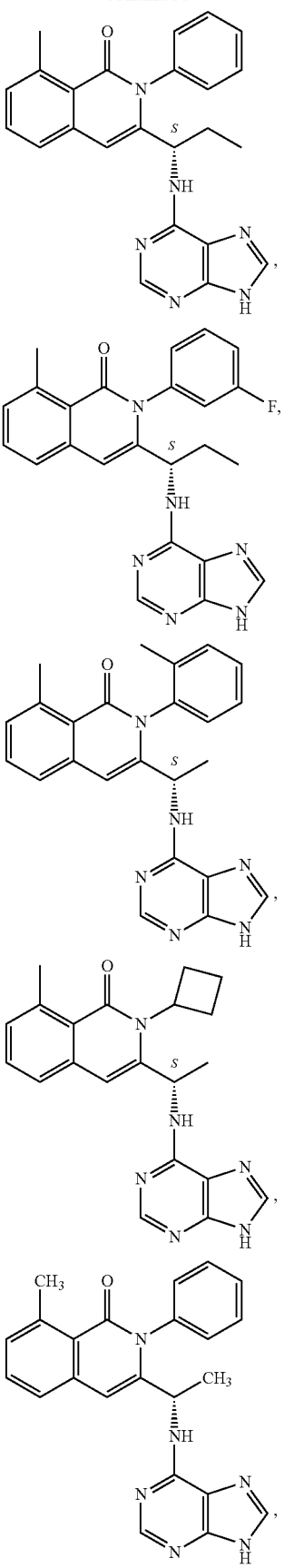
318
-continued
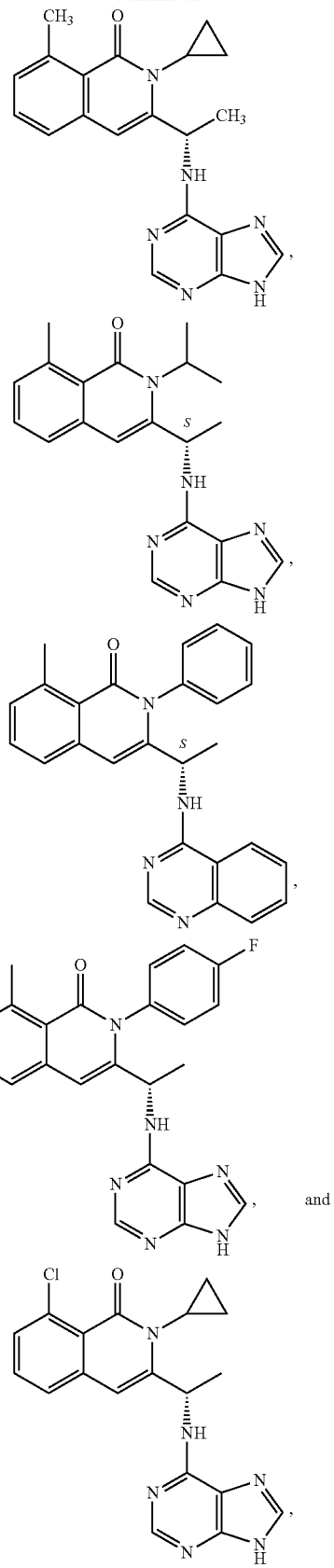
or a pharmaceutically acceptable salt thereof.

18. The method of claim 1, wherein the PI3K inhibitor is a compound of the following structure:

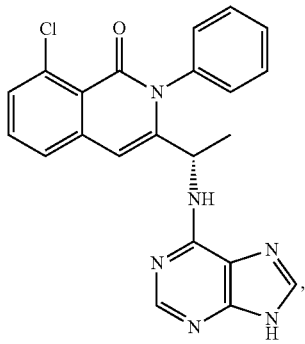 [SMILES: C[C@H](Nc1ncnc2[nH]cnc12)c1cc2cccc(Cl)c2c(=O)n1-c1ccccc1]

or a pharmaceutically acceptable salt thereof.

19. The method of claim 1, wherein the lupus is selected from the group consisting of systemic lupus erythematosus (SLE), cutaneous lupus erythematosus (CLE), drug-induced lupus, and neonatal lupus.

20. The method of claim 19, wherein the lupus is SLE.

21. The method of claim 19, wherein the CLE is acute cutaneous lupus erythematosus (ACLE), subacute cutaneous lupus erythematosus (SCLE), intermittent cutaneous lupus erythematosus, or chronic cutaneous lupus.

22. A method of treating lupus, comprising administering a PI3K inhibitor to a subject in need thereof, in an amount sufficient to treat the lupus in the subject, wherein the PI3K inhibitor is

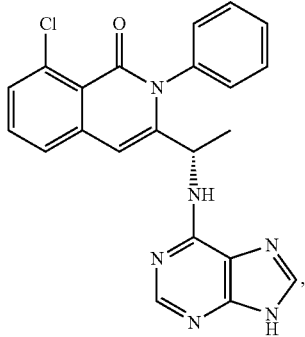 [SMILES: C[C@H](Nc1ncnc2[nH]cnc12)c1cc2cccc(Cl)c2c(=O)n1-c1ccccc1]

or a pharmaceutically acceptable salt thereof, and wherein the treatment results in reduction of levels of one or more of IFN-α, TNF-α, IL-6, IL-8, IL-1, or an anti-dsDNA autoantibody in the subject.

23. A method of treating lupus comprising administering a PIK3 inhibitor to a subject in need thereof, in an amount sufficient to decrease or inhibit the lupus in the subject, wherein the treatment results in reduction of levels of one or more of IFN-α, TNF-α, IL-6, IL-8, or IL-1 in the subject.

24. The method of claim 23, wherein the subject is a mammal.

25. The method of claim 24, wherein the subject is a human.

26. The method of claim 23, wherein the subject is a female.

27. The method of claim 23, wherein the treatment results in reduction of a level of an anti-dsDNA autoantibody in the subject.

28. The method of claim 23, wherein the treatment results in reduction of one or more of nephritis, proteinuria, or spleen inflammation in the subject.

29. The method of claim 23, wherein the treatment results in reduction of levels of immune complexes in the subject.

30. The method of claim 23, wherein the lupus is selected from the group consisting of systemic lupus erythematosus (SLE), cutaneous lupus erythematosus (CLE), drug-induced lupus, and neonatal lupus.

31. The method of claim 30, wherein the lupus is SLE.

32. The method of claim 30, wherein the CLE is acute cutaneous lupus erythematosus (ACLE), subacute cutaneous lupus erythematosus (SCLE), intermittent cutaneous lupus erythematosus, or chronic cutaneous lupus.

33. The method of claim 23, further comprising administration of an additional therapeutic agent.

34. The method of claim 33, wherein the additional therapeutic agent is chosen from one or more of belimumab, AGS-009, rontalizumab, vitamin D3, sifalimumab, AMG 811, IFNα Kinoid, CEP33457, epratuzumab, LY2127399, Ocrelizumab, Atacicept, A-623, SBI-087, AMG557, laquinimod, rapamycin, cyclophosphamide, azathioprine, mycophenolate, leflunomide, methotrexate, CNTO 136, tamibarotene, N-acetylcysteine, CDP7657, hydroxychloroquine, rituximab, carfilzomib, bortezomib, ONX 0914, IMO-3100, or DV 1179.

35. The method of claim 23, wherein the PI3K inhibitor is a compound of Formula I-1:

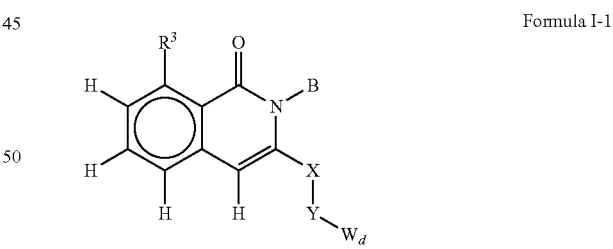

Formula I-1 or a pharmaceutically acceptable salt thereof, wherein
B is a moiety of Formula II:

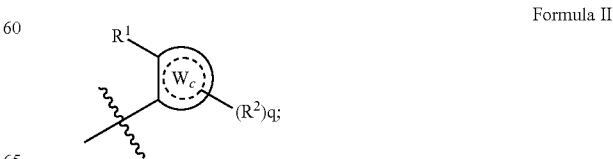

Formula II wherein $W_c$ is aryl, heteroaryl, heterocycloalkyl, or cycloalkyl, and q is an integer of 0, 1, 2, 3, or 4;

X is a bond or —$(CH(R^9))_z$—, and z is an integer of 1;

Y is —$N(R^9)$—;

$W_d$ is:

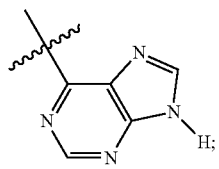

$R^1$ is hydrogen, alkyl, alkenyl, alkynyl, alkoxy, amido, alkoxycarbonyl, sulfonamido, halo, cyano, or nitro;

$R^2$ is alkyl, alkenyl, alkynyl, cycloalkyl, heterocycloalkyl, aryl, heteroaryl, heteroarylalkyl, alkoxy, amino, halo, cyano, hydroxy or nitro;

$R^3$ is hydrogen, alkyl, alkenyl, alkynyl, cycloalkyl, heterocycloalkyl, alkoxy, amido, amino, alkoxycarbonyl sulfonamido, halo, cyano, hydroxy or nitro; and each instance of $R^9$ is independently hydrogen, alkyl, or heterocycloalkyl.

36. The method of claim 35, wherein B is a moiety of Formula II:

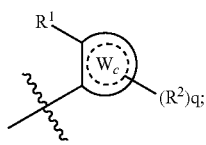

Formula II wherein $W_c$ is aryl, heteroaryl, heterocycloalkyl, or cycloalkyl;

q is an integer of 0 or 1;

$R^1$ is hydrogen, alkyl, or halo;

$R^2$ is alkyl or halo; and $R^3$ is hydrogen, alkyl, or halo.

37. The method of claim 35, wherein X is —$(CH(R^9))_z$—, and Y is —NH—.

38. The method of claim 35, wherein $R^3$ is —H, —$CH_3$, —$CH_2CH_3$, —$CF_3$, —Cl or —F.

39. The method of claim 36, wherein X is —$(CH(R^9))_z$—, wherein $R^9$ is methyl and z=1; and $W_d$ is

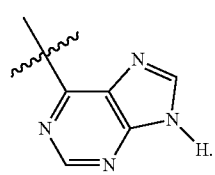

40. The method of claim 35, wherein the compound is predominately in an (S)-stereochemical configuration.

41. The method of claim 35, wherein the compound has a structure of Formula V-A2:

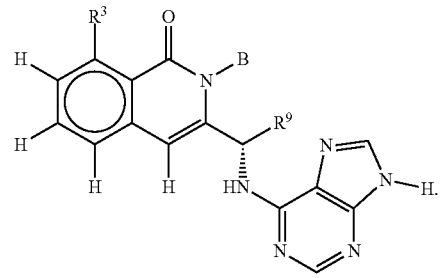

Formula V-A2

42. The method of claim 23, wherein the PI3K inhibitor is a compound selected from the group consisting of:

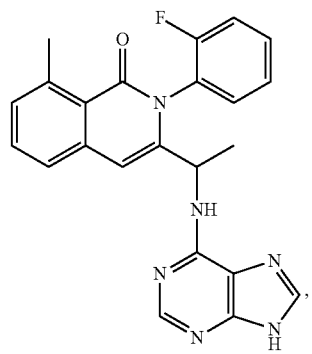

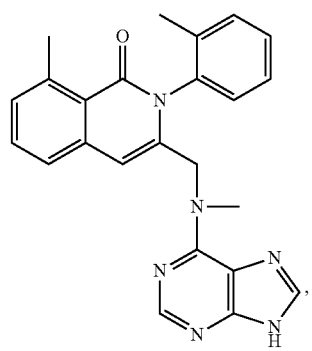

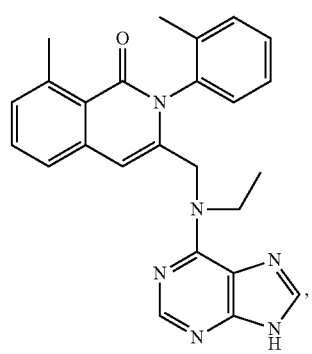

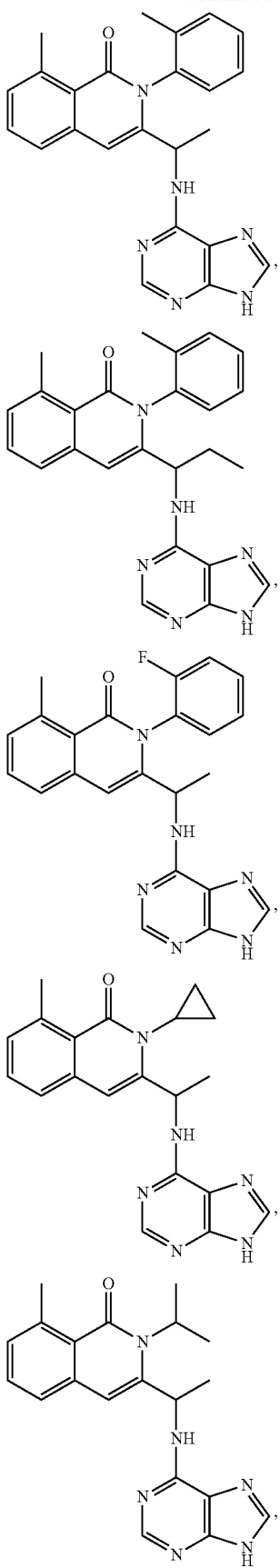
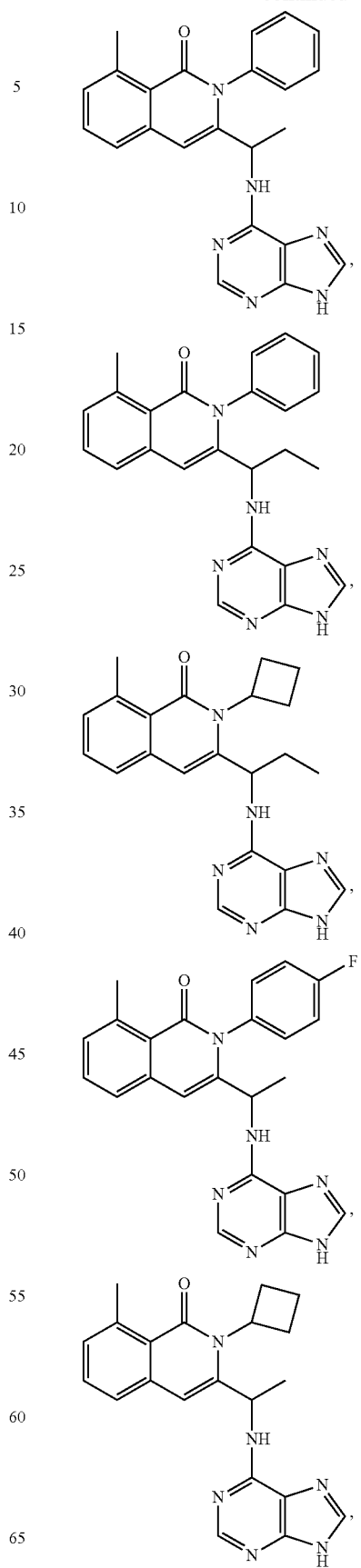

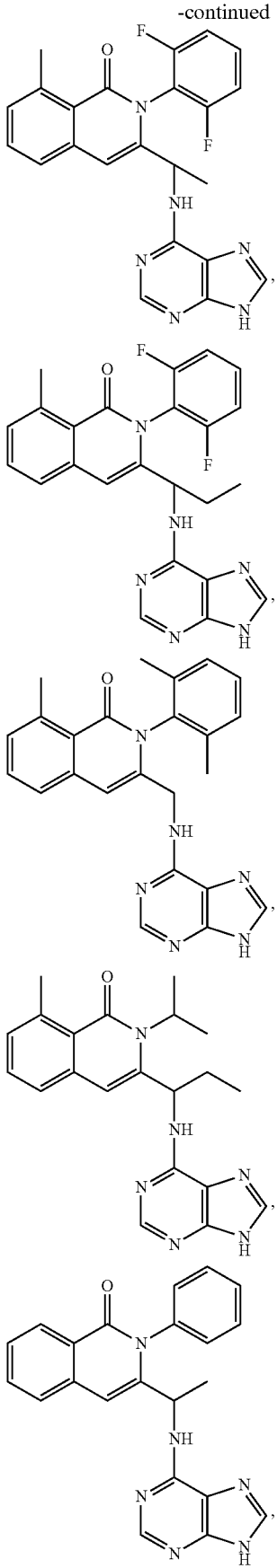
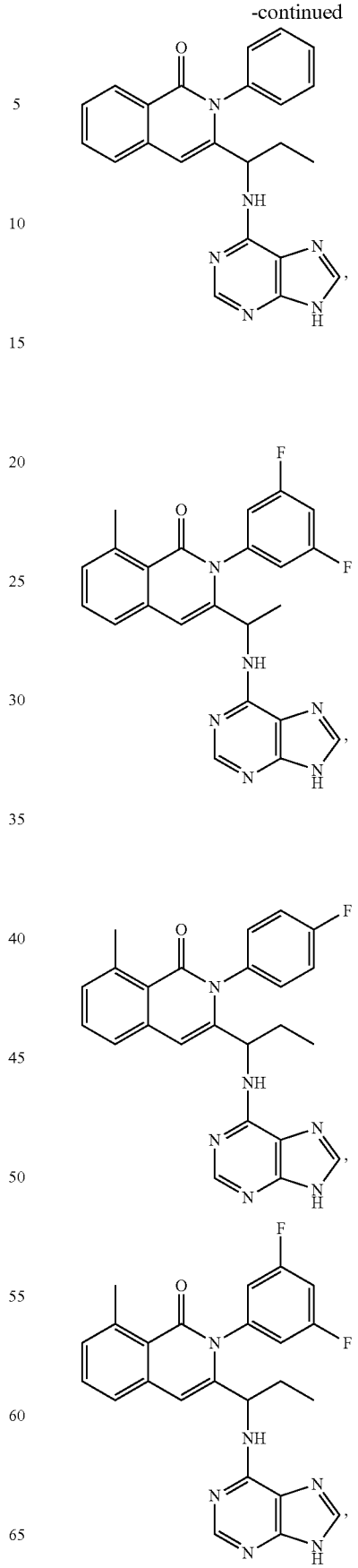

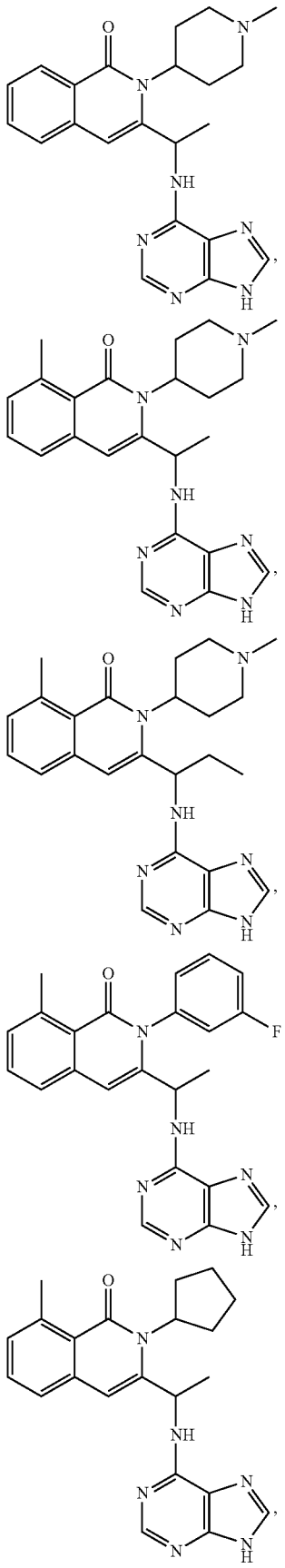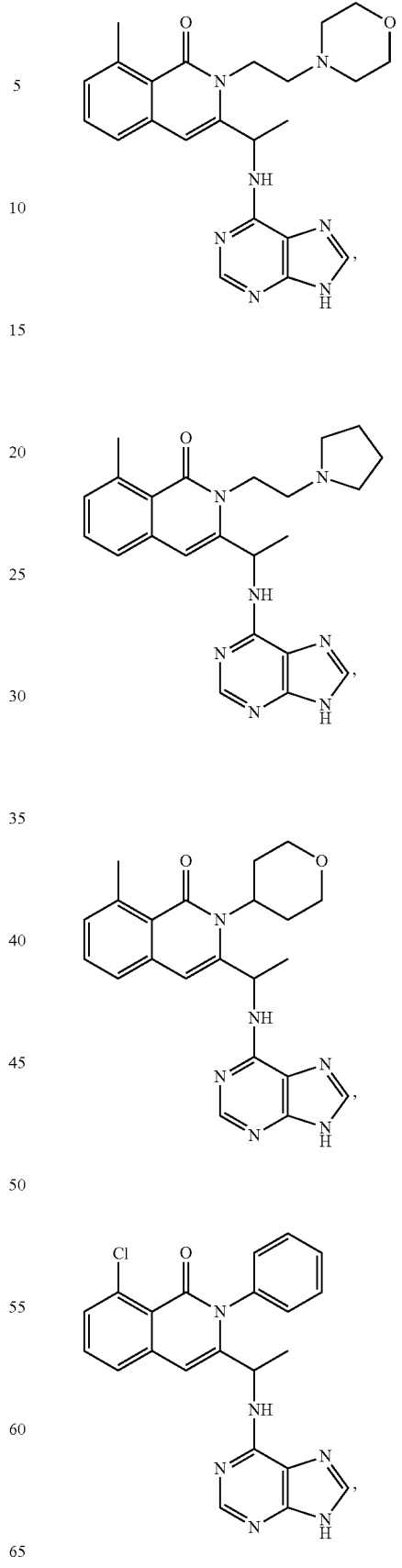
or a pharmaceutically acceptable salt thereof.

43. The method of claim 23, wherein the PI3K inhibitor is a compound selected from the group consisting of:
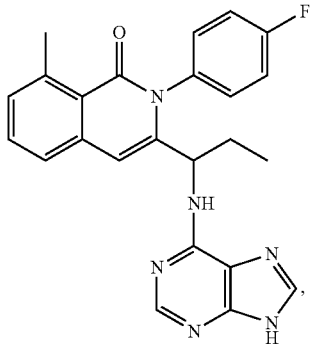
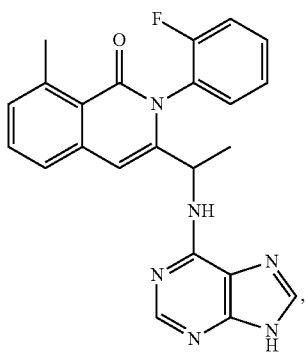
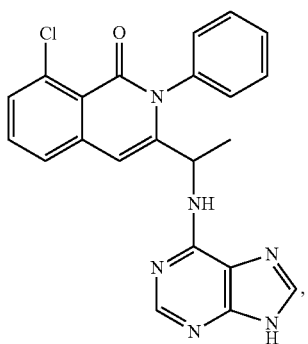 [SMILES: C[C@H](Nc1ncnc2[nH]cnc12)c1cc2cccc(Cl)c2c(=O)n1-c1ccccc1]
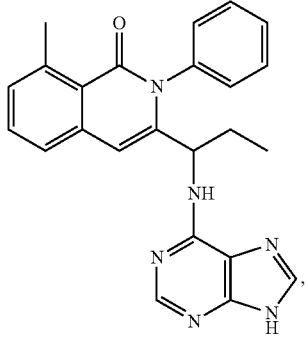
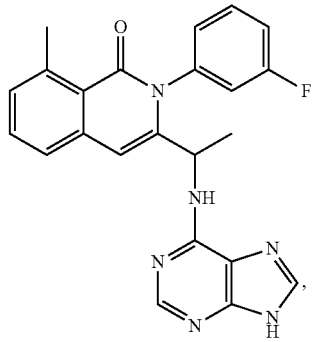
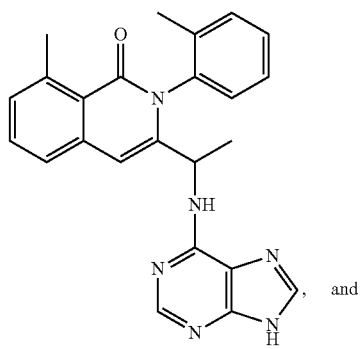
or a pharmaceutically acceptable salt thereof.
44. The method of claim 23, wherein the PI3K inhibitor is a compound selected from the group consisting of:
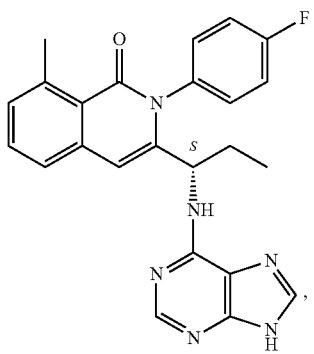

-continued
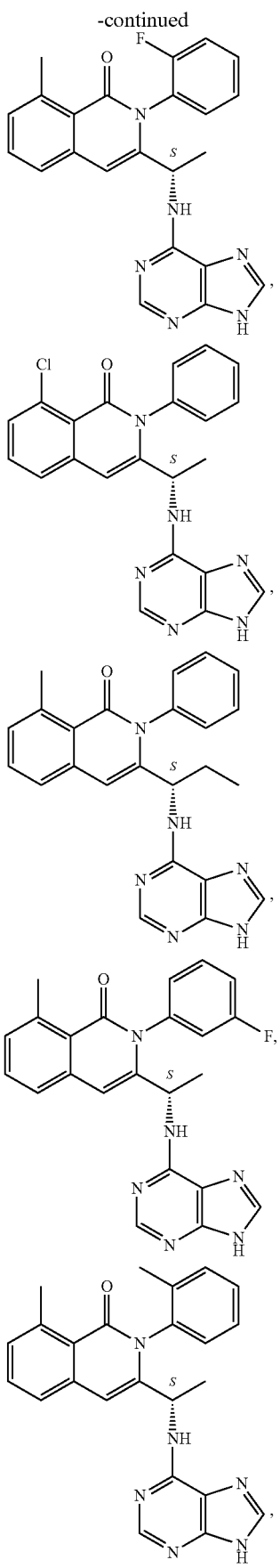
-continued
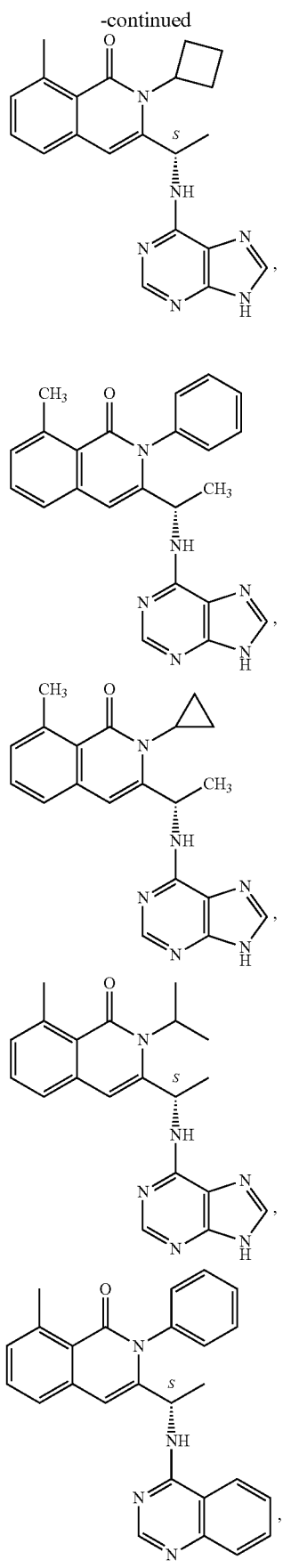

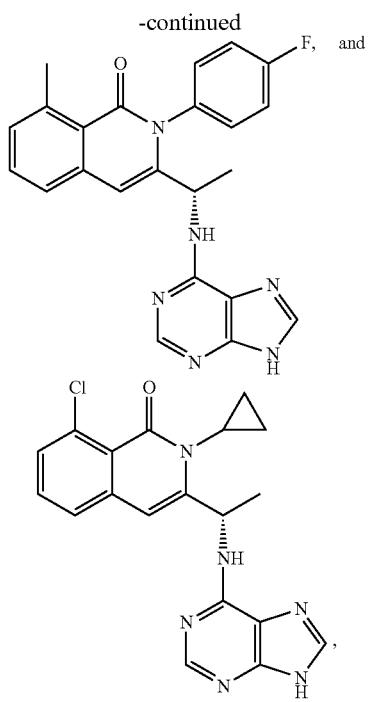

or a pharmaceutically acceptable salt thereof.

45. The method of claim 23, wherein the PI3K inhibitor is a compound of the following structure:

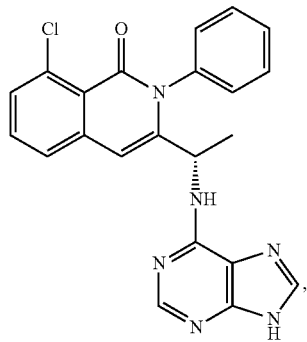

or a pharmaceutically acceptable salt thereof.

46. The method of claim 1, wherein the PI3K inhibitor is a compound of the following structure:

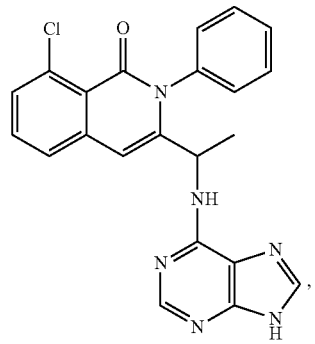 [SMILES: CC(Nc1ncnc2[nH]cnc12)c1cc2cccc(Cl)c2c(=O)n1-c1ccccc1]

or a pharmaceutically acceptable salt thereof.

47. The method of claim 23, wherein the PI3K inhibitor is a compound of the following structure:

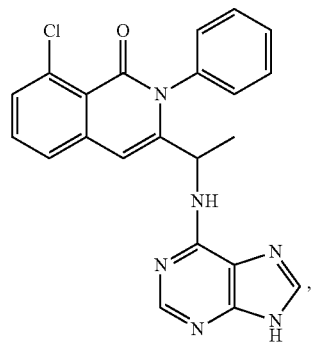 [SMILES: CC(Nc1ncnc2[nH]cnc12)c1cc2cccc(Cl)c2c(=O)n1-c1ccccc1]

or a pharmaceutically acceptable salt thereof.

48. The method of claim 1, wherein the symptom is reduced by at least 10%, at least 20%, at least 30%, at least 40%, at least 50%, at least 60%, at least 70%, at least 80%, at least 90%, or at least 95% relative to a control level.

* * * * *

UNITED STATES PATENT AND TRADEMARK OFFICE
CERTIFICATE OF CORRECTION

PATENT NO.      : 8,828,998 B2
APPLICATION NO. : 13/837195
DATED           : September 9, 2014
INVENTOR(S)     : Palombella et al.

It is certified that error appears in the above-identified patent and that said Letters Patent is hereby corrected as shown below:

In the Claims

In column 306, line 15 (part of claim 3), replace the term "or" before "spleen" with "and" to read:
-- proteinuria, and spleen --.

In column 307, lines 7–8 (part of claim 8), insert a -- , -- between the terms "alkoxycarbonyl" and "sulfonamido" to read:
-- alkoxycarbonyl, sulfonamido --.

In column 307, line 35 (part of claim 12), replace the term "z=1" with "z is 1".

In column 316, approximately lines 38–50 (part of claim 17), replace the structure of the second compound of claim 17 with

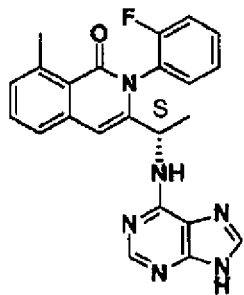

Signed and Sealed this
Fourteenth Day of July, 2015

Michelle K. Lee
*Director of the United States Patent and Trademark Office*

In column 316, approximately lines 54–66 (part of claim 17), replace the structure of the third compound of claim 17 with

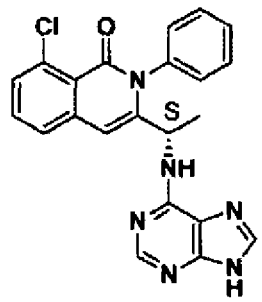

In column 317, approximately lines 15–27 (part of claim 17), replace the structure of the second compound with

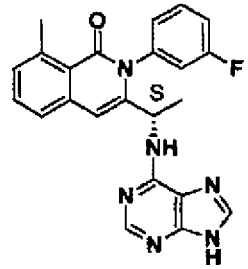

In column 321, lines 24–25 (part of claim 35), insert a -- , -- between the terms "alkoxycarbonyl" and "sulfonamido" to read:

-- alkoxycarbonyl, sulfonamido --.

In column 321, line 54 (part of claim 39), replace the term "z=1" with "z is 1".